United States Patent
Mirel et al.

(10) Patent No.: US 7,205,106 B1
(45) Date of Patent: Apr. 17, 2007

(54) ASSOCIATION OF POLYMORPHISMS IN IL4-RELATED GENES WITH AUTOIMMUNE DISEASE

(75) Inventors: Daniel B. Mirel, Oakland, CA (US); Henry A. Erlich, Oakland, CA (US); Teodorica L. Bugawan, Castro Valley, CA (US); Janelle A. Noble, Berkeley, CA (US); Ann Maria Valdes, Zola Predosa (IT)

(73) Assignee: Roche Molecular Systems, Inc., Alameda, CA (US)

( * ) Notice: Subject to any disclaimer, the term of this patent is extended or adjusted under 35 U.S.C. 154(b) by 0 days.

(21) Appl. No.: 10/267,844

(22) Filed: Oct. 8, 2002

Related U.S. Application Data

(63) Continuation-in-part of application No. 10/264,965, filed on Oct. 4, 2002, which is a continuation-in-part of application No. 10/189,956, filed on Jul. 3, 2002.

(60) Provisional application No. 60/306,912, filed on Jul. 20, 2001.

(51) Int. Cl.
  *C12Q 1/68* (2006.01)
  *C12P 19/34* (2006.01)
(52) U.S. Cl. .................. 435/6; 435/91.1; 435/91.2
(58) Field of Classification Search ............ 435/6, 435/810, 91.1, 91.2; 536/23.1, 24.33, 24.32
See application file for complete search history.

(56) References Cited

U.S. PATENT DOCUMENTS

2003/0152951 A1* 8/2003 Mirel et al. ................. 435/6

FOREIGN PATENT DOCUMENTS

| EP | 1186613 | 3/2002 |
| EP | 02028714 | 7/2003 |
| WO | WO 96/05213 | 2/1996 |
| WO | WO 01/23404 A1 | 4/2001 |
| WO | WO 01/23410 A2 | 4/2001 |

OTHER PUBLICATIONS

Bugawan et al. Association of specific IL4 receptor SNPs with Type 1 diabetes in Filipinos. American Journal of Human Genetics, vol. 69, No. 4, supplement, p. 403, Abstract No. 1291, Oct. 2001).*
Deichmann et al. Common polymorphism in the coding part of the Il4 receptor gene. Biochemical and biophysical research communications, vol. 231, pp. 696-697, 1997.*
Yamada et al. Association between a single nucleotide polymorphism in the promoter of the human IL-3 gene and Rheumatoid Arthritis . . . American Journal of Human Genetics. vol. 68, pp. 674-685, Feb. 14, 2001.*

(Continued)

*Primary Examiner*—Kenneth R. Horlick
*Assistant Examiner*—Cynthia B. Wilder
(74) *Attorney, Agent, or Firm*—Townsend and Townsend and Crew LLP

(57) ABSTRACT

The present invention provides methods and reagents for determining sequence variants present at the IL4 receptor, IL-4 and IL-13 loci, which facilitate identifying individuals at risk for type 1 diabetes.

13 Claims, 2 Drawing Sheets

Figure 1:
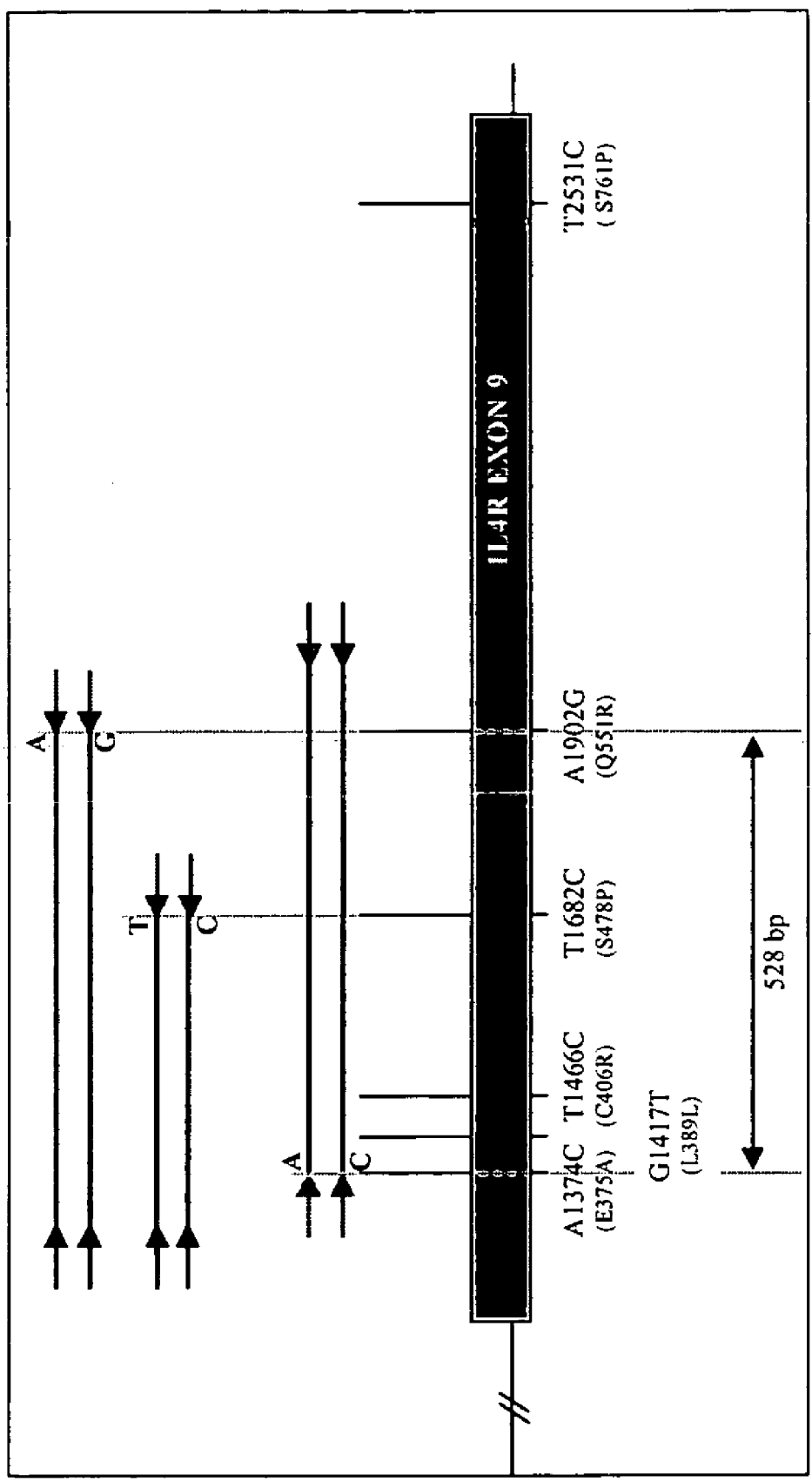

Schematic of Molecular Haplotyping Method for SNPs #3-7.

OTHER PUBLICATIONS

Reimsnider et al. IL4 and IL4R-alpha genes are not linked or associated with type 1 diabetes. Pediatric Research. vol. 47, No. 2, pp. 246-249, 2000.*

Deichmann et al., "Linkage and Allelic Association of Atopy and Markers Flanking the IL4-Receptor Gene," Clin. Exp. Allergy (1998) 28:151-15.

Dupre et al., "Atopy and a Mutation in the Interleukin-4 Receptor Gene," N. Eng. J. Med. (2000) 343:69-70.

Grimbacher et al., "The Interleukin-4 Receptor Variant Q576R in Hyper-IgE Syndrome," N. Eng. J. Med. (1998) 338:1073-1074.

Hackstein et al., "Definition of Human Interleukin-4 Receptor Alpha Chain Haplotypes and Allelic Association with Atopy Markers," Hum. Immunol. (1999) 60:1119-1127.

Hackstein et al., "Analysis of Interleukin-4 Receptor Alpha Chain Variants in Multiple Sclerosis," J. Neuroimmunol. (2001) 113:240-248.

Hershey et al., "The Association of Atopy With a Gain-of-Function Mutation in the Alpha Subunit of the Interleukin-4 Receptor," N. Eng. J. Med. (1997) 337:1720-1725.

Kanemitsu et al., "Association of Interleukin-4 Receptor and Interleukin-4 Promoter Gene Polymorphisms with Systemic Lupus Erythematosus," Arthritis Rheum (1999) 42:1298-1300.

Kruse et al., "The Polymorphisms S503P and Q576R in the Interleukin-4 Receptor Alpha Gene are Associated with Atopy and Influence the Signal Transduction," Immunology (1999) 96:365-371.

Mirel et al., "Association of IL4R Haplotypes With Type 1 Diabetes," Diabetes (2002): 51:3336-3341.

Mitsuyasu et al., "Ile50Val Variant of IL4R Alpha Upregulates IgE Synthesis and Associates with Atopic Asthma," Nat. Genet. (1998) 19:119-120.

Noble et al., "The Role of HLA Class II Genes in Insulin-Dependent Diabetes Mellitus: Molecular Analysis of 180 Caucasian, Multiplex Families," Am. J. Hum. Genet. (1996) 59:1134-1148.

Noguchi et al., "No Association Between Atopy/Asthma and the Ile50Val Polymorphism of IL-4 Receptor," Am. J. Respir. Crit. Care Med. (1999) 160:342-345.

Ober et al., "Variation in the Interleukin 4-Receptor Alpha Gene Confers Susceptibility to Asthma and Atopy in Ethnically Diverse Populations," Am. J. Hum. Genet. (2000) 66:517-526.

Olavesen et al., "Analysis of Single Nucleotide Polymorphisms in the Interleukin-4 Receptor Gene for Association With Inflammatory Bowel Disease," Immunogenetics (2000) 51:1-7.

Peltz "A Role for CD4+ T-Cell Subsets Producing a Selective Pattern of Lymphokines in the Pathogenesis of Human Chronic Inflammatory and Allergic Diseases," Immunological Reviews (1991) 123:23-35.

Reimsnider et al., "IL4 and IL4R Alpha Genes Are Not Linked or Associated With Type 1 Diabetes," Pediatr. Res. (2000) 47:246-249.

Rosa et al., "The R576 IL-4 Receptor Alpha Allele Correlates With Asthma Severity," J. Allergy Clin. Immunol. (1999) 104:1008-1014.

Shirakawa et al., "Atopy and Asthma: Genetic Variants of IL-4 and IL-13 Signalling," Immunol. Today (2000) 21:60-64.

Tan et al., "Interleukin-4 Receptor Variant Q576R: Ethnic Differences and Association With Atopy," Clin. Genet. (1999) 56:333-334.

Youn et al., "Association of the Interleukin-4 Receptor Alpha Variant Q576R with Th1/Th2 Imbalance in Connective Tissue Disease," Immunogenetics (2000) 51:743-746.

Pravdić et al., "Catalytic Hydrogenation of Some 2-Acetamidoaldose Derivatives", Croatica Chemica Acta 45:343-356 (1973).

Bugawan T.L., et al.; "Association of Specific IL4 Receptor SNPs with Type 1 Diabetes in Filipinos"; 2001, XP-002266510.

Bugawan T.L., et al.; "Association of Interaction of the IL4R, IL4, and IL13 Loci with Type 1 Diabetes among Filipinos"; Am. J. Hum. Genet. 2003, vol. 72, pp. 1505-1514.

Hackstein, H., "Definition of Human Interleukin-4 Receptor Alpha Chain Haplotypes and Allelic Association with Atopy Markers"; Human Immunology 1999, vol. 60, pp. 1119-1127.

Jahromi, Mohammed et al.; "A CA Repeat Polymorphism of the IFN Gene is Associated with Susceptibility to Type I Diabetes"; Journal of Interferon and Cytokine Research 2000, vol. 20, pp. 187-190.

Noguchi, Emiko et al.; "Haplotypes of the 5' Region of the IL-4 Gene and SNPs in the Intergene Sequence Between the IL-4 and IL-13 Genes are Associated with Atopic Asthma"; Human Immunology 2001, vol. 62, pp. 1251-1257.

Ohkubo, T. et al.; "A Novel Polymorphism in the Promoter Region of the IL-4 Gene is Associated with Type 1 Diabetes in Japanese"; 2001, XP-002266508.

Maier, LM, et al., "Testing the possible negative association of type 1 diabetes and atopic disease by analysis of the interleukin 4 receptor gene," Genes and Immunity, 2003, vol. 4, pp. 469-475.

Pociot, F., et al., "Genetics of type 1 diabetes mellitus," Genes and Immunity, 2002, vol. 3, pp. 235-249.

* cited by examiner

Figure 1. Schematic of Molecular Haplotyping Method for SNPs #3-7.

ASSOCIATION OF POLYMORPHISMS IN IL4-RELATED GENES WITH AUTOIMMUNE DISEASE

The present patent application is a continuation-in-part of U.S. patent application Ser. No. 10/264,965, filed Oct. 4, 2002, which is a continuation-in-part of U.S. patent application Ser. No. 10/189,956, filed Jul. 3, 2002, which claims priority under 35 U.S.C. § 119(e) to U.S. provisional application No. 60/306,912, filed Jul. 20, 2001, all of which are herein incorporated by reference in their entireties.

1. FIELD OF THE INVENTION

The present invention relates to the fields of immunology and molecular biology. In particular, it relates to methods and reagents for detecting an individual's risk for autoimmune diseases. More specifically, it relates to methods and reagents for detecting an individual's increased or decreased risk for type 1 diabetes.

2. DESCRIPTION OF RELATED ART

The immunological response to an antigen is mediated through the selective differentiation of CD4+ T helper precursor cells (Th0) to T helper type 1 (Th1) or T helper type 2 (Th2) effector cells, with functionally distinct patterns of cytokine (also described as lymphokine) secretion. Th1 cells secrete interleukin 2 (IL-2), IL-12, tumor necrosis factor (TNF), lymphotoxin (LT), and interferon gamma (IFN-γ) upon activation, and are primarily responsible for cell-mediated immunity such as delayed-type hypersensitivity. Th2 cells secrete IL-4, IL-5, IL-6, IL-9, and IL-13 upon activation, and are primarily responsible for extracellular defense mechanisms. The role of Th1 and Th2 cells is reviewed in Peltz, 1991, *Immunological Reviews*, 123: 23–35, incorporated herein by reference.

IL4 and IL13 play a central role in IgE-dependent inflammatory reactions. IL4 induces IgE antibody production by B Cells and further provides a regulatory function in the differentiation of Th0 to Th1 or Th2 effector cells by both promoting differentiation into Th2 cells and inhibiting differentiation into Th1 cells. IL13 also induces IgE antibody production by B Cells.

IL4 and IL13 operate through the IL4 receptor ("IL4R"), found on both B and T cells, and the IL13R, found on B cells, respectively. The human IL4 receptor (IL4R) is a heterodimer comprising the IL4R α chain and the IL2 receptor γ chain. The α-chain of the IL4 receptor also serves as the α-chain of the IL13 receptor. IL4 binds to both IL4R and IL13R through the IL4R α-chain and can activate both B and T cells, whereas IL13 binds only to IL13R through the IL13R α1 chain and activates only T cells.

3. SUMMARY OF INVENTION

The present invention provides methods for detecting an individual's increased or decreased risk for an autoimmune disease such as type 1 diabetes, also known as insulin-dependent diabetes mellitus ("IDDM"). The present invention also provides kits, reagents and arrays useful for detecting an individual's risk for autoimmune diseases such as type 1 diabetes.

In one aspect, the present invention provides a method for detecting an individual's increased or decreased risk for an autoimmune disease such as type 1 diabetes by detecting the presence of a type 1 diabetes-associated polymorphism in the IL4R, IL4 or IL13 loci in a nucleic acid sample of the individual, wherein the presence of said polymorphism indicates the individual's increased risk for type 1 diabetes.

In one aspect, the present invention provides a method for detecting an individual's increased or decreased risk for an autoimmune disease such as type 1 diabetes by detecting the presence of a type 1 diabetes-associated polymorphism in the IL4R, IL4 or IL13 loci in a nucleic acid sample of the individual, wherein the presence of said polymorphism indicates the individual's increased risk for type 1 diabetes.

In one embodiment, the polymorphism is an IL4R polymorphism. In another embodiment, the polymorphism is an IL4 polymorphism. In another embodiment, the polymorphism is an IL13 polymorphism. In another embodiment, an IL4R polymorphism and an IL4 polymorphism are detected. In another embodiment, an IL4R polymorphism and an IL13 polymorphism are detected. In another embodiment, an IL4 polymorphism and an IL13 polymorphism are detected. In another embodiment, an IL4R polymorphism, an IL4 polymorphism and an IL13 polymorphism are detected.

In another embodiment, the IL4R polymorphism is selected from the IL4R polymorphisms listed in Table 21. In another embodiment, the IL4 polymorphism is the IL4(−524) polymorphisms listed in Table 21. In another embodiment, the IL13 polymorphism is selected from the IL4R polymorphisms listed in Table 21. In another embodiment, 2 or more IL4R polymorphisms selected from the IL4R polymorphisms listed in Table 21 are detected. In another embodiment, 6 or more IL4R polymorphisms selected from the IL4R polymorphisms listed in Table 21 are detected. In another embodiment, 7 or more IL4R polymorphisms selected from the IL4R polymorphisms listed in Table 21 are detected. In another embodiment, 8 or more IL4R polymorphisms selected from the IL4R polymorphisms listed in Table 21 are detected. In another embodiment, all 10 IL4R polymorphisms listed in Table 21 are detected.

The individual can belong to any race or population. In one embodiment, the individual is an Asian, preferably a Filipino, or a Caucasian.

The nucleic acid sample can be obtained from any part of the individual's body, including, but not limited to hair, skin, nails, tissues or bodily fluids such as saliva, blood, etc. The nucleic acid sample can, but need not, be amplified by any amplification method including, but not limited to, polymerase chain reaction ("PCR").

The polymorphism can be any predisposing or protective polymorphism in the IL4R, IL4 or IL13 loci. In one embodiment of the invention, the polymorphism can be any polymorphism identified as predisposing or protective by methods taught herein. In one embodiment, the polymorphism can be a single nucleotide polymorphism ("SNP") in the IL-4 receptor ("IL4R"), IL4 or IL13 loci. In another embodiment, specific haplotypes in the IL4R, IL4 and IL13 loci as well as specific combinations of, and interactions between, SNPs at these loci can be indicative of an increased or a decreased risk to an autoimmune disease such as type 1 diabetes.

The polymorphism can be detected by any method known in the art for detecting the presence of a specific polymorphism in a nucleic acid sample. These methods include, but are not limited to, contacting the nucleic acid sample with one or more nucleic acid molecules that hybridize under stringent hybridization conditions to at least one type 1 diabetes-associated IL4R, IL4 or IL13 polymorphism and detecting the hybridization, detection by amplification of the nucleic acid sample by, for example, PCR, and by direct sequencing of the nucleic acid sample.

Another aspect of the invention relates to a kit useful for detecting the presence of a predisposing or a protective polymorphism in the IL4R, IL4 or IL13 loci in a nucleic acid sample of an individual whose risk for type 1 diabetes is being assessed. The kit can comprise one or more oligonucleotides capable of detecting a predisposing or protective polymorphism in the IL4R, IL4 or IL13 loci as well as instructions for using the kit to detect susceptibility for an autoimmune disease such as type 1 diabetes. In preferred embodiments, the oligonucleotide or oligonucleotides each individually comprise a sequence that hybridizes under stringent hybridization conditions to at least one type 1 diabetes-associated IL4R, IL4 or IL13 polymorphism. In some embodiments, the oligonucleotide or oligonucleotides each individually comprise a sequence that is fully complementary to a nucleic acid sequence comprising a type 1 diabetes-associated IL4R, IL4 or IL13 polymorphism.

In some embodiments, the oligonucleotide can be used to detect the presence of a type 1 diabetes-associated IL4R, IL4 or IL13 polymorphism by hybridizing to the polymorphism under stringent hybridizing conditions. In some embodiments, the oligonucleotide can be used as an extension primer in either an amplification reaction such as PCR or a sequencing reaction, wherein the type 1 diabetes-associated IL4R, IL4 or IL13 polymorphism is detected either by amplification or sequencing.

In certain embodiments, the kit can further comprise amplification or sequencing primers which can, but need not, be sequence-specific. The kit can also comprise reagents for labeling one or more of the oligonucleotides, or comprise labeled oligonucleotides. Optionally, the kit can comprise reagents to detect the label.

In some embodiments, the kit can comprise one or more oligonucleotides that can be used to detect the presence of two or more predisposing or protective IL4R, IL4 or IL13 polymorphisms or combinations of predisposing polymorphisms, protective polymorphisms or both.

In another aspect, the invention provides an array useful for detecting the presence of a predisposing or a protective IL4R, IL4 or IL13 polymorphism in a nucleic acid sample of an individual whose risk for type 1 diabetes is being assessed. The array can comprise one or more oligonucleotides capable of detecting a predisposing or protective IL4R, IL4 or IL13 polymorphism. The oligonucleotides can be immobilized on a substrate, e.g., a membrane or glass. In preferred embodiments, the oligonucleotide or oligonucleotides each individually comprise a sequence that can hybridize under stringent hybridization conditions to a nucleic acid sequence comprising a type 1 diabetes-associated IL4R, IL4 or IL13 polymorphism. In some embodiments, the oligonucleotide or oligonucleotides each individually comprise a sequence that is fully complementary to a nucleic acid sequence comprising a type 1 diabetes-associated IL4R, IL4 or IL13 polymorphism. The oligonucleotide or oligonucleotides can, but need not, be labeled. In some embodiments, the array can be a micro array.

In some embodiments, the array can comprise one or more oligonucleotides used to detect the presence of two or more predisposing or protective IL4R, IL4 or IL13 polymorphisms or combinations of predisposing polymorphisms, protective polymorphisms or both.

In certain embodiments, an individual's risk for particular Th1-mediated diseases is diagnosed from the individual's IL4R, IL4 or IL13 genotype. In a preferred embodiment, the Th1-mediated disease is type 1 diabetes. An individual who has at least one polymorphism statistically associated with type 1 diabetes possesses a factor contributing to either an increased or a decreased risk of a type 1 diabetes as compared to an individual without the polymorphism. The statistical association of IL4R, IL4 or IL13 polymorphisms (sequence variants) is shown in the examples.

The genotype can be determined using any method capable of identifying nucleotide variation consisting of single nucleotide polymorphic sites. The particular method used is not a critical aspect of the invention. A number of suitable methods are described below.

In one embodiment of the invention, genotyping is carried out using oligonucleotide probes specific to variant IL4R, IL4 or IL13 sequences. Preferably, a region of the IL4R, IL4 or IL13 genes which encompasses one or several polymorphic sites of interest is amplified prior to, or concurrent with, the hybridization of probes directed to such sites. Probe-based assays for the detection of sequence variants are well known in the art.

Alternatively, genotyping is carried out using allele-specific amplification or extension reactions, wherein allele-specific primers are used which support primer extension only if the targeted allele is present. Typically, an allele-specific primer hybridizes to the IL4R, IL4 or IL13 genes such that the 3' terminal nucleotide aligns with a polymorphic position. Allele-specific amplification reactions and allele-specific extension reactions are well known in the art.

4. BRIEF DESCRIPTION OF THE FIGURES

Figure 2:
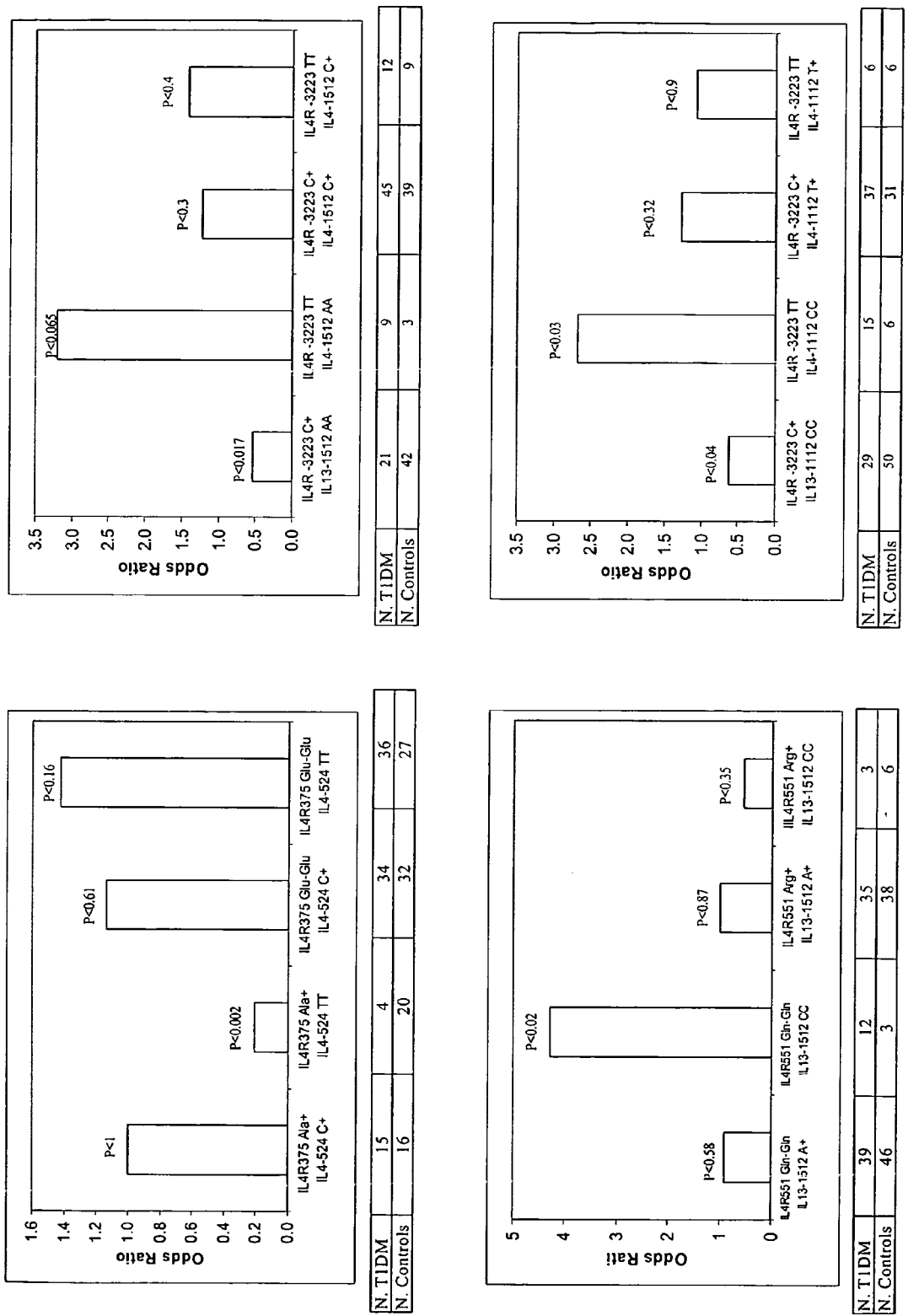

FIG. 1 provides a schematic of a molecular haplotyping method;

FIG. 2 provides an illustration of epistasis between the IL4R SNPs and IL4 and IL13 SNPs.

5. BRIEF DESCRIPTION OF THE TABLES

Table 1 provides the nucleotide sequence of the coding region of an IL4R (SEQ ID NO: 2);

Table 2 provides IL4R, IL4 and IL13 SNPs useful in the methods of the invention;

Table 3 provides probes used to identify IL4R polymorphisms (SEQ ID NO: 3–19);

Table 4 provides computationally estimated haplotype frequencies compared between Filipino controls and diabetics (SEQ ID NO: 20–24);

Table 5 provides genotypes of affected and nonaffected individuals;

Table 6 provides single nucleotide polymorphisms detected;

Table 7 provides amplicon primers and lengths (SEQ ID NO: 25–36);

Table 8 provides hybridization probes and titers (SEQ ID NO: 37–53);

Table 9 provides allele frequency of wildtype allele in HBDI founders;

Table 10 provides D' and Δ values for pairs of IL4R SNPs;

Table 11A provides results of single locus TDT analysis;

Table 11B provides results of single locus TDT analysis;

Table 12 provides allele-specific PCR primers (SEQ ID NO: 54–62);

Table 13 provides IBD distributions for IL4R haplotypes;

Table 14A provides haplotype transmissions;

Table 14B provides haplotype transmissions;

Table 14C provides haplotype transmissions;

Table 15A provides SNP by SNP allele transmissions;

Table 15B provides SNP by SNP allele transmissions;

Table 16A provides a TDT analysis;

Table 16B provides a TDT analysis;

Table 16C provides a TDT analysis;
Table 17A provides a TDT analysis;
Table 17B provides a TDT analysis;
Table 18 provides allele frequencies in Filipino controls and diabetics;
Table 19 provides estimated haplotype frequencies;
Table 20 provides observed haplotype frequencies;
Table 21 provides allele frequencies in diabetics and controls;
Table 22 provides pairwise linkage disequilibrium values for IL4R SNPs;
Table 23 provides pairwise linkage disequilibrium values for IL4 and IL13 SNPs;
Table 24 provides genotype frequencies in patients and controls;
Table 25A provides IL-4R 7-SNP Haplotypes in Filipino diabetics and controls;
Table 25B provides estimated IL4R 10-SNP haplotype frequencies in diabetics and controls;
Table 26 provides estimated IL4 and IL13 5-SNP haplotype frequencies in diabetics and controls;
Table 27 provides correlation between genotype frequencies at IL4R SNPs and five IL4 and IL13 SNPs;
Table 28 provides epistatic interaction between IL4R SNPs and five IL4 and IL13 SNPs;
Table 29 provides probes used to identify IL4 and IL13 polymorphisms (SEQ ID NO: 63–68);
Table 30 provides amplicon primers and lengths for an IL4 promoter and IL13 SNPs (SEQ ID NO: 69–74);
Table 31 provides amplicon primers and lengths for IL4R promoter SNPs (SEQ ID NO: 75–77 and 79–81);
Table 32 provides amplicon primers and lengths for IL13 promoter SNPs (SEQ ID NO: 82–87);

6. DETAILED DESCRIPTION OF THE INVENTION

The present invention provides methods, reagents and kits for detecting an individual's increased or decreased risk for an autoimmune disease. Examples of autoimmune diseases include, but are not limited to, multiple sclerosis, myasthenia gravis, Crohn's disease, ulcerative colitis, primary biliary cirrhosis, type 1 diabetes mellitus (insulin dependent diabetes mellitus or IDDM), Grave's disease, autoimmune hemolytic anemia, pernicious anemia, autoimmune thrombocytopenia, vasculitides such as Wegener's granulomatosis, Behcet's disease, rheumatoid arthritis, systemic lupus erythematosus (lupus), scleroderma, systemic sclerosis, Guillain-Barre syndromes, Hashimoto's thyroiditis spondyloarthropathies such as ankylosing spondylitis, psoriasis, dermatitis herpetiformis, inflammatory bowel diseases, pemphigus vulgaris and vitiligo. In certain preferred embodiments, the autoimmune disease is type 1 diabetes.

Abbreviations and Terminology:

The term "IL4R gene" or "IL4R locus" refers to the genomic nucleic acid sequence that encodes the alpha subunit of the interleukin 4 receptor protein. The nucleotide sequence of a gene, as used herein, encompasses coding regions, referred to as exons, intervening, non-coding regions, referred to as introns, and upstream or downstream regions. Upstream or downstream regions can include regions of the gene that are transcribed but not part of an intron or exon, or regions of the gene that comprise, for example, binding sites for factors that modulate gene transcription. The gene sequence of a Human mRNA for IL4R is provided at GenBank accession number X52425.1 (SEQ ID NO: 1). The coding region is provided as SEQ ID NO: 2. The genomic sequence for the IL4R gene is included in GenBank accession number AC004525.1 (SEQ ID NO: 88).

The term "IL4 gene" or "IL4 locus" refers to the genomic nucleic acid sequence that encodes the interleukin 4 protein. The nucleotide sequence of a gene, as used herein, encompasses coding regions, referred to as exons, intervening, non-coding regions, referred to as introns, and upstream or downstream regions. Upstream or downstream regions can include regions of the gene that are transcribed but not part of an intron or exon, or regions of the gene that comprise, for example, binding sites for factors that modulate gene transcription. The genomic sequence for the IL4 gene is provided at GenBank accession number M23442.1 (SEQ ID NO: 89).

The term "IL13 gene" or "IL13 locus" refers to the genomic nucleic acid sequence that encodes the interleukin 13 protein. The nucleotide sequence of a gene, as used herein, encompasses coding regions, referred to as exons, intervening, non-coding regions, referred to as introns, and upstream or downstream regions. Upstream or downstream regions can include regions of the gene that are transcribed but not part of an intron or exon, or regions of the gene that comprise, for example, binding sites for factors that modulate gene transcription. The genomic sequence for the IL13 gene is provided at GenBank accession number U10307.1 (SEQ ID NO: 90).

The term "allele", as used herein, refers to a sequence variant of the gene. Alleles are identified with respect to one or more polymorphic positions, with the rest of the gene sequence unspecified. For example, an IL4R allele may be defined by the nucleotide present at a single SNP; or by the nucleotides present at a plurality of SNPs. In certain embodiments of the invention, an IL4R is defined by the genotypes of 6, 7, 8 or 10 IL4R SNPs. Examples of such IL4R SNPs are provided in Table 2, below.

For convenience, the allele present at the higher or highest frequency in the population will be referred to as the wild-type allele; less frequent allele(s) will be referred to as mutant-allele(s). This designation of an allele as a mutant is meant solely to distinguish the allele from the wild-type allele and is not meant to indicate a change or loss of function.

The term "predisposing polymorphism" refers to a polymorphism that is positively associated with an autoimmune disease such as type 1 diabetes. The presence of a predisposing polymorphism in an individual could be indicative that the individual has an increased risk for the disease relative to an individual without the polymorphism.

The term "protective polymorphism" refers to a polymorphism that is negatively associated with an autoimmune disease such as type 1 diabetes. The presence of a protective polymorphism in an individual could be indicative that the individual has a decreased risk for the disease relative to an individual without the polymorphism.

The terms "polymorphic" and "polymorphism", as used herein, refer to the condition in which two or more variants of a specific genomic sequence, or the encoded amino acid sequence, can be found in a population. The terms refer either to the nucleic acid sequence or the encoded amino acid sequence; the use will be clear from the context. The polymorphic region or polymorphic site refers to a region of the nucleic acid where the nucleotide difference that distinguishes the variants occurs, or, for amino acid sequences, a region of the amino acid where the amino acid difference that distinguishes the protein variants occurs. As used herein, a "single nucleotide polymorphism", or SNP, refers to a polymorphic site consisting of a single nucleotide position.

"Odds Ratio" ("OR") refers to the ratio of the odds of the disease for individuals with the marker (allele or polymorphism) relative to the odds of the disease in individuals without the marker (allele or polymorphism).

"Linkage Disequilibrium" ("LD") refers to alleles at different loci that are not associated at random, i.e., not associated in proportion to their frequencies. If the alleles are in positive linkage disequilibrium, then the alleles occur together more often than expected assuming statistical independence. Conversely, if the alleles are in negative linkage disequilibrium, then the alleles occur together less often than expected assuming statistical independence.

The term "genotype" refers to a description of the alleles of a gene or genes contained in an individual or a sample. As used herein, no distinction is made between the genotype of an individual and the genotype of a sample originating from the individual. Although, typically, a genotype is determined from samples of diploid cells, a genotype can be determined from a sample of haploid cells, such as a sperm cell.

The term "haplotype" refers to a description of the variants of a gene or genes contained on a single chromosome, i.e., the genotype of a single chromosome. A haplotype is a set of maternally inherited alleles, or a set of paternally inherited alleles, at any locus.

The term "target region" refers to a region of a nucleic acid which is to be analyzed and usually includes at least one polymorphic region.

Individual amino acids in a sequence are represented herein as AN or NA, wherein A is the amino acid in the sequence and N is the position in the sequence. In the case that position N is polymorphic, it is convenient to designate the more frequent variant as $A_1N$ and the less frequent variant as $NA_2$. Alternatively, the polymorphic site, N, is represented as $A_1NA_2$, wherein $A_1$ is the amino acid in the more common variant and $A_2$ is the amino acid in the less common variant. Either the one-letter or three-letter codes are used for designating amino acids (see Lehninger, *Biochemistry 2nd ed.*, 1975, Worth Publishers, Inc. New York, N.Y.: pages 73–75, incorporated herein by reference). For example, I50V represents a single-amino-acid polymorphism at amino acid position 50, wherein isoleucine is the present in the more frequent protein variant in the population and valine is present in the less frequent variant. The amino acid positions are numbered based on the sequence of the mature IL4R protein, as described below.

"Stringent" as used herein refers to hybridization and wash conditions at 50° C. or higher. Other stringent hybridization conditions may also be selected. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 50° C. As other factors may significantly affect the stringency of hybridization, including, among others, base composition, length of the nucleic acid strands, the presence of organic solvents, the extent of base mismatching, the combination of parameters is more important than the absolute measure of any one.

Representations of nucleotides and single nucleotide changes in DNA sequences are analogous. For example, A398G represents a single nucleotide polymorphism at nucleotide position 398, wherein adenine is the present in the more frequent (wild-type) allele in the population and guanine is present in the less frequent (mutant) allele. The nucleotide positions are numbered based on the IL4R coding region sequence provided as SEQ ID NO:2, shown below. It will be clear that in a double stranded form, the complementary strand of each allele will contain the complementary base at the polymorphic position.

Conventional techniques of molecular biology and nucleic acid chemistry, which are within the skill of the art, are fully explained in the literature. See, for example, Sambrook et al., 1989, Molecular Cloning—A Laboratory Manual, Cold Spring Harbor Laboratory, Cold Spring Harbor, N.Y.; Oligonucleotide Synthesis (M. J. Gait, ed., 1984); Nucleic Acid Hybridization (B. D. Hames and S. J. Higgins. eds., 1984); the series, Methods in Enzymology (Academic Press, Inc.); and the series, Current Protocols in Human Genetics (Dracopoli et al., eds., 1984 with quarterly updates, John Wiley & Sons, Inc.); all of which are incorporated herein by reference. All patents, patent applications, and publications mentioned herein, both supra and infra, are incorporated herein by reference.

Association With Type 1 Diabetes

As IL4R, IL4 or IL13 are a small component of the complex system of genes involved in an immune response, the effect of the IL4R, IL4 or IL13 loci is expected to be small. Other factors, such as an individual's HLA genotype, may exert dominating effects which, in some cases, may mask the effect of the IL4R, IL4 or IL13 genotypes. For example, particular HLA genotypes are known to have a major effect on the likelihood of type 1 diabetes (see Noble et al., 1996, *Am. J. Hum. Genet,* 59:1134–1148, incorporated herein by reference). The IL4R, IL4 or IL13 genotypes are likely to be more informative as an indicator of predisposition towards type 1 diabetes among individuals who have HLA genotypes that confer neither increased nor decreased risk. Furthermore, because allele frequencies at other loci relevant to immune system-related diseases differ between populations and, thus, populations exhibit different risks for immune system-related diseases, it is expected that the effect of the IL4R, IL4 or IL13 genotypes may be of different magnitude in some populations. Although the contribution of the IL4R, IL4 or IL13 genotypes may be relatively minor by itself, genotyping at the IL4R, IL4 or IL13 loci will contribute information that is, nevertheless, useful for a characterization of an individual's predisposition towards type 1 diabetes. The IL4R, IL4 or IL13 genotype information may be particularly useful when combined with genotype information from other loci.

Methods for Detecting Risk for Autoimmune Diseases

The present invention provides methods of determining an individual's risk for any autoimmune disease or condition or any Th-1 mediated disease. Such diseases or conditions include, but are not limited to, multiple sclerosis, myasthenia gravis, Crohn's disease, ulcerative colitis, primary biliary cirrhosis, type 1 diabetes mellitus (insulin dependent diabetes mellitus or IDDM), Grave's disease, autoimmune hemolytic anemia, pernicious anemia, autoimmune thrombocytopenia, vasculitides such as Wegener's granulomatosis, Behcet's disease, rheumatoid arthritis, systemic lupus erythematosus (lupus), scleroderma, systemic sclerosis, Gullian-Barre syndromes, Hashimoto's thyroiditis spondyloarthropathies such as ankylosing spondylitis, psoriasis, dermatitis herpetiformis, inflammatory bowel diseases, pemphigus vulgaris and vitiligo. In certain embodiments of the invention, the methods are used to determine an individual's risk for type 1 diabetes. Preferably, the individual is a human.

Nucleic Acids

Accordingly, one embodiment of the invention is an isolated nucleic acid molecule comprising a portion of the IL4R, IL4 or IL13 genes, their complements, or variants thereof. Preferably said variant comprises at least one of the polymorphisms identified herein. Even more preferably, said variant comprises at least one of the polymorphisms identified herein to be associated with type 1 diabetes. Thus, in one embodiment, the nucleic acid molecule comprises at least one of the IL4R, IL4, and/or IL13 polymorphisms provided in Table 2. In a further embodiment, the nucleic acid molecule comprises or consists of primers and probes specific to polymorphisms identified in the IL4R, IL4, or IL13 gene, including but not limited to SEQ ID NOS: 3–19, 25–36, 37–53, 54–62, 69–74, 75–80, and 81–86.

The isolated nucleic acid molecules may be RNA, mRNA, DNA, cDNA, and may be double- or single-stranded. They may encode the sense strand, the non-coding regions, or the antisense strand. The nucleic acid molecule can include all or a portion of the coding sequence of the gene and can further comprise additional non-coding regions such as introns and non-coding 3' and 5' sequences (including regulatory sequences for example). Additionally, the nucleic acid molecule can be fused to a marker sequence, for example, a sequence that encodes a polypeptide to assist in isolation or purification of the polypeptide.

An "isolated" nucleic acid molecule, as used herein, is one that is separated from nucleotide sequences which normally flank the nucleic acid molecule and/or has been completely or partially purified from other biological material (e.g., protein) normally associated with the nucleic acid.

The nucleic acid molecule can be fused to other coding or regulatory sequences and still be considered isolated. Thus, recombinant DNA contained in a vector is included in the definition of "isolated" as used herein. Also, isolated nucleic acid molecules include recombinant DNA molecules in heterologous host cells, as well as partially or substantially purified DNA molecules in solution. "Isolated" nucleic acid molecules also encompass in vivo and in vitro RNA transcripts of the DNA molecules of the present invention. An isolated nucleic acid molecule or nucleotide sequence can include a nucleic acid molecule or nucleotide sequence that is synthesized chemically or by recombinant means. Also, isolated polynucleotides include recombinant DNA molecules in heterologous organisms, as well as partially or substantially purified DNA molecules in solution. In vivo and in vitro RNA transcripts of the DNA molecules of the present invention are also encompassed by "isolated" nucleotide sequences. Such polynucleotides are useful in the manufacture of the encoded polypeptide, as probes for isolating homologous sequences (e.g., from other mammalian species), for gene mapping (e.g., by in situ hybridization with chromosomes), or for detecting expression of the gene in tissue (e.g., human tissue), such as by Northern blot analysis.

The nucleic acid molecules of the invention can comprise one or more modified nucleotide residues. The modification may be at the base, sugar and/or phosphate moiety and include, for example, halogenation, hydroxylation, alkylation, an attached linker and/or label. The modifications can further comprise, for example, labeling, methylation, internucleotide modifications such as uncharged linkages (e.g., methyl phosphonates, phosphotriesters, phosphoamidates, carbamates), charged linkages (e.g., phosphorothioates, phosphorodithioates), pendent moieties (e.g., polypeptides), intercalators (e.g., acridine, psoralen), chelators, alkylators, and modified linkages (e.g., alpha anomeric nucleic acids). Also included are synthetic molecules that mimic nucleic acid molecules in the ability to bind to a designated sequence via hydrogen bonding and other chemical interactions. Such molecules include, for example, those in which peptide linkages substitute for phosphate linkages in the backbone of the molecule.

In certain embodiments, nucleic acid molecules of the invention include, but are not limited to, IL4R, IL4 and/or IL13 mRNA, cDNA and/or genomic DNA molecules. The nucleotide sequence of the coding region of a IL4R mRNA is available from GenBank under accession number X52425.1, nucleotides 176–2653 are provided as SEQ ID NO: 2, shown in a 5' to 3' orientation in Table 1, below. The IL4R mRNA is provided as SEQ ID NO:1. Although only one strand of the nucleic acid is shown in Table 1, those of skill in the art will recognize that SEQ ID NO: 1 and SEQ ID NO: 2 identify regions of double-stranded genomic nucleic acid, and that the sequences of both strands are fully specified by the sequence information provided. The genomic sequence for the IL4R gene is included in GenBank accession number AC004525.1 (SEQ ID NO: 88). The nucleotide sequence of the coding region of a IL4 mRNA is available from GenBank under accession number M23442.1 (SEQ ID NO: 89) and the nucleotide sequence of the coding region of a IL13 mRNA is available from GenBank under accession number U10307.1 (SEQ ID NO: 90).

Primers And Probes

By "oligonucleotide" is meant a single-stranded nucleotide polymer made of more than 2 nucleotide subunits covalently joined together. In one embodiment said oligonucleotides are between about 10 and 1000 nucleotide units, in a further embodiment, said oligonucleotides are between about 12 and 100 nucleotides units. The sugar groups of the nucleotide subunits may be ribose, deoxyribose or modified derivatives thereof such as o-methyl ribose. The nucleotide subunits of an oligonucleotide may be joined by phosphodiester linkages, phosphorothioate linkages, methyl phosphonate linkages or by other linkages, including but not limited to rare or non-naturally-occurring linkages, that do not prevent hybridization of the oligonucleotide. Furthermore, an oligonucleotide may have uncommon nucleotides or non-nucleotide moieties. An oligonucleotide as defined herein is a nucleic acid, preferably DNA, but may be RNA or have a combination of ribo- and deoxyribonucleotides covalently linked. Oligonucleotide probes and amplification oligonucleotides of a defined sequence may be produced by techniques known to those of ordinary skill in the art, such as by chemical or biochemical synthesis, and by in vitro or in vivo expression from recombinant nucleic acid molecules, e.g., bacterial or retroviral vectors. As used herein, an oligonucleotide does not consist of wild-type chromosomal DNA or the in vivo transcription products thereof.

Primer and probe sequences may comprise DNA, RNA (oligonucleotides—see above) or nucleic acid analogs such as uncharged nucleic acid analogs including but not limited to peptide nucleic acids (PNAs) which are disclosed in International Patent Application WO 92/20702 or morpholino analogs which are described in U.S. Pat. Nos. 5,185,444, 5,034,506, and 5,142,047 all of which are herein incorporated by reference in their entireties. Such sequences can routinely be synthesized using a variety of techniques currently available. For example, a sequence of DNA can be synthesized using conventional nucleotide phosphoramidite chemistry and the instruments available from Applied Biosystems, Inc, (Foster City, Calif.); DuPont, (Wilmington, Del.); or Milligen, (Bedford, Mass.). Similarly, and when desirable, the sequences can be labeled using methodologies well known in the art such as described in U.S. Pat. Nos. 5,464,746; 5,424,414; and 4,948,882 all of which are herein incorporated by reference in their entireties. Primers and Probes may be used in a variety of ways and may be defined by the specific use. For example, a "capture probe" is immobilized or can be immobilized on a solid support by any appropriate means, including, but not limited to: by covalent bonding, by adsorption, by hydrophobic and/or electrostatic interaction, or by direct synthesis on a solid support (see in particular patent application WO 92 10092). A "detection probe" may be labeled by means of a marker chosen, for example, from radioactive isotopes, enzymes, in particular enzymes capable of acting on a chromogenic, fluorogenic or luminescent substrate (in particular a peroxidase or an alkaline phosphatase), chromophoric chemical compounds, chromogenic, fluorogenic or luminescent compounds, analogues of nucleotide bases, and ligands such as biotin. A "primer" is a probe comprising, for example, from 10 to 100 nucleotide units and having a hybridization specificity under determined conditions for the initiation of an enzymatic polymerization, for example in an amplification technique such as PCR (Polymerase Chain Reaction), in a process of sequencing, in a method of reverse transcription and the like. One use of a probe is as a hybridization assay probe; probes may also be used as in vivo or in vitro therapeutic amplification oligomers or antisense agents to block or inhibit gene transcription, or translation in diseased, infected, or pathogenic cells.

All of the oligonucleotides, primers and probes of the present invention, whether hybridization assay probes, amplification oligonucleotides, or helper oligonucleotides, may be modified with chemical groups to enhance their performance or to facilitate the characterization of amplification products. For example, backbone-modified oligonucleotides such as those having phosphorothioate or methylphosphonate groups which render the oligonucleotides resistant to the nucleolytic activity of certain polymerases or to nuclease enzymes may allow the use of such enzymes in an amplification or other reaction. Another example of modification involves using non-nucleotide linkers (e.g., Arnold, et al., "Non-Nucleotide Linking Reagents for Nucleotide Probes", EP 0 313 219 hereby incorporated by reference herein in its entirety) incorporated between nucleotides in the nucleic acid chain which do not interfere with hybridization or the elongation of the primer. Amplification oligonucleotides may also contain mixtures of the desired modified and natural nucleotides.

The 3' end of an amplification oligonucleotide may be blocked to prevent initiation of DNA synthesis as described by McDonough, et al., entitled "Nucleic Acid Sequence Amplification", WO94/03472 which enjoys common ownership with the present invention and is hereby incorporated by reference herein in its entirety. A mixture of different 3' blocked amplification oligonucleotides, or of 3' blocked and unblocked oligonucleotides may increase the efficiency of nucleic acid amplification, as described therein.

The 5' end of the oligonucleotides may be modified to be resistant to the 5'-exonuclease activity present in some nucleic acid polymerases. Such modifications can be carried out by adding a non-nucleotide group to the terminal 5' nucleotide of the primer using techniques such as those described by Arnold, et al., supra, entitled "Non-Nucleotide Linking Reagents for Nucleotide Probes", incorporated by reference herein.

Once synthesized, selected oligonucleotide probes may be labeled by any of several well-known methods (e.g., J. Sambrook, supra). Useful labels include radioisotopes as well as non-radioactive reporting groups. Isotopic labels include $^3H$, $^{35}S$, $^{32}P$, $^{125}I$, $^{57}Co$ and $^{14}C$. Isotopic labels can be introduced into the oligonucleotide by techniques known in the art such as nick translation, end labeling, second strand synthesis, the use of reverse transcription, and by chemical methods. When using radiolabeled probes hybridization can be detected by autoradiography, scintillation counting, or gamma counting. The detection method selected will depend upon the particular radioisotope used for labeling.

Non-isotopic materials can also be used for labeling and may be introduced internally into the nucleic acid sequence or at the end of the nucleic acid sequence. Modified nucleotides may be incorporated enzymatically or chemically. Chemical modifications of the probe may be performed during or after synthesis of the probe, for example, through the use of non-nucleotide linker groups as described by Arnold, et al., supra "Non-Nucleotide Linking Reagents for Nucleotide Probes," incorporated by reference herein. Non-isotopic labels include fluorescent molecules, chemiluminescent molecules, enzymes, cofactors, enzyme substrates, haptens or other ligands.

In one embodiment, the probes are labeled with an acridinium ester. Acridinium ester labeling may be performed as described by Arnold et al., U.S. Pat. No. 5,185,439, entitled "Acridinium Ester Labeling and Purification of Nucleotide Probes," issued Feb. 9, 1993 and hereby incorporated by reference herein in its entirety.

TABLE 1

| SEQ ID NO: 2 |
| --- |

| | | | | | |
|---:|---|---|---|---|---|
| 1 | atggggtggc | tttgctctgg | gctcctgttc | cctgtgagct | gcctggtcct gctgcaggtg |
| 61 | gcaagctctg | ggaacatgaa | ggtcttgcag | gagcccacct | gcgtctccga ctacatgagc |
| 121 | atctctactt | gcgagtggaa | gatgaatggt | cccaccaatt | gcagcaccga gctccgcctg |
| 181 | ttgtaccagc | tggttttcct | gctctccgaa | gcccacacgt | gtatccctga gaacaacgga |
| 241 | ggcgcgggt | gcgtgtgcca | cctgctcatg | gatgacgtgg | tcagtgcgga taactataca |
| 301 | ctggacctgt | gggctgggca | gcagctgctg | tggaagggct | ccttcaagcc cagcgagcat |
| 361 | gtgaaaccca | gggcccagg | aaacctgaca | gttcacacca | atgtctccga cactctgctg |
| 421 | ctgacctgga | gcaacccgta | tcccctgac | aattacctgt | ataatcatct cacctatgca |
| 481 | gtcaacattt | ggagtgaaaa | cgacccggca | gatttcagaa | tctataacgt gacctaccta |
| 541 | gaaccctccc | tccgcatcgc | agccagcacc | ctgaagtctg | ggatttccta cagggcacgg |
| 601 | gtgagggcct | gggctcagtg | ctataacacc | acctggagtg | agtggagccc cagcaccaag |
| 661 | tggcacaact | cctacaggga | gcccttcgag | cagcacctcc | tgctgggcgt cagcgttttcc |
| 721 | tgcattgtca | tcctggccgt | ctgcctgttg | tgctatgtca | gcatcaccaa gattaagaaa |

TABLE 1-continued

SEQ ID NO: 2

```
 781 gaatggtggg atcagattcc caacccagcc cgcagccgcc tcgtggctat aataatccag
 841 gatgctcagg ggtcacagtg ggagaagcgg tcccgaggcc aggaaccagc caagtgccca
 901 cactggaaga attgtcttac caagctcttg ccctgttttc tggagcacaa catgaaaagg
 961 gatgaagatc ctcacaaggc tgccaaagag atgcctttcc agggctctgg aaaatcagca
1021 tggtgcccag tggagatcag caagacagtc ctctggccag agagcatcag cgtggtgcga
1081 tgtgtggagt tgtttgaggc cccggtggag tgtgaggagg aggaggaggt agaggaagaa
1141 aaagggagct tctgtgcatc gcctgagagc agcagggatg acttccagga gggaagggag
1201 ggcattgtgg cccggctaac agagagcctg ttcctggacc tgctcggaga ggagaatggg
1261 ggcttttgcc agcaggacat gggggagtca tgccttcttc caccttcggg aagtacgagt
1321 gctcacatgc cctgggatga gttcccaagt gcagggccca aggaggcacc tccctgggggc
1381 aaggagcagc ctctccacct ggagccaagt cctcctgcca gcccgaccca gagtccagac
1441 aacctgactt gcacagagac gcccctcgtc atcgcaggca accctgctta ccgcagcttc
1501 agcaactccc tgagccagtc accgtgtccc agagagctgg gtccagaccc actgctggcc
1561 agacacctgg aggaagtaga acccgagatg ccctgtgtcc ccagctctc tgagccaacc
1621 actgtgcccc aacctgagcc agaaacctgg gagcagatcc tccgccgaaa tgtcctccag
1681 catggggcag ctgcagcccc cgtctcggcc cccaccagtg gctatcagga gtttgtacat
1741 gcggtggagc agggtggcac ccaggccagt gcggtggtgg gcttgggtcc cccaggagag
1801 gctggttaca aggccttctc aagcctgctt gccagcagtg ctgtgtcccc agagaaatgt
1861 gggtttgggg ctagcagtgg ggaagagggg tataagcctt tccaagacct cattcctggc
1921 tgccctgggg accctgcccc agtccctgtc cccttgttca cctttggact ggacagggag
1981 ccacctcgca gtccgcagag ctcacatctc ccaagcagct ccccagagca cctgggtctg
2041 gagccggggg aaaaggtaga ggacatgcca aagcccccac ttcccaggga gcaggccaca
2101 gacccccttg tggacagcct gggcagtggc attgtctact cagcccttac ctgccacctg
2161 tgcggccacc tgaaacagtg tcatggccag gaggatggtg gccagacccc tgtcatggcc
2221 agtccttgct gtggctgctg ctgtggagac aggtcctcgc cccctacaac cccctgagg
2281 gccccagacc cctctccagg tggggttcca ctggaggcca gtctgtgtcc ggcctccctg
2341 gcaccctcgg gcatctcaga gaagagtaaa tcctcatcat ccttccatcc tgcccctggc
2401 aatgctcaga gctcaagcca gaccccaaa atcgtgaact ttgtctccgt gggacccaca
2461 tacatgaggg tctcttag
```

SNPs

In one aspect, the present invention provides a method for detecting an individual's increased or decreased risk for an autoimmune disease such as type 1 diabetes by detecting the presence of one or more IL4R, IL4 or IL13 SNPs in a nucleic acid sample of the individual, wherein the presence of said SNP(s) indicates the individual's increased or decreased risk for type 1 diabetes. The SNPs can be any SNPs in the IL4R, IL4 or IL13 loci including SNPs in exons, introns or upstream or downstream regions. Examples of such SNPs include, but are not limited to those provided in Table 2, below, and discussed in detail in the Examples. In one embodiment, the SNPs present in the IL4R, IL4 or IL13 loci are identified by genotyping the IL4R, IL4 or IL13 SNPs.

In certain embodiments, the genotype of one IL4R, IL4 or IL13 SNP can be used to determine an individual's risk for an autoimmune disease. In other embodiments, the genotypes of a plurality of IL4R, IL4 or IL13 SNPs can be used. For example, in certain embodiments, the genotypes of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 of the SNPs in Table 2 can be used to determine an individual's risk for an autoimmune disease. In other embodiments, certain Examples, below.

TABLE 2

IL4R, IL4 and IL13 SNPs

| dbSNP ID rs# | Exon* | Variation | WT allele | Var allele | Acc X52425.1 (cDNA) | AC004525.1 (genomic) | Formal SNP name |
|---|---|---|---|---|---|---|---|
| IL4RSNPs | | | | | | | |
| | P | C(−3223)T | G | A | NA | 128387 | G128387A |
| | P | T(−1914)C | A | G | NA | 127078 | A127078G |
| | 3 | I50V | A | G | 398 | 94272 | A398G |
| | 4 | N142N | C | T | 676 | 92548 | C676T |
| | 4 | C92516T | C | T | NA | 92516 | C92516T |
| | 4 | A92417T | A | T | NA | 92417 | A92417T |
| 2234896 | 7 | P249P | C | G | 997 | 80189 | C997G |
| 2234897 | 9 | F288F | T | C | 1114 | 76868 | T1114C |
| 1805011 | 9 | E375A | A | C | 1374 | 76608 | A1374C |
| | 9 | E375E | G | A | 1375 | 76607 | G1375A |
| 2234898 | 9 | L389L | G | T | 1417 | 76565 | G1417T |
| 1805012 | 9 | C406R | T | C | 1466 | 76516 | T1466C |
| 2234899 | 9 | C406C | C | T | 1468 | 76514 | C1468T |
| 2234900 | 9 | L408L | T | C | 1474 | 76508 | T1474C |
| 1805013 | 9 | S411L | C | T | 1482 | 76500 | C1482T |
| 1805015 | 9 | S478P | T | C | 1682 | 76300 | T1682C |
| 1801275 | 9 | QS51R | A | G | 1902 | 76080 | A1902G |
| | 9 | V554I | G | A | 1910 | 76072 | G191OA |

TABLE 2-continued

IL4R, IL4 and IL13 SNPs

|  | 9 | P650S | C | T | 2198 | 75784 | C2198T |
|---|---|---|---|---|---|---|---|
| 1805016 | 9 | S727A | T | G | 2429 | 75553 | T2429G |
|  | 9 | G759G | C | T | 2567 | 75455 | C2567T |
| 1805014 | 9 | S761P | T | C | 2531 | 75451 | T2531C |
|  | 9 | P774P | T | C | 2572 | 75410 | T2572C |
| 1049631 | 9 | 3'UTR | G | A | 3044 | 74938 | G3044A |
| 8832 | 9 | 3'UTR | A | G | 3289 | 74693 | A3289G |
| 8674 | 9 | 3'UTR | C | T | 3391 | 74581 | C3391T |

| SNP Description | Exon | Variation | WT allele | Var allele | Genbank Access # | Chromosomal Position | Formal SNP name |
|---|---|---|---|---|---|---|---|
| IL4 SNPs | | | | | | | |
| 5'(−524) | P | (−524) | C | T | M23442.1 | 5q31 | C582T |
| IL13 SNPs | | | | | | | |
| (−1512) | P | (−1512) | A | C | U10307.1 | 5q31 | A(−1512)C |
| (−1112) | P | (−1112) | C | T | U10307.1 | 5q31 | C(−1112)T |
| Intron 3 | — | Intron3 | C | T | U10307.1 | 5q31 | C4045T |
| R110Q | 4 | R110Q | G | A | U10307.1 | 5q31 | G4166A |

P: Promoter region
*The exon numbering is based on the scheme disclosed by Ober etal., 2000, Am J Hum Genet 66:517–526. Other numbering schemes are available and one of skill in the art will be able to identify the SNP and the scheme is used.

Genotyping Methods

In the methods of the present invention, the alleles present in a sample are identified by identifying the nucleotide present at one or more of the polymorphic sites. Any type of tissue containing IL4R, IL4 or IL13 nucleic acid may be used for determining the IL4R, IL4 or IL13 genotypes of an individual. A number of methods are known in the art for identifying the nucleotide present at polymorphic sites. The particular method used to identify the genotype is not a critical aspect of the invention. Although considerations of performance, cost, and convenience will make particular methods more desirable than others, it will be clear that any method that can identify the nucleotide present will provide the information needed to identify the genotype. Preferred genotyping methods involve DNA sequencing, allele-specific amplification, or probe-based detection of amplified nucleic acid.

IL4R, IL4 or IL13 alleles can be identified by DNA sequencing methods, such as the chain termination method (Sanger et al., 1977, Proc. Natl. Acad. Sci,. 74:5463–5467, incorporated herein by reference), which are well known in the art. In one embodiment, a subsequence of the gene encompassing the polymorphic site is amplified and either cloned into a suitable plasmid and then sequenced, or sequenced directly. PCR-based sequencing is described in U.S. Pat. No. 5,075,216; Brow, in PCR Protocols, 1990, (Innis et al., eds., Academic Press, San Diego), chapter 24; and Gyllensten, in PCR Technology, 1989 (Erlich, ed., Stockton Press, New York), chapter 5; each incorporated herein by reference. Typically, sequencing is carried out using one of the automated DNA sequencers which are commercially available from, for example, PE Biosystems (Foster City, Calif.), Pharmacia (Piscataway, N.J.), Genomyx Corp. (Foster City, Calif.), LI-COR Biotech (Lincoln, Nebr.), GeneSys technologies (Sauk City, Wis.), and Visible Genetics, Inc. (Toronto, Canada).

IL4R, IL4 or IL13 alleles can also be identified using amplification-based genotyping methods. Various nucleic acid amplification methods known in the art can be used in to detect nucleotide changes in a target nucleic acid. A preferred method is the polymerase chain reaction (PCR), which is now well known in the art, and described in U.S. Pat. Nos. 4,683,195; 4,683,202; and 4,965,188; each incorporated herein by reference. Examples of the numerous articles published describing methods and applications of PCR are found in PCR Applications, 1999, (Innis et al., eds., Academic Press, San Diego), PCR Strategies, 1995, (Innis et al., eds., Academic Press, San Diego); PCR Protocols, 1990, (Innis et al., eds., Academic Press, San Diego); and PCR Technology, 1989, (Erlich, ed., Stockton Press, New York); each incorporated herein by reference. Commercial vendors, such as PE Biosystems (Foster City, Calif.) market PCR reagents and publish PCR protocols.

Other suitable amplification methods include the ligase chain reaction (Wu and Wallace, 1988, Genomics 4:560–569); the strand displacement assay (Walker et al., 1992, Proc. Natl. Acad. Sci. USA 89:392–396, Walker et al. 1992, Nucleic Acids Res. 20:1691–1696, and U.S. Pat. No. 5,455,166); and several transcription-based amplification systems, including the methods described in U.S. Pat. Nos. 5,437,990; 5,409,818; and 5,399,491; the transcription amplification system (TAS) (Kwoh et al., 1989, Proc. Natl. Acad. Sci. USA, 86:1173–1177); and self-sustained sequence replication (3SR) (Guatelli et al., 1990, Proc. Natl. Acad. Sci. USA, 87:1874–1878 and WO 92/08800); each incorporated herein by reference. Alternatively, methods that amplify the probe to detectable levels can be used, such as Qβ-replicase amplification (Kramer et al., 1989, Nature, 339:401–402, and Lomeli et al., 1989, Clin. Chem., 35:1826–1831, both of which are incorporated herein by reference). A review of known amplification methods is provided in Abramson et al., 1993, Current Opinion in Biotechnology, 4:41–47, incorporated herein by reference.

Genotyping also can also be carried out by detecting and analyzing IL4R, IL4 or IL13 mRNA under conditions when both, maternal and paternal, chromosomes are transcribed. Amplification of RNA can be carried out by first reverse-transcribing the target RNA using, for example, a viral reverse transcriptase, and then amplifying the resulting cDNA, or using a combined high-temperature reverse-transcription-polymerase chain reaction (RT-PCR), as described in U.S. Pat. Nos. 5,310,652; 5,322,770; 5,561,058; 5,641,864; and 5,693,517; each incorporated herein by reference (see also Myers and Sigua, 1995, in PCR Strategies, supra, chapter 5).

IL4R, IL4 or IL13 alleles can also be identified using allele-specific amplification or primer extension methods, which are based on the inhibitory effect of a terminal primer mismatch on the ability of a DNA polymerase to extend the primer. To detect an allele sequence using an allele-specific amplification or extension-based method, a primer complementary to the IL4R, IL4 or IL13 genes is chosen such that the 3' terminal nucleotide hybridizes at the polymorphic position. In the presence of the allele to be identified, the primer matches the target sequence at the 3' terminus and primer is extended. In the presence of only the other allele, the primer has a 3' mismatch relative to the target sequence and primer extension is either eliminated or significantly reduced. Allele-specific amplification- or extension-based methods are described in, for example, U.S. Pat. Nos. 5,137,806; 5,595,890; 5,639,611; and U.S. Pat. No. 4,851,331, each incorporated herein by reference.

Using allele-specific amplification-based genotyping, identification of the alleles requires only detection of the presence or absence of amplified target sequences. Methods for the detection of amplified target sequences are well known in the art. For example, gel electrophoresis (see Sambrook et al., 1989, supra.) and the probe hybridization assays described above have been used widely to detect the presence of nucleic acids.

Allele-specific amplification-based methods of genotyping can facilitate the identification of haplotypes, as described in the examples. Essentially, the allele-specific amplification is used to amplify a region encompassing multiple polymorphic sites from only one of the two alleles in a heterozygous sample. The SNP variants present within the amplified sequence are then identified, such as by probe hybridization or sequencing.

An alternative probe-less method, referred to herein as a kinetic-PCR method, in which the generation of amplified nucleic acid is detected by monitoring the increase in the total amount of double-stranded DNA in the reaction mixture, is described in Higuchi et al., 1992, *Bio/Technology*, 10:413–417; Higuchi et al., 1993, *Bio/Technology*, 11:1026–1030; Higuchi and Watson, in PCR Applications, supra, Chapter 16; U.S. Pat. Nos. 5,994,056 and 6,171,785; and European Patent Publication Nos. 487,218 and 512,334, each incorporated herein by reference. The detection of double-stranded target DNA relies on the increased fluorescence that DNA-binding dyes, such as ethidium bromide, exhibit when bound to double-stranded DNA. The increase of double-stranded DNA resulting from the synthesis of target sequences results in an increase in the amount of dye bound to double-stranded DNA and a concomitant detectable increase in fluorescence. For genotyping using the kinetic-PCR methods, amplification reactions are carried out using a pair of primers specific for one of the alleles, such that each amplification can indicate the presence of a particular allele. By carrying out two amplifications, one using primers specific for the wild-type allele and one using primers specific for the mutant allele, the genotype of the sample with respect to that SNP can be determined. Similarly, by carrying out four amplifications, each with one of the possible pairs possible using allele specific primers for both the upstream and downstream primers, the genotype of the sample with respect to two SNPs can be determined. This gives haplotype information for a pair of SNPs.

Alleles can be also identified using probe-based methods, which rely on the difference in stability of hybridization duplexes formed between a probe and its corresponding target sequence comprising an IL4R, IL4 or IL13 allele. Under sufficiently stringent hybridization conditions, stable duplexes are formed only between a probe and its target allele sequence and not other allele sequences. The presence of stable hybridization duplexes can be detected by any of a number of well known methods. In general, it is preferable to amplify a nucleic acid encompassing a polymorphic site of interest prior to hybridization in order to facilitate detection. However, this is not necessary if sufficient nucleic acid can be obtained without amplification.

A probe suitable for use in the probe-based methods of the present invention, which contains a hybridizing region either substantially complementary or exactly complementary to a target region of SEQ ID NOS: 2, 88, 89 or 90 or the complement of SEQ ID NOS: 2, 88, 89 or 90, wherein the target region encompasses the polymorphic site, and exactly complementary to one of the two allele sequences at the polymorphic site, can be selected using the guidance provided herein and well known in the art. Similarly, suitable hybridization conditions, which depend on the exact size and sequence of the probe, can be selected empirically using the guidance provided herein and well known in the art. The use of oligonucleotide probes to detect nucleotide variations including single base pair differences in sequence is described in, for example, Conner et al., 1983, *Proc. Natl. Acad. Sci. USA*, 80:278–282, and U.S. Pat. Nos. 5,468,613 and 5,604,099, each incorporated herein by reference.

In preferred embodiments of the probe-based methods for determining the IL4R, IL4 or IL13 genotypes, multiple nucleic acid sequences from the IL4R, IL4 or IL13 genes which encompass the polymorphic sites are amplified and hybridized to a set of probes under sufficiently stringent hybridization conditions. The alleles present are inferred from the pattern of binding of the probes to the amplified target sequences. In this embodiment, amplification is carried out in order to provide sufficient nucleic acid for analysis by probe hybridization. Thus, primers are designed such that regions of the IL4R, IL4 or IL13 genes encompassing the polymorphic sites are amplified regardless of the allele present in the sample. Allele-independent amplification is achieved using primers which hybridize to conserved regions of the IL4R, IL4 or IL13 genes. The IL4R, IL4 or IL13 genes contain many invariant or monomorphic regions and suitable allele-independent primers can be selected routinely from SEQ ID NOS: 1, 88, 89 or 90. One of skill will recognize that, typically, experimental optimization of an amplification system is helpful.

Suitable assay formats for detecting hybrids formed between probes and target nucleic acid sequences in a sample are known in the art and include the immobilized target (dot-blot) format and immobilized probe (reverse dot-blot or line-blot) assay formats. Dot blot and reverse dot blot assay formats are described in U.S. Pat. Nos. 5,310,893; 5,451,512; 5,468,613; and 5,604,099; each incorporated herein by reference.

In a dot-blot format, amplified target DNA is immobilized on a solid support, such as a nylon membrane. The membrane-target complex is incubated with labeled probe under suitable hybridization conditions, unhybridized probe is removed by washing under suitably stringent conditions, and the membrane is monitored for the presence of bound probe. A preferred dot-blot detection assay is described in the examples.

In the reverse dot-blot (or line-blot) format, the probes are immobilized on a solid support, such as a nylon membrane or a microtiter plate. The target DNA is labeled, typically during amplification by the incorporation of labeled primers. One or both of the primers can be labeled. The membrane-probe complex is incubated with the labeled amplified target DNA under suitable hybridization conditions, unhybridized target DNA is removed by washing under suitably stringent conditions, and the membrane is monitored for the presence of bound target DNA. A preferred reverse line-blot detection assay is described in the examples.

Probe-based genotyping can be carried out using a "TaqMan" or "5'-nuclease assay," as described in U.S. Pat. Nos. 5,210,015; 5,487,972; and 5,804,375; and Holland et al., 1988, *Proc. Natl. Acad. Sci. USA*, 88:7276–7280, each incorporated herein by reference. In the TaqMan assay, labeled detection probes that hybridize within the amplified region are added during the amplification reaction mixture. The probes are modified so as to prevent the probes from acting as primers for DNA synthesis. The amplification is carried out using a DNA polymerase that possesses 5' to 3' exonuclease activity, e.g., Tth DNA polymerase. During each synthesis step of the amplification, any probe which hybridizes to the target nucleic acid downstream from the primer being extended is degraded by the 5' to 3' exonuclease activity of the DNA polymerase. Thus, the synthesis of a new target strand also results in the degradation of a probe, and the accumulation of degradation product provides a measure of the synthesis of target sequences.

Any method suitable for detecting degradation product can be used in the TaqMan assay. In a preferred method, the detection probes are labeled with two fluorescent dyes, one of which is capable of quenching the fluorescence of the other dye. The dyes are attached to the probe, preferably one attached to the 5' terminus and the other is attached to an internal site, such that quenching occurs when the probe is in an unhybridized state and such that cleavage of the probe by the 5' to 3' exonuclease activity of the DNA polymerase occurs in between the two dyes. Amplification results in cleavage of the probe between the dyes with a concomitant elimination of quenching and an increase in the fluorescence observable from the initially quenched dye. The accumulation of degradation product is monitored by measuring the increase in reaction fluorescence. U.S. Pat. Nos. 5,491,063 and 5,571,673, both incorporated herein by reference, describe alternative methods for detecting the degradation of probe which occurs concomitant with amplification.

The TaqMan assay can be used with allele-specific amplification primers such that the probe is used only to detect the presence of amplified product. Such an assay is carried out as described for the kinetic-PCR-based methods described above. Alternatively, the TaqMan assay can be used with a target-specific probe.

Examples of other techniques that can be used for probe-based genotyping include, but are not limited to, AMPLIFLUOR™ nucleic acid probe technology, Dye Binding-Intercalation, Fluorescence Resonance Energy Transfer (FRET), Hybridization Signal Amplification Method (HSAM), HYBPROBE™ nucleic acid probe technology, Invader/Cleavase Technology (Invader/CFLP™ nucleic acid probe technology), MOLECULAR BEACONS™ nucleic acid probe technology, ORIGEN™ nucleic acid probe technology, DNA-Based Ramification Amplification technology, Rolling circle amplification technology (RCAT™ nucleic acid detection system), SCORPIONS™ nucleic acid probe technology, and Strand displacement amplification (SDA).

The assay formats described above typically utilize labeled oligonucleotides to facilitate detection of the hybrid duplexes. Oligonucleotides can be labeled by incorporating a label detectable by spectroscopic, photochemical, biochemical, immunochemical, radiological, radiochemical or chemical means. Useful labels include $^{32}$P, fluorescent dyes, electron-dense reagents, enzymes (as commonly used in ELISAs), biotin, or haptens and proteins for which antisera or monoclonal antibodies are available. Labeled oligonucleotides of the invention can be synthesized and labeled using the techniques described above for synthesizing oligonucleotides. For example, a dot-blot assay can be carried out using probes labeled with biotin, as described in Levenson et al., 1989, in *PCR Protocols: A Guide to Methods and Applications* (Innis et al., eds., Academic Press. San Diego), pages 99–112, incorporated herein by reference. Following hybridization of the immobilized target DNA with the biotinylated probes under sequence-specific conditions, probes which remain bound are detected by first binding the biotin to avidin-horseradish peroxidase (A-HRP) or streptavidin-horseradish peroxidase (SA-HRP), which is then detected by carrying out a reaction in which the HRP catalyzes a color change of a chromogen.

Whatever the method for determining which oligonucleotides of the invention selectively hybridize to IL4R, IL4 or IL13 allelic sequences in a sample, the central feature of the typing method involves the identification of the IL4R, IL4 or IL13 alleles present in the sample by detecting the variant sequences present.

The present invention also relates to a kit, a container unit comprising useful components for practicing the present method. A useful kit can contain oligonucleotide probes specific for IL4R, IL4 or IL13 alleles as well as instructions for their use to determine risk for an autoimmune disease such as type 1 diabetes. In some cases, detection probes may be fixed to an appropriate support membrane. The kit can also contain amplification primers for amplifying regions of the IL4R, IL4 or IL13 loci encompassing the polymorphic sites, as such primers are useful in the preferred embodiment of the invention. Alternatively, useful kits can contain a set of primers comprising an allele-specific primer for the specific amplification of IL4R, IL4 or IL13 alleles. Other optional components of the kits include additional reagents used in the genotyping methods as described herein. For example, a kit additionally can contain an agent to catalyze the synthesis of primer extension products, substrate nucleoside triphosphates, reagents for labeling and/or detecting nucleic acid (for example, an avidin-enzyme conjugate and enzyme substrate and chromogen if the label is biotin) and appropriate buffers for amplification or hybridization reactions.

The present invention also relates to an array, a support with immobilized oligonucleotides useful for practicing the present method. A useful array can contain oligonucleotide probes specific for IL4R, IL4, IL13 alleles or certain combinations of IL4R, IL4 and/or IL13 alleles. The oligonucleotides can be immobilized on a substrate, e.g., a membrane or glass. The oligonucleotides can, but need not, be labeled. In some embodiments, the array can be a micro-array. In some embodiments, the array can comprise one or more oligonucleotides used to detect the presence of two or more IL4R, IL4, IL13 alleles or certain combinations of IL4R, IL4 and/or IL13 alleles.

The examples of the present invention presented below are provided only for illustrative purposes and not to limit the scope of the invention. Numerous embodiments of the invention within the scope of the claims that follow the examples will be apparent to those of ordinary skill in the art from reading the foregoing text and following examples.

7. EXAMPLE 1

Genotyping Protocol: Probe-Based Identification of IL4R, IL4 and IL13 Alleles This example describes a method of genotyping SNPs in the IL4R, IL4 and IL13 loci that are associated with type 1 diabetes. Two different genotyping methods, line blot assays and kinetic thermocycling, were used, depending on the region and gene genotyped.

Line Blot Assay for Identifying 8 IL4R SNPs, 1 IL4 SNP and 2 IL13 SNPs

Eight exemplary SNPs in the human IL4R gene (listed in Table 6), one exemplary SNP in the human IL4 gene (Table 2) and two exemplary SNPs in the human IL4R gene (Table 2) were genotyped using this method. Each SNP is described by its position in the reference GenBank accession sequence. For example, SNP 1 of Table 6 is found at position 398 of X52425.1 (SEQ ID NO: 1), where an "A" nucleotide is present. The variant allele at this position has a "G" nucleotide. The SNPs will be referred to by the SNP # in the subsequent text.

The regions of the IL4R, IL4 and IL13 genes that encompass the SNPs were amplified and the nucleotide present identified by probe hybridization. The probe detection was carried out using an immobilized probe (line blot) format.

Amplicons and Primers

The pairs of primers used to amplify the regions encompassing the eight IL4R SNPs are listed in Table 7 (SEQ ID NO: 25–36) and those used to amplify the regions encompassing the IL4 SNP and two IL13 SNPs are listed in Table 30 (SEQ ID NO: 69–74). IL4R SNP numbers 3, 4, and 5 (Table 6) were co-amplified on the same 228 basepair fragment. The primers were modified at the 5' phosphate by conjugation with biotin. Reagents for synthesizing oligonucleotides with a biotin label attached to the 5' phosphate are commercially available from Clontech (Palo Alto, Calif.) and Glenn Research (Sterling, Va.). A preferred reagent is Biotin-ON from Clontech.

Amplification Primers

Amplification of six regions of the IL4R gene, which encompass eight polymorphic sites, the one region of the IL4 gene, which encompass one polymorphic site, and the two regions of the IL13 gene, which encompass two polymorphic sites, was carried out using the primer pairs shown below. All primers are shown in the 5' to 3' orientation.

The following primers amplify a 114 base-pair region encompassing nucleotide position 398 the IL4R gene.

RR192B CAGCCCCTGTGTCTGCAGA (SEQ ID NO:25)

RR193B GTCCAGTGTATAGTTATCCGCACTGA (SEQ ID NO:31)

The following primers amplify a 163 base-pair region encompassing nucleotide position 676.

DBM0177B CTGACCTGGAGCAACCCGTA (SEQ ID NO:26)

DBM0178B ACTGGGCCTCTGCTGGTCA (SEQ ID NO:32)

The following primers amplify a 228 base-pair region encompassing nucleotide positions 1374, 1417, and 1466 of the IL4R gene.

DBM0023B ATTGTGTGAGGAGGAGGAGGAGGTA (SEQ ID NO:27)

DBM0022B GTTGGGCATGTGAGCACTCGTA (SEQ ID NO:33)

The following primers amplify a 129 base-pair region encompassing nucleotide position 1682 of the IL4R gene.

DBM0097B CTCGTCATCGCAGGCAA (SEQ ID NO:28)

DBM0098B AGGGCATCTCGGGTTCTA (SEQ ID NO:34)

The following primers amplify a 198 base-pair region encompassing nucleotide position 1902 of the IL4R gene.

RR200B GCCGAAATGTCCTCCAGCA (SEQ ID NO:29)

RR178B CCACATTTCTCTGGGGACACA (SEQ ID NO:35)

The following primers amplify a 177 base-pair region encompassing nucleotide position 2531 of the IL4R gene.

DBM0112B CCGGCCTCCCTGGCA (SEQ ID NO:30)

DBM0071B GCAGACTCAGCAACAAGAGG (SEQ ID NO:36)

The following primers amplify a 107 base-pair region encompassing nucleotide position 582 in the promoter region of the IL4 gene.

RR169B ACTAGGCCTCACCTGATACGA (SEQ ID NO:69)

RR170B CATAGAGGCAGAATAACAGGCAGA (SEQ ID NO:72)

The following primers amplify a 118 base-pair region encompassing nucleotide position 4045 in intron 3 of the IL13 gene.

DBM0165B CTCGGACATGCAAGCTGGAA (SEQ ID NO:70)

DBM0166B ACTGAATGAGACAGTCCCTGGA (SEQ ID NO:73)

The following primers amplify a 187 base-pair region encompassing codon 4166 in exon 4 of the IL13 gene.

DBM0167B AATCGAGGTGGCCCAGTTTGTA (SEQ ID NO:71)

DBM0168B CCTAACCCTCCTTCCCGCCTA (SEQ ID NO:74)

Amplification

The PCR amplification was carried out in a total reaction volume of 25–100 µl containing the following reagents:
0.2 ng/µl purified human genomic DNA
0.2 mM each primer
800 mM total dNTP (200 mM each dATP, dTTP, dCTP, dGTP)
70 mM KCl
12 mM Tris-HCl, pH 8.3
3 mM $MgCl_2$,
0.25 units/µl AMPLITAQ GOLD™ DNA polymerase*

* developed and manufactured by Hoffmann-La Roche and commercially available from Applera (Foster City, Calif.).

Amplification was carried out in a GENEAMP™ PCR System 9600 thermal cycler (Applera, Foster City, Calif.), using the specific temperature cycling profile shown below.

| Pre-reaction incubation: | 94° C. for 12.5 minutes |
| --- | --- |
| 33 cycles: | |
| denature: | 95° C. for 45 seconds |
| anneal: | 61° C. for 30 seconds |
| extend: | 72° C. for 45 seconds |
| Final extension: | 72° C. for 7 minutes |
| Hold: | 10° C.–15° C. |

Detection Probes

Preferred probes used to identify the nucleotides present at the 8 SNPs present in the amplified IL4R nucleic acids are described in Table 3. Two probes are shown for the detection of T1466; a mixture of the two probes was used. Preferred probes used to identify the nucleotides present at the one SNP present in the amplified IL4 nucleic acids and the two SNPs present in the amplified IL13 nucleic acids are described in Table 29. All probes are shown in the 5' to 3' orientation.

Probe Hybridization Assay, Immobilized Probe Format

In the immobilized probe format, the probes were immobilized to a solid support prior to being used in the hybridization. The probe-support complex was immersed in a solution containing denatured amplified nucleic acid (biotin labeled) to allow hybridization to occur. Unbound nucleic acid was removed by washing under stringent hybridization conditions, and nucleic acid remaining bound to the immobilized probes was detected using a chromogenic reaction. The details of the assay are described below.

For use in the immobilized probe detection format, described below, a moiety was attached to the 5' phosphate of the probe to facilitate immobilization on a solid support. See Cheng et al., 1999, Genome Res 9:936–949, incorporated herein by reference. Preferably, Bovine Serum Albumin (BSA) is attached to the 5' phosphate essentially as described by Tung et al., 1991, *Bioconjugate Chem.*, 2:464–465, incorporated herein by reference. Alternatively, a poly-T tail is added to the 5' end as described in U.S. Pat. No. 5,451,512, incorporated herein by reference.

The probes were applied in a linear format to sheets of nylon membrane (e.g., BIODYNE™ B nylon filters, Pall Corp., Glen Cove, N.Y.) using a Linear Striper and MULTISPENSE2000™ controller (IVEK, N. Springfield, Vt.). The detection of the wildtype allele of SNP #5 (table 6) was carried out using a mixture of two probes as listed; this mixture enables the detection of SNP #5 indiscriminately of another nearby SNP. Probe titers were chosen to achieve signal balance between the allelic variants; the titers used are provided in the table of probes, above. Each sheet was cut to strips between 0.35 and 0.5 cm in width. To denature the amplification products, 20 µl of amplification product (based on a 50 µl reaction) were added to 20 µl of denaturation solution (1.6% NaOH) and incubated at room temperature to complete denaturation.

The denatured amplification product (40 µl) was added to the well of a typing tray containing 3 ml of hybridization buffer (4× SSPE, 0.5% SDS) and the membrane strip. Hybridizations were allowed to proceed for 15 minutes at 55° C. in a rotating water bath. Following hybridization, the hybridization solution was aspirated, the strip was rinsed in 3 ml warm wash buffer (2× SSPE, 0.5% SDS) by gently rocking strips back and forth, and the wash buffer was aspirated. Following rinsing, the strips were incubated in 3 ml enzyme conjugate solution (3.3 ml hybridization buffer and 12 µl of strepavidin-horseradish peroxidase (SA-HRP)) in the rotating water bath for 5 minutes at 55° C. Then the strips were rinsed with wash buffer, as above, incubated in wash buffer at 55° for 12 minutes (stringent wash), and finally rinsed with wash buffer again.

Target nucleic acid, now HRP-labeled, which remains bound to the immobilized amplification product was visualized as follows. A color development solution was prepared by mixing 100 ml of citrate buffer (0.1 M Sodium Citrate, pH 5.0), 5 ml 3,3',5,5'-tetramethylbenzidine (TMB) solution (2 mg/ml TMB powder from Fluka, Milwaukee, Wis., dissolved in 100% EtOH), and 100 µl of 3% hydrogen peroxide. The strips were first rinsed in 0.1 M sodium citrate (pH 5.0) for 5 minutes, then incubated in the color development solution with gentle agitation for 8 to 10 minutes at room temperature in the dark. The TMB, initially colorless, is converted by the target-bound HRP, in the presence of hydrogen peroxide, into a colored precipitate. The developed strips were rinsed in water for several minutes and immediately photographed.

Kinetic Thermocycling to Identify 2 IL4R Promoter and 2 IL13 Promoter SNPs

The two IL4R promoter and the two IL13 promoter SNPs were genotyped using allele-specific PCR on a PE9700 thermal cycler (ABI) measuring SyBr Green (Molecular Probes) fluorescence (Higuchi, Fockler, Dollinger, Watson. Biotechnology 11:1026–30 (1993)). For each DNA, two amplifications were set up in parallel. One contained the common primer and one allele-specific primer; the other contained the common primer and the other allele-specific primer. The primers used to genotype the two IL4R promoter SNPs are provided in Table 31 and the primers used to genotype the two IL13 promoter SNPs are provided in Table 32. The amplification of the DNA with a particular allele-specific primer indicated the presence of the corresponding allele. An increase in the fluorescence of SyBr Green was indicative of the accumulation of amplification product. One of skill in the art will be able to correlate the change in fluorescence with the presence or absence of amplification product, and thus, the presence or absence of the corresponding allele.

The PCR amplification was carried out in a total reaction volume of 100 µl containing the following reagents:

| Volume (µl) | Component |
| --- | --- |
| 1 | 1 M Tris pH 8.0 |
| 12 | 25 mM MgCl2 |
| 1 | 100X dNTPs (50 mM each dA, dC, dG; 25 mM dT; 75 mM dU) |
| 1 | 20X SYBR Green |
| 1 | 200 µM ROX |
| 2 | 1 U/µl UNG |
| 2.5 | 80% Glycerol |
| 4 | 100% DMSO |
| 1 | 20 µM primer 1 |
| 1 | 20 µM primer 2 |
| 1 | 12 U/µl CEA2 Gold DNA Polymerase* |
| 2 | 10 ng/µl genomic DNA |
| to 100 µl | sterile water |

*Developed and manufactured by Roche Molecular Systems. Alternatively, 1 µl of AmpliTaq Gold DNA Polymerase, also developed and manufactured by Roche Molecular Systems and sold commercially by Applied Biosystems, Inc, (Foster City, Calif.), can be used.

-continued

Amplification was carried out in a GENEAMP ™ PCR System 9600 thermal cycler (Applera, Foster City, CA), using the specific temperature cycling profile shown below.

| | |
|---|---|
| Pre-reaction incubation: | 2 minutes at 50 ° C. |
| | 12 minutes at 94 ° C. |
| 50 cycles: | |
| denature: | 20 seconds at 95 ° C. |
| anneal: | 20 seconds at 58 ° C. |
| Final extension: | 5 minutes at 72 ° C. |

8. EXAMPLE 2

Association of IL4R SNPs with Type 1 Diabetes in HBDI Families

This example demonstrates the association of IL4R SNPs with type 1 diabetes in HBDI families.

IL4R genotyping was carried out on individuals from 282 Caucasian families ascertained because they contained two offspring affected with type 1 diabetes. The IL4R genotypes of all individuals were determined. IL4R genotyping was carried out using a genotyping method essentially as described in Example 1. In addition to the 564 offspring (2 siblings in each of 282 families) in the affected sibling pairs on which ascertainment was based, there were 26 other affected children. There were 270 unaffected offspring among these families.

The family-based samples were provided as purified genomic DNA from the Human Biological Data Interchange (HBDI), which is a repository for cell lines from families affected with type 1 diabetes. All of the HBDI families used in this study are nuclear families with unaffected parents (genetically unrelated) and at least two affected siblings. These samples are described further in Noble et al., 1996, Am. J. Hum. Genet. 59:1134–1148, incorporated herein by reference.

It is known that the HLA genotype can have a significant effect, either increased or decreased depending on the genotype, on the risk for type 1 diabetes. In particular, individuals with the HLA DR genotype DR3-DQB1*0201/DR4-DQB1*0302 (referred to as DR3/DR4 below) appear to be at the highest risk for type 1 diabetes (see Noble et al., 1996, Am. J. Hum. Genet., 59:1134–1148, incorporated herein by reference). These high-risk individuals have about a 1 in 15 chance of being affected with type 1 diabetes. Because of the strong effect of this genotype on the likelihood of type 1 diabetes, the presence of the DR3-DQB1*0201/DR4-DQB1*0302 genotype could mask the contribution from the IL4R allelic variants.

Individuals within these families also were genotyped at the HLA DRB1 and DQB1 loci. Of the affected sibling pairs, both siblings have the DR3/DR4 genotype in 90 families. Neither affected sibling has the DR 3/4 genotype in 144 families. Exactly one of the affected pair has the DR 3/4 genotype in the remaining 48 families.

Statistical Analysis, Methods and Algorithms

Since the eight SNPs in IL4R are both physically and genetically very closely linked to each other, the presence of a particular allele at a particular SNP is correlated with the presence of another particular allele at a nearby SNP. This non-random association of two or more SNPs' alleles is known as linkage disequilibrium (LD).

Linkage disequilibrium among the eight IL4R SNPs was assessed using the genotypes of the 282 pairs of parents. These 564 individuals are not related to each other except by marriage. A summary of the calculated frequency of the WT allele for each SNP in this group of 564 individuals (the "HBDI founders") is shown in Table 9.

The calculation of LD can be performed in several ways. Two complementary methods to assess LD between all pairs of IL4R SNP loci were used. In the first method, the values of two distinct but related metrics for LD, namely D and Δ (Devlin and Risch 1995, Genomics, 29(2): 311–22), using the Maximum Likelihood Estimation algorithm of Hill (Hill, 1974, Heredity, 33(2): 229–39) were calculated. The values for D and Δ for all pairs of IL4R SNPs are shown in Table 10, in the lower left triangular portion. Both D and Δ can have values that range between −1 and +1. Values near +1 or −1 suggest strong linkage disequilibrium; values near zero indicate the absence of LD.

A second measure of LD uses a permutation test method implemented in the Arlequin program (Excoffier et al., 1995, Mol Biol Evol, 12:921–7, University of Geneva, CH) (Slatkin et al., 1996, Heredity, 76:377–83). This method maximizes the likelihood ratio statistic (S=−2 $\log(L_{H'}/L_H)$) by permuting alleles and recalculating S over a large number of iterations until S is maximized. These iterations allow the determination of the null distribution of S, and thus the maximum S obtained can be converted into an exact P-value (significance level). These P-values are listed in the upper right triangular portion of Table 10.

Table 10 of pairwise LD shows that there is significant evidence for LD between SNPs 1 and 2, and among (all combinations of) SNPs 3, 4, 5, 6, 7 and 8. SNPs 3 through 8 are known to exist within 1200 basepairs of each other in a single exon (exon 9) of the IL4R gene, and the LD between these SNPs is evidence for very small genetic distances as well.

The Transmission Disequilibrium Test (TDT) of Spielman (Spielman and Ewens, 1996, Am J Hum Genet, 59(5): 983–9; Spielman and Ewens, 1998, Am J Hum Genet, 62(2): 450–8) was performed on the IL4R genotype data for the 282 affected sib pairs (namely, a family structure consisting of the two parents and the two affected children). The TDT was used to test for the association of the individual alleles of the eight IL4R SNPs to type 1 diabetes. The TDT assesses whether an allele is transmitted from heterozygous parents to their affected children at a frequency that is significantly different than expected by chance. Under the null hypothesis of no association of an allele with disease, a heterozygous parent will transmit or will not transmit an allele with equal frequency to an affected child. The significance of deviation from the null hypothesis can be assessed using the McNemar chi-squared test statistic (=$(T-NT)^2/(T+NT)$, where T is the observed number of transmissions and NT is the observed number of non-transmissions). The significance (P-value) of the McNemar chi-squared test statistic is equal to the Pearson chi-squared statistic with one degree of freedom (Glantz et al., Primer of biostatistics., New York, McGraw-Hill Health Professions Division, 1997).

The results of the single SNP locus TDT results are shown in tables 11A and 11B. The TDT/S-TDT program (version 1.1) of Spielman was used to perform the counting of transmitted and non-transmitted alleles (Spielman, McGinnis et al., 1993, Am J Hum Genet, 52(3): 506–16; Spielman and Ewens, 1998, supra). The table lists the observed transmissions of the wildtype allele at each SNP locus. Since these are biallelic polymorphisms, the transmission counts of the variant allele are equal to the non-transmissions of the wildtype allele.

The counts of transmissions and non-transmissions of alleles to the probands only shown in Table 11A do not quite reach statistical significance, at α=0.05. However, it is valid to count transmission events to all affected children. However, when the TDT is used in this way (or, for that matter, with more than one child per family), then a significant test statistic is evidence of linkage only, not of association and linkage. Table 11B shows the TDT analysis when 26 additional affected children are included. The results presented in Table 11B below show that there is a significant deviation from the expected transmission frequencies for alleles of SNPs 3, 4, 5 and 6. Inspection of the "% transmission" values for these SNPs indicates that the wildtype allele is transmitted to affected children at frequencies greater than the expectation of 50%.

The evidence for strong LD among the eight IL4R SNPs suggested that the transmission of the ordered set of alleles from each parent to each affected child in the HBDI cohort could be detected. This ordered set of alleles corresponds physically to one of the two parental chromosomes, and is called a haplotype. By inferring the parental haplotypes and their transmission or non-transmission to affected children, more statistical information is expected to be obtained than that from alleles alone.

Haplotypes were inferred using a combination of two methods. As the first step, the GeneHunter program (Falling Rain Genomics, Palo Alto, Calif.) (Kruglyak, et al., 1996, *Am J Hum Genet*, 58(6): 1347–63) was used as it very rapidly calculates haplotypes from genotype data from pedigrees. Each HBDI family pedigree was then inspected individually using the Cyrillic program (Cherwell Scientific Publishing, Palo Alto, Calif.), to resolve any ambiguous or unsupported haplotype assignments. Unambiguous and non-recombinant haplotypes could be confidently assigned in all but six of the 282 families. The haplotype data for these 276 families were used in subsequent data analysis.

The IL4R gene has the property that many of the SNPs reside within the 3'-most exon (exon 9), whose coding region is approximately 1.5 kb long. A method was developed for directly haplotyping up to five of these exon 9 alleles (namely, SNPs #3–7) without needing parental genotypes. As many of these SNPs direct changes to the amino acid sequence of the IL4R protein, different haplotypes encode different proteins with likely different functions.

Haplotypes, in an individual for which no parental genotypic information is known, can be inferred unambiguously only when at most one of the SNP sites of those is heterozygous. In other cases, the ambiguity must be resolved experimentally.

Two allele-specific primers with one common primer to perform PCR reactions (using STOFFEL GOLD™ DNA polymerase) to separately amplify the DNA from each chromosome, as shown in FIG. 1 below were used. The alleles on each amplicon were then detected by the same strip hybridization procedure, and the linked alleles called directly. The choice of allele-specific (colored or shaded arrows) and common (black arrows) primers depends on which SNP loci are heterozygous. The primers were modified at the 5' phosphate by conjugation with biotin, and are shown in Table 12 (SEQ ID NO: 54–62).

For each haplotyping assay, two PCR reactions were set up for each DNA to be tested. One reaction contained the common primer and the wildtype allele-specific primer, the other contained the common primer and the variant allele-specific primer. Each PCR reaction was made in a total reaction volume of 50–100 μl containing the following reagents:

0.2 ng/ml purified human genomic DNA 0.2 mM each primer 800 mM total dNTP (200 mM each dATP, dTTP, dCTP, dGTP)

10 mM KCl 10 mM Tris-HCl, pH 8.0

2.5 mM $MgCl_2$ 0.12 units/ml STOFFEL GOLD™ DNA polymerase*

*developed and manufactured by Roche Molecular Systems.

Amplification was carried out in a GeneAmp™ PCR System 9600 thermal cycler (PE Biosystems, Foster City, Calif.), using the specific temperature cycling profile shown below:

| Pre-reaction incubation: | 94° C. for 12.5 minutes |
|---|---|
| 33 cycles: | |
| Denature: | 95° C., 45 seconds |
| Anneal: | 64° C., 30 seconds |
| Extend: | 72° C., 45 seconds |
| Final Extension: | 72° C., 7 minutes. |
| Hold: | 10° C.–15° C. |

Following amplification, each PCR product reaction was denatured and separately used for hybridization to the membrane-bound probes as described above.

Haplotype Sharing in Affected Sibs

Evidence for linkage of IL4R to type 1 diabetes (as opposed to association) can be assessed by the haplotype sharing method. This method assesses the distribution over all families of the number of chromosomes that are identical-by-descent (IBD) between the two affected siblings in each family. For example, if in a family, the father transmits the same one of his two IL4R haplotypes to both children, and the mother transmits the same one of her two IL4R haplotypes to both children, then the children are said to share two chromosomes IBD (or, to be IBD=2). If both parents transmit different IL4R haplotypes to their two children, the children are said to be IBD=0.

Under the null hypothesis of no linkage of IL4R to type 1 diabetes, the proportion of families IBD=0 is 25%, IBD=1 is 50% and IBD=2 is 25%, as expected by random assortment (see Table 13). Evidence for a statistically significant difference from this expectation can be assessed using the chi-square statistic.

Identity-by-descent (IBD) values of parental IL4R haplotypes in the affected sibs could be determined unambiguously in 256 families. In the rest of the families, one or both parents were homozygous and/or the parental source of the child's chromosomes could not be determined. The distribution of IBD is shown in Table 13.

It is known that the HLA genotype can have a significant effect, either increased or decreased depending on the genotype, on the risk for type 1 diabetes. In particular, individuals with the HLA DR genotype DR3-DQB1*0201/DR4-DQB1*0302 (referred to as DR3/4 below) appear to be at the highest risk for type 1 diabetes (see Noble, Valdes et al., 1996), incorporated herein by reference). These high-risk individuals have about a 1 in 15 chance of being affected with type 1 diabetes. Because of the strong effect of this genotype on the likelihood of type 1 diabetes, the presence of the DR3/4 genotype could mask the contribution of IL4R alleles or haplotypes.

The distribution of IBD in families was stratified into two groups based on the DR3/4 genotype of the children. The first group contains the families in which one or both of the sibs are DR3/4 ("Either/both sib DR3/4", n=119). The second group contains the families where neither child is DR3/4 ("Neither sib DR3/4", n=137). The IBD distribution in these subgroups is shown in Table 13. There was no statistically significant departure from the expected distribution of IBD sharing in the "either/both sib DR3/4" subgroup of families. There is a statistically significant departure from the expected distribution of IBD sharing in the "neither sib DR3/4" subgroup of families (Table 13). This indicates that there is evidence for linkage of the IL4R loci to IDDM in the "neither sib DR3/4" families.

Association by AFBAC

Association of IL4R haplotypes with type 1 diabetes was assessed using the AFBAC (Affected Family Based Control) method (Thomson, G., 1995, *Am J Hum Genet* 57:487–98). In essence, two groups of haplotypes, and the haplotype frequencies in the groups, are compared with each other as in a case/control scheme of sampling. These two groups are the case (transmitted) and the control (AFBAC) haplotypes.

The case haplotypes, namely those transmitted to the affected children, were collected and counted as follows. For every pair of siblings, regardless of the status of the parents (homozygote or heterozygote) all four transmitted chromosomes were counted. However, the haplotypes in the two siblings in a pair are not independent of each other. The way to make a statistically conservative and valid enumeration is to divide all counts by two.

The control (AFBAC) haplotypes are those that are never transmitted to the affected pair of children (Thomson, 1995). The AFBAC haplotypes permit an unbiased estimate of control haplotype frequencies. AFBACs can only be determined from heterozygous parents, and furthermore, only when the parent transmits one haplotype to both children; the other, never-transmitted haplotype is counted in the AFBAC population. The AFBAC population serves as a well-matched set of control haplotypes for the study.

Table 14A shows the comparison of transmitted and AFBAC frequencies for all HBDI haplotypes that were observed at least five times in the complete sample set. Each row represents data on an individual haplotype. However, in all 16 distinct haplotypes were observed in the HBDI data set, although some very rarely. The seven rarest haplotypes are grouped together in the "others" row. Each haplotype is listed by the ordered set of alleles (namely, from SNPs 1-2-3-4-5-6-7-8) present at each of the eight IL4R SNPs as described in Table 6. A "1" denotes the presence of the reference allele, a "2" the presence of the variant allele for each SNP. The "reference" allele for each SNP is that present in GenBank Accession X52425.1 as described in Table 6.

Tables 14B and 14C show the comparison of transmitted and AFBAC frequencies for all HBDI haplotypes seen in the "either/both sib DR3/4" and the "neither sib DR3/4" subgroups of families, respectively. These tables show that stratifying the families based on the DR3/4 genotype of the children permits the identification of haplotypes that are associated with IDDM. In particular, in the "neither sib DR3/4" subgroup one haplotype (labeled "2 1 2 2 2 2 2 1") is significantly underrepresented in the pool of transmitted chromosomes (P<0.005).

From the transmitted and AFBAC haplotype frequency information in Tables 14B and 14C, one can derive by counting the frequencies of transmitted and AFBAC alleles. The locus-by-locus AFBAC analyses are shown in Tables 15A and 15B.

The data present in Tables 15A and 15B show that there statistically significant evidence, in the "neither sib DR3/4" subgroup of families, that alleles of SNPs numbers 3, 4 5, 6, and 7 are associated with IDDM. The evidence for association is especially strong for SNP #6. In the "either/both sib DR3/4" subgroup, there is the same trend of allelic association, although the trend does not quite reach statistical significance.

Association by Haplotype-Based TDT

The TDT analysis can be utilized for determining the transmission (or non-transmission) of 8-locus haplotypes from parents to affected children, once the haplotypes have been inferred or assigned by molecular means. Tables 16A, B, and C summarize the TDT results for the HBDI families. Each haplotype is listed by the ordered set of alleles (namely, from SNPs 1-2-3-4-5-6-7-8) present at each of the eight IL4R SNPs as described in Table 6. A "1" denotes the presence of the reference allele, a "2" the presence of the variant allele for each SNP. The "reference" allele for each SNP is that present in GenBank Accession X52425.1 as described in Table 6. Table 16A counts informative transmission events only to one child (the proband) per family, Table 16B counts informative transmissions to the two primary affected children per family, and Table 16C counts informative transmissions to all affected children. The 8-locus haplotype TDT results reach statistical significance when all affected children (2 or more per family) are included.

The TDT analyses can be performed on families after stratifying for the DR3/4 genotype of the children. The summary of counts of informative transmissions to the two primary affected children per family, in the "either/both sib DR3/4" and the "neither sib DR3/4" subgroups of families, are shown in tables 17A and 17B respectively. Each haplotype is listed by the ordered set of alleles (namely, from SNPs 1-2-3-4-5-6-7-8) present at each of the eight IL4R SNPs as described in Table 6. A "1" denotes the presence of the reference allele, a "2" the presence of the variant allele for each SNP. The "reference" allele for each SNP is that present in GenBank Accession X52425.1 as described in Table 6.

As presented above, there is significant evidence of linkage of IDDM to IL4R in the "neither sib DR3/4" subgroup. The data in Table 17B indicate that there is significant evidence of association of IL4R haplotypes to IDDM, in the presence of this linkage. In particular, in the "neither sib DR3/4" subgroup one haplotype (labeled "2 1 2 2 2 2 2 1") is significantly under-transmitted to affected children.

9. EXAMPLE 3

Association of IL4R With Type 1 Diabetes in Filipino Samples

This example demonstrates the association of IL4R SNPs with type 1 diabetes in a Filipino population.

As used in this section, "patients" refers to individuals with the disease, namely individuals with type 1 diabetes and "controls" refers normal individuals, those without the disease.

Ninety patients (n=90) were selected for this study from amongst the Filipino population. The patients included in the study were affected by type 1 diabetes as defined by the recent ADA classification (the Expert Committee on the Diagnosis and Classification of Diabetes Mellitus 1997). The patients were born in the Philippines and all had two Filipino parents. These patients had been characterized for C-peptide levels below 0.3 mmol/l and for autoantibodies to islet cell autoantigens (Medici et al., 1999, *Diabetes Care*, 9:1458–62). Samples were also collected from ninety-four Filipino normal subjects without a family history for diabetes. This was the control group. All patients and controls were from the southern region of Luzon, Philippines. The study was approved by the local Ethics Committee and informed consent was given by patients. In addition, independent samples from a previous study of HLA class II loci in Filipinos (Bugawan et al., 1994, *Genetics*, 54:331–340) originating from the same region were used, following a statistical test of heterogeneity, to supplement the control samples. These comprised a total of 194 chromosomes taken from family and individual samples.

The individuals were genotyped as described above. The genotypes of the affected and unaffected individuals are shown in Table 4 (SEQ ID NO: 20–24). Both the actual numbers and the frequencies are provided for each genotype. The data (Table 5) confirm the presence of an association of IL4R SNP variants with type 1 diabetes.

Statistical Methods & Algorithms

Allele and haplotype frequencies between groups were compared using the z-test. Haplotype compositions and frequencies were estimated from the genotype data using the EM algorithm in the Arlequin program (L. Excoffier, University of Geneva, CH) (Excoffier et al., 1995, *Mol Biol Evol*, 12:921–7; Slatkin et al., 1996, *Heredity*, 76:377–83).

Results

The wildtype allele frequencies for each of the eight IL4R SNPs in the Filipino control and diabetic groups are shown in Table 18. Table 18 provides evidence that the allele frequencies for SNPs #3 and 4 are significantly different between the two groups, and suggests an association to IDDM.

It is also possible to infer and construct the multi-locus IL4R haplotypes in the Filipino subjects, either computationally by Maximum-likelihood estimation (MLE), or by using molecular haplotyping methods described previously. Table 19 lists the five most frequent computationally estimated haplotypes and their frequencies in the Filipino diabetics and controls, and presents the significance of the differences in frequencies. Each haplotype is listed by the ordered set of alleles (namely, from SNPs 1-2-3-4-5-6-7-8) present at each of the eight IL4R SNPs as described in Table 6. A "1" denotes the presence of the reference allele, a "2" the presence of the variant allele for each SNP. The "reference" allele for each SNP is that present in GenBank Accession X52425.1 as described in Table 6.

Table 20 lists the observed haplotypes as derived and inferred by molecular haplotyping; the unambiguous seven-locus haplotypes (SNP#1 allele not shown, as indicated by the "x") are compiled. Each haplotype is listed by the ordered set of alleles (namely, from SNPs 1-2-3-4-5-6-7-8) present at each of the eight IL4R SNPs as described in Table 6. A "1" denotes the presence of the reference allele, a "2" the presence of the variant allele for each SNP. The "reference" allele for each SNP is that present in GenBank Accession X52425.1 as described in Table 6. Tables 18 and 19 both provide evidence of a statistically significant difference in the frequency of one or more haplotypes between the Filipino control and diabetic populations, and support the presence of an association of IL4R to IDDM. In particular, the haplotype (labeled "x 1 2 2 2 2 2 1") is significantly underrepresented in the Filipino diabetics group.

10. EXAMPLE 4

Association of IL4R, IL4 and IL13 SNPs With Type 1 Diabetes in Filipino Samples

This example demonstrates the association of IL4R, IL4 and IL13 SNPs with type 1 diabetes in the same Filipino population as described above, in Example 3.

As used in this section, "patients" refers to individuals with the disease, namely individuals with type 1 diabetes and "controls" refers normal individuals, those without the disease.

The individuals were genotyped as described above.

Individual SNPs

The distributions of alleles at the individual SNPs in the IL4R locus (n=10), the IL4 locus (n=1) and the IL13 locus (n=4) among patients and controls are shown in Table 21. Linkage disequilibrium patterns were estimated using maximum likelihood approaches from individual genotype data from unrelated individuals (Slatkin and Excoffier, 1996 *Heredity* 76:377:383). The patterns of pairwise linkage disequilibrium (LD) for these SNPs inferred among the control population are shown in Tables 22 and 23. Among the individual IL4R SNPs, three (E375A, L389L, and C406R) showed a nominally significant association with type 1 diabetes while the variant allele at two additional SNPs (I50V, p=0.062 and S478G, p=0.064) was decreased among patients (Table 21).

The two promoter SNPs were not significantly associated with type 1 diabetes, although the variant allele of the −3223 SNP was slightly increased among patients (OR=1.45, p=0.10). With the exception of this promoter SNP and the I50V SNP, with which it is in strong LD, the variant allele at each SNP was underrepresented among patients. Some of the polymorphic amino acid residues in this chain appear to be biologically important and affect IL-4 receptor signaling (Kruse et al., 1999, *Immunology*, 96:365–71).

Of the 10 IL4R SNPs typed, the L389L SNP showed the strongest association with type 1 diabetes in this population, with significantly lower frequencies among patients than controls (OR=0.34; p=0.001). Without being bound by theory, it is believed that because this is a silent (synonymous) polymorphism, it is unlikely that this SNP is responsible for the observed protective effect for type 1 diabetes. This SNP is in very strong LD (Table 22) with the nonsynonymous flanking SNPs (E375A, C406R, S478P and Q551R) and that these SNPs all show a trend toward protection (negative association). The L389L SNP is also in strong negative LD with the −3223 promoter SNP (Table 22).

In the comparison of genotypes at the individual IL4R SNPs (Table 24), the protective effect is dominant in that the heterozygote for IL4R 389 has an OR=0.29. Among the individual SNPs on chromosome 5q31, only the variant alleles at the two IL13 promoter SNPs were increased among patients (OR=1.58 and p=0.05 for −1512 and OR=1.49 and p=0.12 for −1112) (Table 21) When genotype frequencies are compared, however, the IL13 R110Q showed a nominally significant association in this population (p=0.03; Table 24). These data suggest that the variant homozygote, but not the heterozygote, may be at increased risk for type 1 diabetes. In Table 24, each haplotype is listed by the ordered set of alleles (namely, from SNPs 1-2-3-4-5-6-7-8) present at each of the eight IL4R SNPs as described in Table 6. The letters refer to the actual allele (nucleotide) present, as described in Table 6.

Haplotypes

IL4R

IL4R haplotypes were estimated based on an expectation-maximization (EM) method (Excoffier et al., 1995, *Mol. Biol. Evol.*, 12:921–927.) and were directly determined by molecular haplotyping methods, described in Example 4. The molecular haplotyping method allowed the unambiguous assignment of phase for 7 IL4R SNPs (C676T, A1374C, G1417T, T1466C, T1682C, A1902G and T2531C). Using molecular haplotyping of these 7 SNPs, 7 different IL4R haplotypes were determined in this population and their frequencies among patients and controls compared (Table 25A). In Table 25A each haplotype is listed by the ordered set of alleles (namely, from SNPs 2-3-4-5-6-7-8) present at seven of the eight IL4R SNPs as described in Table 6. The letters refer to the actual allele (nucleotide) present, as described in Table 6.

One specific haplotype (CCTCCGT)) was significantly underrepresented among patients (OR=0.4, p=0.013). This same haplotype was also found to be protective (significant negative association), by the TDT methods, in the HBDI families, as described in Example 2. This protective effect has thus been observed in two different populations and in two different study designs, namely case/control (Filipino) and TDT, in addition to the biological plausibility (i.e., functional consequences) of these SNPs. This strongly suggests that variants of the IL4R molecule influence the susceptibility to type 1 diabetes. In particular, this specific haplotype of IL4R appears to confer a dominant protective effect.

In the HBDI families, stratification based on the highest risk HLA genotype (HLA-DRB1*0301-DQB1*0201/HLA-DRB1*04-DQB1*0302) was necessary to demonstrate the protective effect of the IL4R haplotype. A significant negative association was found only among those families in which neither affected sib was DR3/4, presumably because the effect of the IL4R polymorphism was relatively modest compared to the risk conferred by this high risk HLA genotype, which confers a disease risk higher than DR3/3 or DR4/4 homozygotes. Among Filipinos, a significant protective effect of a specific IL4R haplotype was observed without stratification (Table 25). Without being bound by theory, this may reflect the absence among Filipinos of a higher risk associated with DR3/4 than with DR3/3 or DR4/4 genotypes. The lack of the "DR3/4 effect," well-established by many studies of Caucasian type 1 diabetes, can be attributed among Filipinos to the differing patterns of linkage disequilibrium of DQB1 alleles with DRB1*04 alleles between Asians and Caucasians.

The molecular haplotyping approach used in this example did not assign phase for the two promoter SNPs and the I50V SNP in the IL4R locus. Consequently, the EM approach was used to estimate frequencies for 10-SNP haplotypes for these 3 individual SNPs and the 7-SNP haplotype previously determined by molecular methods (Table 25B). In Table 25B, each haplotype is listed by the ordered set of alleles (namely, from SNPs 1-2-3-4-5-6-7-8-9-10) present at each of the ten IL4R SNPs described in Table 21 (SNPs in order: C(-3223)T-C(-1914)T-I50V-N142N-E375A-L389L-C406R-S478P-Q551R-S761P). The letters refer to the actual allele (nucleotide) present, as described in Table 21.

Of the 17 10-SNP haplotypes with an estimated frequency >1%, in either group, only one 10-SNP haplotype containing the protective 7-SNP haplotype (H5A or CCA-CCTCCGT) appeared strongly negatively associated (OR=0.0; 95% CI [0–0.5]; p=0.001) with disease. Interestingly, the other haplotype which contained the same 7-SNP haplotype (H$_5$B or CTA-CCTCCGT) was not significantly associated with disease (OR=0.66 p=0.33). This suggests that a specific combination of IL4R promoter SNPs with a particular coding sequence variant contributes to the risk for type 1 diabetes.

IL4 and IL13

The IL4 and the IL13 SNPs are in strong LD (Table 23). The estimated frequencies for these 5-SNP haplotypes were compared among patients and controls (Table 26). In Table 26, each haplotype is listed by the ordered set of alleles present at the one IL4 SNP and the four IL13 SNPs as described in Table 21. The order is IL4 C(-524)T-IL13 A(-1512)C-IL13 C(-1112)T-IL13 intron3-IL13 R110Q. The letters refer to the actual allele (nucleotide) present, as described in Table 21.

The overall distributions were different (p=0.005) and one haplotype, TCTTA, was strongly associated with type 1 diabetes (OR=3.47, p=0.004). Two other haplotypes showed a nominally significant association (p=0.02 and 0.03). One surprising observation was that the IL13 haplotype CTTA appeared to be associated with disease only in combination with the T allele at the IL4-524 promoter SNP because the CCTTA haplotype showed no disease association. These data could reflect LD between the associated 5-SNP haplotype with some nearby causal gene or suggest that a particular combination of a promoter variant at IL4 and promoter and coding variants at IL13 are responsible for an elevated type 1 diabetes risk (gene—gene interaction).

13. EXAMPLE 7

Dependence of Risk for Type 1 Diabetes Conferred by IL4R SNPs on Genotype at IL4 and IL13 in Filipino Samples: Evidence for Epistasis This example demonstrates epistasis, the interaction between SNPs on the IL4R locus on chromosome 16 and those on the IL4 and IL13 loci on chromosome 5.

Because IL4 and IL13 both serve as ligands for a receptor composed, in part, of the IL4R alpha chain, there is a likelihood of gene—gene interactions between polymorphisms in the IL4R locus on chromosome 16p11 and the five SNPs in the IL4 and IL13 loci on chromosome 5q31. In one approach, the statistical independence for genotypes at the 10 IL4R SNPs and the genotypes at each of the IL4 and IL13 SNPs (Table 27) was examined. Gene by gene interactions at SNPs in different genes were evaluated by assessing whether the genotype frequencies at unlinked loci were independent (i.e., the IL13 and IL4 SNPs on chromosome 5 and the IL4R SNPs on chromosome 16) among patients. These analyses were done for each pair of unlinked SNPs carrying out a chi-square test in contingency tables with marginals defined by genotype counts either in patients or controls. The chi-square values and the corresponding degrees of freedom for each IL4R SNP comparisons were summed and p-value of the sum of chi-squares computed.

No deviation from independence was found for these SNPs among controls but a significant deviation was found for the IL4-524 promoter SNP (p=0.001) and the IL13 intron 3 SNP (p=0.019) among patients.

To assess whether the effect on type 1 diabetes susceptibility due to IL4R SNPs was modified by the IL4 or the IL13 SNPs, epistasis was modeled using a logistic regression model (see below). For each of the five IL4 and IL13 SNPs, we tested whether the effect of the combined IL4R SNP genotypes on type 1 diabetes susceptibility differed depending on the IL4 and IL13 SNPs. The results (Table 28) indicate that there is indeed an epistatic interaction between the IL4R genotypes and IL4 and IL13 genotypes. To address the issue of multiple comparisons, we carried out permutation analysis on this test. In 22/200 permutations one or more of the 5-SNP tests showed a p<0.035, in 13/200 one or more of the SNP tests had p<0.035 and another one had p<0.075. In 9/200 one or more of the 5-SNP tests showed a p<0.035, another had a p<0.075 and another had a p<0.135. Thus, the pattern observed in Table 28 has a probability of p<0.045. The conclusion from this is that the epistatic interaction observed between the IL4 and IL13 SNPs and the IL4R genotypes is statistically significant indicating that, in this data set, the genotypes in the IL4, IL13 region affect the genetic susceptibility to type 1 diabetes conferred by IL4R.

To illustrate this interaction, the odds ratios for individual IL4R SNPs as a function of the IL4 and IL13 SNP genotype were also calculated. The differences among the Odds Ratios were greatest for the IL4R −3223 SNP and the four IL13 SNPs. The odds ratios with the 95% confidence intervals and the p values from the stratified contingency table analyses are shown in FIG. 2. FIG. 2 shows the Odds ratios, patient and control counts of specific IL4R and IL4, IL13 genotypes. FIG. 2A shows the interaction of IL4R Ala375Glu with and IL4-524 (promoter). FIG. 2B shows the interaction of IL4R Gln551Arg with IL13 A-1512C. FIG. 2C shows the interaction between IL4R C-3223T and IL13 A-1512C and FIG. 2D shows the interaction between IL4R C-3223T and IL13 C-1112T. The p-value The most striking observation was that the IL4R-3223 SNP CT genotype had an OR of 8.55 (95% CI=1.05, 69.8) when present with the TT IL13-1112 genotype and an OR 0.53 (95% CI=0.29, 0.98) when present with the CC genotype. Without being bound by theory, the observation of an interaction between polymorphisms in the IL13 and IL4 genes and polymorphism in the gene encoding the receptor for the products of these two genes represents an interesting and biologically plausible hypothesis that, given the multiple comparisons, requires further testing. A recently published study of asthma patients reported a gene—gene interaction between IL4R and IL13 in the determination of serum IgE levels (Howard et al., 2002, *Am J Hum Genet,* 70:230–6).

As described above, the IL4R association data obtained in this Filipino case control study indicate that the 7-SNP haplotype, composed primarily of variant alleles at these SNPs, confers dominant protection to type 1 diabetes (Table 25A), consistent with our recent observations, based on TDT and AFBAC analysis in a set of multiplex Caucasian families (the HBDI registry). The replication of this observation in two different populations and in two different study designs strengthens this inference. The analysis of 10-SNP IL4R haplotypes among Filipinos suggests that a specific promoter variant in combination with specific coding sequence variants may be responsible for the observed protection (Table 25B). Several recent studies have shown that the reference or wild-type allele at several of these IL4R SNPs is associated with atopic asthma and increased IgE levels (Howard et al., 2002, *Am J Hum Genet,* 70:230–6, Sandford et al., 2000, *J Allergy Clin Immunol,* 106:135–40). Thus, it appears that the same alleles at IL4R SNPs confer an increased risk to a canonical Th1 (type 1 diabetes) and a Th2 disease (atopic asthma). Without being bound by theory, these associations argue against an effect on Th1/Th2 balance mediated by polymorphism in the IL4R gene and suggest instead that this polymorphism may influence some aspect of immune regulation and homeostasis in Th1 and Th2 pathways and possibly, B cell activation. Conceivably, the observed patterns of disease association reflect the effect of IL4R polymorphisms on the balance between the activation of Th1 and Th2 cells and that of T regulatory cells. In conclusion, the extent of risk for type 1 diabetes may be determined by specific combinations of variants at the IL4R locus and at the genes encoding its two ligands, IL4 and IL13.

Calculations Performed to Achieve the Results of Table 28

For each IL4R SNP, the homozygote genotype with the highest odds ratio was given a value of 2, the heterozygote was given a value of 1, the other homozygote was 0. A logistic regression was carried out on nine IL4R polymorphisms (S761P did not show the variant) in this way and a new numerical variable "il4r" was derived given by: il4r=$\alpha_1 G_{-3223}+\alpha_2 G_{-1914}+\alpha_3 G_{50}+\alpha_4 G_{142}+\alpha_5 G_{375}+\alpha_6 G_{389}+\alpha_7 G_{406}+\alpha_8 G_{478}+\alpha_9 G_{551}$ where Gi denotes the genotype (0, 1 or 2) at the ith position and $\alpha j$ denotes the coefficient fitted by logistic regression. The coefficients fitted by the regression were $\alpha 1=0.368$; $\alpha 2=0.053$; $\alpha 3=0.37$; $\alpha 4=0.061$; $\alpha 5=0.66$; $\alpha 6=1.08$; $\alpha 7=0.57$; $\alpha 8=0.54$ and $\alpha 9=0.22$. Epistasis was then tested independently for each of the five chromosome 5 SNPs by fitting the following logistic regression model: $P(T1DM)=\exp(X)/(1+\exp(X))$ Where $X=C+\beta_1 il4r+\beta_2 G_{chr5i}+\beta_3(il4r \cdot G_{chr5i})$ and $G_{chr5i}$ is the genotype of one of the chromosome 5 SNPs (values 0, 1 or 2).

Permutation Analysis.

Because five different SNPs were compared, it was important to correct for multiple tests. However, a Bonferroni or a Dunn-Sidak correction was not appropriate since the IL4 and IL13 SNPs are not independent (see Table 23). Therefore permutation analysis was carried out, keeping constant the patient and control genotype frequencies, but permutating the IL4 and IL13 genotypes and the IL4R genotypes within the patient and within the control groups separately. In this way, only the epistatic interaction between the two genetic regions was tested and not the individual IL4 or IL13 and IL4R genetic associations. 200 permutations were carried testing for epistasis at all five chromosome 5 SNPs each time. Analyses were carried out using S-Plus version 6.0 Professional (Insightful Corporation).

Various embodiments of the invention have been described. The descriptions and examples are intended to be illustrative of the invention and not limiting. Indeed, it will be apparent to those of skill in the art that modifications may be made to the various embodiments of the invention described without departing from the spirit of the invention or scope of the appended claims set forth below.

All references cited herein are hereby incorporated by reference in their entireties.

TABLE 3

| Variant | Probe | Probe Sequence | Seq ID No: | titer (μl) |
|---|---|---|---|---|
| A398 | DBM0081P | CCACACGTGTATCCCTGAGAA | 3 | 1.0 |
| 398G | DBM0082P | TCTCAGGGACACACGTGTG | 4 | 4.0 |
| C676 | DBM0172P | TGGAGTGAAAACGACCCGGCAG | 5 | 1.0 |
| 676T | DBM0073P | CTGCCGGGTCATTTTCGCTCC | 6 | 1.0 |
| A1374 | DBM0043RC | GAGGGAAGGGAGGGCATTGTG | 7 | 1.0 |
| 1374C | DBM0139P | AGGGAAGGGCGGGCATTGT | 8 | 4.0 |
| G1417 | DBM0124P | CTCTCCGAGCAGGTCCAGG | 9 | 1.0 |
| 1417T | DBM0046RC | TCCTGGACCTTCTCGGAGAGG | 10 | 1.0 |
| T1466 | DBM0076P | AAGGTGGAAGAAGGCATGACTCC | 11 | 1.0 |
|  | DBM0132P | AAGGTGGGAGAAGACATGACTCC | 12 | 1.0 |
| 1466C | DBM0171P | GGAGTCACGTCTTCTCCTACCTT | 13 | 2.0 |
| T1682 | DBM0157P | TGGCTCAGAGAGTTGCTGAAGC | 14 | 2.0 |
| 1682C | DBM0094P | TTCAGCAACCCCCTGAGCC | 15 | 2.0 |
| A1902 | KW86 | AGTGGCTATCAGGAGTTTGT | 16 | 1.6 |
| 1902G | KW85 | AGTGGCTATCGGGAGTTTGT | 17 | 0.8 |
| T2531 | DBM0080P. | CTCTTCTCTGAGATGCCCGAG | 18 | 0.5 |
| 2531C | DBM0048RC | CTCGGGCATCCCAGAGAAGAG | 19 | 0.5 |

TABLE 6

| | | SNPs detected | | |
|---|---|---|---|---|
| SNP # | LOCUS | SNP | Variation | Genbank Access # |
| 1 | IL4R | A398G | I50V | X52425 |
| 2 | IL4R | C676T | N142N | X52425 |
| 3 | IL4R | A1374C | E375A | X52425 |
| 4 | IL4R | G1417T | L389L | X52425 |
| 5 | IL4R | T1466C | C406R | X52425 |
| 6 | IL4R | T1682C | S478P | X52425 |
| 7 | IL4R | A1902G | Q551R | X52425 |
| 8 | IL4R | T2531C | S761P | X52425 |

TABLE 4

Computationally estimated haplotype frequencies compared between Filipino controls and diabetics.

| haplotype | Seq ID No: | label | MLE frequency | MLE frequency | O.R. | COUNT: control | COUNT: diabetics | Total count | exp control | exp diabetic | chi-square | P-value |
|---|---|---|---|---|---|---|---|---|---|---|---|---|
| ACATTTAT | 20 | H-1 | 0.318 | 0.329 | 1.1 | 59.7 | 58.5 | 118.2 | 60.7 | 57.5 | 0.033 | 0.855 |
| ACAGTTGT | 21 | H-6 | 0.074 | 0.074 | 1.0 | 14.0 | 13.2 | 27.2 | 14.0 | 13.2 | 0.000 | 0.987 |
| ACCTCCGT | 22 | H-3 | 0.145 | 0.058 | 0.4 | 27.3 | 10.3 | 37.6 | 19.3 | 18.3 | 6.727 | 0.009 |
| GCAGTTAT | 23 | H-2 | 0.390 | 0.441 | 1.2 | 73.3 | 78.5 | 151.8 | 78.0 | 73.8 | 0.582 | 0.445 |
| GCCGCCGT | 24 | H-10 | 0.032 | 0.051 | 1.6 | 6.0 | 9.0 | 15.0 | 7.7 | 7.3 | 0.776 | 0.378 |
| | | n = | 188 | 178 | | | | 366 | | | | |
| | | | | | | | | | | overall | 8.118 | 0.0987 |

TABLE 5

| SNP | Affected Genotypes (n = 89) | | | Control Genotypes (n = 94) | | |
|---|---|---|---|---|---|---|
| A398G (50 I/V) | AA = 21 (0.236) | AG = 40 (0.449) | GG = 28 (0.315) | AA = 32 (0.340) | AG = 41 (0.436) | GG = 21 (0.223) |
| C676G (142 N/N) | CC = 89 (1) | | | CC = 92 (0.979) | CG = 2 (0.021) | |
| A1374C (375 E/A) | AA = 70 (0.787) | AC = 17 (0.191) | CC = 2 (0.023) | AA = 55 (0.630) | AC = 30 (0.341) | CC = 3 (0.034) |
| G1417T (389 L/L) | GG = 78 (0.876) | GT = 10 (0.112) | TT = 1 (0.011) | GG = 63 (0.670) | GT = 29 (0.309) | TT = 2 (0.022) |
| T1466C (406 C/R) | TT = 70 (0.787) | TC = 17 (0.191) | CC = 2 (0.023) | TT = 60 (0.638) | TC = 32 (0.340) | CC = 2 (0.022) |
| T1682C (478 S/P) | TT = 70 (0.787) | TC = 17 (0.191) | CC = 2 (0.023) | TT = 61 (0.649) | TC = 31 (0.330) | CC = 2 (0.022) |
| A1902G (551 Q/R) | AA = 50 (0.562) | AG = 35 (0.393) | GG = 3 (0.034) | AA = 50 (0.532) | AG = 36 (0.383) | GG = 8 (0.085) |
| T2531C (761 S/P) | TT = 89 (1) | | | TT = 94 (1) | | |

TABLE 7

Amplicon primers and lengths

| SNP # | Amplicon size, bp | Amplicon Left Primer Name | Left primer sequence | Seq ID No: | Amplicon Right Primer Name | Right primer sequence | Seq ID No: |
|---|---|---|---|---|---|---|---|
| 1 | 114 | RR192B | CAGCCCTGTGTCTGCAGA | 25 | RR193B | GTCCAGTGTATAGTTATCCGCACTGA | 31 |
| 2 | 163 | DBM0177B | CTGACCTGGAGCAACCCGTA | 26 | DBM0178B | ACTGGGCCTCTGCTGGTCA | 32 |
| 3, 4, 5 | 228 | DBM0023B | ATTGTGTGAGGAGGAGGAGGAGGTA | 27 | DBM0022B | GTTGGGCATGTGAGCACTCGTA | 33 |
| 6 | 129 | DBM0097B | CTCGTCATCGCAGGCAA | 28 | DBM0098B | AGGGCATCTCGGGTTCTA | 34 |
| 7 | 198 | RR200B | GCCGAAATGTCCTCCAGCA | 29 | RR178B | CCACATTTCTCTGGGGACACA | 35 |
| 8 | 177 | DBM0112B | CCGGCCTCCCTGGCA | 30 | DBM0071B | GCAGACTCAGCAACAAGAGG | 36 |

TABLE 8

Hybridization probes and titers

| SNP # | WT allele probe name | WT allele probe sequence | Seq ID No: | WT allele probe titer ($\mu M$) | Variant allele probe name | Variant allele probe sequence | Seq ID No: | Variant allele probe titer ($\mu M$) |
|---|---|---|---|---|---|---|---|---|
| 1 | DBM0081P | CCACACGTGTATCCCTGAGAA | 37 | 1.0 | DBM0082P | TCTCAGGGACACACGTGTG | 46 | 4.0 |
| 2 | DBM0172P | TGGAGTGAAAACGACCCGGCAG | 38 | 1.0 | DBM0073P | CTGCCGGGTCATTTTCGCTCC | 47 | 1.0 |
| 3 | DBM0043RC | GAGGGAAGGGAGGGCATTGTG | 39 | 1.0 | DBM0139P | AGGGAAGGGCGGGCATTGT | 48 | 4.0 |
| 4 | DBM0124P | CTCTCCGAGCAGGTCCAGG | 40 | 1.0 | DBM0046RC | TCCTGGACCTTCTCGGAGAGG | 49 | 1.0 |
| 5 | DBM0076P + DBM0132P | AAGGTGGAAGAAGGCATGACTCC AAGGTGGGAGAAGACATGACTCC | 41 42 | 1.0 1.0 | DBM0171P | GGAGTCACGTCTTCTCCTACCTT | 50 | 2.0 |
| 6 | DBM0157P | TGGCTCAGAGAGTTGCTGAAGC | 43 | 2.0 | DBM0094P | TTCAGCAACCCCCTGAGCC | 51 | 2.0 |
| 7 | KW86 | AGTGGCTATCAGGAGTTTGT | 44 | 1.6 | KW85 | AGTGGCTATCGGGAGTTTGT | 52 | 0.8 |
| 8 | DBM0080P. | CTCTTCTCTGAGATGCCCGAG | 45 | 0.5 | DBM0048RC | CTCGGGCATCCCAGAGAAGAG | 53 | 0.5 |

TABLE 9

Allele Frequency Of wildtype allele in HBDI founders

| SNP # | WT Allele Frequency |
|---|---|
| 1 | 0.53 |
| 2 | 0.90 |
| 3 | 0.89 |
| 4 | 0.89 |
| 5 | 0.89  |
| 6 | 0.83 |
| 7 | 0.79 |
| 8 | 0.99 |

TABLE 10

Pairwise Linkage Disequilibrium Measures

| SNP | 1 | 2 | 3 | 4 | 5 | 6 | 7 | 8 |
|---|---|---|---|---|---|---|---|---|
| 1 |  | 0.000 | 0 067 | 0.068 | 0.069 | 0 000 | 0 000 | 0.003 |
| 2 | 1.00 (0.35) |  | 0.000 | 0.000 | 0.000 | 0.000 | 0.000 | 0.000 |
| 3 | 0.23 (0.09) | -1.00 (-0.12) |  | 0.000 | 0.000 | 0.000 | 0.000 | 0.779 |
| 4 | 0 23 (0 09) | -1.00 (-0.12) | 1 00 (1 00) |  | 0.000 | 0 000 | 0.000 | 0 782 |
| 5 | 0.22 (0 08) | -1 00 (-0 11) | 1.00 (0 97) | 1 00 (0 97) |  | 0 000 | 0.000 | 0 807 |
| 6 | 050 (0 24) | 0 39 (0 29) | 0.97 (0 78) | 0 97 (0 78) | 1 00 (0 78) |  | 0 000 | 0 000 |
| 7 | 0 30 (0 16) | 0.36 (0.23) | 0.99 (0.70) | 0.99 (0.70) | 0.99 (0.68) | 0 99 (0 87) |  | 0.000 |
| 8 | 1.00 (0.11) | 0 90 (0 29) | -0.58 (-0.02) | -0.58 (-0 02) | -0.49 (-0.02) | 1.00 (0.23) |  |  |

Above diagonal

Exact P-value by permu test

Below diagonal:

D' (and Δ)

TABLE 11A

Results of single locus TDT analysis, to the 282 probands only

| SNP # | Transmissions of WT allele to affected (T) | Non-transmissions of WT allele to affected (NT) | Total observed Transmissions (T + NT) | McNemar chi-squared statistic | Significance |
|---|---|---|---|---|---|
| 1 | 144 | 138 | 282 | 0.128 | N.S. |
| 2 | 55 | 39 | 94 | 2.723 | N.S. |
| 3 | 62 | 46 | 108 | 2.370 | N.S. |
| 4 | 62 | 46 | 108 | 2.370 | N.S. |
| 5 | 61 | 46 | 107 | 2.103 | N.S. |
| 6 | 90 | 67 | 157 | 3.369 | N.S. |
| 7 | 103 | 81 | 184 | 2.630 | N.S. |
| 8 | 5 | 7 | 12 | 0.333 | N.S. |

TABLE 11B

Results of single locus TDT analysis, to 564 primary affected and 26 additional children

| SNP # | Transmissions of WT allele to affected (T) | Non-transmissions of WT allele to affected (NT) | Total observed Transmissions (T + NT) | McNemar chi-squared statistic | Significance | % Transmission T/(T + NT) |
|---|---|---|---|---|---|---|
| 1 | 311 | 280 | 591 | 1.626 | N.S. | |
| 2 | 107 | 90 | 197 | 1.467 | N.S. | |
| 3 | 130 | 98 | 228 | 4.491 | P < 0.05 | 57.0% |
| 4 | 130 | 98 | 228 | 4.491 | P < 0.05 | 57.0% |
| 5 | 128 | 98 | 226 | 3.982 | P < 0.05 | 56.6% |
| 6 | 189 | 149 | 338 | 4.734 | P < 0.05 | 55.9% |
| 7 | 212 | 180 | 392 | 2.612 | N.S. | |
| 8 | 12 | 13 | 25 | 0.040 | N.S. | |

TABLE 12

Allele-specific PCR primers and amplicon lengths

| SNP detected allele-specifically | Amplicon Size, bp | Other SNPs spanned by amplicon | Common Primer Name | Common Primer Sequences | Seq ID No: |
|---|---|---|---|---|---|
| 3 | 678 | 4,5,6,7 | RR178B | CCACATTTCTCTGGGGACACA | 54 |
| 7 | 639 | 3,4,5,6 | DBM0023B | ATTGTGTGAGGAGGAGGAGGAGGTA | 55 |
| 6 | 413 | 3,4,5 | DBM0023B | ATTGTGTGAGGAGGAGGAGGAGGTA | 56 |

| SNP detected allele-specifically | Wildtype Allele-Specific Primer Sequence | Wildtype Allele-specific Primer Sequence | Seq ID No: | Variant Allele-Specific Primer Name | Variant Allele-specific Primer Sequence | Seq ID No: |
|---|---|---|---|---|---|---|
| 3 | DBM0149B | TTCCAGGAGGGAAGGGA | 57 | DBM015CB | TTCCAGGAGGGAAGGGC | 60 |
| 7 | DBN9155B | CACCGCATGTACAAACTCCT | 58 | DBM0156B | CACCGCATGTACAAACTCCC | 61 |
| 6 | DBM0194B | GGTGACTGGCTCAGGGA | 59 | DBM0195B | GGTGACTGGCTCAGGGG | 62 |

TABLE 13

IBD Distributions for IL4R haplotypes

| Group (n) | IBD = 2 | IBD = 1 | IBD = 0 | P-value |
|---|---|---|---|---|
| All families (256) | 30.7% | 47.9% | 21.5% | N.S. |
| Either/both sib DR3/4 (119) | 26.1% | 50.4% | 23.5% | N.S. |
| Neither sib DR3/4 (137) | 34.7% | 45.6% | 19.7% | 0.03 |
| Expectation | 25% | 50% | 25% | |

TABLE 14A

Haplotype transmissions by AFBAC method: all families

| IL4R 8-locus Haplotype | Counts | | | Observed Frequency | | Chi-squared | |
|---|---|---|---|---|---|---|---|
| | Transmitted | AFBAC | Total | Transmitted | AFBAC | Statistic | p-value |
| 1 1 1 1 1 1 1 1 | 259.5 | 109.5 | 369 | 46.3% | 41.8% | 0.82 | 0.36 |
| 2 1 1 1 1 1 1 1 | 170.5 | 71.5 | 242 | 30.4% | 27.3% | 0.60 | 0.44 |
| 2 1 2 2 2 2 2 1 | 29.5 | 23.5 | 53 | 5.3% | 9.0% | 3.79 | 0.05 |
| 2 2 1 1 1 1 1 1 | 23.5 | 13 | 36.5 | 4.2% | 5.0% | 0.24 | 0.63 |
| 1 1 2 2 2 2 2 1 | 23 | 12.5 | 35.5 | 4.1% | 4.8% | 0.18 | 0.67 |
| 2 2 1 1 1 2 2 1 | 20.5 | 14 | 34.5 | 3.7% | 5.3% | 1.20 | 0.27 |
| 1 1 1 1 1 1 2 1 | 19 | 9 | 28 | 3.4% | 3.4% | 0.00 | 0.98 |
| 2 1 1 1 1 1 2 1 | 3.5 | 3 | 6.5 | 0.6% | 1.1% | 0.61 | 0.43 |
| 2 2 1 1 1 2 2 2 | 4.5 | 2 | 6.5 | 0.8% | 0.8% | 0.00 | 0.95 |
| Others | 6.5 | 4 | 10.5 | 1.2% | 1.5% | 0.19 | 0.67 |
| TOTAL | 560 | 262 | 822 | | | 7.64 | 0.94 |

TABLE 14B

Haplotype transmissions by AFBAC method: "Either/both sib DR3/4" subgroup of famlies

| IL4R 8-locus Haplotype | Counts | | | Observed Frequency | | Chi-squared | |
|---|---|---|---|---|---|---|---|
| | Transmitted | AFBAC | Total | Transmitted | AFBAC | Statistic | p-value |
| 1 1 1 1 1 1 1 1 | 254 | 50.5 | 304.5 | 46.7% | 41.6% | 0.57 | 0.45 |
| 2 1 1 1 1 1 1 1 | 156 | 30 | 186 | 28.7% | 24.7% | 0.56 | 0.45 |
| 2 1 2 2 2 2 2 1 | 35 | 11 | 46 | 6.4% | 9.1% | 0.99 | 0.32 |
| 2 2 1 1 1 1 1 1 | 24 | 7 | 31 | 4.4% | 5.8% | 0.39 | 0.53 |
| 1 1 1 1 1 1 2 1 | 20 | 6 | 26 | 3.7% | 4.9% | 0.40 | 0.52 |
| 1 1 2 2 2 2 2 1 | 18 | 7 | 25 | 3.3% | 5.8% | 1.59 | 0.21 |
| 2 2 1 1 1 2 2 1 | 18 | 4 | 22 | 3.3% | 3.3% | 0.00 | 0.99 |
| 2 2 1 1 1 2 2 2 | 8 | 2 | 10 | 1.5% | 1.6% | 0.02 | 0.89 |
| 2 2 1 1 1 2 2 2 | 8 | 1 | 9 | 1.5% | 0.8% | 0.31 | 0.58 |
| 2 1 1 1 1 1 2 1 | 1 | 2 | 3 | 0.2% | 1.6% | 4.71 | 0.03 |
| 2 1 1 1 1 2 2 1 | 2 | 1 | 3 | 0.4% | 0.8% | 0.46 | 0.50 |
| TOTAL | 544 | 121.5 | 665.5 | | | 10.00 | 0.44 |

TABLE 14C

Haplotype transmissions by AFBAC method: "neither sib DR3/4" subgroup of famlies

| IL4R 8-locus Haplotype | Counts | | | Observed Frequency | | Chi-squared | |
|---|---|---|---|---|---|---|---|
| | Transmitted | AFBAC | Total | Transmitted | AFBAC | Statistic | p-value |
| 1 1 1 1 1 1 1 1 | 267 | 62.5 | 329.5 | 45.7% | 40.7% | 0.68 | 0.409 |
| 2 1 1 1 1 1 1 1 | 185 | 43 | 228 | 31.7% | 28.0% | 0.53 | 0.467 |
| 2 1 2 2 2 2 2 1 | 24 | 15.5 | 39.5 | 4.1% | 10.1% | 8.14 | 0.004 |
| 1 1 2 2 2 2 2 1 | 30 | 6 | 36 | 5.1% | 3.9% | 0.38 | 0.540 |
| 2 2 1 1 1 2 2 1 | 23 | 10 | 33 | 3.9% | 6.5% | 1.80 | 0.179 |
| 2 2 1 1 1 1 1 1 | 23 | 7.5 | 30.5 | 3.9% | 4.9% | 0.26 | 0.607 |
| 1 1 1 1 1 1 2 1 | 17 | 5 | 22 | 2.9% | 3.3% | 0.05 | 0.825 |
| 2 1 1 1 1 1 2 1 | 8 | 1 | 9 | 1.4% | 0.7% | 0.51 | 0.473 |
| 2 2 1 1 1 2 2 2 | 3 | 1 | 4 | 0.5% | 0.7% | 0.04 | 0.837 |
| 1 1 1 1 1 2 2 1 | 2 | 1 | 3 | 0.3% | 0.7% | 0.29 | 0.593 |
| 2 1 2 2 1 1 2 1 | 2 | 1 | 3 | 0.3% | 0.7% | 0.29 | 0.593 |
| TOTAL | 584 | 153.5 | 737.5 | | | 12.97 | 0.226 |

TABLE 15A

SNP by SNP allele transmissions by AFBAC method:
"either/both sib DR3/4" subgroup of familes

| | Transmitted (n = 540) | | | AFBAC (n − 121.5) | | | |
|---|---|---|---|---|---|---|---|
| | allele counts | | variant allele | allele counts | | variant allele | Chi-squared | p-value |
| SNP # | wt | variant | frequency | wt allele | variants | frequency | Statistic | (df = 1) |
| 1 | 296 | 244 | 45.2% | 64.5 | 57 | 46.9% | 0.12 | 0.730 |
| 2 | 490 | 50 | 9.3% | 107.5 | 14 | 11.5% | 0.58 | 0.446 |
| 3 | 485 | 55 | 10.2% | 103.5 | 18 | 14.8% | 2.17 | 0.141 |
| 4 | 485 | 55 | 10.2% | 103.5 | 18 | 14.8% | 2.17 | 0.141 |
| 5 | 485 | 55 | 10.2% | 103.5 | 18 | 14.8% | 2.17 | 0.141 |
| 6 | 457 | 83 | 15.4% | 96.5 | 25 | 20.6% | 1.97 | 0.161 |
| 7 | 436 | 104 | 19.35 | 88.5 | 33 | 27.2% | 3.77 | 0.052 |
| 8 | 532 | 8 | 1.5% | 119.5 | 2 | 1.6% | 0.02 | 0.893 |
| TOTAL | | | | | | | | |

TABLE 15B

SNP by SNP allele transmissions by AFBAC method:
"neither sib DR3/4" subgroup of familes

| | Transmitted (n = 588) | | | AFBAC (n − 158.5) | | | |
|---|---|---|---|---|---|---|---|
| | allele counts | | variant allele | allele counts | | variant allele | Chi-squared | p-value |
| SNP # | wt | variant | frequency | wt allele | variants | frequency | Statistic | (df = 1) |
| 1 | 320 | 268 | 45.6% | 77.5 | 81 | 51.1% | 1.53 | 0.216 |
| 2 | 539 | 49 | 8.3% | 139 | 19.5 | 12.3% | 2.36 | 0.124 |
| 3 | 529 | 59 | 10.0% | 132 | 26.5 | 16.7% | 5.50 | 0.019 |
| 4 | 529 | 59 | 10.0% | 132 | 26.5 | 16.7% | 5.50 | 0.019 |
| 5 | 534 | 54 | 9.2% | 136 | 22.5 | 14.2% | 3.41 | 0.065 |
| 6 | 502 | 86 | 14.6% | 121 | 37.5 | 23.7% | 7.38 | 0.007 |
| 7 | 475 | 113 | 19.2% | 115 | 43.5 | 27.4% | 5.10 | 0.024 |
| 8 | 584 | 4 | 0.7% | 157.5 | 1 | 0.6% | 0.00 | 0.946 |

TABLE 16A

TDT analysis of 8-loocus haplotypes to probands only.

| haplotype | transmitted to affected | NOT transmitted to affected | TOTAL TRANSMISSIONS OBSERVED | McNemar chi-squared statistic | P-value (1 df) | % TRANSMISSION |
|---|---|---|---|---|---|---|
| 11111111 | 140 | 131 | 271 | 0.299 | 0.585 | 51.7% |
| 21111111 | 130 | 105 | 235 | 2.660 | 0.103 | 55.3% |
| 21222221 | 27 | 39 | 66 | 2.182 | 0.140 | 40.9% |
| 22111111 | 19 | 28 | 47 | 1.723 | 0.189 | 40.4% |
| 11222221 | 19 | 24 | 43 | 0.581 | 0.446 | 44.2% |
| 22111221 | 17 | 23 | 40 | 0.900 | 0.343 | 42.5% |
| 11111121 | 18 | 15 | 33 | 0.273 | 0.602 | 54.5% |
| 22111222 | 6 | 5 | 11 | 0.091 | 0.763 | 54.5% |
| 21111121 | 1 | 5 | 6 | 2.667 | 0.102 | 16.7% |
| 11111221 | 1 | 3 | 4 | 1.000 | 0.317 | 25.0% |
| 11221221 | 2 | 0 | 2 | 2.000 | 0.157 | 100.0% |
| 21221121 | 1 | 1 | 2 | 0.000 | 1.000 | 50.0% |
| 21221221 | 0 | 2 | 2 | 2.000 | 0.157 | 0.0% |
| 11221111 | 0 | 1 | 1 | 1.000 | 0.317 | 0.0% |
| 11111222 | 1 | 0 | 1 | 1.000 | 0.317 | 100.0% |
| total | 382 | 382 | 764 | | | |

TABLE 16B

TDT analysis of 8-loocus haplotypes to two primary affected children per family.

| haplotype | transmitted to affected | NOT transmitted to affected | TOTAL TRANSMISSIONS OBSERVED | McNemar chi-squared statistic | P-value (1 df) | % TRANSMISSION |
|---|---|---|---|---|---|---|
| 21222221 | 52 | 80 | 132 | 5.939 | 0.015 | 39.4% |
| 21111111 | 245 | 225 | 470 | 0.851 | 0.356 | 52.1% |
| 11111111 | 283 | 259 | 542 | 1.063 | 0.303 | 52.2% |
| 22111111 | 43 | 51 | 94 | 0.681 | 0.409 | 45.7% |
| 11221221 | 3 | 1 | 4 | 1.000 | 0.317 | 75.0% |
| 11222221 | 44 | 42 | 86 | 0.047 | 0.829 | 51.2% |
| 22111221 | 37 | 43 | 80 | 0.450 | 0.502 | 46.3% |
| 11111121 | 36 | 30 | 66 | 0.545 | 0.460 | 54.5% |
| 22111222 | 11 | 11 | 22 | 0.000 | 1.000 | 50.0% |
| 21111121 | 3 | 9 | 12 | 3.000 | 0.083 | 25.0% |
| 21221121 | 2 | 2 | 4 | 0.000 | 1.000 | 50.0% |
| 21221221 | 0 | 4 | 4 | 4.000 | 0.046 | 0.0% |
| 11111221 | 4 | 4 | 8 | 0.000 | 1.000 | 50.0% |
| 11221111 | 0 | 2 | 2 | 2.000 | 0.157 | 0.0% |
| 11111222 | 1 | 1 | 2 | 0.000 | 1.000 | 50.0% |

TABLE 16c

TDT analysis of 8-loocus haplotypes to all affected children.

| haplotype | transmitted to affected | NOT transmitted to affected | TOTAL TRANSMISSIONS OBSERVED | McNemar chi-squared statistic | P-value (1 df) | % TRANSMISSION |
|---|---|---|---|---|---|---|
| 11111111 | 295 | 272 | 567 | 0.933 | 0.334 | 52.0% |
| 21111111 | 259 | 236 | 495 | 1.069 | 0.301 | 52.3% |
| 21222221 | 55 | 88 | 143 | 7.615 | 0.006 | 38.5% |
| 22111111 | 45 | 53 | 98 | 0.653 | 0.419 | 45.9% |
| 11222221 | 44 | 43 | 87 | 0.011 | 0.915 | 50.6% |
| 22111221 | 40 | 46 | 86 | 0.419 | 0.518 | 46.5% |
| 11111121 | 38 | 30 | 68 | 0.941 | 0.332 | 55.9% |
| 22111222 | 12 | 11 | 23 | 0.043 | 0.835 | 52.2% |
| 21111121 | 3 | 10 | 13 | 3.769 | 0.052 | 23.1% |
| 11111221 | 6 | 4 | 10 | 0.400 | 0.527 | 60.0% |
| 21221221 | 1 | 5 | 6 | 2.667 | 0.102 | 16.7% |
| 11221221 | 3 | 2 | 5 | 0.200 | 0.655 | 60.0% |
| 21221121 | 3 | 2 | 5 | 0.200 | 0.655 | 60.0% |
| 11221111 | 0 | 2 | 2 | 2.000 | 0.157 | 0.0% |
| 11111222 | 1 | 1 | 2 | 0.000 | 1.000 | 50.0% |
| TOTAL | 805 | 805 | 1610 | | | |

TABLE 17A analysis of 8-loocus haplotypes to two primary affected children per family: "either/both sib DR3/4" subgroup.

| haplotype | transmitted to affected | NOT transmitted to affected | TOTAL TRANSMISSIONS OBSERVED | McNemar chi-squared statistic | P-value (1 df) | % TRANSMISSION |
|---|---|---|---|---|---|---|
| 11111111 | 133 | 121 | 254 | 0.567 | 0.451 | 52.45 |
| 21111111 | 105 | 101 | 206 | 0.078 | 0.780 | 51.0% |
| 21222221 | 30 | 36 | 66 | 0.545 | 0.460 | 45.5% |
| 22111111 | 22 | 26 | 48 | 0.333 | 0.564 | 45.8% |
| 11222221 | 19 | 19 | 38 | 0.000 | 1.000 | 50.0% |
| 22111221 | 16 | 22 | 38 | 0.947 | 0.330 | 42.1% |
| 22111222 | 14 | 14 | 28 | 0.000 | 1.000 | 50.0% |
| 22111222 | 8 | 6 | 14 | 0.286 | 0.593 | 57.1% |
| 21111121 | 1 | 5 | 6 | 2.667 | 0.102 | 16.7% |
| 11111221 | 2 | 0 | 2 | 2.000 | 0.157 | 100.0% |
| TOTAL | 350 | 350 | 700 | | | |

TABLE 17B

TDT analysis of 8-loocus haplotypes to two primary affected children per family:

"neither sib DR3/4" subgroup.

| haplotype | transmitted to affected | NOT transmitted to affected | TOTAL TRANSMISSIONS OBSERVED | McNemar chi-squared statistic | P-value (1 df) | % TRANSMISSION |
|---|---|---|---|---|---|---|
| 11111111 | 138 | 126 | 264 | 0.545 | 0.460 | 52.3% |
| 21111111 | 128 | 112 | 240 | 1.067 | 0.302 | 53.3% |
| 21222221 | 22 | 44 | 66 | 7.333 | 0.007 | 33.3% |
| 22111111 | 23 | 29 | 52 | 0.692 | 0.405 | 44.2% |
| 11222221 | 28 | 20 | 48 | 1.333 | 0.248 | 58.3% |
| 22111111 | 21 | 25 | 46 | 0.348 | 0.555 | 45.7% |
| 11111121 | 17 | 11 | 28 | 1.286 | 0.257 | 60.7% |
| 22111222 | 3 | 5 | 8 | 0.500 | 0.480 | 37.5% |
| 11111221 | 2 | 4 | 6 | 0.667 | 0.414 | 33.3% |
| 21111121 | 2 | 4 | 6 | 0.667 | 0.414 | 33.3% |
| 11221221 | 3 | 1 | 4 | 1.000 | 0.317 | 75.0% |
| 21221121 | 2 | 2 | 4 | 0.000 | 1.000 | 50.0% |
| 21221221 | 0 | 4 | 4 | 4.000 | 0.046 | 0.0% |
| 11221111 | 0 | 2 | 2 | 2.000 | 0.157 | 0.0% |
| 11111222 | 1 | 1 | 2 | 0.000 | 1.000 | 50.0% |
| TOTAL | 390 | 390 | 780 | | | |

TABLE 18

Allele frequencies compared between Filipino controls and diabetics.

| SNP # | WT Allele Frequency in controls | WT allele frquency in diabetics | P-value by z- test |
|---|---|---|---|
| 1 | 0.559 | 0.461 | 0.077 |
| 2 | 0.989 | 1.000 | 0.480 |
| 3 | 0.793 | 0.882 | 0.031 |
| 4 | 0.824 | 0.933 | 0.003 |
| 5 | 0.809 | 0.882 | 0.075 |
| 6 | 0.814 | 0.882 | 0.097 |
| 7 | 0.723 | 0.770 | 0.362 |
| 8 | 1.000 | 1.000 | 1.000 |
| n = | 188 | 178 | chromosomes |

TABLE 19

Computationally estimated haplotype frequencies compared between Filipino controls and diabetics.

| | MLE frequency: controls | MLS frequency: Diabetics | O.R. | COUNT: control | COUNT: diabetics | Total count | exp control | exp diabetic | chi-square | P-value |
|---|---|---|---|---|---|---|---|---|---|---|
| IL4R | | | | | | | | | | |
| 11111111 | 0.318 | 0.329 | 1.1 | 59.7 | 58.5 | 118.2 | 60.7 | 57.5 | 0.033 | 0.855 |
| 11111121 | 0.074 | 0.074 | 1.0 | 14.0 | 13.2 | 27.2 | 14.0 | 13.2 | 0.000 | 0.987 |
| 11222221 | 0.145 | 0.058 | 0.4 | 27.3 | 10.3 | 37.6 | 19.3 | 18.3 | 6.727 | 0.009 |
| 21111111 | 0.390 | 0.441 | 1.2 | 73.3 | 78.5 | 151.8 | 78.0 | 73.8 | 0.582 | 0.445 |
| 21212221 | 0.032 | 0.051 | 1.6 | 6.0 | 9.0 | 15.0 | 7.7 | 7.3 | 0.776 | 0.378 |
| n = | 188 | 178 | | | | 366 | | | | |

TABLE 20

Observed haplotypes and frequencies compared between Filipino controls and diabetics.

| haplotype | calc frequency: controls | calc frequency: Diabetics | O.R. | COUNT: control | COUNT: diabetics | Total count | exp control | exp diabetic | chi-square | P-value |
|---|---|---|---|---|---|---|---|---|---|---|
| IL4R | | | | | | | | | | |
| x1111111 | 0.707 | 0.770 | 1.4 | 133.0 | 137.0 | 270.0 | 138.7 | 131.3 | 0.480 | 0.489 |
| x1111121 | 0.074 | 0.112 | 1.6 | 14.0 | 20.0 | 34.0 | 17.5 | 16.5 | 1.413 | 0.235 |
| x1222221 | 0.154 | 0.067 | 0.4 | 29.0 | 12.0 | 41.0 | 21.1 | 19.9 | 6.155 | 0.013 |
| x1212221 | 0.032 | 0.051 | 1.6 | 6.0 | 9.0 | 15.0 | 7.7 | 7.3 | 0.776 | 0.378 |

TABLE 20-continued

Observed haplotypes and frequencies compared between Filipino controls and diabetics.

| haplotype | calc frequency: controls | calc frequency: Diabetics | O.R. | COUNT: control | COUNT: diabetics | Total count | exp control | exp diabetic | chi-square | P-value |
|---|---|---|---|---|---|---|---|---|---|---|
| x1222111 | 0.005 | 0.000 | 0.0 | 1.0 | 0.0 | 1.0 | 0.5 | 0.5 | 0.947 | 0.331 |
| x2111111 | 0.011 | 0.000 | 0.0 | 2.0 | 0.0 | 2.0 | 1.0 | 1.0 | 1.894 | 0.169 |
| x1221121 | 0.016 | 0.000 | 0.0 | 3.0 | 0.0 | 3.0 | 1.5 | 1.5 | 2.840 | 0.092 |
| n = | | | | 188.0 | 178.0 | 366 | | overall | 14.504 | 0.024 |

TABLE 21

Allele Frequencies in Patients and Controls

| Gene | SNP Description | Major allele | Minor allele | Freq in Controls | Freq in T1D patients | p-value[a] | O.R.[b] | 95% CI |
|---|---|---|---|---|---|---|---|---|
| IL4R | 5'(−3223)[c] | C | T | 41.9% | 51.1% | 0.10 | 1.45 | 0.96, 2.19 |
|  | 5'(−1914)[c] | C | T | 44.1% | 42.7% | 0.86 | 1.06 | 0.70, 1.60 |
|  | I50V[d] | A | G | 44.1% | 53.9% | 0.06 | 1.48 | 0.98, 2.23 |
|  | N142N[d] | C | G | 1.1% | 0.0% | 0.17 | 0.00 | |
|  | E375A[d] | A | C | 20.7% | 11.7% | 0.02 | 0.50 | 0.28, 0.90 |
|  | L389L[d] | G | T | 17.6% | 6.7% | 0.001 | 0.34 | 0.17, 0.67 |
|  | C406R[d] | T | C | 19.1% | 11.7% | 0.05 | 0.56 | 0.31, 0.99 |
|  | S478P[d] | T | C | 18.6% | 11.7% | 0.06 | 0.58 | 0.32, 1.04 |
|  | Q551R[d] | A | G | 27.7% | 23.3% | 0.34 | 0.80 | 0.50, 1.27 |
|  | S761P[d] | T |  | 100.0% | 100.0% | n.a. | n.a. | |
| IL4 | 5'('524)[e] | C | T | 30.9% | 34.4% | 0.46 | 1.18 | 0.76, 1.82 |
| IL13 | 5'(−1512)[f] | A | C | 30.6% | 41.0% | 0.05 | 1.58 | 1.03, 2.42 |
|  | 5'(−1112)[f] | C | T | 23.1% | 30.9% | 0.117 | 1.49 | 0.94, 2.37 |
|  | Intron 3[f] | C | T | 40.4% | 45.6% | 0.32 | 1.23 | 0.82, 1.86 |
|  | R110Q[f] | G | A | 39.9% | 46.1% | 0.23 | 1.29 | 0.85, 1.95 |

[a]Differences in allele frequencies between cases and controls were tested using a chi-square test.
[b]Odds ratios refer to the minority allele.
[c]Accession sequence AC004525.1;
[d]Accession sequence X52425.1;
[e]Accession sequence M23442.1;
[f]Accession sequence U10307.1

TABLE 22

Pairwise Linkage Disequilibrium Between IL4R SNPs

|  | −3223 (T) | −1914 (T) | 50 (G) | 142 (G) | 375 (C) | 389 (T) | 406 (C) | 478 (C) | 551 (G) |
|---|---|---|---|---|---|---|---|---|---|
| −3223 (T) | — | −0.183*** | 0.176*** | 0.004 | −0.063*** | −0.068*** | −0.061*** | −0.059*** | −0.068*** |
| −1914 (T) | −1.0 | — | −0.068*** | −0.005 | 0.105 | 0.029* | 0.014 | 0.011 | 0.027 |
| 50 (G) | 0.75 | −0.81 | — | 0.006 | −0.049** | −0.067*** | −0.043** | −0.039** | −0.079*** |
| 142 (G) | 1.0 | −1.0 | 1.0 | — | −0.002 | −0.002 | −0.002 | −0.002 | −0.003 |
| 375 (C) | −0.70 | 0.70 | −0.53 | −1.0 | — | 0.139*** | 0.152*** | 0.147*** | 0.145*** |
| 389 (T) | −0.93 | 0.29 | −0.86 | −1.0 | 1.0 | — | 0.126*** | 0.122*** | 0.122*** |
| 406 (C) | −0.74 | 0.13 | −0.49 | −1.0 | 1.0 | 0.89 | — | 0.150*** | 0.133*** |
| 478 (C) | −0.74 | 0.62 | −0.48 | −1.0 | 1.0 | 0.85 | 1.0 | — | 0.135*** |
| 551 (G) | −0.56 | 0.17 | −0.65 | −1.0 | 0.96 | 0.96 | 0.96 | 1.0 | — |

Top diagonal (D = $P_{ab} - P_a \cdot P_b$). Bottom diagonal D' (normalized linkage disequilibrium, D' = D/Dmax). All values refer to the minority allele indicated in the table. Statistically significant linkage disequilibrium values are indicated as follows:
*p < 0.05;
**p < 0.01;
***p < 0.0001

TABLE 23

Pairwise Linkage Disequilibrium Between IL4 and IL13 SNPs

| | IL4-524 (C) | IL13-1512(C) | IL13-1112(T) | IL13 intr (T) | IL13 110(A) |
|---|---|---|---|---|---|
| IL4-524 (C) | — | 0.062*** | 0.069*** | 0.024 | 0.063*** |
| IL13-1512(C) | 0.29 | — | 0.163*** | 0.057*** | 0.058** |
| IL13-1112(T) | 0.41 | 1.0 | — | 0.077*** | 0.078** |
| IL13 intr (T) | 0.13 | 0.31 | 0.54 | — | 0.201 |
| IL13 110(A) | 0.34 | 0.31 | 0.55 | 0.84 | — |

Top diagonal (D = $P_{ab} - P_a \cdot P_b$). Bottom diagonal D' (normalized linkage disequilibrium, D' = D/Dmax).
Statistically significant linkage disequilibrium values are indicated as follows: *p < 0.05; p < 0.01; *p < 0.0001

TABLE 24

Genotype Frequencies in Diabetics and Controls.

| | genotype | controls | T1DM | Fisher's exact test | OR | 95% CI |
|---|---|---|---|---|---|---|
| IL4R_3223 | CC | 29.0% | 24.1% | 0.1584 | 0.78 | (0.40, 1.51) |
| | CT | 58.1% | 51.7% | | 0.77 | (0.43, 1.38) |
| | TT | 12.9% | 24.1% | | 2.15 | (0.99, 4.68) |
| IL4R_1914 | CC | 31.2% | 36.0% | 0.6636 | 1.24 | (0.67, 2.29) |
| | TC | 49.5% | 42.7% | | 0.76 | (0.43, 1.36) |
| | TT | 19.4% | 21.3% | | 1.13 | (0.55, 2.33) |
| IL4R 50 | AA | 34.7% | 23.6% | 0.1846 | 0.58 | (0.30, 1.11) |
| | AG | 43.2% | 44.9% | | 1.08 | (0.60, 1.93) |
| | GG | 22.1% | 31.5% | | 1.62 | (0.84, 3.13) |
| IL4R 142 | CC | 97.9% | 100.0% | 0.4978 | | |
| | CG | 2.1% | 0.0% | | | |
| IL4R 375 | AA | 62.1% | 78.7% | 0.038 | 2.25 | (1.17, 4.33) |
| | AC | 34.7% | 19.1% | | 0.44 | (0.23, 0.87) |
| | CC | 3.2% | 2.2% | | 0.70 | (0.12, 4.32) |
| IL4R 389 | GG | 67.4% | 87.6% | 0.002 | 3.43 | (1.60, 7.37) |
| | GT | 30.5% | 11.2% | | 0.29 | (0.13, 0.63) |
| | TT | 2.1% | 1.1% | | 0.53 | (0.05, 5.93) |
| IL4R 406 | CC | 2.1% | 2.2% | 0.0585 | 1.07 | (0.15, 7.76) |
| | TC | 33.7% | 19.1% | | 0.46 | (0.24, 0.92) |
| | TT | 64.2% | 78.7% | | 2.05 | (1.06, 3.97) |
| IL4R 478 | CC | 2.1% | 2.2% | 0.0904 | 1.07 | (0.15, 7.76) |
| | TC | 32.6% | 19.1% | | 0.49 | (0.25, 0.96) |
| | TT | 65.3% | 78.7% | | 1.96 | (1.01, 3.79) |
| IL4R 551 | AA | 52.6% | 57.3% | 0.5613 | 1.21 | (0.68, 2.16) |
| | AG | 38.9% | 38.2% | | 0.97 | (0.53, 1.76) |
| | GG | 8.4% | 4.5% | | 0.51 | (0.15, 1.76) |
| IL4-590 | CC | 10.5% | 12.4% | 0.8143 | 1.20 | (0.48, 2.98) |
| | CT | 40.0% | 42.7% | | 1.12 | (0.62, 2.01) |
| | TT | 49.5% | 44.9% | | 0.83 | (0.47, 1.49) |
| IL13INT3 C | CC | 33.7% | 31.5% | 0.5413 | 0.90 | (0.49, 1.68) |
| | CT | 50.5% | 46.1% | | 0.84 | (0.47, 1.49) |
| | TT | 15.8% | 22.5% | | 1.55 | (0.74, 3.25) |
| IL13 110 | AA | 12.6% | 27.0% | 0.0252 | 2.55 | (1.19, 5.49) |
| | GA | 54.7% | 38.2% | | 0.51 | (0.28, 0.92) |
| | GG | 32.6% | 34.8% | | 1.10 | (0.60, 2.03) |
| IL13_1512 | AA | 48.4% | 34.8% | 0.1363 | 0.57 | (0.31, 1.03) |
| | AC | 41.9% | 48.3% | | 1.29 | (0.72, 2.32) |
| | CC | 9.7% | 16.9% | | 1.89 | (0.78, 4.57) |
| IL13_1112 | CC | 60.2% | 51.7% | 0.2429 | 0.71 | (0.39, 1.27) |
| | CT | 33.3% | 34.8% | | 1.07 | (0.58, 1.97) |
| | TT | 6.5% | 13.5% | | 2.26 | (0.81, 6.31) |

TABLE 25A

Molecular IL-4 R Haplotypes in Filipino Diabetics and Controls

| 7 SNP Haplotype | Frequency in Controls | Frequency in Diabetics | chi-square p-value | O.R. | 95% CI |
|---|---|---|---|---|---|
| CAGTTAT | 70.7% | 77.0% | 0.49 | 1.38 | (0.9, 2.2) |
| CCTCCGT | 15.4% | 6.7% | 0.013 | 0.40 | (0.2, 0.8) |
| GAGTTAT | 1.1% | 0.0% | 0.50 | 0.0 | (0.0, 5.8) |
| CAGTTGT | 7.4% | 11.2% | 0.23 | 1.57 | (0.8, 3.2) |
| CCGCCGT | 3.2% | 5.1% | 0.38 | 1.62 | (0.6, 4.6) |
| CCTTTGT | 1.6% | 0.0% | 0.27 | 0.0 | (0.0, 3.5) |
| CCTGTAT | 0.5% | 0.0% | 0.98 | 0.0 | (0.0, 15.8) |
| total (6 d.f.) | | | 0.076 | | |
| n = | 188 | 178 | | | |

TABLE 25B

Estimated IL4R 10-SNP Haplotype Frequencies in Diabetics and Controls

| 8 locus H-ID | IL4R 10 Locus Haplotype | Controls[a] N = 188 | std dev | T1DM N = 180 | std dev | O.R. | 95% CI | P-value[b] |
|---|---|---|---|---|---|---|---|---|
| H-5A | CCACCTCCGT | 5.8% | (1.7%) | 0.0% | | 0.00 | (0.0, 0.8) | 0.001 |
| H-5B | CTACCTCCGT | 8.5% | (2.3%) | 5.8% | (2.2%) | 0.66 | (0.3, 1.6) | 0.33 |
| H-3A | CTGCCTCCGT | 0.9% | (0.6%) | 0.0% | | 0.00 | (0.0, 6.0) | 0.21 |
| H-3B | TCGCCTCCGT | 0.0% | | 0.9% | (1.1%) | n.a. | | 0.19 |
| | Total (23 d.f.) | | | | | | | 0.04 |

[a]Maximum likelihood haplotype frequencies were computed using an Expectation-Maximization (EM) algorithm (see Excoffier and Slatkin 1995) as implemented by the Arlequin software program L. Excoffier, University of Geneva, CH). The standard deviation was computed carrying out 100 boostrap replicates. 24 of the possible 512 haplotypes were observed. The four shown here all include the disease associatedseven SNP haplotype. The two 8 SNP haplotypes containing the seven SNP haplotype were designated H-3 and H-5 in reference Mirel et al, (in press) The standard deviation was computed carrying out 100 boostrap replicates.
[b]Differences in allele frequencies between cases and controls were tested using a chi-square test

TABLE 26

Estimated IL4 and IL13 5-SNP Haplotype Frequencies in Diabetics and Controls

| 5 locus haploytpe | Controls N = 188 | Sd | T1DM N = 176* | Sd | Odds Ratio | P-value |
|---|---|---|---|---|---|---|
| C A C C A | 4.1% | (1.3%) | 3.5% | (1.7%) | 0.84 | |
| C A C C G | 8.9% | (2.2%) | 10.6% | (2.9%) | 1.21 | |
| C A C T A | 1.3% | (1.1%) | 3.0% | (1.8%) | 2.26 | |
| C A T T A | 0.0% | | 0.6% | (0.5%) | n.a. | |
| C C C C G | 1.5% | (1.0%) | 0.9% | (0.9%) | 0.61 | |
| C C T C G | 1.1% | (0.9%) | 5.5% | (2.3%) | 5.19 | 0.02 |
| C C T T A | 12.6% | (2.4%) | 9.3% | (2.0%) | 0.71 | |
| C C T T G | 0.0% | | 0.4% | (0.7%) | n.a. | |
| T A C C G | 33.6% | (3.8%) | 21.9% | (3.9%) | 0.55 | 0.03 |
| T A C T A | 16.4% | (3.3%) | 16.3% | (3.0%) | 0.99 | |
| T A C T G | 5.0% | (1.7%) | 3.2% | (1.4%) | 0.62 | |
| T C C C G | 4.6% | (1.8%) | 9.8% | (2.9%) | 2.23 | 0.06 |
| T C C T A | 1.3% | (1.1%) | 0.0% | | 0.00 | |
| T C C T G | 0.2% | (0.5%) | 0.0% | | 0.00 | |
| T C T C G | 5.3% | (2.4%) | 1.7% | (1.2%) | 0.31 | 0.07 |
| T C T T A | 4.1% | (2.1%) | 12.8% | (2.2%) | 3.47 | 0.004 |
| T C T C A | 0.0% | | 0.6% | (0.7%) | n.a. | |
| Total (16 d.f.) | | | | | | 0.005 |

*due to missing genotypes.
(order of the SNPs: 1L4-524, 1L13-1512, 1L13-1112, IL13INT3, IL13R110)

TABLE 27

Test For Independence Between Genotype Frequencies at IL4R SNPs and Genotype Frequencies at Five IL4 and IL13 SNPs.

| Chromsome 5 SNP | controls | T1D |
|---|---|---|
| IL4-524 | 0.15 | 0.001 |
| IL13-1512 | 0.77 | 0.78 |
| IL13-1112 | 0.93 | 0.73 |
| IL13 110 | 0.99 | 0.91 |
| IL3 intron 3 | 0.99 | 0.019 |

TABLE 28

Epistasis Between IL4R and Five IL4 and IL13 SNPs

| | $\beta_3$ | Std.Error | Odds ratio | Walds Chi-sq | Nominal p-value |
|---|---|---|---|---|---|
| IL4-524:il4r | −0.22 | 0.10 | 0.81 | 4.55 | 0.033 |
| IL13-1512:il4r | 0.04 | 0.15 | 1.04 | 0.06 | 0.811 |
| IL13-1112:il4r | 0.10 | 0.16 | 1.10 | 0.37 | 0.545 |
| IL13 110:il4r | 0.14 | 0.09 | 1.15 | 2.24 | 0.135 |
| IL13INT3:il4r | 0.17 | 0.09 | 1.18 | 3.19 | 0.074 |

The Overall p-Value For All Five Tests By Permutation Analysis Was p < 0.045 (see text).

TABLE 29

Probes For IL4 and IL13

| SNP | Allele | Probe | Probe Sequence | Seq ID No: | Conc. (μM) |
|---|---|---|---|---|---|
| IL4P C582T | C | KW66 | AACATTGTCCCCCAGTGC | 63 | 1.2 |
| IL4P C582T | T | KW89 | AGCACTGGGGAACAATGTTC | 64 | 0.9 |
| IL13 Int 3 | C | DBM0161P | TTCTACTCACGTGCTGACCT | 65 | 1.0 |
| IL13 Int 3 | T | DBM0164P | GGTCAGCACATGAGTAGAACG | 66 | 0.3 |
| IL13 Ex 4 R110Q | | DBM0136P | TCAGTTGAACCGTCCCTCG | 67 | 1.0 |
| IL13 Ex 4 R110Q | | DBM0181P | GAGGGACAGTTCAACTGAAAC | 68 | 1.0 |

TABLE 30

Amplicon Primers and Lengths

| Exon | Amplicon Size | Forward Primer | Seq ID No | Sequence | Reverse Primer | Seq ID No | Sequence |
|---|---|---|---|---|---|---|---|
| IL4P | 107 | RR169B | 69 | ACTAGGCCTCACCTGATACGA | RR170B | 72 | CATAGAGGCAGAATAACAGGCAGA |
| IL 13 in 3 | 118 | DBM0165B | 70 | CTCGGACATGCAAGCTGGAA | DBM0166B | 73 | ACTGAATGAGACAGTCCCTGGA |
| IL 13 ex 4 | 187 | DBM0167B | 71 | AATCGAGGTGGCCCAGTTTGTA | DBM0168B | 74 | CCTAACCCTCCTTCCCGCCTA |

TABLE 31

Amplicon Primers and Lengths for IL4R

| Exon | Amplicon Size | Allele | Primer | Seq ID No | Sequence |
|---|---|---|---|---|---|
| T(−1914)C | 49 | T | DBM0659 | 75 | ACTGACTTATCTTTACTGTCACTTCT |

TABLE 31-continued

Amplicon Primers and Lengths for IL4R

| Exon | Amplicon Size | Allele | Primer | Seq ID No | Sequence |
|---|---|---|---|---|---|
| | | | DBM0661 | 76 | GCAAGACAGCCACCAACCC |
| T(−1914)C | 49 | C | DBM0660 | 77 | TGACTTATCTTTACTGTCACTTCC |
| | | | DBM0661 | 76 | GCAAGACAGCCACCAACCC |
| C(−3223)T | 42 | C | DBM0672 | 79 | CCTGCTCCCAGGACTGAC |
| | | | DBM0667 | 80 | CCCAGACTTTATCTGTGACTGCTC |
| C(−3223)T | 42 | T | DBM0671 | 81 | CCTGCTCCCAGGACTGAT |
| | | | DBM0667 | 80 | CCCAGACTTTATCTGTGACTGCTC |

TABLE 32

Amplicon Primers and Lengths for IL13

| Exon | Amplicon Size | Allele | Primer | Seq ID No | Sequence |
|---|---|---|---|---|---|
| A(−1512)C | 44 | A | DBM0650 | 82 | GGAAACAGGCCCGTAGA |
| | | | DBM0652 | 83 | GAGTGCCGCTACTTGGCC |
| A(−1512)C | 43 | C | DBM0651 | 84 | GAAACAGGCCCGTAGC |
| | | | DBM0652 | 83 | GAGTGCCGCTACTTGGCC |
| C(−1112)T | 55 | C | DBM0656 | 85 | TCTGGAGGACTTCTAGGAAAAC |
| | | | DBM0658 | 86 | TGCAGCCATGTCGCCTTT |
| C(−1112)T | 55 | T | DBM0657 | 87 | TCTGGAGGACTTCTAGGAAAAT |
| | | | DBM0658 | 86 | TGCAGCCATGTCGCCTTT |

What is claimed is:

1. A method for determining a non-diabetic individual's risk for type 1 diabetes comprising, detecting the presence of at least one type 1 diabetes-associated Interleukin-4 receptor (IL4R) polymorphism in a nucleic acid sample of the individual, wherein the polymorphism is a minor allele selected from the group consisting of A1374C (E375A), G1417T (L389L), and T1466C (C406R); and wherein the presence of the minor allele polymorphism in the individual indicates a decreased risk for type 1 diabetes relative to the presence of a major allele of the polymorphism in the individual.

2. The method of claim 1, further comprising detecting at least one other IL4R polymorphism and wherein said polymorphisms comprise a haplotype, wherein the haplotype is a 7 SNP haplotype CCTCCGT comprising polymorphic positions C676T (N142N), A1374C (E375A), G1417T (L389L), T1466C (C406R), T1682C (S478P), A1902G (Q551R), and T2531C (S761P).

3. The method of claim 1, wherein the nucleic acid sample comprises DNA.

4. The method of claim 1, wherein the nucleic acid sample comprises RNA.

5. The method of claim 1, wherein the nucleic acid sample is amplified.

6. The method of claim 5, wherein the nucleic acid sample is amplified by a polymerase chain reaction.

7. The method of claim 1, wherein the at least one polymorphism is detected by amplification.

8. The method of claim 7, wherein the at least one polymorphism is detected by a polymerase chain reaction.

9. The method of claim 1, wherein the at least one polymorphism is detected by sequencing.

10. The method of claim 1, wherein the at least one polymorphism is detected by amplification of a target region containing the at least one polymorphism; and hybridization with at least one sequence-specific oligonucleotides that hybridizes under stringent conditions to the at least one polymorphism and detecting the hybridization.

11. The method of claim 1, wherein the at least one polymorphism is a combination of 2 or more IL4R polymorphisms selected from the IL4R polymorphisms listed in claim 1.

12. The method of claim 1, wherein the at least one polymorphism is a combination of the 3 IL4R polymorphisms selected from the IL4R polymorphisms listed in claim 1.

13. The method of claim 1, further comprising detecting a polymorphism that is in linkage disequilibrium with an IL4R polymorphism listed in claim 1.

* * * * *

SEQUENCE LISTING

<160> NUMBER OF SEQ ID NOS: 90

<210> SEQ ID NO 1
<211> LENGTH: 3597
<212> TYPE: DNA
<213> ORGANISM: Homo sapiens

<400> SEQUENCE: 1

```
ggcgaatgga gcagggcgc gcagataatt aaagatttac acacagctgg aagaaatcat      60
agagaagccg ggcgtggtgg ctcatgccta taatcccagc acttttggag gctgaggcgg     120
gcagatcact tgagatcagg agttcgagac cagcctggtg ccttggcatc tcccaatggg     180
gtggctttgc tctgggctcc tgttccctgt gagctgcctg gtcctgctgc aggtggcaag     240
ctctgggaac atgaaggtct tgcaggagcc cacctgcgtc tccgactaca tgagcatctc     300
tacttgcgag tggaagatga atggtccac caattgcagc accgagctcc gcctgttgta     360
ccagctggtt tttctgctct ccgaagccca cacgtgtatc cctgagaaca cggaggcgc     420 ggggtgcgtg tgccacctgc tcatggatga cgtggtcagt gcggataact atacactgga     480
cctgtgggct gggcagcagc tgctgtggaa gggctccttc aagcccagcg agcatgtgaa     540
acccagggcc ccaggaaacc tgacagttca caccaatgtc tccgacactc tgctgctgac     600
ctggagcaac ccgtatcccc ctgacaatta cctgtataat catctcacct atgcagtcaa     660
catttggagt gaaaacgacc cggcagattt cagaatctat aacgtgacct acctagaacc     720
ctcccctccg catcgcagcca gcaccctgaa gtctgggatt tcctacaggg cacgggtgag     780
ggcctgggct cagtgctata acaccaccctg gagtgagtgg agccccagca ccaagtggca     840
caactcctac agggagccct tcgagcagca cctcctgctg ggcgtcagcg tttcctgcat     900
tgtcatcctg gccgtctgcc tgttgtgcta tgtcagcatc accaagatta gaaagaatg     960
```

-continued

```
gtgggatcag attcccaacc cagcccgcag ccgcctcgtg gctataataa tccaggatgc    1020 tcagggtca  cagtgggaga agcggtcccg aggccaggaa ccagccaagt gcccacactg    1080
gaagaattgt cttaccaagc tcttgccctg ttttctggag cacaacatga aaagggatga    1140
agatcctcac aaggctgcca aagagatgcc tttccagggc tctggaaaat cagcatggtg    1200
cccagtggag atcagcaaga cagtcctctg ccagagagc atcagcgtgg tgcgatgtgt     1260
ggagttgttt gaggccccgg tggagtgtga ggaggaggag gaggtagagg aagaaaaagg    1320
gagcttctgt gcatcgcctg agagcagcag ggatgacttc caggagggaa gggagggcat    1380
tgtggcccgg ctaacagaga gcctgttcct ggacctgctc ggagaggaga atgggggctt    1440
ttgccagcag gacatggggg agtcatgcct tcttccacct tcgggaagta cgagtgctca    1500
catgccctgg gatgagttcc caagtgcagg gcccaaggag gcacctccct ggggcaagga    1560
gcagcctctc cacctggagc caagtcctcc tgccagcccg acccagagtc cagacaacct    1620
gacttgcaca gagacgcccc tcgtcatcgc aggcaaccct gcttaccgca gcttcagcaa    1680
ctccctgagc cagtcaccgt gtcccagaga gctgggtcca gacccactgc tggccagaca    1740
cctggaggaa gtagaacccg agatgccctg tgtcccccag ctctctgagc caaccactgt    1800
gccccaacct gagccagaaa cctgggagca gatcctccgc cgaaatgtcc tccagcatgg    1860
ggcagctgca gcccccgtct cggcccccac cagtggctat caggagtttg tacatgcggt    1920
ggagcagggt ggcacccagg ccagtgcggt ggtgggcttg ggtcccccag gagaggctgg    1980
ttacaaggcc ttctcaagcc tgcttgccag cagtgctgtg tccccagaga aatgtgggtt    2040
tggggctagc agtggggaag agggtgtataa gcctttccaa gacctcattc ctggctgccc   2100
tggggaccct gccccagtcc ctgtcccctt gttcaccttt ggactggaca gggagccacc    2160
tcgcagtccg cagagctcac atctcccaag cagctcccca gagcacctgg gtctggagcc    2220
gggggaaaag gtagaggaca tgccaaagcc cccacttccc caggagcagg ccacagaccc    2280
ccttgtggac agcctgggca gtggcattgt ctactcagcc cttacctgcc acctgtgcgg    2340
ccacctgaaa cagtgtcatg gccaggagga tggtggccag accctgtca tggccagtcc     2400 ttgctgtggc tgctgctgtg gagacaggtc ctcgcccct acaaccccc tgagggcccc      2460 agaccctct ccaggtgggg ttccactgga ggccagtctg tgtccggcct ccctggcacc     2520
ctcgggcatc tcagagaaga gtaaatcctc atcatccttc catcctgccc ctggcaatgc    2580
tcagagctca agccagaccc ccaaaatcgt gaactttgtc tccgtgggac ccacatacat    2640
gagggtctct taggtgcatg tcctcttgtt gctgagtctg cagatgagga ctagggctta    2700
tccatgcctg ggaaatgcca cctcctggaa ggcagccagg ctggcagatt tccaaaagac    2760
ttgaagaacc atggtatgaa ggtgattggc cccactgacg ttggcctaac actgggctgc    2820
agagactgga ccccgcccag cattgggctg ggctcgccac atcccatgag agtagagggc    2880
actgggtcgc cgtgccccac ggcaggcccc tgcaggaaaa ctgaggccct tgggcacctc    2940
gacttgtgaa cgagttgttg gctgctccct ccacagcttc tgcagcagac tgtccctgtt    3000
gtaactgccc aaggcatgtt ttgcccacca gatcatggcc cacgtggagg cccacctgcc    3060
tctgtctcac tgaactagaa gccgagccta gaaactaaca cagccatcaa gggaatgact    3120
tgggcggcct tgggaaatcg atgagaaatt gaacttcagg gaggtggtc attgcctaga     3180 ggtgctcatt catttaacag agcttcctta ggttgatgct ggaggcagaa tcccggctgt    3240
caaggggtgt tcagttaagg ggagcaacag aggacatgaa aaattgctat gactaaagca    3300
```

-continued

| | |
|---|---|
| gggacaattt gctgccaaac acccatgccc agctgtatgg ctgggggctc ctcgtatgca | 3360 |
| tggaaccccc agaataaata tgctcagcca ccctgtgggc cgggcaatcc agacagcagg | 3420 |
| cataaggcac cagttaccct gcatgttggc ccagacctca ggtgctaggg aaggcgggaa | 3480 |
| ccttggggttg agtaatgctc gtctgtgtgt tttagtttca tcacctgtta tctgtgtttg | 3540 |
| ctgaggagag tggaacagaa ggggtggagt tttgtataaa taaagtttct ttgtctc | 3597 |

<210> SEQ ID NO 2
<211> LENGTH: 2478
<212> TYPE: DNA
<213> ORGANISM: Homo sapiens

<400> SEQUENCE: 2

| | |
|---|---|
| atggggtggc tttgctctgg gctcctgttc cctgtgagct gcctggtcct gctgcaggtg | 60 |
| gcaagctctg ggaacatgaa ggtcttgcag gagcccacct gcgtctccga ctacatgagc | 120 |
| atctctactt gcgagtggaa gatgaatggt cccaccaatt gcagcaccga gctccgcctg | 180 |
| ttgtaccagc tggttttct gctctccgaa gcccacacgt gtatccctga gaacaacgga | 240 |
| ggcgcggggt gcgtgtgcca cctgctcatg gatgacgtgg tcagtgcgga taactataca | 300 |
| ctggacctgt gggctgggca gcagctgctg tggaagggct ccttcaagcc cagcgagcat | 360 |
| gtgaaaccca gggccccagg aaacctgaca gttcacacca atgtctccga cactctgctg | 420 |
| ctgacctgga gcaacccgta tccccctgac aattacctgt ataatcatct cacctatgca | 480 |
| gtcaacattt ggagtgaaaa cgacccggca gatttcagaa tctataacgt gacctaccta | 540 |
| gaaccctccc tccgcatcgc agccagcacc ctgaagtctg ggatttccta cagggcacgg | 600 |
| gtgagggcct gggctcagtg ctataacacc acctggagtg agtggagccc cagcaccaag | 660 |
| tggcacaact cctacaggga gcccttcgag cagcacctcc tgctgggcgt cagcgtttcc | 720 |
| tgcattgtca tcctggccgt ctgcctgttg tgctatgtca gcatcaccaa gattaagaaa | 780 |
| gaatggtggg atcagattcc caacccagcc cgcagccgcc tcgtggctat aataatccag | 840 |
| gatgctcagg ggtcacagtg ggagaagcgg tcccgaggcc aggaaccagc caagtgccca | 900 |
| cactggaaga attgtcttac caagctcttg ccctgttttc tggagcacaa catgaaaagg | 960 |
| gatgaagatc ctcacaaggc tgccaaagag atgccttttc agggctctgg aaaatcagca | 1020 |
| tggtgcccag tggagatcag caagacagtc ctctggccag agagcatcag cgtggtgcga | 1080 |
| tgtgtggagt tgtttgaggc cccggtggag tgtgaggagg aggaggaggt agaggaagaa | 1140 |
| aaagggagct tctgtgcatc gcctgagagc agcaggatg acttccagga gggaagggag | 1200 |
| ggcattgtgg cccggctaac agagagcctg ttcctggacc tgctcggaga ggagaatggg | 1260 |
| ggcttttgcc agcaggacat ggggagtca tgccttcttc caccttcggg aagtacgagt | 1320 |
| gctcacatgc cctgggatga gttcccaagt gcagggccca aggaggcacc tcctgggc | 1380 |
| aaggagcagc tctccacct ggagccaagt cctcctgcca gcccgaccca gagtccagac | 1440 |
| aacctgactt gcacagagac gccctcgtc atcgcaggca accctgctta ccgcagcttc | 1500 |
| agcaactccc tgagccagtc accgtgtccc agagagctgg gtccagaccc actgctggcc | 1560 |
| agacacctgg aggaagtaga acccgagatg ccctgtgtcc cccagctctc tgagccaacc | 1620 |
| actgtgcccc aacctgagcc agaaacctgg gagcagatcc tccgccgaaa tgtcctccag | 1680 |
| catggggcag ctgcagcccc cgtctcggcc ccaccagtg gctatcagga gtttgtacat | 1740 |
| gcggtggagc agggtggcac ccaggccagt gcggtggtgg gcttgggtcc ccaggagag | 1800 |
| gctggttaca aggccttctc aagcctgctt gccagcagtg ctgtgtcccc agagaaatgt | 1860 |

```
gggtttgggg ctagcagtgg ggaagagggg tataagcctt tccaagacct cattcctggc   1920
tgccctgggg accctgcccc agtccctgtc cccttgttca cctttggact ggacagggag   1980
ccacctcgca gtccgcagag ctcacatctc ccaagcagct ccccagagca cctgggtctg   2040
gagccggggg aaaaggtaga ggacatgcca aagcccccac ttccccagga gcaggccaca   2100 gaccccttg tggacagcct gggcagtggc attgtctact cagcccttac ctgccacctg    2160
tgcggccacc tgaaacagtg tcatggccag gaggatggtg gccagacccc tgtcatggcc   2220
agtccttgct gtggctgctg ctgtggagac aggtcctcgc ccctacaac cccctgagg     2280 gccccagacc cctctccagg tggggttcca ctggaggcca gtctgtgtcc ggcctccctg   2340
gcaccctcgg gcatctcaga gaagagtaaa tcctcatcat ccttccatcc tgcccctggc   2400
aatgctcaga gctcaagcca gaccccaaa atcgtgaact tgtctccgt gggacccaca    2460 tacatgaggg tctcttag                                                 2478
```

<210> SEQ ID NO 3
<211> LENGTH: 21
<212> TYPE: DNA
<213> ORGANISM: Artificial sequence
<220> FEATURE:
<223> OTHER INFORMATION: Description of artificial sequence: Probe used to identify IL4R polymorphisms

<400> SEQUENCE: 3

```
ccacacgtgt atccctgaga a                                              21
```

<210> SEQ ID NO 4
<211> LENGTH: 19
<212> TYPE: DNA
<213> ORGANISM: Artificial sequence
<220> FEATURE:
<223> OTHER INFORMATION: Description of artificial sequence: Probe used to identify IL4R polymorphisms

<400> SEQUENCE: 4

```
tctcagggac acacgtgtg                                                 19
```

<210> SEQ ID NO 5
<211> LENGTH: 22
<212> TYPE: DNA
<213> ORGANISM: Artificial sequence
<220> FEATURE:
<223> OTHER INFORMATION: Description of artificial sequence: Probe used to identify IL4R polymorphisms

<400> SEQUENCE: 5

```
tggagtgaaa acgacccggc ag                                             22
```

<210> SEQ ID NO 6
<211> LENGTH: 21
<212> TYPE: DNA
<213> ORGANISM: Artificial sequence
<220> FEATURE:
<223> OTHER INFORMATION: Description of artificial sequence: Probe used to identify IL4R polymorphisms

<400> SEQUENCE: 6

```
ctgccgggtc attttcgctc c                                              21
```

<210> SEQ ID NO 7
<211> LENGTH: 21
<212> TYPE: DNA

```
<213> ORGANISM: Artificial sequence
<220> FEATURE:
<223> OTHER INFORMATION: Description of artificial sequence:  Probe
      used to identify IL4R polymorphisms

<400> SEQUENCE: 7
gagggaaggg agggcattgt g                                              21

<210> SEQ ID NO 8
<211> LENGTH: 19
<212> TYPE: DNA
<213> ORGANISM: Artificial sequence
<220> FEATURE:
<223> OTHER INFORMATION: Description of artificial sequence:  Probe
      used to identify IL4R polymorphisms

<400> SEQUENCE: 8
agggaagggc gggcattgt                                                 19

<210> SEQ ID NO 9
<211> LENGTH: 19
<212> TYPE: DNA
<213> ORGANISM: Artificial sequence
<220> FEATURE:
<223> OTHER INFORMATION: Description of artificial sequence:  Probe
      used to identify IL4R polymorphisms

<400> SEQUENCE: 9
ctctccgagc aggtccagg                                                 19

<210> SEQ ID NO 10
<211> LENGTH: 21
<212> TYPE: DNA
<213> ORGANISM: Artificial sequence
<220> FEATURE:
<223> OTHER INFORMATION: Description of artificial sequence:  Probe
      used to identify IL4R polymorphisms

<400> SEQUENCE: 10
tcctggacct tctcggagag g                                              21

<210> SEQ ID NO 11
<211> LENGTH: 23
<212> TYPE: DNA
<213> ORGANISM: Artificial sequence
<220> FEATURE:
<223> OTHER INFORMATION: Description of artificial sequence:  Probe
      used to identify IL4R polymorphisms

<400> SEQUENCE: 11
aaggtggaag aaggcatgac tcc                                            23

<210> SEQ ID NO 12
<211> LENGTH: 23
<212> TYPE: DNA
<213> ORGANISM: Artificial sequence
<220> FEATURE:
<223> OTHER INFORMATION: Description of artificial sequence:  Probe
      used to identify IL4R polymorphisms

<400> SEQUENCE: 12
aaggtgggag aagacatgac tcc                                            23

<210> SEQ ID NO 13
<211> LENGTH: 23
<212> TYPE: DNA
<213> ORGANISM: Artificial sequence
```

```
<220> FEATURE:
<223> OTHER INFORMATION: Description of artificial sequence:   Probe
      used to identify IL4R polymorphisms

<400> SEQUENCE: 13
ggagtcacgt cttctcctac ctt                                          23

<210> SEQ ID NO 14
<211> LENGTH: 22
<212> TYPE: DNA
<213> ORGANISM: Artificial sequence
<220> FEATURE:
<223> OTHER INFORMATION: Description of artificial sequence:   Probe
      used to identify IL4R polymorphisms

<400> SEQUENCE: 14
tggctcagag agttgctgaa gc                                           22

<210> SEQ ID NO 15
<211> LENGTH: 19
<212> TYPE: DNA
<213> ORGANISM: Artificial sequence
<220> FEATURE:
<223> OTHER INFORMATION: Description of artificial sequence:   Probe
      used to identify IL4R polymorphisms

<400> SEQUENCE: 15
ttcagcaacc ccctgagcc                                               19

<210> SEQ ID NO 16
<211> LENGTH: 20
<212> TYPE: DNA
<213> ORGANISM: Artificial sequence
<220> FEATURE:
<223> OTHER INFORMATION: Description of artificial sequence:   Probe
      used to identify IL4R polymorphisms

<400> SEQUENCE: 16
agtggctatc aggagtttgt                                              20

<210> SEQ ID NO 17
<211> LENGTH: 20
<212> TYPE: DNA
<213> ORGANISM: Artificial sequence
<220> FEATURE:
<223> OTHER INFORMATION: Description of artificial sequence:   Probe
      used to identify IL4R polymorphisms

<400> SEQUENCE: 17
agtggctatc gggagtttgt                                              20

<210> SEQ ID NO 18
<211> LENGTH: 21
<212> TYPE: DNA
<213> ORGANISM: Artificial sequence
<220> FEATURE:
<223> OTHER INFORMATION: Description of artificial sequence:   Probe
      used to identify IL4R polymorphisms

<400> SEQUENCE: 18
ctcttctctg agatgcccga g                                            21

<210> SEQ ID NO 19
<211> LENGTH: 21
<212> TYPE: DNA
<213> ORGANISM: Artificial sequence
<220> FEATURE:
```

```
<223> OTHER INFORMATION: Description of artificial sequence:   Probe
      used to identify IL4R polymorphisms

<400> SEQUENCE: 19
ctcgggcatc ccagagaaga g                                              21

<210> SEQ ID NO 20
<211> LENGTH: 8
<212> TYPE: DNA
<213> ORGANISM: Artificial sequence
<220> FEATURE:
<223> OTHER INFORMATION: Description of artificial sequence:   Sequences
      used to determine computationally estimated haplotype frequencies
      compared between Filipino controls and diabetics

<400> SEQUENCE: 20 acatttat                                                              8

<210> SEQ ID NO 21
<211> LENGTH: 8
<212> TYPE: DNA
<213> ORGANISM: Artificial sequence
<220> FEATURE:
<223> OTHER INFORMATION: Description of artificial sequence:   Sequences
      used to determine computationally estimated haplotype frequencies
      compared between Filipino controls and diabetics

<400> SEQUENCE: 21 acagttgt                                                              8

<210> SEQ ID NO 22
<211> LENGTH: 8
<212> TYPE: DNA
<213> ORGANISM: Artificial sequence
<220> FEATURE:
<223> OTHER INFORMATION: Description of artificial sequence:   Sequences
      used to determine computationally estimated haplotype frequencies
      compared between Filipino controls and diabetics

<400> SEQUENCE: 22 acctccgt                                                              8

<210> SEQ ID NO 23
<211> LENGTH: 8
<212> TYPE: DNA
<213> ORGANISM: Artificial sequence
<220> FEATURE:
<223> OTHER INFORMATION: Description of artificial sequence:   Sequences
      used to determine computationally estimated haplotype frequencies
      compared between Filipino controls and diabetics

<400> SEQUENCE: 23 gcagttat                                                              8

<210> SEQ ID NO 24
<211> LENGTH: 8
<212> TYPE: DNA
<213> ORGANISM: Artificial sequence
<220> FEATURE:
<223> OTHER INFORMATION: Description of artificial sequence:   Sequences
      used to determine computationally estimated haplotype frequencies
      compared between Filipino controls and diabetics

<400> SEQUENCE: 24 gccgccgt                                                              8

<210> SEQ ID NO 25
```

```
<211> LENGTH: 19
<212> TYPE: DNA
<213> ORGANISM: Artificial sequence
<220> FEATURE:
<223> OTHER INFORMATION: Description of artificial sequence:  Amplicon
      primer

<400> SEQUENCE: 25
cagcccctgt gtctgcaga                                                  19

<210> SEQ ID NO 26
<211> LENGTH: 20
<212> TYPE: DNA
<213> ORGANISM: Artificial sequence
<220> FEATURE:
<223> OTHER INFORMATION: Description of artificial sequence:  Amplicon
      primer

<400> SEQUENCE: 26
ctgacctgga gcaacccgta                                                 20

<210> SEQ ID NO 27
<211> LENGTH: 25
<212> TYPE: DNA
<213> ORGANISM: Artificial sequence
<220> FEATURE:
<223> OTHER INFORMATION: Description of artificial sequence:  Amplicon
      primer

<400> SEQUENCE: 27
attgtgtgag gaggaggagg aggta                                           25

<210> SEQ ID NO 28
<211> LENGTH: 17
<212> TYPE: DNA
<213> ORGANISM: Artificial sequence
<220> FEATURE:
<223> OTHER INFORMATION: Description of artificial sequence:  Amplicon
      primer

<400> SEQUENCE: 28
ctcgtcatcg caggcaa                                                    17

<210> SEQ ID NO 29
<211> LENGTH: 19
<212> TYPE: DNA
<213> ORGANISM: Artificial sequence
<220> FEATURE:
<223> OTHER INFORMATION: Description of artificial sequence:  Amplicon
      primer

<400> SEQUENCE: 29
gccgaaatgt cctccagca                                                  19

<210> SEQ ID NO 30
<211> LENGTH: 15
<212> TYPE: DNA
<213> ORGANISM: Artificial sequence
<220> FEATURE:
<223> OTHER INFORMATION: Description of artificial sequence:  Amplicon
      primer

<400> SEQUENCE: 30
ccggcctccc tggca                                                      15

<210> SEQ ID NO 31
<211> LENGTH: 26
```

```
<212> TYPE: DNA
<213> ORGANISM: Artificial sequence
<220> FEATURE:
<223> OTHER INFORMATION: Description of artificial sequence:   Amplicon
      primer

<400> SEQUENCE: 31
gtccagtgta tagttatccg cactga                                          26

<210> SEQ ID NO 32
<211> LENGTH: 19
<212> TYPE: DNA
<213> ORGANISM: Artificial sequence
<220> FEATURE:
<223> OTHER INFORMATION: Description of artificial sequence:   Amplicon
      primer

<400> SEQUENCE: 32
actgggcctc tgctggtca                                                  19

<210> SEQ ID NO 33
<211> LENGTH: 22
<212> TYPE: DNA
<213> ORGANISM: Artificial sequence
<220> FEATURE:
<223> OTHER INFORMATION: Description of artificial sequence:   Amplicon
      primer

<400> SEQUENCE: 33
gttgggcatg tgagcactcg ta                                              22

<210> SEQ ID NO 34
<211> LENGTH: 18
<212> TYPE: DNA
<213> ORGANISM: Artificial sequence
<220> FEATURE:
<223> OTHER INFORMATION: Description of artificial sequence:   Amplicon
      primer

<400> SEQUENCE: 34
agggcatctc gggttcta                                                   18

<210> SEQ ID NO 35
<211> LENGTH: 21
<212> TYPE: DNA
<213> ORGANISM: Artificial sequence
<220> FEATURE:
<223> OTHER INFORMATION: Description of artificial sequence:   Amplicon
      primer

<400> SEQUENCE: 35
ccacatttct ctggggacac a                                               21

<210> SEQ ID NO 36
<211> LENGTH: 20
<212> TYPE: DNA
<213> ORGANISM: Artificial sequence
<220> FEATURE:
<223> OTHER INFORMATION: Description of artificial sequence:   Amplicon
      primer

<400> SEQUENCE: 36
gcagactcag caacaagagg                                                 20

<210> SEQ ID NO 37
<211> LENGTH: 21
<212> TYPE: DNA
```

```
<213> ORGANISM: Artificial sequence
<220> FEATURE:
<223> OTHER INFORMATION: Description of artificial sequence:
      Hybridization probe

<400> SEQUENCE: 37
ccacacgtgt atccctgaga a                                          21

<210> SEQ ID NO 38
<211> LENGTH: 22
<212> TYPE: DNA
<213> ORGANISM: Artificial sequence
<220> FEATURE:
<223> OTHER INFORMATION: Description of artificial sequence:
      Hybridization probe

<400> SEQUENCE: 38
tggagtgaaa acgacccggc ag                                         22

<210> SEQ ID NO 39
<211> LENGTH: 21
<212> TYPE: DNA
<213> ORGANISM: Artificial sequence
<220> FEATURE:
<223> OTHER INFORMATION: Description of artificial sequence:
      Hybridization probe

<400> SEQUENCE: 39
gagggaaggg agggcattgt g                                          21

<210> SEQ ID NO 40
<211> LENGTH: 19
<212> TYPE: DNA
<213> ORGANISM: Artificial sequence
<220> FEATURE:
<223> OTHER INFORMATION: Description of artificial sequence:
      Hybridization probe

<400> SEQUENCE: 40
ctctccgagc aggtccagg                                             19

<210> SEQ ID NO 41
<211> LENGTH: 23
<212> TYPE: DNA
<213> ORGANISM: Artificial sequence
<220> FEATURE:
<223> OTHER INFORMATION: Description of artificial sequence:
      Hybridization probe

<400> SEQUENCE: 41
aaggtggaag aaggcatgac tcc                                        23

<210> SEQ ID NO 42
<211> LENGTH: 23
<212> TYPE: DNA
<213> ORGANISM: Artificial sequence
<220> FEATURE:
<223> OTHER INFORMATION: Description of artificial sequence:
      Hybridization probe

<400> SEQUENCE: 42
aaggtgggag aagacatgac tcc                                        23

<210> SEQ ID NO 43
<211> LENGTH: 22
<212> TYPE: DNA
<213> ORGANISM: Artificial sequence
```

```
<220> FEATURE:
<223> OTHER INFORMATION: Description of artificial sequence:
      Hybridization probe

<400> SEQUENCE: 43
tggctcagag agttgctgaa gc                                         22

<210> SEQ ID NO 44
<211> LENGTH: 20
<212> TYPE: DNA
<213> ORGANISM: Artificial sequence
<220> FEATURE:
<223> OTHER INFORMATION: Description of artificial sequence:
      Hybridization probe

<400> SEQUENCE: 44
agtggctatc aggagtttgt                                            20

<210> SEQ ID NO 45
<211> LENGTH: 21
<212> TYPE: DNA
<213> ORGANISM: Artificial sequence
<220> FEATURE:
<223> OTHER INFORMATION: Description of artificial sequence:
      Hybridization probe

<400> SEQUENCE: 45
ctcttctctg agatgcccga g                                          21

<210> SEQ ID NO 46
<211> LENGTH: 19
<212> TYPE: DNA
<213> ORGANISM: Artificial sequence
<220> FEATURE:
<223> OTHER INFORMATION: Description of artificial sequence:
      Hybridization probe

<400> SEQUENCE: 46
tctcagggac acacgtgtg                                             19

<210> SEQ ID NO 47
<211> LENGTH: 21
<212> TYPE: DNA
<213> ORGANISM: Artificial sequence
<220> FEATURE:
<223> OTHER INFORMATION: Description of artificial sequence:
      Hybridization probe

<400> SEQUENCE: 47
ctgccgggtc attttcgctc c                                          21

<210> SEQ ID NO 48
<211> LENGTH: 19
<212> TYPE: DNA
<213> ORGANISM: Artificial sequence
<220> FEATURE:
<223> OTHER INFORMATION: Description of artificial sequence:
      Hybridization probe

<400> SEQUENCE: 48
agggaagggc gggcattgt                                             19

<210> SEQ ID NO 49
<211> LENGTH: 21
<212> TYPE: DNA
<213> ORGANISM: Artificial sequence
<220> FEATURE:
```

```
<223> OTHER INFORMATION: Description of artificial sequence:
      Hybridization probe

<400> SEQUENCE: 49
tcctggacct tctcggagag g                                              21

<210> SEQ ID NO 50
<211> LENGTH: 23
<212> TYPE: DNA
<213> ORGANISM: Artificial sequence
<220> FEATURE:
<223> OTHER INFORMATION: Description of artificial sequence:
      Hybridization probe

<400> SEQUENCE: 50
ggagtcacgt cttctcctac ctt                                            23

<210> SEQ ID NO 51
<211> LENGTH: 19
<212> TYPE: DNA
<213> ORGANISM: Artificial sequence
<220> FEATURE:
<223> OTHER INFORMATION: Description of artificial sequence:
      Hybridization probe

<400> SEQUENCE: 51
ttcagcaacc ccctgagcc                                                 19

<210> SEQ ID NO 52
<211> LENGTH: 20
<212> TYPE: DNA
<213> ORGANISM: Artificial sequence
<220> FEATURE:
<223> OTHER INFORMATION: Description of artificial sequence:
      Hybridization probe

<400> SEQUENCE: 52
agtggctatc gggagtttgt                                                20

<210> SEQ ID NO 53
<211> LENGTH: 21
<212> TYPE: DNA
<213> ORGANISM: Artificial sequence
<220> FEATURE:
<223> OTHER INFORMATION: Description of artificial sequence:
      Hybridization probe

<400> SEQUENCE: 53
ctcgggcatc ccagagaaga g                                              21

<210> SEQ ID NO 54
<211> LENGTH: 21
<212> TYPE: DNA
<213> ORGANISM: Artificial sequence
<220> FEATURE:
<223> OTHER INFORMATION: Description of artificial sequence:
      allele-specific PCR primer

<400> SEQUENCE: 54
ccacatttct ctggggacac a                                              21

<210> SEQ ID NO 55
<211> LENGTH: 25
<212> TYPE: DNA
<213> ORGANISM: Artificial sequence
<220> FEATURE:
<223> OTHER INFORMATION: Description of artificial sequence:
``` allele-specific PCR primer

<400> SEQUENCE: 55
attgtgtgag gaggaggagg aggta                25

<210> SEQ ID NO 56
<211> LENGTH: 25
<212> TYPE: DNA
<213> ORGANISM: Artificial sequence
<220> FEATURE:
<223> OTHER INFORMATION: Description of artificial sequence:
      allele-specific PCR primer

<400> SEQUENCE: 56
attgtgtgag gaggaggagg aggta                25

<210> SEQ ID NO 57
<211> LENGTH: 17
<212> TYPE: DNA
<213> ORGANISM: Artificial sequence
<220> FEATURE:
<223> OTHER INFORMATION: Description of artificial sequence:
      allele-specific PCR primer

<400> SEQUENCE: 57
ttccaggagg gaaggga                17

<210> SEQ ID NO 58
<211> LENGTH: 20
<212> TYPE: DNA
<213> ORGANISM: Artificial sequence
<220> FEATURE:
<223> OTHER INFORMATION: Description of artificial sequence:
      allele-specific PCR primer

<400> SEQUENCE: 58
caccgcatgt acaaactcct                20

<210> SEQ ID NO 59
<211> LENGTH: 17
<212> TYPE: DNA
<213> ORGANISM: Artificial sequence
<220> FEATURE:
<223> OTHER INFORMATION: Description of artificial sequence:
      allele-specific PCR primer

<400> SEQUENCE: 59
ggtgactggc tcaggga                17

<210> SEQ ID NO 60
<211> LENGTH: 17
<212> TYPE: DNA
<213> ORGANISM: Artificial sequence
<220> FEATURE:
<223> OTHER INFORMATION: Description of artificial sequence:
      allele-specific PCR primer

<400> SEQUENCE: 60
ttccaggagg gaagggc                17

<210> SEQ ID NO 61
<211> LENGTH: 20
<212> TYPE: DNA
<213> ORGANISM: Artificial sequence
<220> FEATURE:
<223> OTHER INFORMATION: Description of artificial sequence:
      allele-specific PCR primer

```
<400> SEQUENCE: 61
caccgcatgt acaaactccc                                              20

<210> SEQ ID NO 62
<211> LENGTH: 17
<212> TYPE: DNA
<213> ORGANISM: Artificial sequence
<220> FEATURE:
<223> OTHER INFORMATION: Description of artificial sequence:
      allele-specific PCR primer

<400> SEQUENCE: 62
ggtgactggc tcagggg                                                 17

<210> SEQ ID NO 63
<211> LENGTH: 18
<212> TYPE: DNA
<213> ORGANISM: Artificial sequence
<220> FEATURE:
<223> OTHER INFORMATION: Description of artificial sequence:   Probe
      used to identify IL4 and IL13 polymorphisms

<400> SEQUENCE: 63
aacattgtcc cccagtgc                                                18

<210> SEQ ID NO 64
<211> LENGTH: 20
<212> TYPE: DNA
<213> ORGANISM: Artificial sequence
<220> FEATURE:
<223> OTHER INFORMATION: Description of artificial sequence:   Probe
      used to identify IL4 and IL13 polymorphisms

<400> SEQUENCE: 64
agcactgggg aacaatgttc                                              20

<210> SEQ ID NO 65
<211> LENGTH: 20
<212> TYPE: DNA
<213> ORGANISM: Artificial sequence
<220> FEATURE:
<223> OTHER INFORMATION: Description of artificial sequence:   Probe
      used to identify IL4 and IL13 polymorphisms

<400> SEQUENCE: 65
ttctactcac gtgctgacct                                              20

<210> SEQ ID NO 66
<211> LENGTH: 21
<212> TYPE: DNA
<213> ORGANISM: Artificial sequence
<220> FEATURE:
<223> OTHER INFORMATION: Description of artificial sequence:   Probe
      used to identify IL4 and IL13 polymorphisms

<400> SEQUENCE: 66
ggtcagcaca tgagtagaac g                                            21

<210> SEQ ID NO 67
<211> LENGTH: 19
<212> TYPE: DNA
<213> ORGANISM: Artificial sequence
<220> FEATURE:
<223> OTHER INFORMATION: Description of artificial sequence:   Probe
      used to identify IL4 and IL13 polymorphisms
```

```
<400> SEQUENCE: 67
tcagttgaac cgtccctcg                                                    19

<210> SEQ ID NO 68
<211> LENGTH: 21
<212> TYPE: DNA
<213> ORGANISM: Artificial sequence
<220> FEATURE:
<223> OTHER INFORMATION: Description of artificial sequence:  Probe
      used to identify IL4 and IL13 polymorphisms

<400> SEQUENCE: 68
gagggacagt tcaactgaaa c                                                 21

<210> SEQ ID NO 69
<211> LENGTH: 21
<212> TYPE: DNA
<213> ORGANISM: Artificial sequence
<220> FEATURE:
<223> OTHER INFORMATION: Description of artificial sequence:  Amplicon
      primer

<400> SEQUENCE: 69
actaggcctc acctgatacg a                                                 21

<210> SEQ ID NO 70
<211> LENGTH: 20
<212> TYPE: DNA
<213> ORGANISM: Artificial sequence
<220> FEATURE:
<223> OTHER INFORMATION: Description of artificial sequence:  Amplicon
      primer

<400> SEQUENCE: 70
ctcggacatg caagctggaa                                                   20

<210> SEQ ID NO 71
<211> LENGTH: 22
<212> TYPE: DNA
<213> ORGANISM: Artificial sequence
<220> FEATURE:
<223> OTHER INFORMATION: Description of artificial sequence:  Amplicon
      primer

<400> SEQUENCE: 71
aatcgaggtg gcccagtttg ta                                                22

<210> SEQ ID NO 72
<211> LENGTH: 24
<212> TYPE: DNA
<213> ORGANISM: Artificial sequence
<220> FEATURE:
<223> OTHER INFORMATION: Description of artificial sequence:  Amplicon
      primer

<400> SEQUENCE: 72
catagaggca gaataacagg caga                                              24

<210> SEQ ID NO 73
<211> LENGTH: 22
<212> TYPE: DNA
<213> ORGANISM: Artificial sequence
<220> FEATURE:
<223> OTHER INFORMATION: Description of artificial sequence:  Amplicon
      primer

<400> SEQUENCE: 73
```
actgaatgag acagtccctg ga                    22

<210> SEQ ID NO 74
<211> LENGTH: 21
<212> TYPE: DNA
<213> ORGANISM: Artificial sequence
<220> FEATURE:
<223> OTHER INFORMATION: Description of artificial sequence: Amplicon
      primer

<400> SEQUENCE: 74
cctaaccctc cttcccgcct a                     21

<210> SEQ ID NO 75
<211> LENGTH: 26
<212> TYPE: DNA
<213> ORGANISM: Artificial sequence
<220> FEATURE:
<223> OTHER INFORMATION: Description of artificial sequence: Amplicon
      primer

<400> SEQUENCE: 75
actgacttat ctttactgtc acttct           26

<210> SEQ ID NO 76
<211> LENGTH: 19
<212> TYPE: DNA
<213> ORGANISM: Artificial sequence
<220> FEATURE:
<223> OTHER INFORMATION: Description of artificial sequence: Amplicon
      primer

<400> SEQUENCE: 76
gcaagacagc caccaaccc                   19

<210> SEQ ID NO 77
<211> LENGTH: 24
<212> TYPE: DNA
<213> ORGANISM: Artificial sequence
<220> FEATURE:
<223> OTHER INFORMATION: Description of artificial sequence: Amplicon
      primer

<400> SEQUENCE: 77
tgacttatct ttactgtcac ttcc              24

<210> SEQ ID NO 78
<211> LENGTH: 0
<212> TYPE: PRT
<213> ORGANISM: Homo sapiens

<400> SEQUENCE: 78

000

<210> SEQ ID NO 79
<211> LENGTH: 18
<212> TYPE: DNA
<213> ORGANISM: Artificial sequence
<220> FEATURE:
<223> OTHER INFORMATION: Description of artificial sequence: Amplicon
      primer

<400> SEQUENCE: 79
cctgctccca ggactgac                    18

```
<210> SEQ ID NO 80
<211> LENGTH: 24
<212> TYPE: DNA
<213> ORGANISM: Artificial sequence
<220> FEATURE:
<223> OTHER INFORMATION: Description of artificial sequence:   Amplicon
      primer

<400> SEQUENCE: 80
cccagacttt atctgtgact gctc                                              24

<210> SEQ ID NO 81
<211> LENGTH: 18
<212> TYPE: DNA
<213> ORGANISM: Artificial sequence
<220> FEATURE:
<223> OTHER INFORMATION: Description of artificial sequence:   Amplicon
      primer

<400> SEQUENCE: 81
cctgctccca ggactgat                                                     18

<210> SEQ ID NO 82
<211> LENGTH: 17
<212> TYPE: DNA
<213> ORGANISM: Artificial sequence
<220> FEATURE:
<223> OTHER INFORMATION: Description of artificial sequence:   Amplicon
      primer

<400> SEQUENCE: 82
ggaaacaggc ccgtaga                                                      17

<210> SEQ ID NO 83
<211> LENGTH: 18
<212> TYPE: DNA
<213> ORGANISM: Artificial sequence
<220> FEATURE:
<223> OTHER INFORMATION: Description of artificial sequence:   Amplicon
      primer

<400> SEQUENCE: 83
gagtgccgct acttggcc                                                     18

<210> SEQ ID NO 84
<211> LENGTH: 16
<212> TYPE: DNA
<213> ORGANISM: Artificial sequence
<220> FEATURE:
<223> OTHER INFORMATION: Description of artificial sequence:   Amplicon
      primer

<400> SEQUENCE: 84
gaaacaggcc cgtagc                                                       16

<210> SEQ ID NO 85
<211> LENGTH: 22
<212> TYPE: DNA
<213> ORGANISM: Artificial sequence
<220> FEATURE:
<223> OTHER INFORMATION: Description of artificial sequence:   Amplicon
      primer

<400> SEQUENCE: 85
tctggaggac ttctaggaaa ac                                                22

<210> SEQ ID NO 86
```

```
<211> LENGTH: 18
<212> TYPE: DNA
<213> ORGANISM: Artificial sequence
<220> FEATURE:
<223> OTHER INFORMATION: Description of artificial sequence:  Amplicon
      primer

<400> SEQUENCE: 86
tgcagccatg tcgcctt                                                    18

<210> SEQ ID NO 87
<211> LENGTH: 22
<212> TYPE: DNA
<213> ORGANISM: Artificial sequence
<220> FEATURE:
<223> OTHER INFORMATION: Description of artificial sequence:  Amplicon
      primer

<400> SEQUENCE: 87
tctggaggac ttctaggaaa at                                              22

<210> SEQ ID NO 88
<211> LENGTH: 130020
<212> TYPE: DNA
<213> ORGANISM: Homo sapiens

<400> SEQUENCE: 88
aagcttcact ctcacgctct gtggtgtgac atccactcag caaagaggtg caaacctgga     60
cccccagagt gtgaatcaca gacacctctt atacccagc ccctctgctg ggaatctagc    120
ggcagaaact cccgagctca tgggcggggc cttcctgagg gcaggctccc tttgcagcct   180
gtgtttgcct ctggggccgc tttgggtaca cacatacaca cacacacaca cacacacaca   240
ccatgccaaa gccacctccc aggcccttcc atgccctgcc tagttctgtt ttgttttgtt   300
tgagacggag tctcactctg acgcccaggc tggagtgcgg tggcatgatc ttggctcatt   360
gcaacctctg tctcccaggt tcaaacaatt ctcctgcctc agcctcccga gtagccggga   420
ttacgggcgt gtgccaccac gcccggcaaa ttttttttgta ttttttagtag agatgggtt   480 tcaccatgtt gcccaggctg gtctcgaaca cctgacctca acgatccac ctgcctcagc    540 ttcccaaagt gctgggatta gaggcgtgag ccacagtgcc tggcccctgc cctggttctt   600
gttttgtgtt ttgagatgag gtctcgctat attgcccagg ttggtcttaa agccccaggt   660
tcaagcaatc ctcctgcctc agccttccaa agtgttggaa ttacaggcat gagccacctc   720
gccctgccac ctgccctaat tctgaactca cagataaaac tgctcccacc aaccaggccc   780
tcctgcccct gggaccccc tctacctcca gcctggaggg aaattccagg cctccctgga   840
gcttatgaag gggaaaaaac ccaagagggt ttttttttc tgtaactcag tgtcgtccat    900
tcgcctcatt atggggtcag gatcccagaa agtcagggtt aaaaggacat ttgctctaca   960
aatagggaag ctgtcccaga ggtaggtatg cctcatccat ggtcacacag atgggcagag  1020
ctgagccgga acacgaaccc agaagtcccg ggtcccagcc tagctccttc aatacctctc  1080
aaacctatta tcaaccttc acactttagt aaaaaatagc gcaactcaaa acagaactct   1140
aaggtgtagt gaggacatag gccaggtcag atctgatgga aggaggagag ctggcccaga  1200
gggcagggag tagggaccc agcccctacc tataatccta gcactttggg aggccaaggc   1260
aagtggatcg ctggagccca ggagttcgag actggcctgg gcaacatggc aagatccccg  1320
tctctactaa aaatacaaaa attagctggg tgtagtggtg tacacctgtt gtcccagcta  1380
cacgggaggc tgaggtggga ggatcacctg agcccagaga ggtcagggct gcggtgagct  1440
```

-continued

```
aagattgagt gccaccctaa gcctggggtc ccaggatact cactgctctc agccaggaga   1500
aagctgccac actcctggga gtagttgcca gactggtctg tgatgttgac actgaaaatg   1560
tcgtcggcca tgaagtggaa tacatccatg tggcaggtgt aggtggcatg cgtggcattg   1620
tgggccgacc tgtggaggct gcaggaggtg gcctcgtcct tcagctcttc atactggtct   1680
tgccttcaag gacaaagcag ccggtcatgg ctggaagcca ggggcagggg ggatggtggt   1740
gggctcagtg ctcagggcca gggcagaagc ccagactctc agggctggga gggatttgag   1800
gcagggctgg ggggtggtca cctggtccaa ccaacctttt cccagggaag gtatcacctc   1860
ccctacagca tcctcaatga attgtgtccg ggctcagctt gcacacctcc caggggccag   1920
gaactcacta cctcatttag ggcagcagct ctcaattttg gaaatttggg ccattcttgc   1980
ttggactaag cctaaatctg tccctgttgg tcccaacaac cagatggctg tcctgcagga   2040
agggcgctag gcattttggg tttccttctc tcctttctgt ccaacatcca tttttttgag   2100
acagggtctc actctggccc caggctggag tatagtagtg tgatcatggc ttactgcagc   2160
ctcgaccttc ccaggctcag ctgatcctcc cacctcagcc tcctcagtac ctgggactac   2220
atgcatgcac caccatgccc agctaacttt ttgtattttt tgtagagatg gggtcccacc   2280
atgttgctta ggctggtctc aaactcctgg gctcaagtga tctgccagcc ttggcctccc   2340
aaagtgctgg gattacagga ctgagccacc tcgcccagtc cccaaatcca ctgaatatct   2400
aataatagcc tgtgctgagg gccaggaaaa gagctaaatg aacctcatct cctcctctgg   2460
gtggacttct gggaaagttg gtgggatggg attagggaaa atgctgtggc ttttaactc    2520 ccactggaca aaaatgatgg gttttgaagt atgtatagta gtttaccgga tattaatttc   2580
cctacctaga tgttcaggat ctgaacatga ccactctcta ggcccagtag ggatgtgtgg   2640
actgagttct ctgccaaatt tgctggaata caagttcctg ctgaataaat gctctccaag   2700
cctcccagcc tgaacttgct ccttattccc cctcacctgc ctcactccac tccagccaca   2760
ctgacctcct cctattcct caaacgcacc agctcttctc ccacagggcc tttgcactgg    2820
cagtgccctc tgcccagctc cctggcttcc tccttctcac tagcagttgt ggtcccttta   2880
cctgaggtcc agtgttctgt ccttgatata gcacccagta ttattagaaa gtatcctgtt   2940
tggggcagaa cacggtggct tatgcctgta atcccaacac tttgggaggc tggccatgcg   3000
gcagaccggc catcccgggg tctcaaaacc atgggcgacc tgtgtgggcg agagagtggt   3060 cttttgaagct ggtggataga ccaacctgc gggctcctga cttttcaagt cctgtgagcc   3120
ctgagtggtt gtctgaaagg cgggtacagt gggcggatca cttgaggcca ggagttcgag   3180
accaggtggg ctaacatgac aaaaccctgt ctctacttaa aatacaaaaa ttagccaggc   3240
atggtggtgc acacctggat gcaatcccag atacttggga ggttgaggca ggagaattgc   3300
ttgaacccag gaggtggagg ttgcagtgag ccgagatcat gccaccgcac tccagcctgg   3360
gcaacagagt gagactccgt ctccaaaaaa aagaaagaaa gaaagtgtcc tgtttgggcc   3420
tggcatggtg gctcacacct gtaatcccag cactttggga ggctgaggtg ggcagattgc   3480
ttgagcccag gagtttgaat ccagcctggg taacatggca aaaccctgtc tttacaaaaa   3540
ctacaaaaat tatccaggta tggtgatgca tgcctgtagt cccagctact caggaggctt   3600
aggtggaggg attgcttgag cccaggaggt caaggctaca gtgagttctg atcccaccac   3660
tgcactccag cctgggcaac agagcaagac cctgtctcaa aaaataaaa taaaataaaa    3720 taaaataaaa taaaaagag aaagcacctt gttggttgtt ttgtgtgtct gtctccccca    3780
```

```
gcctccgccc caccgtggta cgtcagttcc aaggcatctg gggcctggtc agtcttgctc    3840
tgctgaatcc ccagtgcctg caacagtgtc tggcaggaac ttaatacatg ttttgttttg    3900
ttttgttttg tttttgagtt gggatcttgc ttttttgccc aggctggagt gcagtggcgt    3960
gatcatagct cactgcagcc tcgacctcct gagcttggtc cccctgcctt agactctcaa    4020
gtagctggga ttacaggatt gtgccaccac gcccgactga tttattttt gtagagacag     4080 ggttttgtga tgttgcccag gctggtctca aactcctggg ctcaagtgat cctccttcct    4140
tggcctccca aagtgctggg gttagaaaca tgagccactg cacctggcct ataaatggtt    4200
ttgaatgaat gaatgagctg atggataaca gaagctcttc tttatcctga gctgcatagg    4260
gtctaaaagg gacccatgga ctttggagtt gggcggtctg aatttgaatc ccagctccag    4320
cattcactgg ctgtgtgacc ttaggcaagt tgcttaacct ctctgaacct caatgtcctc    4380
atctgtaaaa tgggagtaat cattgtgagg gttgggggtg accattcatg ggaagcgtgt    4440 agttggggc ctggtaccta agtgcttgaa aaatcatgcg ggaaaccagc catcccgggg     4500
tctcaaaacc atggccgacc tgtgtgggtg agagagtggc ctttgaagct ggtggataga    4560
ccaaccctgc gggctcctga cttttcaagt cctgtgagcc ctgagtggtt gtctgaaagg    4620
cggacacagt ggtcctcagt gcacagtgtc ctcctggggg aatcactgag caggcaccct    4680
gaattgcatc cccgggggact ggtgaggccc ggctacttac caggtaaggg tgagcgtgct   4740
ggggtggagg ttccacattt ccaggatgca gatgaccgtc tggaggtaat cggtgtagca    4800
gacgaggtcg gggcagcccc agcctggagg gtcagtgggg agagaggcct tggtgggggg    4860
tggcttggga ctgcagagct tcctctccat ccctcgagg gctggaggaa gaatgggtgc     4920 agggtcccc aggccgggac aaatatgagg actcaggagc tgcttagatg taggcctggc     4980 acccagggg cctcaccacc tggaaattcc ttgtttgagc accaatgttt caaggctggc     5040
tatgaagaca ggatgcatgt gatggcaaat aatataaaac tagctggtcc ccagctcagc    5100
accctcctcc agagccctgc gcccggccac caggtctgtg tccctcctgg ccaagctccc    5160
actcagaatg gcaatatcct aaatgcccca gatgtggtag gaaccagcc agagcacacg     5220 cacacacccc aagagggtca ggacctcata gagtcaagga cagctatgct gaaaatgtcc    5280
caaaaccctg acaaggaaga ggactcggct ctacagaagt tggatccaca ggacacccac    5340
tctcggagat tcaggaagtg cttcaaggag taggaaaccg tgagagaatt aaaaagccct    5400
cggacacttt tgcataaagg tctgcgtgat cctgcggcca aaaatgccac cgccaccaag    5460
aagtcttcta ggtattgccc tatgaggcaa ttttgttgga agatttaaca cctttccatc    5520
ctgctcccca aacattaatt gtttcgctgt gttctaaaac aggggtgcaa tcatcatcta    5580
cattttgtta aatgtggaca aaatcaatgg aataatttgt agctttgttt tgtatattcg    5640
agtgccaatt ccactatttt ttgctgctat ttactagaaa cttgtaccgc tcacctcttt    5700
ttgagatagg atctcttgct ctgttgccca ggctggaatg cagtggtgcg atctcagctc    5760
actgcagcct ccacctcctg ggctcaagca gtcctcccac ttcaacttcc tgagtagctg    5820
agactacagt tgtgcaccac catgcctgga taatttttgt gttttgtag agacagggtt     5880 tcaccatgtt gcccaggctg gtctcaatct cctgagctca agcgatccac ctgcctcagc    5940
ctcccaaagt gctgggattg taagaatgag ccatcgtgcc tgaccttgtt cccctttta    6000 agtaggttca ttttggtgg cttttttccta tttttccctgg actaatgaag acccctgagg    6060
tggtggtggt agattccctt cctgggtctc actctaggac agaacctata tgcggagcca    6120
agaatactgt gtctggaaat atcctttagt tcattgtaga gatgagaaca ctgaggctcc    6180
```

```
aagactagac catgcctctt gtctctcttg gtctgggctg ctgagacact cacccaggga    6240
aggaaatacc tagtctgtgc tagtttttca tagccgcaca catgacagat attgctaatg    6300
gatcacagca ctccctcccc taggtgtgac ctcggaatgc ttctcaactt ctctcgaggc    6360
agtggctacc aagggatctg agtcatggaa gtaaatcttg ctctaggagg gggctttcct    6420
cagggagaca cacagaactt gtcggtggag tgaaaaggag ctagttccag cacttggtgg    6480
agaaaacagg actgattttg gcaaaacctc aacacagagc ctctaagtag ctgtgtcatc    6540
tctgagttcg tatcctcgtg gttctttctc agagctctgg gaatttggag aggagctacc    6600
attcctagcc aggctcaaag ctaccaaggg acagggtttg tctccaaact tggggaggca    6660
acggcagccc ctgagtggca gggaggtggc accaggatg agagggtggg aaaatgccct    6720
gtcagtaccc cagccacagg gcagagagcc ccagggccat cccatgtctg gggttatgaa    6780
agcgtgcagg aggcagtgag aggtgcacaa agtagctctg tgactgcaaa catgtgactc    6840
aaaactgctt ctcctcccca tgtgtaagcc ggagacactg cttgccctag aggctgttga    6900
ggtgttgaga tgagatcatg cctgtgcctg catgctgccc gcacatggct atcactccac    6960
agatagcagc acagcatggt gaaggccgtg ctacggtttg acgtctgtgt ctccccagaa    7020
actcagttgc caatgtgatc atattaaaag gtggggactc taggagatga ttaagtcatg    7080
ggggcagagc ccccctgaat gaattattga tgctataaga gggctggacg aacccaacat    7140
tcagacccct tttgcccttc tgccatgtga ggatgcagcg tgtgtcccct ctgggggtgg    7200
tgcagcgttc aatgtggcat cttaaaggca aagatggggg ctgggtgcgg taatcccagc    7260
acttttggga ggccgaggcg ggtggatcat ttgaggtcag gagttcaaga ccatcctggc    7320
caacatggtg aaaccccaac tctactaaaa atacgaaaat tagccatggc atgtgcctgt    7380
tatcccagct gctcgggagg ctgaggcatg agaattgctt gaacctggga ggcagaggtt    7440
gcagtgagcc aagattgcac cattgcactc cagcctgtgt gagaaagcaa ggctcagtct    7500
caaaaaaaaa aagcaaagat gggcccctca ccggaatcaa agctactgct ggtgccttga    7560
tcttggactt cccagcctcc agaactgcga gcagtaaatg tctattattt ataaattacc    7620
cagtctcacg tattcagtta cagcagcaca gacagactaa gacagacccc aagagcaaac    7680
tgatcccagc tctgcctctt ccgggtagtg tggccatgca cctgtctctt agcctctctg    7740
agcctcctca gccaaaaaac tgggcgtcat tacaacatgc gccttgtggg gctgttggga    7800
cagtggaatg ggatgacgct ccgagctttg catgcagcca gggcttgtta tctgcacccg    7860
ccagatgtgg agccatggtg ggtgacccaa aggcttttta gaaccaagat gaggatgctt    7920
gccactcaga aagggaaaat caaagcttga catctgtttc ctgaaggagc tatttgaggt    7980
cctgggtctt ctggtaaaaa ccagagaaaa atgcccatga gtcagcagag cagctgttga    8040
gttcctcccc tgcccctagg ccggcctcca cacaagtctg tgctggatcc cgcctcctca    8100 tggcccccctc ctccaggaag ccctccagga tctcttagtc ctaggcagtg cccttttcagt    8160 cggactcctg gtcttcccag ttctgctttc taacgtcacc ccctctaacc acaacatctg    8220
gtcctctggg ggctgcctac caaggttcag tctccttttg gctcttcctc ctgtccccag    8280
cccagggacc accagtgcct gctaagaatc tagcgatttt tttgtttgtt tattgttgtt    8340
gttgttgctg ttgttttgag acagggtctc gctctgttgc ccaggctgga gtacagttgt    8400
caccttgact cactgtaacc tccacctccc aggctcaagc aatcctcccg cctcagcccc    8460
acaaaaagct gagactacaa gcatgcgctc ctatgcctgg ctaattttttt ttcttttgta    8520
```

```
gagacagggc ttcaccatgt tgcccaggct ggtcttgaga tcctgagctc aagcgaccta    8580
ccctcctcag cctcccaaag ggctgggatt ccagtaggag ccaccgcacc cggtgcagca    8640
attgttgaaa acatttcca aggagagtca ttacataagg agaaactgag gttagatgga    8700
aggcagaact tcctcactca gagagttggg agccagccaa ggcagaggtc aggggaaatg    8760
aaggacgaag cctttcatcc ccccagtgac acccgaagac acaagcctgt gggctgggcc    8820
acctgagact catgtctacc gcttctgttt catggagccc tttggtggat ggattctgat    8880
tagtggagag ccggctactg gactcgtgtc agcctcaagg gcatggatgt catcttttct    8940
gaatctgtgg actctagccg tgttttgag cccagaaagc cagcccggcc ctggctcagc    9000
tctgtgatgg gggccctccc cacccgcaga ccacgggca gccacttacc tccctggagc    9060
agcagcagga gcaaggggc ggcccagcca cgcggcatgc tgactcccac gggcctgcaa    9120
gagacgtaca gtggagggtg agccaggcgg gctcagggct cccccggcct cccctcatc    9180
ctgtctcttc ccaggcagac ttgccccga ttccttgaac tgtcttaaga aaatgcaag    9240
atcccgaggg gcctgtggat gaccccaaga actcccacct cttagaaatg gcagattcac    9300
cccaagaatc ccttctccca ccttcttcct gcccccgccc catcacgtca caaatgcaaa    9360
gtgaatttgt tttattattt tattttaata ttttttagaga tgggggtcatg ttctgttgcc    9420
caggctggag tgcaatggcg caatcacggc tcactgcagc ctcaacctcc tgggctcaag    9480
cgatcctcct gcatcagcct cccgagtagc tgggaccaaa ggcacgtgcc accacgcctg    9540
gctaattttt aaaacatttt tgtagaggcg gcatcttgct atgttgccca ggctggtctc    9600
aaactcctgg gatcacatga tcctcctacc tcggcctctc aaagtgctgg gattgacaggc    9660
atgagtcacc acgcccagca caaggtgaat ttaaagaggg aggagactgc tgactatttt    9720
gcccttgctg agcctattga tgtagcattg tgtgtgaaat taaacttgtg tatttatcta    9780
tctaacaaag aaagagggag gaaaaaagag aggaagggag agagaaaagg agaaaaaact    9840
agtttggaaa gggggatctg ctgaggagca attttggatc ttccttccta taaacatcca    9900
tgttgtaaaa aaagccagt aaattggctt ttttatgttt attttttaga caaagtctca    9960
ctctatcgcc caggctggag tgcagtggcc cgatcttggc tcactgcaac ctctacctcc   10020
caggttcaag cgattctcct gcctcagctt cccaagtagc tgggaataca ggtggccgcc   10080
accacgcctg gctaattttt gtattttag tagagacagg gttttgccat gtggactagg   10140
ctggtctcga actcctggcc acaggtgatc cacccacctc agcctctcaa agtgctggaa   10200
ttacaggcat gagccactgc acccagccat caataaattg gcttcttact gaataataaa   10260
tccaaagtta acccacaaag ttaaccactg ctgaatactt aagataaggt tagcccaata   10320
atgaggctcc ttactccatc acaaagccca gattagccca ctcgggagca tgctaggaaa   10380
tccaggcctg accaaacaga gacaacctga cctcctaatt tgggccagga tggagaagga   10440
acctctttgg ggagcagagt gagtttatcc agaaagagtg ccctctactg tcttgggcag   10500
aggaatgccc caccagtctg gcgatgccag gcttctcctg ggacttgtct gtttcaccca   10560
ccagctctgt gtctgtttga ggaagtgcca gccagagggc agtggtccac ctgcccgagc   10620
tcaggagccc ctcccagacc agcccctata gacaagaatg gagctaaagc taaacctaag   10680
agggatgccc catgcaggac ccaagtcaca ggcatggctt tctccagacg ccatccctga   10740
ctccacaagg ggaagatcct cctcctctgt gccggggttc ccaaagatcc tactctggcc   10800
ccatccatag ttccctctga cctccctcac agagccatca agaaccctg ggcagggca    10860
caggctgggg ggccaggaag gttcagatga ccagctgtgt ggctccgggc cagtcccttg   10920
```

```
ccctctctga gccttgtaaa gtggaaacag caaggcctgc ttccaggctt gtgagaattc   10980
aaggaggtga tttgcataaa accctgcaga tggcccccat cacataaaca ctcaaacaac   11040
agctgtaatt gatggagaag gtagagcctc agaaacagag ggggtctcag aatgatctag   11100
ccaagagttg ccaaaatatc tcatatccaa aattttggcc atatttgtat attgtgtgca   11160
ctgttgttta ttttaataca tattttaata tattttctat agataagcac acttaaaaat   11220
ttaactccag catcatccta agcaataaca tcactactca aataaaataa tgttgaggta   11280
gatgcagttt caacctgctt ttaggaatat gaatcctgtg tgattccaac ccctgcagag   11340
gtcctgttat cacactttga agatgtggcc tctgatcgca ggaggggggag tctgtgtctg   11400
cccctcact attctgtcca catccatcac cccagccacg gtgcgagtcc tgacatagct   11460
ctgtccccgt cactccctga tggttttatc ttgaccacag cacagcaaaa agtgcaaact   11520
cctttgccca gattcaatat tcctcatctc cagcttgacc aacatagcaa gaccttgtct   11580
ctaccaaaaa taaaaataga agtaaaaata agttagccgg gtgctgtgtg cctgtggtcc   11640
cagctattcg ggagactgag gaaggaggat cacttgagtg ccggaggtcc aggctgcagt   11700
gagccatgat tgcactattg cactccagcc tgaatgaaag agtgagaccc tgtctttaaa   11760
aaaacaaaca gacaaacaaa aaactcctca tccctcctaa tttcttacct ctgcctacat   11820
cacagagccc tagggatgtg gagggggtac ctgctgcttc tgcctgcccg gcgtctcttc   11880
ccaaagagct cctctatctg agctgcctct agtggtttgc ctgaggctga ctccacccca   11940
tgctccacaa agtgggctcc tgacccaggc ttggccaatc aaaacacccc atctgtctga   12000
ccacagtgat tgcatcaggg atggatgtca acccaggcaa ggccagtgaa agcagtcctg   12060
agatttttt tctagaactc tagaaaactg acacttttt tggtatcttc tcagagcttg   12120
tagccatctt tgtcacctct tagagacagc ctccttgaaa atgacagcca tactgagaaa   12180
tacaggtcag gagtccccat ggcatcatgg gaggtcctgg atccagccat atctgatgtc   12240
caccctgtgg atttctcatt cccatgagcc aaaaaccacc tatgttgctt aatcatgttg   12300
aattctatttt ctgtcacttg ccaccaaaga tccctgacac agtggagttg agaaaagggc   12360
tcagaatttg aagccagaag atcttgaagc aaatagtagc tcttctctgg ctcttttatt   12420
ctctgaactc agttaccatc tctgaaatgg ggacaatagt gctcactgca cctggcagtg   12480
aagaagaggc tgtgagaaag cagatgtggt agtgcttcat ggactgtgaa gtgctgtacc   12540
agtgcacggg tttcctgcca ttactggctg actgccctga attactcatc gtctccccgg   12600
cagcccaggc ttcgtcatgc atctttgcct ctgctggagc agactcctgc cctccaacac   12660
ctttccctc ccatcctctc aactcaactt tcatggtcca tgtgctgtat ccctgcagcc   12720
acactggagt gttccagaac tcctgccact agcctattgc gtttgaggtt ttcactggtg   12780
ctactattaa ttatccactt actattgatc tttaccttgc ctcctatttt ttactccaat   12840
aaacatgtct caaaatatt atatcatgac catcagcaga taactggcat gaaataggca   12900
gtgtgcgcca tgctggtcaa gacacagact atggagctgg ctggtctcag ttcaaatccc   12960
agctctgcca cttataggct ttgtggcctt gggcagtttg cttaaccttt ctgggcctca   13020
tctgtaaaat gggagtaatg ataatcacag cacctgcctc ataggtcttt gggagaatta   13080
aattagtcaa catttataaa gcatttagaa cagtgcctgg catatagcag atattatata   13140
agtgttactt aaacaaaaca atcaacttac cataaaacta aatacaatac aacataaaaa   13200
ctaaatacaa gaaaaacaaa ggcagtaatt gaattttagt gacatgctac tgcctgcctg   13260
```

```
agagtcctag aaactggaga tgtggtttgt ctttgtttaa agttaagaaa gggaggccgg   13320
gcacactggg tcatgcctgt aatcccagca ctttgggagg ccgaggtggg aggatcattt   13380
gaggtcagga gttcgagacc agcctggcca acacggcgaa accccatctc tactaaaaat   13440
acaaaaatta gccgggtgtg atggtgtgtg cctataatcc cagctactca ggaggctgag   13500
acaggagaat tgcttgaacc caggaagagg cggaggttgc agtgagcaga gattacacca   13560
ctgtactcca gcctgggcaa cagagcaaga cactctgtct caaaaaaaaa caaaacaaaa   13620
cacaaaaaaa gagagagtag tgtttaagat gcgatagcac caaattgaga atcttgcctc   13680
ctccatcagc agggcaagtg atgaaagagc ctacgctttc actaggggat ccagggatat   13740
ttaacactgt ttaaaataaa ctgctcactt ctgggaaaca tcagcttaaa aacacagact   13800
ttctccatca ctccctcctc atgctcccac agcaccaaat ggggcctacc ctaattccac   13860
tgccttctct gccccgaatc catccccttt tgggtctttg cacgcaggct gacccctgag   13920
ggcaacagca ccttatcctc agatacagat cgggccacca tgtgtgtttc ctacaaggac   13980
agaaggtgtc ttaggaggct tcctgctaca ggagccccct gatatggttt ggatatttgt   14040
cccacccaaa tctcatgttg aaatgtcatc cccaatgttg gaggtggggc ctggtgggag   14100
gtgattggat catggggggcg gatttctcat gaatggctta gtgccatccg cttggtgatg   14160
agtgagttca cctgagatct aattgttcag aagtgcgtgg cgcctccccc ttttgctcca   14220
gctgtcgcta tgtgatgtgt ctgcttctgc ttcaccttca gccttgagta aaggctccct   14280
gagggcctcc ttaccagaag ccgagaagat gctggcagta tgcttgtaca gcctgcagaa   14340
ccatgagcca attaaacctc ttttctttat aaattaccca gtctcaggta ttgctttatg   14400
gcaatgcaag aatggcctga cacaccgctg cagcacccaa cctctgcagt ctcctacgga   14460
ggagtgaagt gcacctgact tggagtgtgc caggtcccag ctgtgcgtct ttgggcaagt   14520
tctctaaccc ctctgattct ctgttttctc atccataaaa tggaggtcat caatctttgc   14580
tgcaggtttg tcatgagcat taaaagtgtc atcgaatttg aagtcctgta ggtgcattta   14640
tccaccagtt tcagtgctga gaaatgtttc ctggagttgc tgtaattcac cctaaaagtt   14700
gaccaaattt caagagattc tggggaaatg gagaagcttg gggcaggaaa ttagattgaa   14760
gtgagtgcta tggagaatat aaggtgctta acttcatggt caacgtggtg gctcatgcct   14820
gtaatcccaa tactttggga ggccgaggtg ggtggatcac ctgaggtcag gagttcgaga   14880
ccagcctggc caacatggtg aaaccccatct ctactaaaaa tacaaaaatt agccaggtgt   14940
ggtggtgggc acctgtaatc ccagctactc tggaggctga ggcaggagaa ttgcttgaac   15000
ccgggaggtg gaggttgcag tgagccgaga ttgcaccact gcactccagc ctgggtgaca   15060
gagcgagact ccatctcaaa aaaagaaaa agaagagaaa agaaatacaa agaaaaacca   15120
caatgacata ccatttttaat tttgtcggat tggcaaaaac tgaaagtctg atgacatcac   15180
atattgctca ggatatgata taataggaac tctcatttat agccagagga aatgtaaatt   15240
attacaactg gtctggtaaa aagtttggca tgacctaata aaagcgaaca catgccctac   15300
ctaaaaccca gtaacttcac tcttatgtaa actggtaaag aaattcttcc tgcatgtcta   15360
tagcagcatt gattttaata gtgaaaaatt ggaaacaatc taaatagcca tcatcaggag   15420
agtgaaaaaa taaatcgcaa tactgtcact cagtgtaaac atgaatcatt tacagccaca   15480
cacaacaaag tgaatgactc tcacaaacaa aatttggagt gaaaaaagga agttagagaa   15540
cagcataagc ataataacac cattgacacc acactgaaaa ccatacaaaa tcatcctata   15600
tattgtttag gtaagcacac ccatcataaa aatatttaaa aattcatggg gataataaca   15660
```

```
tcaaattttg aatagtgtgg aaaaggaggg ggtgtgagaa ggaggaatgt tcaagggtct    15720
caacagtttg gtaaagcttg gtgaagctac catgggtgtt gattatattt tatgcccttt    15780
tgtatgttca aactatttca taccatttta aatgtaagtg aggcttagtt ttgtaaaata    15840
aaatatggat gagggacttc cacttctggc tataatgaag tagctgttgt cacactaatc    15900
ctcccactga gggcaactac taagcagaaa aaaaaaaaac tgcacaagag agtgccaact    15960
tatatagtac ttaagagagg aaaaatgcat tgaaattctg catgcaattt cccctcaaat    16020
catgtgcaaa gtcattgaaa ataagtagca tgccaagaaa cttagcaaaa aaacacctgc    16080
taataggtgg gaaaactaag aaggaatttt cacagtttta caagctgagg gaagaattag    16140
agttcagggc ctggcaaaaa aagatgggc cctggtgagt acccagctat ttagaaaata    16200
ctattccttg ggaataagga aaaattagaa atagttcatt cttgactgca tcaaggtgta    16260
atctgcttat atgctatatg tctgctagaa gaaaatttaa attgatctag aaaaagttag    16320
cttcatccaa agcctctata cttttatac ataatgtcca actttcagtt aaaattacaa    16380
ggtaaaccaa caagcagtat caaatgatca acaatgaaga taaaatagac aatagaaaag    16440
ttacttaggt gaattggaaa atggcattat cagatatgat ttaaaataac tatgattaat    16500
gtgttcaaaa attctatcag aaatttggaa cctatttaaa aagtagaaat cctggaactg    16560
aaaaatataa taactgaagt ttataaggac tgaagagatg gatttggcaa catactagta    16620
acatcagaag agaggattag taaactggaa gattggtcaa tagaaaatac caagattgaa    16680
gcatgcagag aaaaaaagtt caaaaataca gaaaagagca aaagagacat agaagacatt    16740
gtgaaatgat ctaacataca tgcatttgca attaagaagc agaagagaga gaaaacaagt    16800
aagaagaaat agcagtgatc ttaaaatttt tttccaaact aacaaaagac attaagccac    16860
agatttaaat agctctacaa accacaaata ggataaatac aaagaaaacc acatctaggc    16920
atatcataga aaaactattt taaaaaataa aagacaaaga tatgcagtat gcagaaaaaa    16980
aagacacttc accttcaagg aagaaacaat aagactggca ggggactttt taacaaaatg    17040
atggaagaca gcagacaatg gaacaacttc tttcaatgct gaaatttcaa aagccaattt    17100
agaattttat atccagaaaa aaatctctta aaaaataaaa gtaaggtcaa tatgatacag    17160
acagctataa aaatattaca gttaacatca tacttaatgg taaagaaatg aaagctttgc    17220
tcctaagatc atgaacaaga caagtatgtt cactcttgtg acttttataa aacatttttac    17280 tagaggttct agccgaggca attaggtaag gaaaagaaat aaaagacttt cagattggaa    17340
aggaagaagt aaaccatttc tctttgcaga taatatgatc ttgtatatac aaaactaaag    17400
gaatttacac ctaaaacgaa caaaaaccaa ttagagctaa taaacaaatt tagcctagtt    17460
gtagaatata agattaatag acacaaataa tgatatttta tacacactgg caataaataa    17520
tctgaagatg aaattaagaa agtgatttca tttacaataa tacaaaacag aacaaaatgg    17580
ttaaagtaaa tttaacaaaa ttcattagtt atgttaatat gagatgaatt tgtttattag    17640
tgtgagactt gtgcaataaa acctacaaat gttattgaaa taaattatag aaaacctaaa    17700
taaatggagg atataccatg ttcatagatt ggaaaactta atgttatcaa gatgacgcct    17760
caaattgatc tacagattca aagtaatctc tataaaaaat cccagctggc tcttttttt    17820 tttttttttt tttttgcag aaattgacaa actagtccta aaatttatag ggaaatgtaa    17880
gggactagaa tagccaaaaa ggttttgaga aagaacacag ttggaggagt caaacttcct    17940
tatttcaaag cttactacaa agctacactt atcaacactg tggtactgac acatagatgt    18000
```

-continued

| | | | | |
|---|---|---|---|---|
| acatatagat | caatgggatt | gaactgagag | ttcagaaaga | agtgcatata tttatgttta | 18060 |
| accgattctt | gatgagggtg | ccaaaacaat | tcaatggggg | aaagaatagt ctttaaaaca | 18120 |
| aatggtacca | cacaaatgga | tatccacaat | gcaatataat | gaagctagat ttctacttca | 18180 |
| caccgtatac | aaaaatttac | tcaaaataga | ttaaagacta | gatgtaaaaa gtaaaactat | 18240 |
| taaactctta | gaataaacct | aggtgtaaat | cttcatgacc | ttgtatgaga caataatagt | 18300 |
| tttttaaata | tgacacaaaa | gcataagtaa | acaagaaaa | aatagatcta ttaaactgta | 18360 |
| tcaaaattta | aaatgtttgt | gcttcaaaaa | atactatcaa | gaaagtaaaa ctataacata | 18420 |
| cagcatggga | aaaaaagcat | ttgcaaatca | cgtatttgtt | aaaggtctgg tatttagaat | 18480 |
| atgcaaagaa | ttcttgcaac | tcaagatcta | aaaggcaaga | attaaaattt aaaatgggca | 18540 |
| aaagatttgg | atagacattt | ctccaaagaa | gatatccaaa | caacaaacac atgaaaaggt | 18600 |
| ggccattgac | attactctct | agagagatgc | aaatcaagaa | cataatgaga taccacttca | 18660 |
| catgcattag | gatggtaata | ataataatca | atcacaagtg | tgaatgaggg ggcggagggt | 18720 |
| gagaatgtaa | aatggtgcag | ccactgtgga | aaacagtttt | gcagttcttc aaaatgttaa | 18780 |
| atacagtcac | gtgctgcata | atgatatttc | attcaatgac | agactgcatg tacataggcg | 18840 |
| ggcccatagg | actataatga | aggtgaataa | ttcctattgt | ctagtgacgt catgacacaa | 18900 |
| cactttactc | atgggcttgt | gatgatgctg | gtggaaacaa | atttactgca ctgccagtca | 18960 |
| tataaaagta | tagcatatgc | agggctaggt | gcggtggctc | acgcctgtaa tcccagcact | 19020 |
| ttgggaggcc | aaggcaggca | gatcatttga | ggtcaggact | tcaagaccag tgtgacaaac | 19080 |
| atggtgaaac | cccgtttcaa | ctaaaaacac | aaaaaactta | gccaggcgtg gtgacacatg | 19140 |
| cctgtagtcc | cagctactca | ggaggccgag | gcaggagaat | cacttgaatg gggaggcaga | 19200 |
| ggtagcagtg | agccgagatt | gcgccactgc | actccagcct | ggacaacaga gtgagactcc | 19260 |
| gtctcaaaaa | aaaaaaaaaa | agatagcata | tacaattatg | tattgtacat aatgcttgat | 19320 |
| aataataata | ataataataa | taaactatgt | tactggtgta | tgtatttact atactatatc | 19380 |
| ttaaatcact | attttagggt | gtgctccttg | tacttactta | aaaaaaaatg ttggagggc | 19440 |
| acagtggctt | acgcctgtaa | tcccagcact | ttgggaggct | gaggcaggca gatcacttga | 19500 |
| ggtcaggagt | tggaaaccag | cctggccaac | atggtgaaac | cccatctcta ctaaaaatac | 19560 |
| aaaaattagc | caggcacggt | ggtgtgtgct | tgtaattcca | gctattcgtg agactgaggc | 19620 |
| acaagaatcg | catgaaccca | ggaggtggag | gctgcagtga | gccaagattg tgccactgca | 19680 |
| ctccagcctg | ggtgacagag | caagactctt | aaaaacaaac | aaaaaatgtt aacttgtaaa | 19740 |
| acagcctcag | gcaggtcctt | caggatggat | tccggaagaa | ggcatcatta tcataggaga | 19800 |
| tgccagctcc | atgtgtgttt | ttgccactga | agaccttcca | gtgggacaaa atgtggaggt | 19860 |
| ggaagacagt | catattggtg | atcttgaccc | tgtgtaggcc | taggctaatg tgtctgcctg | 19920 |
| tgtcttagat | ttttttgtttt | ttgttttctg | ggtttttttg | agatggagtt ttgctcttgt | 19980 |
| tgcctaggct | ggagtgcaat | ggcgtggtgt | tggttttccc | gggttcaagt gattctcctg | 20040 |
| tctcagcctc | ccaagtagct | gggattacag | gcgcccgcca | ccatgcttgg ccaattttgt | 20100 |
| attttagta | gagatggggc | tttcaccatg | ttggccaggc | tggtctcgaa ttcctgattg | 20160 |
| caggcgatcc | gccctccttg | gcctcccaaa | gtgctgggat | tacgggcatg agccaccatg | 20220 |
| ccccgcgtgt | cttaggtttt | aacaaaaaaa | atttttttaa | gtaaaaaaat aaaaaataaa | 20280 |
| aaattttaaa | atataatata | taaaaaggct | tttagaataa | gaatataaag aaaaatattt | 20340 |
| tgtatagctg | tacaatgtgt | ttgtgtctta | agtgttagta | caagagtgca cgaaaacact | 20400 |

```
taagtgttat tacaataaga taactgttat tacaaaagtg ttattcaaaa agttttaaaa    20460
agttaaaatg tttataaaga aaaaatgttg gcggggcgca gcggctcatg cctgtaatcc    20520
cagcactttg ggaggccaag gcgggcagat cacgaggtca ggtgatcaag actatcctgg    20580
ctaacatggt gaaacccgt ctctactaaa aataccaaaa aaattagccg agcgtggtgg    20640
cgcgcacctg tagtcccagc tactctggag gctgagacag gagaattgcc tgaacctggg    20700
aggcggaggt tgcagtgagc tgagatcgcg acactgcact ccagcctggg tgatagagtg    20760
agactctgtc tcaaaaaatg aaataaaata gggccgggcg cggtagctta cgcctgtaat    20820
cccagcgctt tggaagggcg agacgggcag atcacaaggt caggagatcg agaccatcct    20880
ggttagcacg tgaaacccca tctctactaa aaatacaaaa aattagccgg gcgcagtggc    20940
aggcgcctgt agtcccagct acttgggagg ctgaggcagg agaatggcgt gaacccggga    21000
ggcggagctt gcagtgagcc gagatcacgc cactgcactc cagcctgggc gatagagcga    21060
acctccgtct aaataaaat aaaataacat aaataaaata aaataaaata aaataaaata    21120
aaataaaata aataggaaaa atgttacagt aagccaaagt taatttatta ttttaaaaat    21180
tcaaataaat ttagagtagc ctaagagttc agtgttgata aagtttacag gagtgtacag    21240
caatgtcctg ggccttcaca ttccctcagc acttaatcac tgacacccag agcaacttcg    21300
aatcctgcaa actgcattca tggtaagtgc cctacacagg tgtgccgttt tttcatattt    21360
tatattatgt tttcactgta ccttttctat gtttagatac acaaatactt acaattgtgt    21420
tacagttgcc tacagtattc agtaccgtat catgctgtgc aggtttgtag ccaattagca    21480
ataggctgta agatacagcc taggtgtgta gtaggctata ccacctaggt ttgtgtaagt    21540
gcactctatg acgttcacac aatgacaaaa ttacctaatg acacatttct cagaatgtat    21600
cctcgtcatt aagcaatgta tgactgtttc catatgacca agaaatttca cacctagtta    21660
tatagtgaaa agaattgacc agatgcagta gctcatgcct gtaatcccag catactggga    21720
ggccaaggcg ggagggttgc ttgagcccag gagtttgaga ctagcctggg taacatggca    21780
agacctcatc tctacaaaaa ttaaaatgaa aacattttct gggcatggtg gtatgtacct    21840
gtggccccag ctactcagga ggctaaggtg ggaggatcac atgagcccaa gagtttgagg    21900
ctacagtgag ctgttttcac accattgcag tccagcctgg gtgacagagt gtgaccctgt    21960
ctcaaaaaaa aaaaaaaaa agaaaagaaa aagaaagaa aaggaaaga aaacaattgc    22020 ggatatatgt ccagaaagaa atgtacaaac cattgtagac aaatattcac agcaacatta    22080
ttcataatac caaaaaactg gaaacaagca aaatttctat cgactggtga atggataaag    22140
aaatgtagta tatccatgca gtagaatgtt atttagccat ataagggaat gaactactga    22200
tacctgctac aaaatggatg aactttaaaa attcatgcta aagtaaagac accagacaca    22260
aaaggcctca tattgtatga ctccatatgt atgaaatgtc cagcattggc agatccatag    22320
agacagaaag taggttagtg gttgccagga gctgaggctg aggggagggg ggatagagag    22380
taacagcaat ggatgtaggt ttgttttttgg agtgatgaaa atatagagtt agtggtgatg    22440
actgcacaac tttgttgaat tgcacatctt aagagtacat tttcagtttt gtgaattaca    22500
tctgaaatac agattttga aaatgaaggc aaaataagga ttttttttca gacaaaaata    22560
agtaagagat tttgtcactg atagacctgc atcaagagat atacaacagt gagttttca    22620 ggtaaaagaa aaataattcc agatgggaag caagttactg tagggtgaaa tgaagagcaa    22680
cagaaagtac tctaaatata tgaattaggc tgggtgcggt ggttcacgcc tgtaatccca    22740
```

```
gcactctggg aggcctaggt gggtggatga cctgaggtca ggagttcgag atcagcctgg   22800
acaacatggc aagacccagt ctctactaaa aacacaaaaa attagccagg tgtggtggcg   22860
caaacctgta gtgtaggcta ctagggaggc agaggcagga gaatcgcttg aatccggaag   22920
gtggagcttg cagtgagctg caactccagc ctgggtgaga aagtgagact ccagcctggg   22980
tgagaaagtg agactctgta tcaaaataaa taaataaata agtgaattac tatgattttt   23040
aatttcttaa catactaatg atgtaaacta tatgcagaat taaaatacac gaccatgaaa   23100
ccccaaaggt aagaagaggt gaataaagtt aaagaggact ttgtacaaga ggacttcaaa   23160
ttgtacaaga ggacttcaaa aagctcatgg aaacatggaa ttaaagataa caattaaaaa   23220
ataaactcta tttctcaaca taaattcagt caaggtcaag gcacttttgt aagtgatgat   23280
accaggcaca tagtccatct ccaaagaact gggggtcct gggaatatag ccatgtcaat   23340
gcaggctttt ttacattatt aactaaagaa aaatgggtga tcgttaaaga ttgcttaaga   23400
ttaggagaca aaaagaagtc agaaggagcc aaacaggact ttaaggtgga tgcctaattt   23460
ctcatggaag ctgtaaaatt gcccttattt gatgagaaga atgagcagga gcattgctat   23520
ggtggaggac tctctggtga agcttttcctg cgcgttttc tgctaaagct ttggctaatt   23580
tccccaaaac actctcatga taagcagatg ttatcattct ttggctgtcc agaaagtcaa   23640
caagcaaaat gccttgagca tcccaaaaac ctgttgccat gacctttgct tttcttgacc   23700
ggtctgcttt tgtcttgact gaacctcgtc tacctctttg gagccactgc tttgtcttca   23760
ggatgaactg gtaaagccac gtttaatctc ctgttacaat tatgtgagga aatgcttctg   23820
aatcttgatc ctattagttt aaaatttgca tggaagtttc tgctgttgtc tgcagctgat   23880
ctgggcacag tggtttggca cccagtaagt gggaagtttg cccaacttta attttttggt   23940
cagaattgtg taacctgaac taattgagat gtctatggtg ttggctattg tttgggctgt   24000
taatagttgg tcctcttcaa ttagggcatg aacaagatga attttttcct aacaaattga   24060
tatggatgat cggccacgga gggctttatc tttatcattg atttcgccat ccttccaccc   24120
tagttgcacc ataaatttga tgtttgttcc tgcttcaatt ttagcagaat tcatgttgca   24180 atgataggg cttttttgca aacagacgcc ttatccttct tagtgcctca aactagatcc   24240
tgttcagaca tgttatagca agttagtaca agtttatttt ggtgcagaaa aaagtttgaa   24300
ctttatgcat agttttttca taatttgaat tttccatgaa cttttggaag aattcatatt   24360
aggtagatcc taataataat aagtatgcat gttgtaatct ctaagataag cacaaaaaga   24420 atataaaga aagtacaatg aacaaactaa taggaaaaat ggaataataa ttttaaaac   24480 ttgattttct aaaaactaga acaaagaagg aagaatagat aggtcaaaaa agaaaacaaa   24540
tagcaagatg gtagacataa tcccagcacc atcagtgctt tcattgatgt ctgaaataaa   24600
aggcagtctt aataccaaaa cttgacatta aggaaagta gaattacagg tcaatctttc   24660
ccataaataa tctaaaaaat atctgaaaca aaatattaac aagtcaaatc taataatatt   24720
tataaaaata gataacatat tattatcaca ttggtttatt tcaggaatgt aaggttagta   24780
tgacatttag aaaccataat caatttcacc acattaactc aataaacaag aaatttata   24840 ttatcattta ataagttcag aaagcacatt taataaattg caacacccat tcatgatttt   24900
taaaccctgt caggaaagca gaaatagagg agtcttcttt aatctaatta cgatcacaca   24960
cacacacaca cacacacaca cacacacaca cactatacat agctaacatt atccttaatt   25020
gtgaaatatt gaacacttcc ttactgaggt caggcaaaaa acaaaaacat cttatactag   25080
aggtgctaat taacataata aggcaatgat aagaaacttt taatttataa agattagaaa   25140
```

-continued

```
actatgtgtt taagttatat aagaattgag gaaccagaaa agtccacgat actcaacaaa      25200
taaactatta gaataataat tgttattatt attcaaagaa gctgaagatg agatcaatat      25260
aaaaatctat tgtgtttcta acaatcagca aaattgacaa acccttagtt aaactaagaa      25320
aaaaagagag aagactcaaa ttaactaaaa tcagaaatga agaggagac attgtaacta       25380
tgtcacagag ataaaaagga ttctaagaga ctactatgaa caattatatg ccaacgaatt      25440
ggatacttca aataaattag taaattccta gacatataca acctacccat actgatcatg     25500
acaaaataga aaatctaagc agacctaaac tagaaaggag attgaatcag taatcgaaaa     25560
cctcctagaa aaaaaaaaaa aaaggccaag accaaatggc ttcactagag aatgctacca    25620
aatacttaaa gaatcaacac caattcatcc ctaacacttc caaaaattga acagtaggga     25680
acacttccaa actcatttta tgatgcccca gtaccaaagc cagacaaaga tgcaagaaaa     25740
caaaaccata gaccagtact cttgatgaat actgatgcaa aaatcctcaa caaaatgcta    25800
gcaaaccaaa tttaacaaca cattaaaagg ctatacacca tgaccaagta ggatttatct     25860
gcagaattca aggatagtta caaaaatcag ataaatgtaa tacatgaaat taacacaaag    25920
aaggacaaaa atcacatggt catctcacct gatgcagaaa agtatttga aaaaattcaa     25980
tactctttca tgataaagaa acattcaag gaactagaaa tagaaataaa ttacctcaac     26040
ataacaaagt ttatatataa aaagcccaca gtgaatatat tcaacagtaa aaaactgaaa    26100
ccttttcctc taagatcagg aacaaggcat ggatgcccac acttgccatt tctattcaac    26160
tggaagttct agccagagca attaggtaag aaaaagaaat aaaaggtatc taaattgaaa   26220
aggaagaaat gcaattatct ctgttcacag attacgtgat tttatatgta ggaaacccta    26280
aatattaaaa aaatggttag aactaatacg tgaattaagc aaagttgcag gatacaaagt    26340
caacactcaa aactcagttg cattttttac attaacaatg gacaatccaa aaagaaactt    26400
aagcaaaaaa tttcatttac aatagcatca aaaagagaaa agtacttagg aataaactta    26460
gccaaggagg agaaagactt gtataaaaca tttttgaagg aaattaaaga acacagataa    26520
gtgaaaagac atcccatgat catggattgg aagacttaat attgttaaga tgacaatact    26580
actcacagaa aactgaattt aatataagcc ctatcaaaat ctcaatgaca gttttttgcag 26640
aaataaaaaa agaattcatc ctaaaattca tatggaactt caagggaccc taaatagcca   26700
aaataatctt gagaaagaag aacactctaa aaaaaaaag aagaagaaga aggagaagga    26760
gaaggagaag gagaagaaag ctggaggcct cacatttcct gatttcaaaa tgtattaaaa    26820
agctacagta atcaatatag tatggtactg gcatacagat agatatacag accaatggaa    26880
aagaatagag agcccagaaa taaacccttg tgtatatagt caaatgatct acaaaggcac    26940
taagtctata caagagggaa aaggaagttt gttcaaggag atagtgctgg aagaaccaaa    27000
tatccatatg caaagaatg atgttggatc cttattttac tccatatgca aacattaact   27060
caaaatgggt taaagaccca acataagac ctgaaactat aaaactccta gaagaaaaca   27120
tatgggaaaa tcttcgtgaa attggaatgg caatgatttt cttgtgtgtg ataacaaaag  27180
cacaggcaac aaaagtaaaa atagacatat gagactacat caaactttaa aacttctgtt   27240
cagcagagga aataatcaac ggaatcaaaa ggcaacctat ggaatgggac aaaatatttg   27300
caaaccatac aagagatatg gggttaatat ctagaatata caaagaactc ctacaactca   27360
ataacaacac aaaaacaaat aactcaattt aaaaatggcc gggtgtggtg gctcacacct    27420
gtaatcccag cattttggga ggccgaggcg ggcgaatcac ctgaggtcag gagttcaaga   27480
```

```
ccagcctggc caagatggcg aaatcccatc tctactaaca aatacaaaaa ttagccaggc  27540
atggtggcag gcacctgtaa ttccagttac tcaggaggct gaggcaggag aattgcttga  27600
acctgggagg cggaggttgc agtgagccaa gatcacacca ctgcactcca gcctgggcaa  27660
cagagcaaga ctctgtctca aaaaaaaaa aaaaaaaaa aaaaggacaa aggacatgaa  27720
tagacatttc cccaaagaag atcagcaaat gcccattaag catacgaaaa gatgctcaat  27780
atcactaatc atcagggaaa tacaaattaa aactacaatg agatatcatc ttgcacttgt  27840
taggatggtt attataaaaa aaagaaaag aacaaatggt ggtgaagatg tagagaattg  27900
aaacccttgt gcacttttag tgggattgta aaatgatgcg aaactttaaa aaatttttt  27960 aattaaaaaa atagaaatac cagacatata tccaaaagaa ataaaaacag catctcaaag  28020
agatatttgc acacctgttt ctgcagcatt atttacaata gctaagatga gcaagtaacc  28080
taaatttatt gataggtgaa tggataaaga aaatgtagta catacataat ggaatattat  28140
tcagacttta aaaggagga agtcctgtca tatgttacga catggatgct tcttgaggac  28200
attctgcaaa gtgaaataaa ccaattgcaa aaaacaaat actgcattgt atcacttata  28260
tgatgtatgt aaagtaatca atctcataga aacagaaagt ggaatgctga ttgccaggga  28320
ctgggggagg gagaaatgaa aagttgtttt tcaatgggta tagagtttca cccatgcaat  28380
aggaaaaagt tctagagatc tcttgtaaac caatgtgcat acagtttaca atattgtact  28440
gcacatctaa aaattgttaa gggtaaaaaa gatctactgg ttaataaaat ccaaacccgg  28500
gacactatac tttgcactac aatacccctct cttgttagat tagcaaagga aaggatccat  28560
aaacattaca aaagcaaaga aaggcaggaa gccctcaact ggttgtcagt tgaagtgggc  28620
tgggtttgat agctatttct tttaacatct ggaactttag ctttaaaaag tgttaataaa  28680
gttgtaaagt ataaaaactc attatatttc tgtacactac aaacagtcaa gaaattttaa  28740
aattatgcca tttacatcag catcaaaaaa tcaaatatcc gagaagaaat ctaatgaaag  28800
atgtacaaga cttttttttt tttttgaga tggagtcttg ctctgtcact cagctctgtc  28860
actagaggca cagtctctgc tcactgcaac ctccgcctcc tgggttcaag caattctgcc  28920
tcagcctcct gagtagctgg gattacaagc atgcaccacc acactcagct aattttttgta  28980 tttttagtgg agacagggtt tcaccacatt ggccaggctg gtctcgaact cctgacctca  29040
aaagatccac ccaccttggc ctcccaaagt gctgggatta caggtgtcag ccactgcacc  29100
tagttgatgt acaagacttc tacacagaaa cctacaagac attactaaga aaaattagag  29160
aaaacataaa taagtggtgg tacatactat gttcatggat tggaaaattt aatactttaa  29220
ggatgctagt cccccccaaa ttgaagtaaa gtttcagtaa aatccaaagt ttcaagaaaa  29280
aaatctccag caagattttc tttggtggaa attgacaaga tagttctaaa atttatatag  29340
aaatacaaag gactgaaaat agtttagaca attttgaaga agaatgtcaa gatttataaa  29400
gtaatttaga aagtatggca ttgttgcaag gaaaaacaaa ctaaccaatg gaaagaaca  29460 gaaacagtag aaataaactc atgtattcaa ccacttgatt ttcagtaagt caccagtgca  29520
aggcagtgga gagaaaacat gatgtttctc taaatgatgg tatattaatt gaatattcat  29580
atggaaaaag taaccttga cccctacctt acaccataca gaaaaataaa ctacagatag  29640
actgtagacc taaatgtgaa aggtaaaaca gtaaatcgtc tagaagaaaa cacagaataa  29700
tatttttatc actttattgc aggcaacact tcttaaacag cacatagaaa gttctggtca  29760
taaagaaaga tttataaata aacttcatga aaattaagat tttttattga tcaaaagttt  29820
ccattaagag aatggaaaag aaactgaaag aggaagaggg aaagaattat atatatgtaa  29880
```

```
atttataata aaatataaat ataaaaatat ttatttataa atattatata tatttataaa   29940
atataaatta tatataataa acatatataa tttatttttta taaatatata tatggagaga   30000
gagagaaata aacacaattc caagtgctga aaaggataca gagtaactaa actctctgtc   30060
tctactcaat attctggtaa gagtgtaaat cgacacaacc actttggaaa acttctgctg   30120
agcagagact caacatttcc acttccaagt tatataacca aagagaaatg caagcatatg   30180
tgcccaagca gacatgtacc agcatgttca tagcagccat tatttacaac ctccccacac   30240
tggaaagaac ccaagttctt ggtttccctg tatcttttt ctgtcacacg attgaggaat    30300
gggatgcgtc tagttcctca agtcggccat tctctgcaat gtgacccagg tagggacatg   30360
gggctgaaag tgaaaggtgg gtagtgtggt aaaagtaaaa tggccctatt tcctataggg   30420
atcacaaaga aatgaggtgg gcgaagaggg actccccaga agtgccagga acaggagcca   30480
acaggtcacc agaagaggaa gtgttaaggc ggagggactt cccgagaggg aacacagaag   30540
aaagaactcc taaagttatc cagggtcttc aaggacttct gcccacctgc tctcctgctg   30600
gtcctcctct ctgaccttcc tgctatagct acagagctgt ggttcctcca actccattct   30660
tactccaacc gtgtcattcc atggctctct gttatccaca aaagaaaaac cccaaattcc   30720
ttgtctggta ttcaaggcat ttcgggatct agccccagt attcatactg gacttcaggc    30780
tcatcagacc actgacagcc tcaccaacat gctccattca cctggcttgc acacctgtgc   30840
atgtgctgtt ttagccacgg aaactatctg cccttttga ctgactgtta gcctcctact    30900
cagtcttcaa aatcccattc aaatggcagc tcctctgtca atctttgacc tctccaaaga   30960
gcatgagtca ctccttcctc tggggtccac cctccacata gtacatagct catggtgttt   31020
tcatctatat tctgggcacc atctaggcag ggacagtgtg tttctttgtt actgctgaat   31080
ccccagtaac taaccagtgc ctacagtggg tgctcaaaac atttgctaca tgagtgacta   31140
aatgaaagag aatgctttct atggaaacga attgtgaaca aacattatcc tcaatgttaa   31200
gacctatgta gaccgtacac tccaaagtta aatcttaccc tttttgaccc attttctgg    31260
agcttagggg attgagagcc ttatgtattt ggtgaggata cgttttttgt tgttgtttgt   31320
tttgttttgt ttttgagatg gagtcttgct ctgttgccca tgctggagtg cagtggcacg   31380
atcttggctc actgcaacct ccgcctcccg ggttcaagtg agtctcctgc ctcagcctcc   31440
caagtagctg ggattacagg catgggctac caagcttggc taactttgta ttttagtag    31500
agacagggtt tcaccatgtt ggtcaggctg atctcaaact cctgacctca ggtgatccac   31560
cctccttggc ctcccaaaat actgggatta caggcatgag ccaccgcacc tggccgagga   31620
taaaagcttt aatgcttcaa tctttttttc ctgcatcagg gcctttggac atgcctttcc   31680
ctctgcctag aatgcttttc ccccagcttc tttccttct catcctcagg tttcaagttc     31740
agtgttgcct cttcaaagag gcaaccctat ctgaactggg tctacgccac agatctctgt   31800
agcccacatc ccctagtttg tctccttcat agcaggtgta agatgaggaa tcgttttgta   31860
aatgtctctg tgtatgtgtt tgtaacttgt ttctgtactg aagcatgagc tctcagaggc   31920
tgggtaattg acctattttg ttcagcacag tatccctagt gcagagaagg ggacctgtag   31980
gtgccccata agtagctgaa gaagaatgtt aagtgaatga atgaatgagg ctaaaaatgg   32040
agacagcccc taagaggtcc tgctttcctc attagcttcc tcactgtccc cagaaactcc   32100
ccccagaccc acctcaggca acatcttctg cttccagagt gtgaataatc atgactaatg   32160
tcatcagatt agtaacaagg aactttcaga gaaggacagt gggctgccca gggtcacaca   32220
```

-continued

```
gcaagttctc atctcagtgg gttctcaggc tggggaagaa ctagcccagt ggccctgggt    32280
cagaaagcag actctgccat tcactcacag tgggaacttg gccgtatctc tgcctttctt    32340
tgagcctcag ctttcctcat ctgtggaatg ggggcagcag gcttagcctg gatgcggagt    32400
gtgaggcagg ttagtgtggt tagtattagg tgtgtggtta tgttagttg cttttcatct    32460
tttttttttt cgccagtggc aaggggtggg ttatgggtgt ctgaaggcag gtatgttggg    32520
gacctcaggc ttacagttaa tcagtagaag acgaaggtga gaggaaggc cttctcctcc    32580
ccagctcgtg caacctctga ggctgtgcga cctctcagcc tatctctctc tcctagccag    32640
gcagcaaatc tctattagct ccagcaatct ttccctcctg gcacttcttc cagcctgtgc    32700
aacctctcct agctgtggag catgaggtcc cagtcgcagc accgcacccc cccactcccc    32760
accccgctg cctgtgcaat ctctatctcc ctgcaagccc tgccatcctc tgcagccttg    32820
cccaaacctt gcaacctctc agcctctgca ccagatctc actccagctc catttcctcc    32880
agcccaggag gggccgcttg tagagcagtg aaaggaggct ttgaactatg ccacgagatg    32940
gagcggagct ggccacccac cgtctctctc ccctcagttc cagcagccc catcagccc     33000
gccctggccc tggccaaagt ggactggtgt tactgattca ttctggggaa agttggcaag    33060
ccctcgtcct agtcaagccc gcttggcaga tggggaaagg aggcccagag aggcccaggg    33120
ccttgtcctg ttcacacagt gggggatggc aggggcctgg gctaggaccc gggctggtgc    33180
acttgcccca actccccggg gacaattcag ggcagggtc ggggtggcca gatccttcct    33240
gtgggctgca gagatcagca ggctgggttc ctgatgcaga tgtcctgggc agtcggggc    33300
cctccttgtg gccctgccc cccagcctgg ggaatattct caggtcgttt cagaagttcc    33360
aagtttactc agaggtctca tttgagctgt catgaaaagt ccctttggcc tggggccagg    33420
gcagggagtg ggggcggtgg cacctgtgag ccaggggtgg gggtgggttc ctcccattgc    33480
cccctctccc tccccttcac gtgtccgggg gctccggagg gcagggaagg agggcatgtg    33540
aggaaggggc tgcgagggca agaagaccct cttcctggag gaagcatctg ttcccctctt    33600
ttcactgctc ccttctagac ggttccctga gtgaccctag aaaaaccccc acctgctct    33660
gaacttcagt ttccccatct gtaaaagggg ggaagcagaa tcatcataag agctcttatt    33720
tactgaggtc tcatatatgc caatatgacc aataatattt attattttt ttctgtattt    33780
tcatagctaa aagcaaagag ctcttacata tttaaagtaa acataggcc ggccacggtg    33840
gctcatgtct ataatcccag cactttggga gactgagaca ggcagatcac ttgagcccag    33900
gagttcaaga ccagcctggc caacatggtg aaaccccgcc tccactaaaa atacaaaaat    33960
tagccaggtg tggtggcagg tgcctgtagt cccagctact cgggaggctg aggcaggaga    34020
atcgcttgaa cctgggagat gaaggttgca gtgagttgag attgcgccac cgcactccag    34080
cctgggcaac agagcaagac tctgtctcaa aaaaaatta aaaaaaaaa aaagtaaaac    34140
atgatagcgg gcacttctca tgagccatct gtgcccagct cttttgcctt ccccatcaca    34200
ctggctctct ctgtgtaccc cagagcttca ggacctaggg aggtgcctgg gccatggtag    34260
atgttccata aagaataggt tgagtaaatc ctcaccacag acctaagaca ggcattctta    34320
ttcctatttc cactcttaca gatgcagcaa ctgagctgca gaaaggttag gtggcttcct    34380
caaggtcaca caggtactaa gcggtggact tgaacccagg tctggccagt tccacagctc    34440
aaagtcacaa ggggtggtgt gctgggaagc cagttccagt tcccccatct aaccgcaggc    34500
accccttcct agttgtgtgg agaaggcccc tgtgcctgcc tgtgaggatg ctgaaggcgc    34560
tagcttccct ctctggctgt ggaaggaacg gatacccgt tcctttcatt catttattta    34620
```

```
tcaggcacct gggttgtcct gatgctacaa agaggtgggt tcctcccaga acttctggtg   34680
gctggctttc tcttgaatgg gcctcctcct ctggtatcca cccccctactc tactgcccac   34740 aagcccctta ctggctctaa tccccacctc ccagtttctt ctcctagcct gaaaccagga   34800
acgctgggca gtgggagcct gcagtctgag ctcagagctg tctttgcctt gctctcccca   34860
cctctcctgg tcctggattc tgcctcctcc tatcacaagg gcttttagct acctccactg   34920
tgggactgag taaggatccg gacaccctcc tggcagagga gcgggcagga cagggcatc   34980 gctgagccca cggtggggag caggtgagca gggcctctcc tctgggggtt gcctgtcctc   35040
gtgggaatga atactccgcc atccccatcc aatgctgctt cccagaagct acccaagccc   35100
atgagtcttg ttttcatgtt attctatcta gcaggtggtg gccttgtcct acagactggc   35160
atccaatccc agctccatgt catctggtca cagttaacct ggggcaaggt tgtccccact   35220
aagcctcact cttgtcatct gtgaaatggg ctgaatgagg ctgcccgctt cacctgttga   35280
ggactatggg agacgcttaa gtgcctacaa catggtgagt tggcactggg ggggccagag   35340
ccaggtggct ggccaggcag gaccacagca gcctgagtgt gtcgctcccc ctctgtcact   35400
cttggagtcg ggcccgtctc catgggctca aagcttctca tgccacaaac tctcttcctc   35460
aaaggaaaag ggccattagg agcacagctt tcaccctgtt cggccctgag gtccccacaa   35520
ctagctccac caggatgggg gtaccttggt ccccatttca tagatgagaa aaccatggct   35580
tctcaaggct agaagcagag agacttgccc aagttcaccg agtgaggaag gcgcgtggcc   35640
gggttttgac ctggcaggtt ttccccgact ccaccatgtg cttctgaaag ccccactctc   35700
cccccaggga atcacagatg tcctcctcgc agcagcctcc tggctttgaa tgtcccgcac   35760
ctggtcttct gccttcactg agcagagacg tcattcctgc ggcaagtcct aagttcccgc   35820
tccccagggc tcctccacca ggaatgttct tcctttccca tccttcaagg ctcagcctcc   35880
actgacctcc ccaccctcct ctcctccaca tgcacaggga actgggttgg cctcttacca   35940
tccgacccgt tccccgtgct tcatgagaaa gatgcagcga cagctcatgg ggtcacctgg   36000
cttgactgcc cgacctgcta cgtcccagtt gagtcaccga gggaaaatca ctctacctct   36060
cgcagcctca ttgcctcatc tgcgaaatgg gcacaccagc cattgttttg aatgactggg   36120
tggaatcaag gtggtaagac atagaaactg acacagaatg gtcccatca ggctctacac   36180 ccatgcccgt cacctcccga ctcagccgcc cagaatcggg tgattgacat gttatgtttg   36240
gcttgaaact ggctttcctt ccccagcccg ctacattttg gaggctggtt ttcaagatag   36300
agggtcgtct cagccacatc cctgctgctg ggcccctaag ctgtgctgaa caagagaccc   36360
caacctcatt tctgcccagc ctcactgcat gaatcttctt tgcctcagtg tccccaattg   36420
tgacttgggc acagtcctcc gagccctccc actgtgacac tagatgcagc aggcagggaa   36480
cagtccctcc tgggcagaga aggcaccctg gtcccagcag aaaaccaggg ctggaattac   36540
cttctgtttc ggcttctttc tcagaaatcc attccgtgtg ctgggggcag tctgatgggc   36600
ttctgggggt ggcagctggg ttcagcgtgg gggtgacaga tgagggtctg agaaagcagg   36660
cagaggcctg gggtgagaat ccacacccag cccgagtcac caatcaggct gtcataagac   36720
ctgtcactct gatgacgggc agctgggcct ccaggcaggt gtcccacaga gcagcagaca   36780
gaggaaagag acgcaaggaa aggtaccagg cggccgcagc agggatgcac gggccgcaga   36840
cagacagaca cagctgcgtg gctgtcagcc acactcaggg agaggcaggc agagggccag   36900
acgccgagct tacggtcact cagcagagag acgccagtgg gtctgtctga ggccgctggc   36960
```

```
tgccacccag ccgcatgtgc agagtgggga ggaagaggag gatgtggtga gccgctcccc    37020
gccagccccg cccacccgca gctgggctcc tcctgggagg gagtgagaaa gaggtgggag    37080
ggggcctggc cccacagcag gcacccactg tcaccaaagg tcacctgcaa gtaagacatt    37140
tggggccatc ggggtgacac ttccctctta gggacctgtg acatcatccc cacaggcctc    37200
tcagtcataa cccatgaggc aggcagtgcc tcctggagcc accacattgc acagatatgg    37260
aaactgaggc cagaggtgtg aagatgtggc acagtttcac ccgtggaccc agagtcctca    37320
gtggccgact ccagcccctc agcacagaga gaaggaccag aaccttgccc aaggtcccac    37380
ggaagcccct ttttcagact ttgcaaacca gcctgtttct tattcctgag ccttacctgc    37440
ctaatagggt ctgagcttgg gaccctctgc tctggcttga ccccatgcc tctctgcctc     37500 catttccttt ggatccagtc tcctgctgca gagctccagg gagcaggacc ccttgggcac    37560
gtcacatcac ctctctgaat gcctcacttt gcccatctgt caaatggggg cacctagcta    37620
tgaggaagag ggcagacatt aacacatgag aattcaagaa gaaatagag aaagaaatt      37680 ctcaagagag ttttcatctt gctaacatgc cagaggccca tgagagggtc agatgtttct    37740
ggaagacatt caagaaacca ggagacaaaa tgtaacaagc ttaatgccta gtgcagtctc    37800
caaaggagag caagagaatt gctaccacca ccaccgctac caccaccacc actaccactg    37860
ccatcaccac cacctcgaat tactttggtg cctacatgat ctcactttat cccacaaagt    37920
gtgaggcaga caagattagt cccattttac agatggagag actgaggccc agaggagtga    37980
aacgtcacac aagccaagaa gaattagagc tgggatttga acctgggtgt gtttgattcc    38040
taagcttata ccaggctgtg aaaacggggc cataccagga tgaaatgtcc cacagttggg    38100
ggaggctatt ttatgctgtt ttgataacaa gatgcaattt gtagctctcc ctgctgactc    38160 attttttggga atcaacttgc tgttgacttt cgtgaccact ccagagaaaa aagagaaagc    38220
gtcttgctat tctttctttc ttttttttc tagctgtttt tgaggaactt ggtacaaatt      38280
cccctgtggt tgatttgagg gatcctggcc ctgtagagct cttcccagct accgaagtgt    38340
gtcgtgttct ctggagaacg aaccttggga agacaccagc ttttgttttt ctttctcttg    38400
atcttcgggg tgaattctct gataacatgc actgaaattt gtagtggttg aaagatcagg    38460
agaagagaca gtaaaagag ctaatatttg ctgaaagctc attgtgtgcc agggtttaa      38520 ggactttaaa gatgcaccct ctcatttaaa cctcagaaat actcgagaag gctgtgtgca    38580
gcggtgcaca cctataattc catcattttg ggaggctgag gtgggaggat cgattgaggc    38640
taggagttca agaccagtct gggcaacata gcaagaccct gtctctataa aaaatttaa    38700 aaattagaca gtcatggtgg tgcacgcctg tagtcccagc tactctggag gctgaggtgg    38760
gaggaccact tgagccaagg agctgaaggc tgcagtgagc tatgactgta gtgctgcact    38820
caagcctggg caacagagca agactctgtc ttcaaaaata aaatcccaa aatgaaaaag    38880 aatgagtcta gaagatagtt atcatcatca tcatcatcgt ccctgtttta cagatgagga    38940
aactgaggct cagagaggtt aagtgacttg tccaaggtca cacagctgat gagtgccaga    39000
gttgggattt gaactcagtc atttgggctc cagagcccgc actcttaact cactacactg    39060
ctctggggtg tgtatgaaaa caaggatatt caatttctcc tccctccctc ctgcctgcct    39120
tctttatcta cctgctttct acccaccac ctacctatcc acccattcat tcttctctgc      39180
acccacccac ccagccattc cttgcttcct cccctaata tttattgagc aggctcagag    39240
aggttaagtg acttgtccaa aatcacgcag cttggctaca tcctgggct agcccacaga    39300 aatatacaca cagtgacagc ccccatggag cctatattct agtagggaga gttagacaaa    39360
```

```
aagaagtaac agacaaactc aatgtaaact gtactaaatg tcatagaaaa ccaatgagag    39420
atcaaggttg tgacatttgg gggtacacta ggtgctaaga agtgcccagc catgggaaga    39480
acattatcgg cagaaggatc tgcaagtgca aaggcactga ggtaggaaag aatgtggctg    39540
gctccaggaa cttgagaaca gcatggcgta atacagtgag caaatggagg aatagtagaa    39600
ggtgaaggca cggaaatcac acatctacac cacatgggac ctcacggttt tgggtgagga    39660
aggtagattg ttccaaagga aatgggaagt catcattgga gggtttcatc ttaagagtgg    39720
cttaatccag tttacatttt cagttccagc caggagttgg ggaatgggtg ggatcagcag    39780
gggtcacagt cccttggtgc ttaaaaagta gatgcatttg gagctgccag gcccatgtcc    39840 actgggtaa acatgagtcc cctcagaaat agacatgtgg tcccttgagg ggttcctctg     39900
ggtctgtaaa tgtctcataa gtatggcctc tatacccttg gaaggaaggt gccataggat    39960
ctcagcggcc ctccaaccat gcctcagtgc tgatagctgg tcagcgggga ggaagtggtc    40020
acatttgcat ttcagccaag gggcctcctg ggaaaaaata attgacacac cccctccctc    40080
aacccatttc ctctttttta ttttttatttt aagagcttta tttagctatg ttttacataa    40140
cataaaatca agccactgta aatgtacagt tcaatgattt ttagtgaatt tatcgaattg    40200
tgcaattata accacgatcc aattttaaaa caatcccatc actcctgaaa ggttccttgt    40260
gcctgcttat agtcaatctc cattcccatt cccagggcca ctcgtctact ttatgcctct    40320
actgattttg cttttttttt ttcctaggca tctcatatca atatgttgtc ttttgtgttt    40380
agtttctttc agcatcgcgt gtttgggggtt caaccacgtt gtagcgtgtg ttggcaccac    40440
atatctaaaa atccattttt aggccaggcg cggtggctca tgcctgtaat ctcaacactt    40500
tgggaggcca aggtgggcgg atcacttgag atcaggagtt cgagaccagc ttggacaaca    40560
tggtaaaacc ccgcctctac taaaaaatac aataattagc ctggtgtggt tgcacacgcc    40620
gggagattga gaccagcctg gccaacatgg tgaaaccctg ttctactaaa aatacaaaaa    40680
ttagttaggt atggtgacgt gcacctgtag ccctagctac tcaggaggct gaggcaggag    40740
aattgcttga acacgggaag tggaggttgc agtgagcaga gctagtgcca ctgccctcca    40800
gcctgggaga cagagcgaaa ctccatctca aaaaaataaa aataaaaat tgattttat      40860 tgctgaagaa tattcacattg catagatatg ccacattcat ttatcctttc atgagatgat    40920
ggacatttgg agtatgtcca cttttttcctt tactacaaac aagcatgcta tgaacacttg    40980
catgcgagtc tttgtgtaga catgcatttt caaatctttt ggatatatac ccagaaggag    41040
acttgttgag ttaaaggtag tttaacttat taacttttaa ataagtttaa cttattaaga    41100
aactgacaaa ctgttttca cagcagctgc cctgtattat attcccacca gcaatgtctg     41160
aaggttccca tttctctacg tccttgacaa tatgtatttt ctttttttttt tttttctttt    41220 tttttttttt tttgagatgg agtctcggtc tgtcgcccag gctggagtgc agtgcgcga     41280 tctcggctca ctgcaagctc cgcctcccgg gttcacgcca ttctcctgcc tcagcttccc    41340
gagtagctgg gactacaggt gcctgccacc acgcctggct aatttttttgt attttctttt    41400 gtagagacgg ggtttcaccg tgttagccag gatggtctcg atctcctgac ctcgtgatgc    41460
gcccgcctcg gcctcccaaa gtgctgggat tacaggcgtg agccaccgca cccagcagac    41520
aatatgtatt ttctgttggt ttttattata gccatcctag cggatgtgaa gtggtatctc    41580
attgtggttt tgatttgcat ttccctaatg gctaatgatg gtaagcatct tttcatgtgc    41640
ttggtagtca tttgcatatc ttgtttggag taatgtctat tgaagtccct tgccaaattt    41700
```

-continued

```
tatttatttt attttttttt tagacagagt cttgatctgt ctcccacact ggagtgcagt    41760
ggtgtgatct tggctcactg aaacctctac ctcctgggtt caagcgattc ttgtgcctcg    41820
gcctcccgag tagctgggct acaaacgtg tgccaccata tccagctaat ttttgtgttt    41880
ttagtagaga cggttttca ccatgttgac caggctggtc tcgaacccct aacctcaggt     41940
gatccgccca cctcagtctc ccaaagtgct gggattacag gcataagcca ccgtgcccag    42000
ctccttgcca attttaaat ttgattgttc atcatttgtt gttgaatttt aagagttctt     42060
tgtatattct ggaaactcac ctttatcaga tatgaatt acaaatattt ttcccattct      42120
gtggctgtct tttcactttg ttgatagtgt gctttaatgc aaaaaaaatg aaaaaaaatt    42180
gactatagat tcatgggttt atttctgaac tctaagttca attccattga tctatatgtc    42240
tagccttgtg ccaggattat cacactgttt tgattactgt agctctgcag taagttttgt    42300
tttgttttgt ttttgttttt gtgttgtttt gagacagagt ttcgctcttg ttgcccaggc    42360
tggaatgcaa tggcacaatc ttggctctgc agtaaatttt aaaatgggaa atttgagtcc    42420
tccaacttta ttgttttggc ttttctgggt cccttgaaat ttcacatgat ttttaggatc    42480 agttttcca tttttaaaa aaggccattg ggacttttat aggaattgca ttaaatctat      42540
aaattacttt gaggagtgca atgttaaatc ttccattaca ttaacataga atttaaaaaa    42600
ctttatttag gtcttttcta atttttttcag caatatttta tagtgttcag tgtacaaatc   42660
ttgcacctcc ttggttaaat ttattcttaa gtattttatt attttttgatg ctattataaa   42720 tagaatttat ttaatttcct tttgggggttg tttattgcta gtatatacaa acacaattta   42780
tttttgtatg ttgatcttat accctgtcac ttggctgaat ttattagctc taataatttc    42840
tttgtgcgtt ctttagaatt ttccatatat atgatcatgt catctgcgaa taacagtagt    42900
ttttactctt tccttttccc atttgaatgc cttttatttc tttttcttgc tgaattgttc    42960
tggttaaaac tttcagtgca atgttgaata ccagtggtga aagtgggcat cctctttcct    43020
gatcttggtg gaaaagtttt cagtctttca ctgatttagt gtgatgttag cttgttagct    43080
gcgggttttt ctttctttat ttctctttct ttctttctct ctttccttct ttctctgtct    43140
ctctcttttt tatttgagat ggagtctcac tctggtgcag gttggagtgc agtggcatga    43200
tcttagctca ttgcaacctc atgggttcaa gtgattctcc tgcctcagcc tcccaagtag    43260
ctgggattac aggtgtgtgc caccacatcc aactaatttt tgtattttta gtagagacag    43320
catttcacca tgttgccag gctggtctcg aactcctgat ctcaggtgat ctgcctgtct     43380
cggcctccca aagtgctggt attacaggca tgagccactg tgcccagcca ggttttcat     43440 atatggtctt tcatgttg agggagttct ctcttattcc tactttactg agtgttttta     43500
tcatgaaagg gtgttaaatt ttgtcaaatg cttttctgca tcaatttgga tgatcgtgtg    43560
ggttttctta ttctattaat gttatgtatt gtattgatta attttcttat gttgaaccac    43620
ccttgcattc ctgggataaa tcctttttgg tcacactgta taatccttt aatgtgctgt     43680 agaattagtt tgcttgtatt tttgtgaaat tttatatcta tattcataag gaatattagt    43740
ctgtagtttt gttttcttgt ggttctcttg tctggatttc tctcctgttt tgtggaggag    43800
tttgagaaga actgatgtta attcttcttc caatgtttag tggaattcac cagtgtagcc    43860
atctgactct ggacttttct tcattgggag gttttgatt caactccttta cttgttgtat    43920 gtttattaag attttctatt tcttcttgag tcagttttgg cagtttgtgt taccaaactt    43980
taatatttaa gttgacaact attattatct aatttgttgg catacagtca ttcacagtac    44040
tcccttatga tcctttttat ttctgtatga tttgtagtaa tattcccact tccatttctg    44100
```

```
attttagtga tttgtattgt ttcttttgct tagtccaact aaaggcttgt caattttgtc  44160 aatcttttg aagaaacgac tcttggtttc tttcatctct attgattttg tattctttat  44220
tttgcttgtt tgcactctaa tctttattat ttccttcctt ctgctacctt tgggtttcat  44280
ttgtccttct ttttttagtt cctttaaaag taaagttagg ttatgatttg tgatcttatt  44340
tgttgttttt tttaatgaa ggcatgtagg gctacacatt tccctgttag cactgctttt  44400
gctacatccc ataattctgg gtgtgttttt ggtgctttca ttttcatttg tctctaagta  44460
ttttctaatt tccttgtgat ttcttcattg acatgatgac tgtttaaaaa tatgctattt  44520
aatttccaca taattgtaaa ttttccagtt ttccttctgc tattgatacc taacttcatt  44580
gtgatcagag aagacacttc atatgatttc aatcttttaa aatttatcaa gacttgtttt  44640
gtggcttaac atatagtcag tcctggagaa tgttccatgt gcactttgtg gtcactgtta  44700
ttgttgggtg gagtgttcta tgtgtgtcta ttagctctgg ttggtttata gttgtacaag  44760
tcccctactt tcttagtctt ctgtctagat ggtctccaac tattattgta gaactgtcta  44820
ttcctctatt cagttctgtc aatatttgct tcatatattt ttgggctctg atgtttagca  44880
catgtatggt cataattatt atgtcttctt ttttttgaga cagagtgttg ctctgtcaca  44940
caggctggag tgcaatggtg caatctcagc tcactgcaac ctccgcctcc caagttcaag  45000
caattctctt gcctcagcct ctcgagtagc tgggactaca ggtgtgcacc accgtgccct  45060
gctaattttt gtattttag tagagacagg gtttcgccat gttggccagg ctggtctcaa  45120
actcctgacc tcaggtgatc cactcatctt ggcctcccaa agtgctggga tgacaggcat  45180
gagccaccac ctggccaatc ttcttgacaa attaacacat ttatcaacat gtaatgtcct  45240
tgtttgtctc ttgtaacaat ttttactta agactcattt tatctgacat tagtatagcc  45300
acctcagctc tctcttggtt tctattttca tagaatatct ttttccatcc tttcactttt  45360
aacttatttg tgtcttttgga tataaagtga gtctcttgta gacagcatgt agttggatca  45420
tgttttttaa ttccttctgt caatccattc tgtcttctaa tcagtgaatt taatctactt  45480
acatttaaag tgattcatga taaaaggctt accactgcat tttgctattc atttcattta  45540
tatcaaattt tcttttgtta ttcaattccc tcattacctc cttctcttgt attgattgat  45600
tttcttctag tgcaccattt tgatagcctc ctcatttctt ttctgtatat ttttagttat  45660
tttcttagtg gttaccttga ggtttacact tcacaggaaa tttataacaa tatagtatga  45720
attgataaca acttggttta aatagcaata caaaaactct actcctatac agctccctct  45780
actctattct actcctatcc ctcccctct tttgttgtca ttatcacaaa ctacatcttt  45840
atgtggcatg tgctcattag catagattta taattatttt tatgtatgta tcttttaaat  45900
aatataggaa acaaaagag gagtcataag ccaaaatat aattatacta gtttttatat  45960
ttacctttac tagtgttctg tatttattca tatggctttg atttactgcc tagtgtcctt  46020
tcatctcagc ctgaaagact ccctttagtg tttttcatag ggaaagcctc ctagtgatga  46080
aatacttcac cttttttttt tgcaatcttt gaatgtttta atttcttaat cattttggaa  46140
agatagttgt gccagataaa gaattctcag ttggcagggt ttttccttc agcactttaa  46200 atatatcatc cttctgtctt ctggccttgt ggcttctgat gagactttgg tcattaatct  46260
tgttgaggac cccttgtatg tgacaagtta cttctctctt gctagtctcc agattctcga  46320
tttgtctttg tctttcaaca gtttgattat aatgtgtctt ggtgtagatt cctttggttt  46380
tatcctagtt ggagttcact gagcttcctg gatgtatata ctcatacctt tcatcaaatt  46440
```

```
ttggaaatgt tggcctttta ttcaaatatt ctttctggtc ctttcttct cctccttctg   46500
ggattcacat aatgcatatg tttatacctt tttttttttt ttgagatgga gtctcgctct   46560
gttgtctcac aggtctctca ggctctgttt attttattc cttttactt tatgctcctc   46620
agactggatt atttcaattt acctagcttc aagcttattg attctttctt ctgcctactc   46680
aaatctggtg ttggagctct ctaataaatt tttcattttg gctattatat ttttcaggtc   46740
caaaatttct atttggttat tttaaataat gtctagctct tattgatatt atctacttgt   46800
tcacacgtag ttctggttta acttagttct tcactcatgg tttcctttag cttttgagc   46860
atatttaaga caattgattt aatgtctttg tctagcagct ccaatgtctg gactttttta   46920
gggacatttt ctatccattt ttccccgtg aatgggctgg gtgttcctgt ttctttgtat   46980
acgttatagg ttttgttgg aaacttggca ttttgaatgt tacaatgtga taattctaga   47040
aatcacattc tcccttcccc tgtccacaag gcttgctttt gtcatttgct gtgagcttca   47100
gccattcatt tacttagtga cttttccaaa ctatttttgc aaagactata tcccttttg   47160
tgtatgttca ctgaaatctc cattctgtta tctcagcagt tggtcagtga tctgtaagag   47220
gtttccttat atacctgcag ccaaaaagaa aacaaaaata aaagatactc ccctagtctt   47280
tgtaaattgg ctctgagctg ggatactcct ttacacttag ccaggcagac tacaattctg   47340
tcttagcctt cacctctgct tgtgcagagc ccaattagcc agaggtgcaa gcctaggatc   47400
atctcatatc atttctgtgc atgacttcag ccctgggcat atgtgttata ttctagattc   47460
cctggtatac acggaagctt ttcaaagccc ttattccccc atatacattc ctccttagtc   47520
tttttcttct ccagcttttt ggtcggtctc tgcttttgc tttgtctgtc atcctttgcc   47580
ccacatgggt agtgtgtgtc tttaaagttt gtcaacagac attgcctggg aagctgctcc   47640
agcctagagt tcagggaag tgggagggca aaacaaaggc aagcacctga gtggatcctt   47700
tagggagatg ccaaacagat caaaatgtag aaacacaatt ctttgagacc aaggcttgtg   47760
ttgttctttc tggtaccagc aagccatgcc aagaatgcag gctactgtac tcatagccac   47820
gactaagctg atgaatgtga gatggtaggc aagtaagcaa aaatgctaca gtattttctt   47880
accaagaatt agcagccttt tctggttgct aaagggtttt gattagattt caggttccaa   47940
aaaagtttct tttgacactt tcttccagct taatgtttgc tttagtggag gaactgatcc   48000
ttggagttcc ttactctgcc atttttaaat aatgtactta atggtgtttt ttttcttttg   48060
aagcataacc cttttaaatt ttattgaaac ccaatttatc aatttttttc ttttgtggat   48120
tggactttgg gtgccatatc taagaaatct tcacctatac caaagtagca aaaatctcct   48180
ctcatatttt cttctaaaag tttaatagtt ttagctcttg catttttatt ttttattatt   48240
tgtttatttt ctgagacagg gttttgctct gttgcccaga ctggagtcca gtggctcact   48300
gcaatctcag gtcactgcaa ccttggcctc ttgggttcaa gcgattctcc tacctcagcc   48360
tcctgagtag ctgggactat aggtgcatac caccatgtcc gcccaatttt tgtatttttg   48420
gtagatatgg ggtttctcca tgttgctcag gctggtcttg aactccgggc tcaagtgatc   48480
catctgcctt gacctcccaa agtgagccat tgagcccagc cttaccttt taaaattatg   48540
attttgactt aatttgtga atgctgtgag gtaatgatct aaatttatct ttttcatat   48600
aaatatctaa atgtttcagc acaatattta gaaagattg ccctctccct tttgaattgc   48660
cctgacacct attttgataa ttgactataa atatatgggt taatttctgg accctgtatt   48720
ctgattcatt gctttatatg tctatccatt tactagcacc ttactgcctt gattgctgta   48780
gctttgtagt aagttttgaa atcaggaagt agaagtcttc caaatttgtt ctgctttttc   48840
```

```
agaattgttt tggtcattct gagtcctttg catttccatt ataaatatta aattccatat    48900
aagtttcagc ttgctaattt ctgcaaaaac tcctactgga attttgacaa ggattgtctt    48960
gaatcaatag atcagtttga ggaaatctac caccttaaaa acttggagac tttcaatcct    49020
ggatataggc actctctcca tttatttaga tctttgaaaa ttcttctcag acaaccgctt    49080
cctcatccat tcattttttt aaattaattt tttattgtaa taaatacaca tcacatgaca    49140
tgtatgatat ggtttggctg tgtccccacc caaatctcat ctgggattgt agctcccata    49200
gttcccacgt gttgtgggag ggagcctgtg ggagataact gaatcatggg ggtggttttc    49260
cctatactgt tcttgtggta gtgaatgagt ctcacgagat ctgatggttt tataaggaga    49320 aaccccttc acttggttct cattgtcttt tgtctgccgc catgtaagat gtgccctttg    49380 cttctgcct ttcaccatga ttgtgaggcc tccccagcca catcaaactg tgagtccatt    49440
aaacctcttt ttctttataa attacccagt cttgggtatg tctttatcag cagcgtgaaa    49500
acagactaat acgatgtacc atcttatcca atttaagtg taagttcagt ggtattaact    49560
gatgcattcc tttctgaggt ccaacattgt ggggttcctg taatggacca gatggtctgc    49620
tgagagccac agccaagaaa gggcagggga tgtttcatgg ggagcaaacc acaaaggaag    49680
gagacgtcta gagggctgga ttgtgcgcaa catgtggctg aaactgggaa ccccctttc    49740 actcagttac cctgagacag caggtttatt ttaagagcga tggctgaata taagaaaaa    49800 actaataaat agtgccctca gttatgagta acacagaaag aatatgttta tcctgcctta    49860
aaagctcatc ttggtttgta ttaggctctg gactaatagg ggtatcattt aagcagatga    49920
taagactaag aattttgtaa atttcttttcc aaaattagga tctctaatgg gctgatcaga    49980
ctgccctagc cattgatcac atcacttgct gtttggcaca tgagttgtgt cttggttggg    50040
ttcccccaga ggcaaattct aagacaagga tttaaggata agtcatagat ttgggaaata    50100
atcctaggaa acacagggga atggagaagt ggggcaggca aagcgaggaa gccagtaaag    50160
ggcgctttaa ggagaaggcc actgctgttg gcaactggag ctgaatccca ctgggtacct    50220
ctctgggaga caatatagaa catgtctcca acttgtccca aaggagaaac aagaaatctg    50280
ggatatttct tttccaggac ttcatttgtt gttagttgag ggctgcttcc agggccacga    50340
ctctctgaca cttccagctt gccgattgca tgcacctgtt gccaaaaatg aaccctcacg    50400
cagggagttg caggtgtttg cagtacaaat gctttggtgt ataaagctga gaagttaagg    50460
gtaaggcttc aacatctgct acagggacca tgatagggac aattaattgt gtcccagctt    50520
ccatcttgtc cttctttctc atatcaggac catagtgtaa ttctggatgg caacagaccc    50580
agctaataga ccacttttcca gtttcccttg cagctagtga tgggagtgtt cacatggacc    50640
ttctggaagc actctgtggc ccttccagta ttccccttcc tcctttctcc tgcctaaagt    50700
gtacacgtga tggctggagc tcaagcagcc atttagaact aaagaaaaag aataggataa    50760
tcacagagaa cttggccctg atatcatggg tcatgaacaa atgtcagcaa tcatttgtct    50820
ctagacttct cgttccataa aggaattagc tcttaagtgt ttaagccact gtggttggtc    50880
tctattagaa gttggaactt ctaaccatac aagggattg agtgactatc aaaaggatga    50940
agaggcttat ctgtgtaccc aaactggtga agcaagaaat aaccaggtat gctgtgtgta    51000
taaagtactg actaggttga aataaatcat gaagagaggg ttggatgaat aatttataaa    51060
acatctgtga aacagaatac tctgtagcta tgccatgtga ggacataaca agaaggtggc    51120
tgtctgcaag ctagaaaggt tgttcagaag acaaccatca accaccttga cttagactac    51180
```

```
cagcctccag aagtgtggga aaataaactg ttgcctaagc cacacagtct atggtatttt   51240
gctatggcag cctgagctga ctaaaacaga tgtatctgta ttagtcagtg ttctccggag   51300
aaacagaact gtaaccaaca caattattaa taacaataat acaaaattgt ttacagttgt   51360
aagggacttg ccatctgcaa taagctatca aaaccacctt ttattttaat tttgtatttt   51420
tgagacaggg tctcactctg tcgcccaaac tggaatgcaa tggtgtgatc atggtgtgat   51480
cactgcagct taaacctctc aaactcaagc cattctccct cttcactctc ccgagtagct   51540
gggaccacag gtgtgcacca ccgcgcctgg ttaagtttta aaaagctttt tgtaggaatg   51600
aagtctcatt atattgccag ggctggtctc aaactcctgg gttcaagtgg tcctcctgcc   51660
tcagcctcct aaagtgttgg gattacaagc gtgagctgct gtgcccagcc ccaaactacc   51720
ttttaatatc cccatttag acataagaaa acaggtgcag gagactaagc aactggtcca   51780
caggcacata gccagtaagt ggcggggtca agatttgaac ctgggccgtc tagcctcaag   51840
ggttaatagg cccatttctg ggtggtggga attttatttt ttaatttttt atgttattct   51900
gtattatctg attttaaaa tgatatctta cttctggaat ctgggaaaaa taaccaagct   51960
atttccattt tgaagagaaa aaaaaaagga catcacaaaa catcagtatg gtgggaaaag   52020
ggtgcagaga agggaaggta taaaaaaatc tatagagatg tgagccatgg tcccctgaa   52080
gcatgtgacg tcctttactt caagccagat attcaattac atgtatatga agattagaac   52140
cacagaacca acatgtcaca tggaaaatgc ttgcgagatt ttcccaaagt caagagtgtg   52200
tcacagccaa ggggaacctg aagcacccta ggttgcatt aatagaggta tggtgtccag   52260
aacaagggag gctattctca ctgcactggc cacaccttca gtctacgtcc agttctggac   52320
cttcattttt aaagaacatt ggcaaattga tgtatattca gaacaggcaa ccgagaaggt   52380
agagcagctg gtgtggagac agtaaaaaaa accatgagac agcagaagta tttggaaaga   52440
gaagactcag ggtgggggtc atgagcaggt ccagaccagc atagtcagag ttgatgaact   52500
ggagaagaca gtgagctccc tgtccctggt atgtaaacaa ctcctcactg tgggggtatg   52560
gttggattaa ctgagtgtgt ggttggacca agggcaatga agtctccttt catgctgagt   52620
gtctgtgtgt ctctgattct tagaaagaca taggagggct taccatggag ggagataatt   52680
atggaccgaa tgtgctgctt tcaacctctg ccaaattcat atgctgaagg cttaacccac   52740
aatgtggctg tatttggaga tgaggccgct aaggaagtaa ttaaggtgaa atgagctcag   52800
aagggtggga ccctgatctg ataatgttag tgcccttata agaagagaca ccagggagtt   52860
tgccctcaat ctccctcaca gcaagaaggc agctgtctgc cagccaggaa gagagccttc   52920
atcaggcatg gattcagctg cctttctttt ctgactgcag agctggggag atggagtttt   52980
accaaagttt tccagatgct gcacagagaa ttcaggtggt gcactgaaaa tgtgcctacc   53040
agagactggc acaaatgcgc gaaggaattt cctttgcatt ctgatcccta atgttattcc   53100
tggaccaact tgttgatcat ggactttcca gcctccagaa ctgtgagaaa taaacgtctg   53160
ttgtgcaaac cacccatcca ttgtgttata gcatcctgag cagctaagac agagggttac   53220
agcaaccact gagctgattg ggcacctctg caagctttct cttaggggac cctgggggctg   53280
agccccagcc tccaagttca ggggtggggg tgcggtgggg tgagctgatt acagtcttag   53340
ggcagaggag gaattgccca tcttctccct cccctgccac ctccaaaatt ttcacagtta   53400
acaaaacaga tcttcttttc actgtcaaag gttttaaatt caatgggaag gcggatacac   53460
aggtctaaaa gcaaagcact tgagttagtg gcatgtacta agtataagag gtactgccgg   53520
gcatggtggc tcacgcctgt aatcccagca ctttggaagg ccgaggcctt aagctcttaa   53580
```

```
acacttaaga gctaattccc ttatggaatg agaagtctag agacaaatga ttgcttaggc   53640
cgagacctaa gatcaggaat tgagaccat cctggccaac atggtgaaac cccatctgta    53700
ctaaaaatac aaaaattagc cgggcgtggt ggcacatgcc tgtattccca gctcctgggg   53760
aggctgaggc aggacaattg cttgaacccg ggaggtggag gttgcagtga tctgaaatcg   53820
tgccactaca ctccagcctg ggtgataaga gcaaaagtcc atctaaaaaa taaaggtact   53880
tataattgtt gctgtttact agactagtat gattattatt aacagcagta gcatattgtc   53940
tttgttttg ttttttgttt tgttttgttt tgttttgttt tctagtcctg atttactctt    54000
ctcctggtca ctgtatcccg gctgtttctg agatatcatg cccctccat tctcagttcc    54060
tttccctagg agcgtgcatg actctagcct aaaccaatcc actatattcc ctaagccaca   54120
ttaacagatc cagtcagagt ctaacagatc ccacgagact ctagagggat tgatcagggc   54180
aaagactccg cacttggagc cgggagaacg tattcatgtg ttccctgcag ctgctgtatg   54240
tctctgtggc cacacgggag aaactgcctc aggatggggt cgacctggaa gaagtgactc   54300
aagagatgaa ctgggccatc aggaatcagg atcccttgat ccagctatgc ctgaaagcca   54360
agacatttta gttaaatagg acaataaatt ccctcttggc ttcagccagt ttggattaag   54420
taagtttctt tcacttgaaa ctgaaagaat cttgacagat acattactgt gtgaccttaa   54480
agtgctataa tggtggttgg tacaaagtgc tatgacagca gacacgagcg accctgatg    54540
atactggcca cagtgtggag ggagtgtcag ggaaggctgc atggaggagg ggtcacttgt   54600
tctggccttg gaaggatgaa gaacagttca gcgtgttgaa aatataggag agtgcatttc   54660
aaaacgttct gaaatgtgg acaggaaacc aagaaatacg cttctaaatc acccaagaga    54720
caatgagaaa aattgcaatg gaaaattaga aaacattttg aactgaatgg ttttaaaaaa   54780
acaaccacat gtaaacttgt gggttgcagc taaaaagta ctcagaggga aatttgtagc    54840
cttaacagtc acagattagc aaagaagaaa agctaaaaat taatgttcca aacgtctctc   54900
tcgagaagtt agaaaatgac agtgaaataa acccaaaaga aaggaaagga aaattataaa   54960
gatcagaatt ggctgaaaga ggaaggaagc acagcagagg gccaaccaag cctggagtcg   55020
gttctctggt aagccaaaga catgagggcg tgacttcccc gcctgttcgg ggaatgatga   55080
gggccctggt gtgggtgggg agggcagagg gggacaccag agcaaggagg aagtgtcgag   55140
gccatagcct gctggcgaag acagtgccag agcctggaga agtttccctg tagagcagcg   55200
ggagcagaac cccaccccat cgacggccag agccatgaga ggatctcagg aggggagtga   55260
tgggagcaag ctacctttgg tccctatcca actgggctgg gaacttgtag ggtcctggga   55320
gactgtctgc agatgagggt atgtggcccg tgtgcctagg tctgattgga aaggagaaga   55380
taagccacag aggataccaa gtttagtttt ccaggaaccg gcctctgtcg ctggggaaac   55440
tgccaccaca gctgctggct gtccagtgcg accttggcac aggctggctt ccctttcagg   55500
gaggggcacc cagacccatt gagtggtgtc tgagaaggcc ctggagggct gggggggaggc   55560
tgccgagcta cggcatctcc agcccttcaa tagaatattt ggcagggttt ctccaccttg   55620
atagtgttga catttgggct ggatcattta cggtggggc catcctgtgc atggtgggat    55680
ggtgaccagc atccctggcc tcttcccact agatgccttt cccccagttg tgaccaccaa   55740
aggtgtcccc tggagggcaa aattgccccc aggttgagaa cctctgattt catgttgtag   55800
ggggaggagc actggaccca gagtcctaca gaagatgtcg gcagtgccaa actcatccgc   55860
tagggctgca tgaccccagg caagatcctt cctctctctg agcctctaca acccctacct   55920
```

```
gccaattgtg gtgagaatac ttaccccctgc ccccaggata attaggagga tgctgtgcct  55980
ggaagagcag gctgccacaa acagcagagg ttaggtggga atcattgccc ctgtacctgg  56040
agcgaggcta aagagctgaa cggcgtgtgg ggcggggtcc ccatggtgac aatagcatga  56100
tctttcttgc ttccttgctt tctctcacca ccccaatccc acccgttggg aattcctgtt  56160
ggttccactt tcaaaacatg cccagaatcc acagctgtgg tcgccgcctg ctctggacat  56220
tggaaaatta gggcctcccc taccaaaaac atccccttct aactgcagcc agaatgatca  56280
ttttgagaca atcatctgat caagtcactt ccacatccaa agccttccta tggttggtca  56340
aacaaaccct aggtcctgtg tgtggccagt aaggccctcc gtggctgatc cccattgcct  56400
ctgaatttgt ctctttcctc tcccccagtt ttctgactct ggcctcctgg ctgcaccccc  56460
ttcacgccat tcccttccca gggccttcgc acagcccgct ccctcctcct agaacaatct  56520 cttttctccct gtccctccag atatctgcgt ggctcattcc cctagttcac tcaagcctct  56580
attcagacct ccttggtgag gtctttcctg gcacctccta aacagctctc cacccgctaa  56640
tttcccctgg ccccctcccct gcctgtctgt tctgcatagc actcaagccc tctgacgtca  56700
cactgtgggc tcacctgcac atctttggc tctctgtcct cactaggtgt cacttcatga  56760
gagcagggac tctgttctgc tcactgcaga accttcctca gtcccttag ggcagtgcct  56820 tgcacacagt aggtgctcac taaaaagtca gcccctgcttc agccccactt aggattcact  56880
ctgggaaaaa gaatcacccc tgccccctg agtcaggttg gcctacaaat ggcaaggcct  56940
cttcagtctc aaatctcaca tgtggctcac acagctctgc cttttccctcc ggctgaatta  57000 gcctctcacc tcaccctccc ttcttgcatg atgtgcttca gccggaatgg gttgtttcct  57060
cctggctccc acatgggccg tgtcctctac ctggtgcatt ctttctgttg ccatctgttg  57120
gaaaactagt tccagtcctt cagatttaa cttagatgtc atctcctcca ggaagctttc  57180
cctgattgcc caagtctggg tcaattgtcc ctcctctgag cccaagcttc cgagtcttgt  57240
tatgaacaca ctgcattgtt gttgcttatg cacttgatcc caatcccatg caggtagggg  57300
ccagtcttgt atccccccagg gcctaggaca gtgctgggac tcaagaaacg tgattggagt  57360
gaatcagtgg atgaatgaat gctctgaatg acaccacctc aaaggacctg gagcattctc  57420
cttaatcact cttgtggggtg ccaatctcct tgggcgcctt tagaagcact atattttctt  57480
cctgagtact gcagctcttt ttaggcccct gaaaggcacc tggctctttc agttttatgg  57540
gcatttgtga aagaactcag cccaacagac ctctgatggg cacacctaga accacctcca  57600
aatggattca ccatggcaca tgctgggacc accttctacc ttggagagag cttcccaccc  57660
attctctcat ttctgcctcc cctaaacagt gagctggcct ggaaaagtct ggcctctcca  57720 ggtgggagg atggagtcag gtgactatgt cctctttgat gagtgggcag tgaggtcccc  57780
caagaagaag gggcaatgct gagtagagac ccttcccca ccctccagtc atctgagacc  57840
atgacttggt tatcttcttg gaacccacat ggtaatcttg gcacccatca gagactgtcc  57900
ttgtctctct agggctggga tgggggacat gctggaggac ccagatgtgc acaccacagg  57960
tgcccacaac acacaaatga aaacagcagc agtagcaggt gttgagtact tactcggtgc  58020
cagatgctag tatcttattt attccactaa acaactccaa gtctgtgttg ttgctggagg  58080
cttagggtcc ttgggccaca tgtgggggctg aaaataatcc tgatctctgt ccgtctgtga  58140
taagagctag taataataat aatgtctgcc ttctgttgtc tccctgtatt cctgtattag  58200 tctgtttttca cgctgctggt aaagacatac ctgagactgg gcaatttaca aaagaaaggt  58260
ttaattagac ttaacagttc aatatggctg gggaggcctc ataatcatgg ccaaaggcaa  58320
```

-continued

```
ggaggagcaa gttacatctt atgtaaatgg aggcaggcag agagcttgtg caggcaaact    58380
cccgttttta aagccatcag atgtcatgag acttattcac tatcatgaga acagcacagg    58440
aaagacctgt ccccatgatt caattatctc ccactgggtc cctcccacaa cacatgggaa    58500
ttatgggagc tacaagatga gatttgggtg gggacacaga gccaaaccat atcaccsccc    58560
aacaagagaa ggcaggcatt attactagcg catatcacag atggggaaac caagccacag    58620
ggaatttaag taacttgttc attgtcacac agataagaag acatgaacct gggattcaaa    58680
cctggacagt tcggctgcag agcttgagct gttaacgatg acactctcat cttttttcaca   58740 aatgcccaca caagtcccct tctgtacata tcaacatatc tcacttacat atatgtgcaa    58800
atcagcatat gaaatcccgc tcttgctcat gcactcatgg acacatacaa cccaatcaca    58860
aagacataga ttctcctgta gcatgaaatt catcatacat cgtcaatagg cagcgagaat    58920
tcacccgagt cacgcacatt tacacacagg tgtgcatgtc cctgttaata tgcctgcgtg    58980
aaaagcatgc agaaccgcca ctcacaagtt cacacatgtg caagtacaca cacattgtca    59040
cataggcaca gacatatata tgtgtgcaca cttgcatata aacatttctt gagcacctac    59100
tatgtgccag gcactgtgcc ggttctggga atataaaagt gaagaaaacc gagtttctac    59160
tctctcagag tgtgtaatcc aggggagggg gaggcatgcg tgagcaaatc agatagaaag    59220
tgcagtggct catgcctgta atcccaacac ttttagaggc cgaggcaggc acatcacctg    59280
agttcaggag ttcaagacca gcctggccaa catagtgaag ccacgtctct actaaaaata    59340
caaaaattag ctgggcaagg tggcgcatgc tgtaatctca actacttggg aggctgaggc    59400
gggagaatca tctaagcccg ggaggcagag gatgttgcag tgagccaaga tcgtgccact    59460
gcactcaagc ctgggtgaca cagcaagact ccatctcaaa aaaaaaaaa aaagaaagc    59520 tcatagttat ggagtgctta ttatgcataa gttgcagagc tgaatctgcc tcatgcatta    59580
ggggtccgta aacaccacag cccccatgct tacatgcaca catatgaata taaacctccc    59640
tccctgcaga agccacatgg cacaacctgg gcccttgaca ggagtggatg ggtgtagggg    59700
acggggatca gcattatttt cagcccccct cgtgcccaa ggacctcaag cctccagcaa    59760
cttccctgag atgagaccat ggcctgtgcg acaaaatgca catgcaattt gcagacatgt    59820
gtacatctct ccacgtgctt gtatgtgtgc aggtccctca gcagtccccc attctcctca    59880
ggacctcccg ccctatcaag agccctgtc cctaagtcac caacctcctc cccctaccct    59940
catcttgcac cttagggacc tgtgggacgg agacatttgg atcttccaag acgctgcaca    60000
cacaggcgga ggatgggctg caatgactcg gcttccaggc agctgtggtg agtttctgca    60060
aagactccct tcctcaaaga ggctctgctt tactgaaagt tcaggttgcc gtggtttccc    60120
cgcattcaca tgggggaaag gtcagactct cacaaaaata tttaccaaga actgtctgtc    60180
agtcaatcaa caaacattta cagacagctg ctgctcacat gctggggaga gaggggggat    60240
gaataagcac aggccttgtc ctacataaaa gctcagggc catgagggag ctgtgattga    60300
cccagcaagg gacacagtgg ccaggaagag ggaactgctt gtccaaaacc tggcatcaaa    60360
agagtgtgcc ctggtgagac caaaacaacc ttttttttt tttttaatt gagacggagt    60420 cttgctctgt cgcccaggct ggagtgcagg ggcgcgatct cggctcactg caagctccgc    60480
ctcccaggtt cactccattc tcttgcctca gcctcctgag tagctgggac tacaggcacc    60540
cgccaccatg cccggctaat ttttttgtat ttttagtaga cggggtttt caccgtgtta   60600 gccaggatgg tcacgatctc ccgactttgt gatctgcctg cctcggcctc ccaaagtgct   60660
```

```
ggaattacag gagtgagcca ctgtacccag ctcaaaacaa ccattttta tggcccctaa    60720 aatcacaacc agtggtgtgc tggtaagcca acaaaaacaa caggaaacaa accaaaaacc    60780
caatatgtgt gtttgctgca aaatcctgaa acacggtgtt tgctgctttg catggtgtag    60840
atagtctcat tgtggccaat ttcaggctac caaggtgatg tcaggggctg cggaggcaaa    60900
gatgaccaca ggagctggtg caagctggac tcaacacact gtttcttccc acagacacca    60960
ggaggacaga gccagagctt tggtgcctgg aacagagtaa ggagtctcag ttagaagtgc    61020
cagggacaag acccaaacct cttgttcatc ttttgatgca tattccgacc tgttctttca    61080
ttcactcagc acttaccctg tgccaggtac tgtgcacctg aaggtgctga gaccattgct    61140
gcctgtgctg atggggaagt actggtgtta aggagcccag aagagaggca ttaaccaatg    61200
cctggggagc tagaggactt cctggaggag gtagtatcta agctgaaatg gaagggagta    61260
aagcagcaag tgagggtag aaaagagtta tttgcaagca gaggaaatag gatgtgcaac    61320
agcttagtga tctcatgcac cactgggttc ccccagcaaa agcatcctgt tgagcagatt    61380
ttgtaaatga accagcacca tcctaggtgc tttacaagta ttcactcatt taatcctcag    61440
acgatcctat ggggtattta atattcttag ctcctttgta cagatgggac cactgggaca    61500
gatggaagtt atgaataagt caatatgccc aagatcactg gtctgccctt cctctccacg    61560
atgctacctt gaagcatctg aagtaggtgc agcttgggga aattttaggg ggtacccaga    61620
tatgggaaac aactgtaaat ttaattctgg gtttaatgaa atgtcagagt gtgggaagtg    61680
atgggttcag tccctccct gctccctgcc agcccttcac acacaaagac aagagtattg    61740
tccatcatgg acacattgac cgaggctgtc ggtcagccag tcaacagaga tttgtcagaa    61800
tctttatgtc ttggtctggc ctaggactgg gatgtttgca gtgaacctct gctcacattt    61860
ttgttttgtt tttccttttt tttttttttt tttgagacag agtcttgccc tgttgcccag    61920
gctggagtgc aatggcacaa tctcggctaa ctgcaacctc cgcctcccgg gttcaagcga    61980
ttctcctccc tcagcctcct gtgtagctgg gattacaggg gcatgccacc acgcccagct    62040 aatttttgt gtctttagta gagacggggt ttcacaatgt taaccaggct ggtcttgaac    62100
tcctgacctt gtgatctgcc caccttggcc tcccaaagtg ctgggattac aggcgtgagc    62160
caccccatct ggccttgttt tgtttttcta ctgaacactt aatctgggct gggctctagg    62220
ctgaggattg gggcacagaa gaagtaatga atctgtgtcc ctgtcatcaa ggggcatgat    62280
aggagacata caggagacaa ggttttctgt atgtttgaaa tattccatga tttaatataa    62340
aaaataattt ttatattaaa ttttagacac aaggtcttgc tctgttgccc aggctggagt    62400
gcagtggcac gattatgact cactgcagcc tcaaactcct gggcttaaac gatcctcctg    62460
cctcagcctc ctgagtagct gggactacag gcgcaagtag tcaattgcaa taaatgacga    62520
ttacaataag tgatcgaaga ggcccaagga caaggagag aacaattctg cccccccatcg    62580 aggggaggac tcacggggaa aggcctgctg ccactgggcc tgagaagatg atatttaca    62640 gcagttgcca gggaatcagg ggaggacgat ttggacctac agatatggat aaggattttg    62700
gttttttttt agagaagagg caatggtgga aatgttctgg aattacatag tggagatgtg    62760
tgtactacaa cattgtgaat acactgaaac ccactgagtt atatatttt aagtggttga    62820 aatagtgaat tttacgtcat ataaattta tctcaataaa aataagctt atgactgggt    62880 gcagtggctc gcacctataa tcccagcact ttgggaggcc aaggcgagtg gtcacctga    62940 ggtcaggagt ttgagaccaa cctggacaac atggcaaaat gccatctcta ctaaaaaata    63000
caaaaattag ctgagcgtgg tggtgggtgc cagtaatccc agctactaag aaagctgagg    63060
```

-continued

```
caggagaatt ccttgaacct gggaagcaga ggttgcagtg agccaagata gtgccattgc    63120
actccagccc aggcaacaag aatgaaactc catctcaaat aaatacataa ataaataagc    63180
ttatgtttca accacaggga gctttctggt tgtaagtgac aaaaatgcct gtttaaaaac    63240
aaagtttagg ccgggcatgg tggctcacac ctgtaatccc agagctttgg gagactgagg    63300
caggagaatc acttgagact aggagtttga aatcagcctg gcaacattc agcctgggca     63360 acatagcgag acaccatttc tacaaaaaat acaagtatta gccaggcgtg gtcacttgtg    63420
cctgtagtct cagctactca ggaggctgag gcaggaggat cgtttaagcc caggagtttg    63480
aggctgcagt gagccataat cgtgccactg cactccagcc tgggcaacag agcaagacct    63540
tgtgtctaaa ataataataa tacatttaa aaataaataa gaagtttatg aatatagttt      63600
caggcatgga tagatcaagg ttctcaaata atttcttcag gttggaaggt tctactctgg    63660
gatctgcttt cttttgtatt ggctttagtc tcattctcaa gcaagctgag gaagcctcat    63720
tggtggccaa agaaaagcag ggacctcaga agccaagacc taccacctac cagctttcaa    63780
agcccaaagg aaagaaggca tgttttccta atggttccaa tgatgctacc aggaaaagct    63840
ctcattggtc agttttaatc atatgcctgt ccctgaacca atcttcagat tgggaaagga    63900
atgctctgat tggccaagcc tgagtcatgt gccctgttgg aaagctagga gttagatcag    63960
ttctctggca gttagatcag ttctctggaa ctgcgagtgg gaagacgctg tcccggcaag    64020
gaccaccagg tggtgatgtc agaagaaggg agagtagata cagggcaggc aggatagccg    64080
ggttcgtccg gaagagtggt agggagggc gtgcctgcca gagggaaagg catgagaaaa     64140
ggcttggagg ttgaaattgc atggtgtggg ctgggaactg tggctgggtg gtggcgtgta    64200
gtcagatgat ggtgtctaga ggggtcaggt catgtgtctg aagacatgag aagcctcact    64260
tctcactttg aaccagggcc aggtacaaag aggtttggac agggcctgta cgccagtgtt    64320
gcccaaactc tcatccctat gcacacaagt catttctgcc gtatttacat ttttctcca     64380 tcattacatt ttcttcatat tggcctcctc gctttgttta aatcactta ttgtcaaatg      64440 aaacattgtc accatcacac atgaaagatc aggatccttt actgtaaata gaagggaact    64500 gtaaaacaa gcccattgaa accaaaccg agtgattaac ttccagctag atgctgcagc       64560
ctgtggtagg ctaatctgga gaagagaaag agaactgaaa aaggaattgt tttctcagct    64620
cactatgccc acatgccacc taaaatcatc ttagggaccc cagggagcag ggaaggacgc    64680
agtcacaaag atggtcctgg tcctggcatg ggggagtgtt tgataaagac actaccggca    64740
taaacccagg ggttacaata gggaggctga catggctgaa cagaggagct ggagagcagg    64800
gtcccaggga cagactcaca gtaccggaag ttctgcaggg aggaaggagg tagtcaattg    64860
aggagcaccc gctctcttgc tttagcaatc aaaaccagga accagaagga ggaggtttgg    64920
cgaggatgag aaaagagctcg tttggatata ctgaatctga gatgtgggga tgtctctgtg    64980
gagatccatt catctgttca agaagtattt atttatttac ttatttttgt gtatttattt    65040
agagacaggg tctctgtcgc ccaggctgga gtgcagtggc gtgatcgtgg ctcactccaa    65100
cctcgacctc ctgggctcaa gcgatcctct cacctaagcc tccccagtag atgagactac    65160
agttatgcac cgccatgcct ggctactttt tgtattttt gtagagatgg agttttgcca     65220
tgttgcccag gctggtctca aactcctggg ctcaagcagt ccacctgcct tggcctccca    65280
aagtgctggg atgacaggcg tgagccatgg tgcccagcca agaagtattt attgagcacc    65340
tactatgtgc caggcactgt tctaggccct gggataaggc aatgagccaa ccaaactgaa    65400
```

-continued

```
atctctgccc accatgagtc tactttcttt gggggagata tgggagacct ggtgagaaat   65460
aagaaataaa agacttaata atatatacaa tatataataa catatgtcac acgagatagg   65520
aatggctact agctaggaca tgcaaaatgt ttgggtggga gatgtggaaa ctgagacata   65580
cccaactgca gttgaatgta taactctgga gttcaggcaa gagatctcag ctggggagat   65640
atatttagaa gacatcattc attcattcat tcattcactt agtaaatgtt tattgagtat   65700
gctctatgtg ccaagcacag tgctgggctg tggaccacag agttcctgat ccatgcgact   65760
ccagtacaga tttagtgaag gttgtaatta actctgtgga aagaggagag gagatgggga   65820
gggcccaga tgggccctgc ggaccctaa cgtgtaagag agggcagagg agaagacctt   65880
ggaaaagag actggagcca ggtgcggtgg ctcatgcctg taatcccagc actttgggag   65940
accgaggcag gcgaatcaca agatcaagag ctcaagacca gcatggccaa catggtgaaa   66000
ccccgtctct actaaaaata caaaaaatt atccaggtgt ggtggtggtg ggtgcctgta   66060
atcccagcta cttgggaggc tgaggcagga gaatcgtttg aacctgggag atggaggttg   66120
tagtgagctg agactgcgcc actgcactcc agcctgggtg atagagcaag actctgcctc   66180
agaaaaaaag aaaagagac tggacaggaa caaacagcca gtgtcagaga accaagaggg   66240
gccgagtttc aggagtgagg gagatgctag tgccacagag tagtagggat tgaaactgag   66300
acttggcttg ggtggtggag ctggcttcag tgaaagtagt ttagtagcag agtcaggccg   66360
actctgcaca gagagggtag aggagtgggt gcagaggaag gaagtgaagc ccaagagagg   66420
agacagcttt tgagcacaag cactgtggct gggggagaga aggcgagaga gaaataggag   66480
ccggggtgga gggaagcttg ggctgttga agatggaaag acttgagtag atatgtgtgg   66540
caatgaggaa aggccagcag agggaggcag gtgaagacac aggggagtga tggtgtttta   66600
gggtccagag ggagaagaga gctcagcctg ggagagaggg aatgaccccg catcaggaat   66660
ggctgcatca ttggaggggc actgtgcaaa ataaaaatgc aggtcttctt attcaaaaag   66720
ggctgataat ttggccaggc gcggtggttc acgcttgtaa tcccagcact tgggaggcc   66780
aaggcgggcg gatcacttga gtccagcagt ttgagaccag cctggccaac atggtgaaac   66840
cccgtctcta ctaaaaataa aaaattagct gggcatggtg gctcatgcct gcaatcccag   66900
ctacttggga ggctgaggca ggagaattgc ttgtactcgg gaggcagagg ttgcagtgag   66960
ccgagattga gccactgcac tccagcctag gggacaagag cgagactccg tctcaaaaag   67020
aaaaaacaaa agggctgaga atcaagatg tcactcttg gttcctggat tagaagtggg   67080
ctgagttgtg gcttctggct gcccagcaga tacctctggg gtaggaatgg ctgtcaccat   67140
gctccacccc aagtcccgt gaggtgagct actgaccttg atgatccttt gcacctgtgc   67200
ccaggcctcc ttcaagggca gaaggcagca atggtcatgg atggtggtgg aatggggagg   67260
atgagtaggg cctggtgtgc tggggacaga gcagcaggtg gccaggagcc tgtaccaggg   67320
aagcaggcag gtggcagatg tcccagggaa gcaggcagga ggtgggaccc tgtgtgagct   67380
gaggctccaa gccctcaatg ggtgctcctt ggtcccatta aacctcccta taaaacacaa   67440
cttcagagat aaaatttta agaatttctt tttcttttt tattttttt tgaaacaaag   67500
tctcgctctg ttgctcaggc tggagtgcag tggcacagtc ttggctcact gcaacctcca   67560
cctcccgggt tcaagtgatt ctcctgcctc agcctcctg agtagctggg attacaggca   67620
tgcaccacca tgcctggcta atttttgtat ttttagtaga cgggtttt caccatattg   67680
gccaggctgg tctcaaactc ttgacttcga gtgatccgcc cacttggcc tcccaaagtg   67740
ctgggattac aggtgtgggc cactgcgcct ggccaagaat ttcaaaactg ggacttcaga   67800
```

-continued

```
gcatgacact gaagagtagg ggtcctccga gcagggggt acgggctgct gcctggcgca      67860
cagctgtgga gccagcctgc cctacgtcca ctctaacaag aaagggtgga tgccgatatg      67920
gaatgggcag gaatttggca ggatcctctg gaagtgaaga ttgagtgcca ataaagaggg      67980
agaggatggg gattggggaa ggagcttgag gaagagtcca gagcctaaag ttggatgcgt      68040
gaatgcacct gcacgttcat ttcccattgc ttctctgaca aatttccaca agtttagtgg      68100
cctaaaactg aaatttatga tcttgcaatt ccagaggtca gaagtctgaa actggtctca      68160
ctgagctcaa aatcagggtg ttaacaaggc tgtgttcatt ccagaaactc tagggaagtc      68220
tgttccttga cttttccagt ttcaagtggt cacctgcatt ccttagccca tggcccttcc      68280
ctccatcttc aaagccagca gcataatatt ttgaaatctc tctctgactt ggcttctcct      68340
gcatctctca cttatgaaga tccttgggat tatattgggc ctgtctggat aattaaggat      68400
aatctccctc tacatctcag gttcagttga ttagcaaccc tgcttccatc tgtaaccta      68460 atccccccct tgccatgtaa tgtaacatgt tcacaggttc cagggattgg gacatggaca      68520
tcttgggggg ttcattattg tacctactac aattttttaag gttgctttat gactgcaaaa      68580
gaaaactcac agtggtttaa agaaaagcac acttacagtt tatttaagaa tttaaggttg      68640
gtttgatcac ttggtgatgt aatcaaagcc ccaggcaggc cttcttcttc ttccactcca      68700
ccatattcag aatgcctcct ttcatctcca ggcttgtctc ctcatgattg caaaagcacc      68760
atccaaagca gaaaggaagg tgcaaagga gccttctcct ccatgctgct ttttgattag      68820
gaaggagaac tgctgacttg ctctgtggtt ccatggcaga gaggaaggtc aggcagccca      68880
gctatgttga ccaactcaag ctaaatttgc tgctagaaat caggaaatca tggatggtgg      68940 tggaagggg aggatgcgta gggcctggtg tgcccaggc agagcagcag gtggccaaga      69000
gcctgtccca ggaaatgcca gttcctgggt gggatcacgc taaggtgggt catcagtata      69060
taggagtggt ggttcagggc agccagaatc agagatcagc ctatagctgg gatcaaagat      69120
ccatctgtgg tgagggtcag gggtcagcat gtggctgggg ccagcctgca accaggatca      69180
tgagtaagtc agtaacatgg gtcgggactc agttcctggc ttgagtcaga gctgttctgt      69240
ggctgaggac aggaggtgga ctgtggccag gatcagaagt cagtctgtgg ctggatcagg      69300
gtcattctgt ggttggagtc agatatcata atggagttgg gatcaatcag tttagtcttc      69360
tctgtctgtc tttctctctg catctctgct tctctctgtc tcattctcct ttgctgtaaa      69420
cacctgttgg aagctcagca acttgggtcc atggggaaga gggaagttga gtctgggcaa      69480
ggtcctataa gtcccggtat ggaagaacat aagggaaaaa gagaaaaatg tcaggaatat      69540
aaagatattc cctagaaaaa tgtcaggaat ataaatatat gtatgtatga tgagaaatga      69600
atgatataaa accgcaaata cgcaaacact gactctgcat gtaaacaaca cacagaagtg      69660
gcacaaacag atacaaacac aagtgggttg aatgatggga ttgggacaat tttttgtcct      69720
ggattactgt tgctccattc tgcccttttt gtaataaagt caaattaaat ttagaatgtc      69780
attatttcct ctaattatgt tttataccct cacctcccac aaaatccaca gacatattca      69840
gtgtaatatt aaggataatg ttagcagact aggcatggtg gctcacatct gtaatcctag      69900
cactttggga ggccgaggtg gatggattgc ttgaaccta ggagtctggg actagcctag      69960
gcaacatagt gattccctgt ctctacaaaa aattaaaaaa caaattagcc aggcttagtg      70020
gtgtgtgcac ctgtggtcac agctacttga gaggctgaag tgggagaatc acatgagccc      70080
aggtgttcaa ggctgcagtg agccgggatt gggccactgc gctccagcct gggtgacaga      70140
```

```
gaaagaccct gtctcaaaaa aaaaaaaaaa agaagaagaa gaagaatgtt agcaaatact    70200
tttaaggcat taactatttg caggcatagt tcttttttt tgagacagag tcccacttgt    70260
tgcccaggct ggagtgcagt ggcacaatct ccgcttgctg caacctctgc ctcctgggtt    70320
caggcaattc tcctgcctca tcctcccgag tagctgggat tacaggcacc cgccaccatg    70380
tctggctgat ttttgtattt ttaatagaga cagggtttca ccatgttggc caggctggtc    70440
tcaaacgcct acctcaggca atctgcccac cttggcctcc catagtgctg ggattacagg    70500
cgtgagccac tgtgcccagc cgcaggcata gttctaagga cctcacaggt actaacatat    70560
ttaattctca caatagctac atgaggcaga tattataatg attcccattt tacagataac    70620
gaatcaagca cagagaggtt acacgctggc ctggcgccac acagcatatc taatggacat    70680
taggctcttt tgtctggtgc tgggggaatt tctggaaaat gcagagatgg aagagaggtg    70740
ggatcggggc agggcgggtg gggaatctcc caggccaagt tttctgggca cggcctggac    70800
ctggagctgc tgggatggag caggtgctga tgctgatgtg gtcaccagag ggcagcaggg    70860
accagggagc tgacttcctc ttcacacccc ctccacccgg ggcggtgccc ctgacttgtc    70920
aataaacgtc gtggaaacag gtgggatttg tggaagaac tgacacggtc ccgccaccat    70980
cacaggcaag ttaagcttga gagcagcctg gtgtcacctg gcctccaccc accacgtcat    71040
ctgctgctca ccccaccact gtggcgtgca gagtactgct cttgtgtgcc ttttaccaag    71100
gaggaaattt aggcccagag tgggcaaaca cttttcccat ggtcacacag cttggaattg    71160
gaaaggctgg acctaaccag gcagggtgag cgcagagccc ttgttcctct gagtctctgt    71220
tctgagctgg aaccagggaa gatgatgagc ccatggtata tacagggcgg ttagctagga    71280
ctctggtttg aagcctggct atgccactcg gtaacagcac atcgtgggca agtcccatgc    71340
agcctcatcg gctgccggga ggatccagtg acgtcaggcc tccctcgtgg tgggagctca    71400
aacacttgct gggttttttg ttttttcggt gttttgcttt ttgtttttta attaataact    71460
ttcgtgggaa aaataaagtc agaaaggttg ttcaaccgga tgttcacgga gatactacgc    71520
cttcaaaaac aagcgctcat ttcgtgatcg cccacacagt gccagatgct ggggcgggga    71580
tgggatttcc ggtggttttt cttcactttc ctctttatat cttcaggctt tctctgaata    71640
ggaaaaggtc tgcacgtgct gatagagtaa tcagaaaaat gcaataagcc acttttgta    71700 aaaaaaaaaa aaaattcag atgcactcac tgccttcctc ccccctttcc ccctcccctc    71760 atccccaca aattctgtgt aaaggcaggg ctgagggagt accccaaat caacatctct    71820 gaaagctccc ccgcaggggc ccaggccact cagcccactc tggcgctgct acccaggggc    71880
gtcccctcct gccctctggt ccagcccgg aggctgaaac tcccgcagcc ggcatctcac    71940
tgggcctatg accctggact tttcctactt cctgcagggt gggggccagc ctgagttggg    72000
cccacctgat ccaccaggtc ttctcatccc tctgtagctt cccaaagccc agccagttca    72060
gtaatagttg ctgaggccaa caacttggat ttcttttgcc taagatcctt tgttgggctc    72120
ccagtcccat tgcatctcta gcagtcaaat atattttcta tttgctgcct aattttttaaa    72180 ttagatttct ctgagacaat gctcaggcaa agtggattcg agccgacatc tgcgtaggtg    72240
tcaggatgac ataagctgat atatcacggc ggctgggagc tcttaggtca gacccgggtt    72300
caaatcctgg ctccaggatt tcctagctgt gtggttctag gctaatcctc aacctctctg    72360
gacctgtttc cttatctgta aaattgggat aatcattgag cctcccaact agagctgttt    72420
ggagacgtaa atgacacagt ggctggacgg cacttagcat attgcttggc cctaaacaga    72480
taactatttt tatttaaaat tatatttat tataaagagc ttttggaggc aagaagtcca    72540
```

```
gaaggctagt tcaggctctg ccattctctg ggtgactttg ggcaagtccc ttttcctctc   72600
taaaactgtt tctccatctg taaactgtgt gatttgggca gctaaaggga ttgattttgg   72660
cttagaacaa ggttttttt gttttttttt tttttcctg agacagggtc tcactctgtc    72720
atccaagctg gagtgcaatg gcacaatctc agctcactgc aacctccgcg tcccaggttg   72780
aagcaattct accaactcag cctcccaagt agctgagatt acaggcaccc accaccacac   72840
ccggctaatt ttttatttt tggtagagat agggtttcac catattggcc aggctggtct    72900
tgaactcctc acctcaagtg atacacccgc ctcagcctcc caaattgctg ggattacagc   72960
catgagccat catgcctggc gcaaggaggt gtttctaaca acatcaggc tgcatgtgag    73020 gtagagagct ccccatcatt tccagtgtag tatgtaggct cctagagcag gaaggaatct   73080
aaaatggcca agcccctcaa gtgtgaaatc agggcagcta ctcagagaag caaaagtgat   73140
acagacatag gagcttcagg ttcccagcct tccatctaa ggcccacacc atccctctgc    73200
ctgcctcgga tgtgaagcgc agatcactac agagagcctg ggtgatggag acactgtctg   73260
gattccacta tagatctgtt gctaactagc tgtgtgacct tggcagtgta tcatcagcca   73320
ctgttggtgt cctgttcctg tcttcttggt gtgccagagt ctctcaacac ctccaactct   73380
cagttgaaga atttttttt tcctggagta gctggaagtg ctggagaatt aatgctcctg    73440
gaagcagctc tcagccaatg acagatggga gctggtggac aaatacccca gctccctctc   73500 cttttgcaggc ataactgggc atgtgccatg catggtcttc cagagatccc cggcaggtaa  73560
gcatcagtta ctcatgctgg taatctgttg ataactcac ccttttgtca gaggtttatt    73620
taaactggag cttgaagag gggctgggta aatgaggct gagacttact gggctgcatt     73680 cctggggaggt tagggcattc ttagtcatag aatgagacag gaggtcgtca ccgatacaag  73740
tcataaagac cttgctgata aacaggttg cagtaaagaa gatggctcta acccaccaaa    73800
accaagatgg caacaagagt gacctctggt tgtcctcact gctacactcc caacagcgcc   73860
atgacagttt acaaatgcca tggcaacatc aggaagttac cctatatggt ctaaaaggga   73920
ggcataataa tccaccccctt gtttggaata taattaatca ataaccataa aaataggcag  73980
ccagcaaccc tcagggctgc tctgtctacg gagtagccat tcttttattc ctttactttc   74040
ctcattaact tgctttcact gactctatgg actcgctctg aattctttct tgcatgagat   74100
tcaagaaccc tcttttgggg tctgcatctg gacccctttc aggtaacact ttcttggttt   74160
gtgtccttcc ctgcctcagt tccccactac cttagcaggg tttcccggga ttacttccta   74220
aatcaactat ttgaatcctt gtatggggaa cccaaaccca gacggcaagt tcttaaccct   74280
cttgcatcct ggttcctctg gatgggtgaa ttccaggagt taacagagac acagcactca   74340
cagcagtgtc tggaggtatg tttggttaat acataaaaaa taaagagaca agaaactttt  74400
atttatacaa aactccaccc cttctgttcc actctcctca gcaaacacag ataacaggtg   74460
atgaaactaa aacacacaga cgagcattac tcaacccaag gttcccgcct tccctagcac   74520
ctgaggtctg ggccaacatg cagggtaact ggtgccttat gcctgctgtc tggattgccc   74580
ggcccacagg gtggctgagc atatttattc tgggggttcc atgcatacga ggagccccca   74640
gccatacagc tgggcatggg tgtttggcag caaattgtcc ctgctttagt cacagcaatt   74700
tttcatgtcc tctgttgctc cccttaactg aacacccctt gacagccggg attctgcctc   74760
cagcatcaac ctaaggaagc tctgttaaat gaatgagcac ctctaggcaa tgaccaccct   74820
ccctgaagtt caatttctca tcgatttccc aaggccgccc aagtcattcc cttgatggct   74880
```

```
gtgttagttt ctaggctcgg cttctagttc agtgagacag aggcaggtgg gcctccatgt    74940
gggccatgat ctggtgggca aaacatgcct tgggcagtta caacagggac agtctgctgc    75000
agaagctgtg gagggagcag ccaacaactc gttcacaagt cgaggtgccc aagggcctca    75060
gttttcctgc aggggcctgc cgtggggcac ggcgacccag tgccctctac tctcatggga    75120
tgtggcgagc ccagcccaat gctgggcggg gtccagtctc tgcagcccag tgttaggcca    75180
acgtcagtgg ggccaatcac cttcatacca tggttcttca agtcttttgg aaatctgcca    75240
gcctggctgc cttccaggag gtggcatttc ccaggcatgg ataagcccta gtcctcatct    75300
gcagactcag caacaagagg acatgcacct aagagaccct catgtatgtg gtcccacgg    75360 agacaaagtt cacgattttg ggggtctggc ttgagctctg agcattgcca ggggcaggat    75420
ggaaggatga tgaggattta ctcttctctg agatgcccga gggtgccagg gaggccggac    75480
acagactggc ctccagtgga accccacctg gagagggtc tggggccctc aggggggttg    75540 taggggcga ggacctgtct ccacagcagc agccacagca aggactggcc atgacagggg    75600
tctggccacc atcctcctgg ccatgacact gtttcaggtg gccgcacagg tggcaggtaa    75660
gggctgagta gacaatgcca ctgcccaggc tgtccacaag gggtctgtg gcctgctcct    75720 ggggaagtgg gggctttggc atgtcctcta ccttttcccc cggctccaga cccaggtgct    75780
ctggggagct gcttgggaga tgtgagctct gcggactgcg aggtggctcc ctgtccagtc    75840
caaaggtgaa caaggggaca gggactgggg cagggtcccc agggcagcca ggaatgaggt    75900 cttgaaagg cttatacccc tcttccccac tgctagcccc aaacccacat ttctctgggg    75960
acacagcact gctggcaagc aggcttgaga aggccttgta accagcctct cctgggggac    76020
ccaagcccac caccgcactg gcctgggtgc caccctgctc caccgcatgt acaaactcct    76080
gatagccact ggtgggggcc gagacggggg ctgcagctgc cccatgctgg aggacatttc    76140
ggcggaggat ctgctcccag gtttctggct caggttgggg cacagtggtt ggctcagaga    76200
gctgggggac acagggcatc tcgggttcta cttcctccag gtgtctggcc agcagtgggt    76260
ctggacccag ctctctggga cacggtgact ggctcaggga gttgctgaag ctgcggtaag    76320
cagggttgcc tgcgatgacg aggggcgtct ctgtgcaagt caggttgtct ggactctggg    76380
tcgggctggc aggaggactt ggctccaggt ggagaggctg ctccttgccc caggaggtg    76440 cctccttggg ccctgcactt gggaactcat cccagggcat gtgagcactc gtacttcccg    76500
aaggtggaag aaggcatgac tcccccatgt cctgctggca aaagccccca ttctcctctc    76560
cgagcaggtc caggaacagg ctctctgtta gccgggccac aatgccctcc cttccctcct    76620
ggaagtcatc cctgctgctc tcaggcgatg cacagaagct ccctttttct tcctctacct    76680
cctcctcctc ctcacactcc accggggcct caaacaactc cacacatcgc accacgctga    76740
tgctctctgg ccagaggact gtcttgctga tctccactgg gcaccatgct gattttccag    76800
agccctggaa aggcatctct ttggcagcct tgtgaggatc ttcatccctt ttcatgttgt    76860
gctccagaaa acagggcaag agcttggtaa gacaattctt ccagtgtctg caaaagcaaa    76920
ggttggtcag ggttcagttt cgacacttga aaaactccta ttcattcttc aaagcccagc    76980
ctgaaatcac catgtcctga tggctgtcta cttcagacat gccttctaac gttataatca    77040
gtaattgatc agtctatgtt gctagaatga gaaatccctg agggtagggt ctgtgtctt    77100 gggatttcgg gaacccagca catgtcctgg gcaccaaata caagctcaga tctgttgagt    77160
aagaaaaagt ctttatggat gatgataatt aaaagcaaca ccattatccc aagccatgac    77220
caattagaaa ggatatggaa gccgggtgcg gtggctcacg cctgtaatcc cagcacttta    77280
```

```
ggaggctgag gagggaggat cgcttgagct caggagtttg agaacagcct gggcaacaga   77340
gcccaagccg tctcaaacat ctctacaaga attaaaaaaa aggaaaatta gctgggcatg   77400
ttggtgtatg actgtagtcc cagctactta gaaggctgag gctagagaat cacttgagcc   77460
cacgagtttg aggctgcagt gaatcactgc actccagcct gagggacaca gcaagaccct   77520
gcgtccaaaa aaaaaaaaaa aaaaaaaaga tgcgggatcc tagggttgaa gcagggtcct   77580 ggacccccctt tagtttctgg agtatggaaa ggtccagcag gccccaggga agaagctaag   77640
gaggccacag tggcggggca acacagcgag agcttgtctt tacaaaaact ttttttggta   77700 ttatttttttt tgagacaaga gtctcactct gtcgcccagg ctggagtgca gtggcacaat   77760
ctgcgctcac tgcaacctct gcctcccggg ttcaagtgat tctcatgcct cagcctcctg   77820
agtagctgga attacaggca aaaccttttt aaaatagcca ggcgtggtaa tgcacatctg   77880
tagtatcagc tactcgggag gctaagatgg gaggatcact tgagctcagg agtttgaagg   77940
tgcagtgagc tatgatcgca ccactgcaca ccagcctggg ccacagagtg agatcctgta   78000
tattaaaaaa aaggagggga gtgttcagga tagtggctat ttgccgacaa gtatacaatt   78060
aggtcaagat tttaacaaca ggcacggctg ctctggttgt taactataac agcactccca   78120 agggtatca ccatgtacct gacacaccag tgaaactcag ggggcttggc cagcagtcca   78180
cgtttccaga acacccctcc tcctgccgtc ccttgaaggc taatgtcaca gggcaattac   78240
cgaatgcagg gaagagaagg cagacatgga gctaggggct tgcctctcca attctatcac   78300
cttcccaatg catgcaggct gtgacctaag ttcagataca tacgggcact ggctggttc   78360 ctggcctcgg gaccgcttct cccactgtga cccctaaaat acagagacag ccaatgaaag   78420
agcagagtgg ccttgcagcc cggcctggag tacggcaatg ctcaggaagg ggtacaagcc   78480
tcgacatcac acagatcaga agtccaacag gtcacttacg ctttctgagc ctcagattcc   78540
tgggaattaa ttcattgtc ctaatattta cagggactgt ggtcgatggc aaaagtggcc   78600
acagaggagt gctctgaatc tcctcccatc ccttgaatct acactggccc tgggacttgc   78660
ttgggcccat agaatgtgat ggaagtgata tcatgccagt gctgcgccta ggcctcaaga   78720
agccttggga cttcccaccc ttgaaaactg agccactctg taaacaagcc tgggccggcc   78780
tgctggagag tgagaggcac atggctcagg cacctgcact gtcccaggta aaagtcagcc   78840
aactaggctg ggtgcagtgg ctcacgcctg taatcccagc actttgggag gctgaggtgg   78900
gtggatcatc tgatattagg agttccagac cagcctgacc aacatgaaga accccatct   78960 ctattaaaaa tacaaaatta gcctggcgtg gtggcacatg cctgtaatcc cagctacttg   79020
ggaggctgag gcaagaaaat tgcttgaacc caggaggcag aggttgcagt gagccaagat   79080
catgccattg cactcctggg caataagagc aaaactccgt ctcagaaaaa gaaaaaaaaa   79140
aaaaaagcca actgtcagac acggagggag gctacgggga cgggtcagct caattcagat   79200
ctgcccagcc cagcccagcc cagcctcccc cgccaccctc actgctgagc ccagcccaa   79260 atgccagcct gcagaagcat aagctaaata aagttgttgt aaccctctac atttcggggt   79320
catttgttac acagcaaaca ctaactgata cataaatggc acttggtatt tgcaagaggc   79380
tggaatatgc actttatatg tattgtctca ataaattcca atatctgtcc taccaggtaa   79440
acactgttat aacccacaag aggaaactga ggctcagaga attaagcaac ttgctcaagt   79500
ccacactgcc agtgagtggc agagtcagga ttcaaagcca acactagatt ccagagtccc   79560
tggaaaagca aggaccctca gaccttctct tctagacagg acctataatc cccctttctc   79620
```

```
ctacctagag aactctcatc ttgctcaggc aaaccccacc cactcaccca caggaccatc   79680
gccttgggga agctgactcc accoctggct tagggggtggg atacatttca ggccaatgag   79740
aacccggaag ggatttgcta gtgcttcggg ggcagtttcc tatgcttaag aagaagacac   79800
agaaagcctg tcaccctctc cttcctccac tccttctggc ctctagccct ggtactggca   79860 cctcccagg gaatgacaca gtgatgatga cccaagggtc attctcccaa ggggagggaa    79920
aaaaacagga aaccaacccc agagaagccc accccaggct gggattgcca aggggaaggg   79980
cgggaaagcc tctggtctgc taatgacctc attcggcttc tgcctctgtc tccctgcaa    80040 ccctcctgac tgtctatttg ccattccaga agccagtgaa ggtccttaac agcccaggtg   80100
ttctgaacca cacttcttca tgtacacagt cccacatgtc ctcatccacg cctactccta   80160
cctgagcatc ctggattatt atagccacga ggcggctgcg ggctggttg ggaatctgat    80220 cccaccattc tttcttaatc ctgaaaaaca aaaggaaaag gtgttgatct ctgaattatt   80280
gacaggtgaa cgctcctccc ataaaagtgg tcgttatcac caatacttat ttggcatcag   80340
agatcaggct gattagtttc tggaggtcaa accactgact catcattcta acctggtgac   80400
atggattcta ttgctaaccc tattctacag atgaggagag tgaggcccaa ggaggtggag   80460
tgacagctgg taggtggcag agccaggttc acactcccgc attctgttac ccagcacaga   80520
gttcctgagg aggccaccta tgtcctcagt gggaatgaga ccccagggga ttaggaaaga   80580
ctcaaactgc agagagagga ttctaggttc ccctcaacaa tccctttttc agagcagctg   80640
agggcaaatg accagggaat ggcctgggat ggcctgggaa ctgggggac ctacggagaa    80700 acacaaccct tctctcttcc tggcctgcct ggggccatgg tgcatcatca ctgggaggta   80760
aggtcctcag accgcttctg aattagcctc tgcccatggt ttcaataaat aaacacatat   80820
ttattgagca ccttctatgt ttgactcact gtgcctggcc ctgaggctac aacagtgaac   80880
gagacaaaga tgcctgcctt ggtgaaactg accttcaaga gggaaagatg gatgataaat   80940
ggagacagaa atgcttatat gaggccaggc atggcggctc acgcctgtaa tcccagcact   81000
ttgggaggcc aaggcaggtg tatcacctga ggtcagaagt tcgagaccag cctggccaat   81060
atggtgaaac accgtctcta ctaaaaatgc aaaacttagc caggcatggt ggcaggcgcc   81120
tgcaatccca gctactcagg aggctgaggc aggagaatcg cttgaacccg gaaggcggag   81180
gttgcagtga gctgagatcg cgccactgca ctccagcctg ggggacaaca tgagactcca   81240
tctcaaagaa aaaaaaaaa aacgaaaga aatgcttata tgaggtcatt cattcatggt    81300
aataagtgcc atgaataaag ataaagggt agaagttcaa gatcagcctg ggctacataa   81360
gtgacagcca gtctctacaa aatgtaagaa aattggccag gcacagtggc tcatgcctgt   81420
acccagcacc ttgggagaac gaggtgggtg gatcacttga ggtcaggagt tcaagaccat   81480
cctggccaac atggtgaaac cccatctcta ctaaaaatac aaaaattagc tgggtgtcgt   81540
ggcacacgcc tgtaatccca gctagtcggg aggctaaggc aggagaatcg cttgaacccg   81600
ggaggcagag attgcagtga gtcgagatcg caccactgca ctctagcttg gttttttgaga   81660 ctccactctg tcccaaaaaa taaaataaaa ttaaattaaa ataagaaaat tagccaggtg   81720
tggtggcaag cgcctgttgt cccagctgct ctggaagttg aaatgggagg atctctttag   81780
cccaggaatt ggaggctgca gtgagccgta accgcgccac tgcacttcag cctggctaac   81840
agagtgagac cctgtctaaa aacagaaca aaacaagaaa ccaaagacaa agaacagcaa    81900
agaggctggc atgctgggat atagtgatgg ggagtgggaa gaggtacagg tgatgggaa    81960 actgaggctc agagcaaggc gatcagtcca aggttgctcg gaggcatcag tgacaagata   82020
```

```
tggaggggaa tttgcattcc ctgcctacct agtgtgtgct gggccaagag tgggcacttt    82080
catcaatcat gttaataatc cttagccacc tctaatcctg acttagtgag gttgagcttg    82140
ctagtcccat ttcagagatg ggaggactga ggctctgaga ccatgatt ccaagggctg      82200 gcaagagctc tctggaaacg aggctccttc caccacctcc cagccactcg ccactcatct    82260
cctccctcag cctttactgt gatttggcct cttctggctg atgaaatatg ttctcaccat    82320
cactgtcact ctgcaaagca ggaaccccag gctcaggggt ttcagcaact tgtcggccgc    82380
cagctaccaa gctccaaggc caggattcaa acccaggtct cctgactcca tcagggcaat    82440
cgtcgcaaat tcctctggct cctaccacat gccccaaat gccccagtt gcccaggcac      82500 ccagtgttgt aagggatgt gggatgactc catcttgctt atccctggcc agctcattct     82560
ccccagtcag ggcccccctc aaattttccc tccttggaga gccttatcct ggtccccctt    82620
gcaaaaagca ccccagaaga tctctggcct ccaccctggt ctagtgcatt cagagagtgg    82680
gtcactatgg aaaaccacct gtttgtgatt gatatgtatt ttcagtctcc ccagtaggat    82740
gccggtttta gaaatgtgga gtcctggttg ggtgcagtgg ctcacacctg taatcccagc    82800
actttgggag gctgaggcag gcagatcatg aggtcaggag ttcgagacca gcctgaccaa    82860
catggtgaaa ccccatctct accaaaaata caaaaaatta gccgggcata gtggcatgcg    82920
cctgtaatcc cagctactct ggaggctgag gcagaagaat tgcttgaacc cgggaggcgg    82980
aggttactgt taggcaagat tgtgccacta tactccagcc tgggtgacag agtgagactc    83040
cgtctcaaaa aaaaaaaaa aagaaaaaaa gaaaaaagtg gggtccttgt cgatatgttc      83100
tcagctctac tctcaaggtg tgtagtagct gctcagtaaa tacgtattat tgactgagag   83160
gactgcaaag gggcagacta gaggggcaag tccctgccac cctgcactcc agagggactg    83220
ctcggcagca ctgggcccag gactcacttg gtgatgctga catagcacaa caggcagacg    83280
gccaggatga caatgcagga aacgctgacg cccagcagga ggtgctgctc gaagggctcc    83340
ctgtaggctg gaagtgggag gggaagccat gagctgaggt cagccatggt acagcctggg    83400
ctccacttcc caggactgga gacccagggt caggaccctc gtccgagacc ctccacgatc    83460
tgaccgccga ccacccctcc acctcatctc cccaccactc tccctcttgc acattgagtc    83520
ctcgtcacac cggccacctc attgcccct gctcctccaa agctcagtgc cacctccaga     83580
tcttaaactt gctgctcttt cttttccggaa gcacagaagt caaatgcacc aacttaggag   83640
ccggatggct ccttgctgtg tgacacagga caagtccctt atcttctctg tgcctccgca    83700
tcctcatctg tactatgggg ttaatgacag aattgatcgt gcagggctgt tgcgaggatg    83760
acatgatgaa tcaatagata atgcactcag aacagagtgg cctgtccaca tcattagctg    83820
ccatcatctc aacacggttg acttctcctt gttcactttc atcgtcacat tctccaaaaa   83880 gttttcccg acaccctccc taccgttgcc cctgcccat cgctccatcc ccttcctctg      83940
ctttattttt cttcccagca ctcactgtca tccagatcca tgtgatttct ttctttcttt    84000
atatgtttgc ttttttgtctc tccctccaga atgtcagctc cacaagagtg gggatttcta   84060
tctgctttgt tcatcgccga ttccccagtg tctagcacag ggctagccat gtaggaggaa    84120
ctcagcaaat atttgctgaa ataatgaatg agggtcccat acattgttat ctgtttcata    84180
caagctagtt cccttcccca tgccaatggc agatgagaat caattcaaaa ctttcccaag    84240
cacctggttc tgtgctgggt tctggagata cagccatgga gaccctgcct atggagctca    84300
cagcccaggg caggagacac gtggctcaac tgatatccac agtgcaggat gagcaatgct    84360
```

```
gagagggctg tgcggtggca gggtcagggt actgccagct gccactgcac ctaccacgtt   84420
gaagaatctt ctttcattga gttttcacga cagcccttac tcctcccatt atacagatgg   84480
ggaaactgaa gcagtcttct tcactcaaca gcttttcct ctctcccttg tcagggagcc    84540
atgcccaccc taaggcttga gccaatcacg attatcctgt tccttttcc aggcatttga    84600 gttcccagtc ttccttgcaa tgagcaagta ataacagtaa ccatgtaaca tgtaacagtc   84660
ttggccaatg agatgtaagg ggaattttgc tagggaagct tctagaaaga tgtttgcttc   84720
ctgattaaaa aagagatgca caaggtacac tctctcgtag cagcctttcc tttccttcct   84780
gctttatgta agacagtgtg caacggccaa cctgagggca tgggtggcaa gtctaaggat   84840
acaatgccac catgtgaagg acggcagaag ggaagacagc agaagggaag agatatcact   84900
tggctgctgt acaaaaccca gtaggtccat ttgtaagact tcattttatg tgagataatc   84960
aatatttcta ctgcgaaaga cctgtgggat acctcactga aaagagttgt ttctgggatg   85020
taggttccaa gtgagaaagt tcccagcctc ctttgtggct atgtgtagtc atgtgaccat   85080
tttcaccaat agaatttgag aggaagtgat gcggcccact tccgggctgt ctgctttcaa   85140
gaagcagatg tgatctccat aatcacgcct cttctgctgg ctggatacag acaatggtgg   85200
ggccctagag cagggattct tcacttgggg ttgatggacc aacatggctg caggtagaat   85260 tcagggtct gagaacttgg atgggaaaga aattacatct ttactttccc taacctctca    85320
cacctagcat ctccttccat taagaatgga ggaaggggcc aggaacactg gctcccactt   85380
gtaatcccag cactttggga agccaagatg ggaagatcac tggagcccag gaggtcaaaa   85440
gcagcctggg caacatagtg atacctgtc tctatttatt ttaaatttt aaaaataaaa     85500 taaaatacaa ttttaaaaaa agaatggagg gaagagaccc cagtaatgac agcatcagtg   85560
atcctgtccc cagcaaaaca aaactcacag ctattctcat atcacatcac aatttcagta   85620
tcataaagta ttatttatgc ttatctactt tgaaattaca gtatttatgc gagctacccc   85680
tagaacttat tatttataga tcttaataaa gaagcacata tatctctaga ttaaaaatgt   85740
gtttaaatgt tttataactg catttcaata caattagttt cctctgtagt tctatttatt   85800
ttattttatt tcattgtatt tatttatttt tagagatggg ctcttgctct gtcacccagg   85860
tgggagtaaa gtggtacgat cacggctcac tgcagcctca aactcctggg ctcaagtgat   85920
cctcccacct cagccttccc agtacctggg actacaggtg catgccacca tgcctggcta   85980
atttttgtac agatgggggt ttcactatat tgcccaggct gggatttat gtatttaaaa    86040 atattctgaa atgaggtcca taggcttcac caggctgcca aggaaaccca ggacacaaaa   86100
gtaggtaaga atctttgtcc tggagaatga tggcaccaca agatggaaag aacctcactc   86160
cccagatttc tacagggagg gaaaccacct acaaaccagc aacattcacg ttagcttgtt   86220
acatgagcaa gaaatatatt cctatagtgt taagccatgg aaattgtggg cttgtgtgtt   86280
actgcagcct agcctgccta cctggcagat acaccacagc aggtgtatct aatggcagga   86340
ttgccattag aggcatccta tgatataaaa gcccagagac tcagccaggg gaagtgtctg   86400
gccacagggg aagaatggag agtggagatt accattgctt aggcctcttg atactcacag   86460
ttgtgccact tggtgctggg gctccactca ctccaggtgg tgttatagca ctgagcccag   86520
gccctcaccc gtgccctgta ggaaatccca gacttcaggg tgctggctgc gatgcggagg   86580
gagggttcta ggtaggtcac gttatagatt ctgaactggt agagaaaagg gagatgttag   86640
ggcaccagcc gggggcgagg ggcaccagtg cccaccctgg ttgctgtcgt tagctgaccc   86700
caccatgttt aagagccacc agcctgggta tttggttgtt cgtcctgttc aggccattgc   86760
```

-continued

| | |
|---|---|
| ttgccacctc tgtaactgtg accaggctag agcaacatgc gtcaggctcc tcgactaatt | 86820 |
| agctgtatgt tacttaggca agttgtttaa cctttctgag ttttcgtgag ataattcaat | 86880 |
| ctcatctgta aaacaagggt aagagtccct actaccactt cctggctgtg tgaccttaag | 86940 |
| taagtgacat aacctctctg gacctcaatg tcctcatctg caaaatgaag ataataaaag | 87000 |
| tgcctatctc ccttcccgca gggttgtggt gataaggaaa tgggttaata tacgtaagta | 87060 |
| tttcaaatag ggtttggtat acaaaaagca ctgggtgatc tttctaaagg actggcaggg | 87120 |
| tcgaggcatc tctctctgtc cttcatgggc ttcctagtgt ctccatggtc aagtccaaac | 87180 |
| tcactggcct agaatccaat gctctgccca acctagcctc tactgagaag tgacttccaa | 87240 |
| gatctattgt taagtaaaca agggaagatg cagatgtgta tgtgttctct gcttcttttt | 87300 |
| atgtttttg tttgtttgtt tgtttttaa agagagatgg ggctgggcat ggtggctcat | 87360 |
| gcctgtaatc ccagcacttt gggaggccga agtgggtgga tcacttgagg tgaggagttc | 87420 |
| aagaccagcc tggccaacat ggtgaaactc tgtctctact aaaaatacaa aaattagctg | 87480 |
| ggtgtggtgg cggcacctg taatcccagc tactcaggag gctgaggcag aagaatcatt | 87540 |
| tgaacctggg aggcagagat tgtggtaagc tgagatcatg ccactgcact ccagcctggg | 87600 |
| tgacagagtg acgacttcgt ctcggaaaaa aaaaaaaaa aagagagag agagagatgg | 87660 |
| cacagtgatc actgcagaca aacctaagat ggccccgatg atccccactt tgaatcacat | 87720 |
| ctttgtgtca tctggtcttc tcgagtgtgg gcaggacctg ctacttgttt ctaacccaca | 87780 |
| gaatatggta aaggtgatgg gatatataga ggatttcatg gatgtgatta tattacagaa | 87840 |
| gactgtaata tcctacttgc taggcaagtc tctctgcctt gatggctttg caaagggcac | 87900 |
| atgggaagga attcagggtt aactacaacc aacagccagc acgaaactga ggctctcagt | 87960 |
| tcaacagcct gccagggact gaatgtcacc aatattgtat gagcttagaa gtgacccttc | 88020 |
| cccaattgag cctcagatga aactgcagcc ccatcccaca ccttgattat agcctcacga | 88080 |
| gactctaaag cagagaacct ggctaagcta tgtccagact cccaaccaca gaaactatga | 88140 |
| gataataaat gggtgttgtt taaagctgtg aagctggtag taccattatt atgcagcaat | 88200 |
| agaaaactaa gacagcgatg actgaacaca cacatttgct tgtatagaca taagctctct | 88260 |
| ctaaaggatg cacatgccct ctgcctgccc taaccttgcc tcccttccc ttctggcaag | 88320 |
| agacagacag cagtggtcag tctctgggaa gaaaacagg aggctggagt cgggagagaa | 88380 |
| acatgtttcc attctaagtc cttttgtacc atttgtattt ttattttgtg taactattac | 88440 |
| ttttaccctc caaaaaagct ttaaaaagtg atacatgaac gctatattca tgactgaccc | 88500 |
| tgatggcaag tgagcaacct gagttctcat cctgtcaccc ctctccctgc gagatccagg | 88560 |
| gctatgcacc tccctctcct cttcctcagc ccccggcagt ttcttcctgg ttactggcag | 88620 |
| ctccatttct gcttgtggtt ggaagcacat ttggggaaac ctggtgcaaa gtgagccaag | 88680 |
| gggaggtttt ttcacaagaa agaagcaaag ttccaaaaga ttgctggagc aactacagag | 88740 |
| agttcagaga ttttcctatt acagagggag ctgagggtgg ggtgtgagtt gtggggagac | 88800 |
| tggggaaggg agagaaaatt ctcactctct tttgtctttc tttctaaaca tgagcaaaca | 88860 |
| agaagcaaca gctagatgta agttaccgaa gaaatcttac accctggaag ggagctggga | 88920 |
| actgggaaat gttttactaa gaaacaaaag agaaatctga gcttccaaag aactacttgc | 88980 |
| ggtttgtctg ttttttaaca agaaggacag gtgtttggga gaccatctct gagagaaatg | 89040 |
| tccatgggag gaaaaagagc acaggcttgg gagttcaaat actgggtgca aatctcagat | 89100 |

```
ctgggctgga tgcggtggct caagcctgta atcccagcac cttgggaggc tgagccaggg    89160
ggatcacttg aagccaggag atccagacca gcccggacaa catggcgaga ccctgtcgct    89220
actaaaaata caaaaaatta gcctggcgtg gtggcctgtg cctgtagtcc cagctacctg    89280
ggaggcagag gtgggagaat cacctgatcc caggaagtca aggatgcagt gagccatgat    89340 cacgccctg  cattccagcc tgggtgatag agtgagactc tgtctcaaca acaacaacaa    89400
caacaaaaac tcagccctgc catttccagc tgtgtgaccc tgagcaatgt gcctggcaca    89460
tagtaggcat ataaaatatg gaaaccatta tgaggcaggc attcagggct ctaactaaac    89520
ttttggcttt gtttggtgct ttatcgctac acatattccc acatccccca accccataat    89580
cctcaaacat tccatgaatt ttcacaccca taaaccttt  atcatgcagt tccctctgcc    89640
tggtctaccg ttcccttctt tccccatcta gaaaactcct atgcatcctt caatgcccaa    89700
gccaaaactc cccctccact atggaacctt gcctagaaat tatctagggg aatgaatgag    89760
tagctctagc cccaaaattc tatagtaagt tcctaatgtt tctttctgga atttatccca    89820
ctcagtatga gccacagttg gtgcctatag tgctgtggca gatgcaggtg gacacccgcc    89880
cagcttttat gccatcgggt ttaggtgccc actgcttagg acagaactcc actgcctgca    89940
actccagggc caaccctcat tagtctaagc caattgtgcc aatcccatca cctggcctat    90000
cattcatcag agggggagcat gtggccaagc tctggccaat cactaaattc tttatgttca    90060
gctctgttct tgggaaggga gagatgggt  atctcagttg ccactgttcc acccacaaga    90120
gaagctggac ttcattcttc tgcctcagac ctggtatctg gaggcctgtg gcatccctga    90180
gcaccaacat acccctaagc catagcccag gcatgctgac caatccaatc ccatgactgg    90240
catctggtgc cacgtcttaa acctggctgg cattttagcc agcacagtcc tgcttcctct    90300
tccccagttt ccctggga  agccactcct gccttatttt cagttcatct ggtttggatg    90360
gagctgagcc cacctgcagc cctagaggca ggtatgtgac tcctccctgg acaagcaggg    90420
ccctccacca gcaccctctc tccacccaca gccagtgatt ggttcagagg ctggcacagc    90480
atcgaagcca ggccactgag cagcagcctt aggactctta ttagaaccgt caagaaaaaa    90540 aaccttttc  ccactgtggc tttgggatgt aggcctggag caactagtag gcatatctgc    90600
cactacatga gggaagagcc tgcctaaaaa cgaagccaat acagaataaa gcagggcgca    90660
gagctggaca ggttcctaga agctggatcc agccatgcct gaaggcagat ctagaaatat    90720
gaaaatatta ataacatat  ctttggactc tgaaggtggt acctttctct tcccccagc    90780 ccatccttgg gactctctgt aggtcttgca caggcctggg gcatgagaag gagatttatt    90840
gaccaaacaa aacttgcccc actctctagc atctgtgcac tccttccccc catgccccc    90900 gctttctgag cctctgctgt gtgagccaac tgccccattc ctgctctttc cccatacctg    90960
gcccagtgcc aaaggggaaa ccagacctga gagatataaa tcgacacccc tggcttggcc    91020
agattgagag gaagcagtga cagacaccag catgggagct taaggtggcg ggtgcctgct    91080
ccctgagagc caaccaggcc cagcctgggc ccctgggatg cacagagccg ccctcacaa    91140 acctcaagga acaaatgaca gaccagtgtg tgggacagcg ggcagatggg gatctctgtg    91200
gcctggggca ctcaagagaa agggcacatg gcttttagga cacatgtggg ccaaacaggg    91260
gagctcatct gtatcacaca ccttgtactg tcatagccct gtgggcgggt gctcttgtca    91320
ctcctgtgtt acagatgagg aaactgaggc acaaagaggt tatgggatat gcccaacatc    91380
acacagctgg cgagtggcac agcaggcatt ggattcagc  cctgtgggac cccaggtccc    91440
atatgtccag agattgtccc tccaatggga atgtgaggaa ggtggattca gggtggggaa    91500
```

```
acatgggtgg caggaaatga cctccctgca caccagcaga aaataggggg gactcagcca   91560
cccactgtgg acggcccctg ccattactga cctgatagtt tcctgtaaat cctctcgccc   91620
tttttaaaga tgtcaataca tgtacttaag aaggaactcc actggccagg tgcggtggct   91680
cacacctgta atcccagcac tttgggaggc caaggcgagt ggatcatctg aggtcaggag   91740
tttgagacca gcctggccaa cgcagtgaaa ccccatctct actaaatata caaaaattag   91800
ctgggcacgg tggcaggtgc ctgtagtccc ggctgctcag gaggctgagg caggagaatc   91860
gctagaaccc aggaggcgga ggttgcagtg agccaagatc acgccactgt gttccaccct   91920
gggtgacaga gtgagactct gtctcaaaac aaacaacaac aaaaactcca ccaacactac   91980
tgtgaaggga atgtcaggac cagcttccat ggggaacaac caacaaactg atcttgtttt   92040
cttgggaaag tctaagcctg gggtgtggcc tctgctctct tcattaagag gaattagtaa   92100
acgagtcagc tgtatgggga cttcctcctt aacccgttgg cctcaaaagg gaactgacac   92160
gggtcactgt ctcttgagtc agtattattc tcttcaataa tagggttatt caagtgagct   92220
gtcaatgtgc cacctacgat cacttgtgtc ccccaaactg ggaaacacag atgtggccca   92280
cagccctacc tttacagagg aggagcggca tgcagagata actccccttc tctgatgtga   92340
ggggtggggg gccaggaagc aaagggactt gcctagggca gagccaggtg agaagccagg   92400
tctctagctc ctgggatttg ctatccagcc ccagggcttg cctcccaggc tcctggctcc   92460
agggactggg cctctgctgg tcacccaccc tgttccccag aggtcacaga aaaacgtcaa   92520
agcatgccca ctcacatctg ccgggtcgtt ttcactccaa atgttgactg cataggtgag   92580
atgattatac aggtaattgt caggggggata cgggttgctc caggtcagca gcagagtgtc   92640
ggagacattg gtgtgaactg tcaggtttcc tggggccctg ggtttcactg cgggagaagc   92700
ggcctctatg tgaggatcta tgcagtgact cccccatcac ccagcccagc cccggcctac   92760
aaaccacagc caccacccag attttttggtc gacaaaacct ccatagcata cttctggagc   92820
accacacaga ttcagagcca tagcaaagaa gattataata acaataatgt tgctaaaatt   92880
ctacatagaa ctttagtgtt tattaattac cctttttttc ttcttttttg agacagggtc   92940
ccactctgtt gcccaggctg gagtgcagtg gcacaatccc agctcactgc agcctcaata   93000
gcccagggct caagtgatct gcctcgcctg ggctcccaaa gtgctgggat tccaggcatg   93060
agccaccgcg cctggtcttt actaaccacc tttctacagt gaaggcaaag tgtatgagcc   93120
aaagtaaccc aaacttcagc cttttaaaaa atctttttat ttttatttat ttttatttt   93180 ttgagacgta atctcactct gtcgcccagg ctggagggca gtagcatgat ctaagctcac   93240
tgcaacctcc ttctcctggg ttcaagccat tctcctacct cagcctccca agtagctggg   93300
attacaggcg cctgccacca tgccagacta attttttgta tttttagtag agacggggtt   93360
ttaccatgtt gtccaggctg gtctcgaact cctgacctcc ggtgatccgc tgggctcggc   93420
ctcccaaagt gctgggatta taggcatgaa ccaccacacc cggcctcaaa cttcagcttt   93480
tacagctgca tccttcacac cttttggccac atctctgtac tttatgatga tttactgagt   93540
atttttcttt attttgattc atctgttta aaacttggtc tcctttgaag caatcatatc   93600
catgagacct caggttttta ttcctgtgat gcatgtcata tcatgcatca ctggaataca   93660
acgcatgttt taaactcctg tcaccacagc ccagcaagct caaggggat tcctgcaggg   93720 actccgggta ccagaagaag gtcagccttc cacggtcaag accatccaaa gccgcagcag   93780
ctgaccagtg gacacagaat ggaaggaatg ttcccagttc ggttttcaat cagcagcagg   93840
```

-continued

```
catgccttcc agcaagcaca cctcatctca atacgccttc ctgggcactt aagttcaggg    93900
gtggaaacag ctgggctgaa gggggcttgg tggtctactg cgaccagctc cgtttcaaag    93960
gtgggaggac tgaggcccag gcaggggcag gaatcccatc agatttggga aaatacaggc    94020
ggcttcctcc tgctgttgct atgacccccac ctcctcccct gcccacccca ccctcagccc    94080
aggcagctgt gggaacacac ccagccaccc ctgccgcact ccgccctgct caccatgctc    94140
gctgggcttg aaggagccct tccacagcag ctgctgccca gcccacaggt ccagtgtata    94200
gttatccgca ctgaccacgt catccatgag caggtggcac acgcaccccg cgcctccgtt    94260
gttctcaggg atacacgtgt gggctctgca gacacagggg ctgggttagg ctggtcacct    94320
gtaggctggc tgggcccac agctgtgtcc gggacatgcc tccaggaacc gcatcagact    94380
cttccagctt cccgatcacg gatgtgagga cagatctggg ggcttgggag cggccagggt    94440
gtgctggggc agccgactag ggttgcctct cttgctggcc acagcctctt accacatgca    94500
ccaaggatgc tcctcacacc tgcctagctg ccggccctgg tcctgggact tagcttgttc    94560
ctgaaagccc atgaaaggga agaaccggtg gcactaatta atttagaaca acataagctc    94620
tgcatcgcac agtttggcca tcgtaagata attccaatgt tccaccttaa cagccaaccc    94680
acatctcacg ggctaggcca ggggtctgca aacttttttct gtaacaggcc agatagttaa    94740
tattttggac ttcaaaggcc acacaatttc ctttttttttt tttttttttg gttatttgta    94800
taaatttagg gggtacgagt tttttgtttt ttgttttttgt ttttttttcc tgagacaaag    94860
tctcactgtc acccaggcta gagtacagtg atgtgatctc ggctcactgc aacctccacc    94920
tcctgggctc aagcaattct cccgcctcag cctccctagt agctgggatt acaggtgtgc    94980
gccactacac ccagttaatt gttgtatttt tagtagagat ggagcttcac catgttggcc    95040
aggccggtct cgaactcctg acctcaagtg atctgcccac ctcggcctcc caaagggctg    95100
ggattacagc cgcgagccac cacagtgccc ggccttacaa gtgcaatttt gatggcaagc    95160
ctcagatctg ttctcactgg atatgctgcc tagtggtgaa gtctggggtt ctggtgggtc    95220
cgtcacccaa atggtgtaca ctatgcccat taagtaactt ctcttccttc accctctcc     95280
caccctccca agtcttcaat gtctgttatt ccatggtaca tggaataatg cccatgtgta    95340
cacattattt aactcttact tataagtgag aacatgcagt atttgacttt ccatttctga    95400
attatttcaa ttaagataaa ggaggaggcc gggctcagtg gctcatgcct gtaatcccag    95460
cactttggga cgctgaggcg ggtggatcac ctgagttcag gagttcgaga ccagcttggc    95520
caacatgatg aaaaccggtc tctactaaaa atacgaaaaa ttagccgggt gtggtggcag    95580
gcaccattaa tcccaactac tcgggaggct gagacaggag aatcgcttga acccgggagg    95640
cagaggttgc agtgagccga gattgtgcca ctgcactcca gcctgggcaa caagagcgaa    95700
actctgtctc aaagaaaaca aacaaacaaa caaacaaaca aaaacataaa aggagggcca    95760
tgcagtttct gttacaacta cagcagccag tgtgttccaa taaaacttta tttacaaaaa    95820
caagcagtgg gccggatttg gctcacgggc catagtttgc caatccctgg actaagccaa    95880
tggaaacaaa gcacagccca tctaccttag aataatcatg gaataccacc tttactggtg    95940
aacgctgcat gctggtgtgc cgtatatccc cagtctgccc cgtaactgtg tgtcttgtgt    96000
acgtgattat gtcctgggca ccagtgtaac gaagcatcct gtgcaccatg gagtagccca    96060
gggaaccacc tgactcctat gccatgtgtc ctggtccatc caccatcaca gaggactcca    96120
ctctcaacac cgtactcctc aatcaagggt ctagtccagt ggttctcaaa gtgtggtctg    96180
ggcccaccag gtaaaactct tttcatcata atacagggac gttatttgcc ttttcactct    96240
```

```
ctctcactgg cgtacagtgg aattttctag aggctacatg acctgtgatc atgtaattga   96300
tctgaagatt tgttgaatgc gggcttgcat gttgttggga cttaaaattt ctccattttg   96360
ggccggatac agcggctcac gcttgtaatc ccagcacttt gggaggcgga ggcaggagga   96420
tcactggagc ccaggagttt gagagcagcc tgggcaacac agtgagacct ccatttcagt   96480
aagaaaaaaa atttttaatt gttttaattt tttaaaaatt acaccatttc ttcattgcaa   96540
gttctaatta ggtaaacata gaatgatgtg ttacctacac caaagccctt tgggtcctca   96600
ctcatttttta agtgtgaaaa agggtcctga gaccaaaaag tgtgagaact gctggtctag   96660
tccagtattc cagccgtatc catgtgccac gtggaccaac actcccacca tgcgctccac   96720
tgtatcttac ataacatgtc cctggagatg ggacctcccc tctaacacca tataaacagc   96780
agcaaaccat actcagcatc ctgcactcca gcgcaccacc tggacccagc tcactcttgg   96840
ggcaaaccct ttgggcacaa cctccccaaa cctccagctc cagcgcaggc ttactcggag   96900
agcagaaaaa ccagctggta caacaggcgg agctcggtgc tgcaattggt gggaccattc   96960
atcttccact cgcaagtaga gatgctcatg tagtcggaga cgcaggtggg ctcctgcaag   97020
accttcatgt tccctgggga gacacaggag cagcctgagc ggcccaggaa ctcaatgcgt   97080
gaggggact tgcacccaaa caggaccaag gggaatagca caaaagcaca gtgcaggcaa   97140
agttgagggc cagcgcccac agagctgggg ccaggaccag ggctgctgga gcttcccagc   97200
tagtgtcggg atgactgtgg aagctgaaga aatacccatg ggtgcggggg ccattagaca   97260
agaacgaacc aagtgcacct ttatctcaca caaacttgac aacttgttct tggccaaatt   97320
aaagggaaaa tatgtagcag tttaaggagt gccattccat cacaccaagc ctctgccctc   97380
gagctagggg aagtgccact tccccatttg cccactatct gcgcccctct ttgtctccac   97440
cccttctgc cctctctgtg ctcaggaggc tgataccaca gtcttcatca ccgggtaccc   97500
ttggccttta gtttccggtt gggtttggcc aatgggagag aggagatgga tgggctggag   97560
gagacatcgg ggtccttctc ctttcagcgc cctcctagct tgtcagtggc catggcagga   97620
ctggaattgg caggatgtac actgagtttg ctaaaccacc tgagcatgag accactcagg   97680
cgcctccatg ctcccatgct cagtgccacg cccatctcag ctgacaacaa cttgcataag   97740
ggcttaccat gttaaggagc tgtcttagat agcaaataaa tattccaagc ttatctcatg   97800
tccaaaacta actcctgatt cccgcccctc cccaaagtac cttctcttct ggcatccttc   97860
tgcatttcag aaatgacaac cgcgtccttc ccagtagttt aggtcagaaa tcttggagtc   97920
atcctggcca cttctctttc tctgtctttc acctcaattc caatctgtcc tcaaatctac   97980
ctcccagagg gatccggagc ctctcatctc ctccactcca gacctccctc cagacctcct   98040
ggcttccacc ctcttccttt ctccacacgg catcctgaag agtcctttgg aacataatgg   98100
atgatatgga tcctctgctc aaacactgca aggtctttt tgattcagcc actctgtcac   98160
cttgctgacc ttcactgctc cctcctgctg ctcactctcc tccaccacat tccctcctgt   98220
gctcaaccct cccgccaggc tcagtgcagg gcctctctgc caagaatgag ccttccccag   98280
acatctgcac ggttcccgct tcctccaagt cagctcaatg aggccttccc tgacttccct   98340
actttcaact gcaatccccc ccactccacc cagcttcccc aacccctct tatgctgttc   98400
tgtgttcttt ccccatcacc ttctcttttt ttttgacagg gtctcacttt ctcacgcagg   98460
ctggagtgga gtggcgcgat cacagttcac tgcagccttg acctcctgag ttcaagggat   98520
cctcccacct cggcctcctg agtagctggg gctacaggcg tgcactgcca cacctggcta   98580
```

```
atattttatt atttgtagag acaaggtctc cctatgttgc ccaagctgac ctcgaactcc    98640
tgggctcaag cgatcctcct gcctcggcct cctgaagtgc tgggattaca ggtgtgagcc    98700
actgcacccg gctcccatca ctttctaaca atctttagaa tttactgata atcagggcca    98760
cttgtcattg gctgtcccct cccactgcag tgtaatctcc ataaggccag gtgacatact    98820
gcaggaccct ggcacgccat taatagccaa caaatgaatg attgagaagt ggtgacttac    98880
cagagcttgc cacctgcagc aggaccaggc agctcacagg gaacaggagc ccagagcaaa    98940
gccaccccat tgggagatgc caaggcacct gcagagagag aggaagcagg ttagtgctga    99000
cctgtgcttc cagcagagct catcttattc aatatgcaac cctcccctgc cctggccatt    99060
tatttgtttg tttgtttgct tgtttgtttg tttttccgag acagagtctc gctctgtctc    99120
caaggctgga gtgcagtggt gcaatctcag ctcactgcaa cctccacctc ccgggttcaa    99180
gcgattcttc tgcctcagcc tcccgagtag ctgggattac aggtgcccac caccacacct    99240
ggctaatttt tgtatttta gtagagacgg gtttcacca tgttggccag gctggtcttg    99300
aacttctgac ctcatgatct gccctctgg tcttctcgaa gtgctgggat tacaggcctg    99360
agccactgcg gctgcccagc catgcccctgg ccatttgtgt ctctgccgac aacaggtcct    99420
ccacgttcac agagctctct ctataatcat gaaacaacac ccagacccac aaagtccaga    99480
gggtgagcta cacaacaact gtcctgggag atgcttctgg atgtggcctt ccttggacaa    99540
ccctctacac atgtttctct gattatttcc tgaggtttaa atacctgctc tgtcactgac    99600
tagatgtgaa ccttgagcaa gctgtgcttc catgcctcag tttccttatc tataaagtgg    99660
gactaagaat agccccatct gattgaggtg ttgtggggat taaatgagct aacacagaca    99720
gagccctcca acagtgaccg gaacacttta aagtctcaag taacgttaca agtcagctta    99780
gtccatatag gctgctataa caaaaatacc ttagagcagg taatttacaa agaacagaaa    99840
cgtattgctc tattgggtgc aatggtgtgc atctctagtc ccagctactc gggaaggtgg    99900
ggtggatcac ttggagtcca ggggtttgag accagcctag ggaatatagt gagacctcat    99960
ggtgaatttt tgaaaaattg ttttaaattt tattattcag gccagacaca gtagctcaca   100020
cctgtatttc cagcactttg gggagccaag gtgggtggat cacctgaggt cagggagttcg   100080 agatcagcct ggccaacatg gagaaacccc gtctgtacta aaaatacaaa aactagccga   100140
gtgtggtggc gggcacctgt aattccagct actctggagg ctgaggcagg agaatcgctt   100200
gaactggggt aggcagaggt tgcagtgagt cgagatcgcg tcattgtact ccagcctggg   100260
cgacaagagc aagactccat ctcaaaataa ataaataata aataaataaa ttttctaatg   100320
catagttctg gagactggga agtccaagat cacgacacta ggagatccag atctggtgag   100380
agcccattcc tcacggacga tgccatgctg ctgtgtcttc atatgacaga aggggcaaac   100440
acacttcctt cagcccgttc atgagggcac taaccccatt catgaccaac cacagagccc   100500
tcatgactta atcacttctc caaggcccca atctcttaat atgactacaa tgggatgaag   100560
tttcaacata tgaatttggg ggaacacatt cagcccatag caccagctat tatcattaag   100620
aaaaaaatgt tcagaagcca ggtgtggtgg ctcacacctg taatcccagc actttgggag   100680
gctaaggagg gaggatggct tgagcccagg agttcaagac cagcctgggc aacagagtga   100740
gaccttatct ctacaaaaat taaacaaaat cagccaggca cggtggtgca tgcctgtaat   100800
cctagctact tgggaggttg aggtgggaag atcgtttgag cctgggatgt caaggctgca   100860
gtaagccaag actgtaccac tgcactccag caagaccctg tcataaaaaa aaagaaaag   100920 aaaagaaaac agaaagtttg ggaggctgag gtgggcggat cacgaggtca ggagtttgag   100980
```

```
accagcctgg ccaacatagt gaaaccctgt ctctactaaa aatacaaaaa ttagccaagt  101040
gtggtggcgc acacctgtag tcccagctac acgggaggcc gaggtgggag aattgcttga  101100
acccaggagg cggaggttgc agcgagccga gaccatgcca ttgcactcca gcctgggtga  101160
cagagtgaga ctctgtctca aaaaaaaaaa aaaaggaaaa gaaaaaaatg ctaagaagca  101220
gaatctcacg gagtcaagtg tgtacttttc cccagcactc ctggtacata acgtcaaata  101280
ccctccaaaa agtgtgtact ggggccgggc gtggtggctc acatctgtaa tcccagcact  101340
ttaggagttc acaaccagcc tggccaacat ggtgaaacct gtctctacca aaaatacaaa  101400
aaaaaattag ccgggcggta gtggcgcgtg cctgtagtcc cagctactca ggaggctgag  101460
gcaggaaaat cgcttgagcc taggaggtgg aggttgtggt gagccagagat ggcaccactg  101520 cactctaggc tgggcgacac agtgagaccc tgttgcaaaa agagaaaaaa aaaaaaaaga  101580 aaagaaaaa aagaaaacag cacgcgctgg gttatattcc ctgcaacatt tcaagtgccc  101640
atccttcact tcccgcttgg gtctctctcc tgggatctta ttcaaaaaag cagctcccag  101700
gctttgttct gctagtgagt agttcttttgc cattaacagc atttctcttt tggtgctctg  101760
gctgtgtttc tgtggcacag gaatggttcc aaggctaacc tcacaggctt gcagcaaaca  101820
ggaacggagg tgttgcctct gaagtactgt gtgcagtgtc tggggcatca taagaactta  101880
aggccacctc aggagctcta ggcccctgct ggatgctctc cgagtgactt gggcacactt  101940
gaaggccctc cccccagcag ggctccacct ccctctccac ctgggcccag cacccatgca  102000
tcctacgcct gccacctaca cttcttcttt tttgttttttt aacatttat tttattttat  102060 ttcatttat tttttgaga cagagtttca ctcttgttgc ccaggctgga gtgcaatggc  102120
gcgatctcgg ctcactgcaa cctccgcctc ccaggttcaa gcgattctcc tgcctcagcc  102180
ttctgagtag ctgggattac aggcatgggc cacacaccca actaattttg tattttagt  102240 agagacaggg tttctccatg ctggtcaggc tggtcttgaa ctcccgaccc caggtgatcc  102300
gcctgcctca gcctcccaaa gtgctgggat tacaggcgtg agccactgag cccggctgcc  102360
acctgcactt cttaaacaca ccaaactcag tcccacctcc atgccttttc tctctctgtc  102420
ccctccacct ggagggacct tcccttcctc cctttccttt tttttttttt ttttttgag  102480 acagagttta ctctgttacc caagctagag tgtagtggca caacctcgac tccctgcaac  102540
ctccacctcc cgggctcaag caatcttccc acctcagcct cctgagtagc tgggaccaca  102600
gatgtgcacc atgaggcctg gctaagtgtt tgtattttg atagagatgg ggtctcatta  102660
tgttgcccag gctggtctcg aactcctgag ttcaagcgat ctgcccacct tggtctccca  102720
aagtgctggg attacaggcg tgagccactg tacccggccc ttcctccctt acgcgtgctt  102780
ttcctctctt cccctaattt atgatggtgc aaaatcaatg ggtgttcagt agaagcagta  102840
cttggagcac ccatacgacc attctgtttt tcactctcag tattccataa actacacaag  102900
ctattcaaca ctttataaca aaacaggctt tgtgttagat gactttgccc aactgtaggc  102960
taatgcaagt gttccgagct aagttaagct ataacgttca gtaggttagg agtatgaagt  103020
acatttctga cttaataata ttttcaactt atgatgagtt tatgggaca aaaccccatc  103080 attaagaaac atctgtgtat gagacacata aacacactca catatctcca taatgaataa  103140
attaccccaa tacctcagtg tgcatgtcag aaaaacaagg acattctctg cataatcaca  103200
atacaaccat cgaaatcagg aaattaacag tgatgcatca ccactatctc atccacggcc  103260
cctatttatg ttttgctaat tgcctcaata atgccctta tacgtccagg atgcaatcca  103320
```

```
agatcattca tcacatttga ttatcatgcc ttcctagtga ccaggtcttg gcttctaaat   103380
actattctgt actgaaagga accagagcgc cttagagaaa tagctgattc caggagaagg   103440
aaaagtacca gataggcttg gaattcttgt gccagacaat aaggaagtac tcagcagcta   103500
gcctgacctg gacaaaacag gcacatttg agcatcaaaa tgaatattat ggtatccact   103560
tgtaacccct ggagttaaag tccaggagtc tgtattgaca tagatcaata aatggaggag   103620
gccgggtgca gtgtggtgtg tgcctgtaat cccaacttct gggaggctg aggcaggagg   103680 atggcttgag cctgggagtt ggaggctgca gtgagctatg atcgcaccac cgcactccag   103740
cctgggcaac agagtcagac ttcatctcta ataaataaat aaacaggaa gaagggaaag   103800 ctctattta ctatgacagc ctcaaagtaa ctccctgcaa aacttgtatt gtatattaac   103860
taatgagtga aaatacatat caatgaacgt tacaatacag aaacctggca gacaccacct   103920
tcaccaagtg atctaaactc accaacaaga atgggacaaa tccccaacat cacctccctg   103980
aaacaattcc tgagaagagc acagcatgtc ttttcctggg ttcctgccaa ggatgcatac   104040
atcatttgga aacgtcagac aaatgtacac caagggccag tctatataca agaactggcc   104100
gctgctcctc acgaagtgcc gggggtgcaa aggacaagcc agcgtgggac atctgtccct   104160 tttttaaattg tctgtcatcc tgacagccag ggtctgtccc attcactgcc gagtccccag   104220
tatctacaac ggtgcctggc acataggacg tgttcagtaa ctgtttgttg attaaattca   104280
ttttggacat gatgtggggc ccctaactgg ctcagcatga ggctgcaaag ctctctctag   104340
gggaaggctc tgtatcggct caaaggttga actcgtcttc cttgctgaga gttacaaaag   104400
taaagtctca agtaaaggag gggcgggaat ggggtggtgg gttcctgaca ctgatttcct   104460
tggcaagtcc tagtaaccttt tactctcaca actacacaga tgcccacagt atcctgtggc   104520
agagatggca aaggtgtcac tttagcctca attatgaata aagagaaaca gagaggccaa   104580
gacgcctgtc caaagtcaca cagcagaaga cttcatggt aaagtcctcc agggaaacag   104640
gggagtcaac aaccctgtca agattcacta aaacatccca gcatggcgtc aggattgata   104700
tccttaatct gttgtggaag gcacgcccag acttacgcat gcccatgtgc acacacgt   104760 gccgcagcta gcttctcagg gatgtgtggg tgctacattt caggagagat cacagatgca   104820
gtgggagaag aggcttccct gaacatcaga ggcaaaaaga acaaagatgc aggtgagtaa   104880
aagaattaaa aagataagtg ccaggttatc gcgttcaagt acacggcaag aggagatgat   104940
ttcaagttcc cattctaaat caagagactc ctggctgggc gcggtggctc acgcctgtaa   105000
tcccagcact tcgggaggct gaggcaggca gatcatgagg tcaggagatc gagaccatcc   105060
tggctaacat ggtgaaactc agtctctact aaaaatacaa aaaattagct gggcgtggtg   105120
gcgggtgcct gtagtcccag ctactcagga ggctgaggca ggagaatggc ttgaacccgg   105180
gaggcggagc ttgcagtgag ccaagattga gccactgcac tccagcctgg gtgacagagc   105240
aagactgtct cagaaaaaaa aaaagagat tcctgaagtg gtggagttgg aagggtctc   105300 agcggtcacc tgccaagctc aactgccaac ctggacaagg atgtcctgcg aacacccac   105360 ttctgacatg ctgctaggca gtttcagccc atatgccacc acagatggag caatcactct   105420
caggtctcag ttaagcagag ccattggaaa cagcctcctt atgttgagtc aaggctttgt   105480
gtgaacaaaa tccctgcttg cccagcactt accttgtact tgacactttg ctaggtgctt   105540
tagaagtatt acctcaccga atccacacaa gaatcctgaa aggtaggctg ttatcccaac   105600
tgtctagcta aggaaactga ggccagagag gccaaataac ccatccacca ggtcccacag   105660
ctggtaaaag gtcagagcta gaatcagaac ccacgtttgt ttgcttccga gcccaccgtg   105720
```

-continued

```
gattccagta taccagttcc ttcaatctca tctcctaaaa ctgcaggctg aacccaataa  105780
gatgaaataa aatgagccgg gcagagttgg ccatcctgct tgtcaatttc aaacaacagt  105840
tccgcaagtg taggataaga aaatctgact gagcagcaga aaagtcctga ggattttatc  105900
atctgcaaaa tctccaaaag ccaatggtga agcagcaact taaaaaaaaa aaaagagtca  105960
cccgaggtca tattaacaga ggtatccatt tatagactgt tacatctcac aacagcagaa  106020
tatacattct cctcaggttc atgtggaata atcaccaaga cagaccacat tctgggacat  106080
aaaacaacct taagagattg aaaacattag aaatcacaca acatatgctc ttaggccaca  106140
atggattcaa attagaagtc actagcagga agaaagccag aaaatttcca agtatttgga  106200
gatttaaaaa cacacttccg aataacatat ggatcaaaga agaaatcaca agagaaacta  106260
aaaatatttt taactaaata aaaatgaaaa tatagcctat caaaatcggt gagacgtagc  106320
aaaagcagtg cttagaggga aatttatatt attgaatgta tatcttagaa agaaagttct  106380
aaaatcaata atctgtttcc atctagagta ctagaaacag aaaagcaata tatgtctaaa  106440
acaagcagaa gaaaaaaata caaaattgga gcatacatca atgaaattaa aaatagaaaa  106500
ttaatcgagg aaaatcaatg aaatcaaaaa ttggttcttc gaaaagatca atgaaattga  106560
taaatctcta cctaggcgaa tcaaaaaaat gagagagaag gcactaatta ataataatgt  106620
gatatggcct ggctctgtgt ccccacccaa atctcaccttt gaattgtaat atgaattgta  106680
atccccacgt gttggggggaa ggacctcatg ggaggtgatt agattacggg agcagttccc  106740
ccatgctgtt ttcgtgacag tgagtgagtt ctcctgagat ctgatggttt tataaagggc  106800
tttccccccc tttccttggc gtgtctcctt cctgacgtca tgtgaaaaag gatgtctttg  106860
cttccctttc cgccatgata atatgttttcc tgaagcctcc ccagccctgc agaactgtga  106920
gtcaaacctc tttcctttat aaattaccca gtcttgggca tgtccttaga gcagcatgag  106980
aacaaactaa tactattgta aattaaagaa aagttattag aggtggcaca tgcctgtagc  107040
cccagctact gggaaggctg aggcaggagg atcacttgag cccaggaggt taaggctgca  107100
gtgggctgtg ttcatgccac tgaactccag cctgggcaac agagaaagat cctgtctcaa  107160
aaaataaaaa ataaaatttt taaattaaaa aaaagtggca ctatataatg attcgggagt  107220
taattctcca agaagatgta aataacaatc cttaatgtgt aggcaactaa caacaaaggg  107280
tcaaaatatg taaggcaaaa actgagagca gcaaggagaa atagagaaat ctgtgtgatt  107340
attctgaata atactattat tggataataa tagtattatt actattactt caactctttt  107400
ggtaatcgac agatccagca ggcagaaatc agtaaggaca cagttgactt gaacagtgct  107460
gtcaatcaac tggatctaag tgcagtgtgc aaccacaact tggcatccct ttggaaggaa  107520
tactgctgtc atgtatgaca acaaccaaca cagagagggc ctgataatcc caggaggcct  107580
agaaagtctt tacctggaaa gctctgcccct cctatactgg gcagcctcac cattcactta  107640
aacacacaga gtttaccaca tgccaagttt tcttttacat cttttacata caagaatgca  107700
tttaataatc tatgaaatag gtaatattat tttctccatt ttcagatgag gaaaccaagg  107760
cacagaaagg ctgagtgatt tgtctgaggt tgcacagctg tgacagtcat gggtcttaaa  107820
tccagcactc aagctccaaa gctttggttc ttaactacta tctgtctaga agtcagagac  107880
cttagtgttt tggggatcaa tgacctatct gagcatctaa tgtaaacccc aaaccctgtt  107940
tctggcaagg tgcatacact taattctgca ttccatttta ggggttcaca gaatccctga  108000
agcccaagtg aggacctcag gtcaaaggcc tgtcctctaa gcagtgggca gcttttgagg  108060
```

```
gtctttgagc agggagtgg caaattttg agaagtctgg ggggatgtgg gcagttagca   108120
gttgctgcag atgaggctca ccctgcctct tctccacatc acagccagag ccattttaaa   108180
atcagaaatg agaccagggc cagctcacac atccaatgcc ccctggctcc taaagggctt   108240
cttcacaggg gccacagatc cccaggggt tcacagctca ttagagaagc atctctgact   108300
tagaataaaa tccaagccct agagtgaaaa aagccagttc ccagagtaca caccccgtga   108360
ctccatttat gtaacatact tgaaatcaca taaccatgga aatggaaaac acatcagtgg   108420
gtgccagggg ctgaggggt gggtcaggaa gggagttgga tgtggctata aaggagaat   108480
ttgagccatc cttgtgatga tagaactgtg ctggatcctg gctgcataca caaacctatg   108540
ccgtgataaa attgcatagc actaaaccac acatgcgtac gcaaacacaa aaatgagtac   108600
aagtaaatcg ggaatcccca ataaggtcag tagcttatat cagtgtcagt atcccagctg   108660
tgatactgta ttacagattt ctacaatctt gccctcgggg ggaacagcat agaagcaggg   108720
gtctctctgt gattttctttt tcttttttctt ttctttttttt tttttttgag atggagtctc   108780
actctgttgc ccaggctgga gtgcagtggt gtgatctcgg ctcactgcaa cctctacctc   108840
ctaggctcaa gtgattctcc tgcctcagcc tccccagtag ctgggactac aggcaagcca   108900
ccatgcccaa ctaattttg tatttttagt agagatggg tttcatcata ctgaccaggc   108960
tggtctcgaa ctcctgatct caagtgatct gcccgcctca gcctccaaaa gtgctgggat   109020
tataggcatg agccaccacg cccggcttct ctatgatttc ttccagctgt gtgtaaatct   109080
ttaattatct gaaaataaaa agtttaattt aagaaaatga agaaagagc caattccct   109140
gcttatccct ctaacattcc cctcctatcc cctctccctc ttctgcaatc ctccattggc   109200
ctcagccctg ggatacactc ccagctctcc cttttccaag catttgcacc agaaacactt   109260
cagaagcctt ctctgacccc cctcaactaa tgcgggccct ccctgtgact tcttatcaca   109320
gcacctgtt tatgtctgtc ccagtactta tcactatctc taatcagatt aatgaggtta   109380
catgtatgaa tgtttatttt atttcaagat gcagatagca aagatagctt tgactgcaaa   109440
atgttttcaa cttccctaga ttttttttttt ttttttgag acggaggttt gctctgttcc   109500
ccaagctgga gagcagtggc gtgatgtcgg ctcactgcaa cctccacctc ccgggttcaa   109560
gcgattcttg tgtctcagcc tctcgagtag ctggaattac aggtgtgtgc caccacaccc   109620
aactaatttt ttgtgttttt agtagagaca ggtttcccc atgttggcca ggctggtctt   109680
aaactcctga cctcaagtga tccacccgcc ttggcctcca aagtgctggg attacaggca   109740
tgagccactg tgtctggcct agattaaat atgccataag aaaaagacag aactcaagtg   109800
tgttagtcca tttttgcatt gctataaaga aatatctgag actgagtaat ttacaaagaa   109860
aagaggttta attggcttat ggctctgcag gctgtacagg aagcatagca cccgtatcta   109920
cttggcttct ggggaggcct cagggagctt ttattcacgg ggaaggcaag aggggagcag   109980
gcgtacatgg tgacagccag ggcaagagag aggaggggag tgccgcacac ttctaaacaa   110040
ccagatcttg tgagaactca ctcactatgg caaggacaga accaaaccat gagggacccg   110100
tccccatgac ccaacatctc ccaccaggac ccacctccaa cactgggat cacatttcaa   110160
caagagattt agagaggatg acatcccaac tatatcagca agcaaaagac tagaaaaagg   110220
tagcaatcta cattatgaac ggttaatggc cttaatatat gaagagttct acaaatcaa   110280
taagacaaac atccctttaa gaaaaatagg caaagaacat aaatggttca caaagacat   110340
attcctccat cagatgtgaa atagccacct caatatactg ctagttttc aagttgggag   110400
tataataggt aacctcaaat ttaaattatg tatttgtcta taaatgcatt gtttgcctcc   110460
```

```
ctctgagaga ccacaagccc catgagggca gagctttatg tctgctgtgc tcactgcttt    110520
atccccagtg cctgaaacag tgcctgacac aggcatagca tgtgtacaat aaacatatat    110580
taaatgaatg aatggtttaa aagtcagcaa taataggctg ggcacagtgg ctcacgcctg    110640
taatcccagc actttgggag gccgaggcag gtggatcacc tgaggtcagg agttcaccaa    110700
catggtgaaa ccacatctct acaaaaatac aaaaattagc cgggcatgat ggtgggtgcc    110760
tgtattccca gctactcggg aggctgagag gctgaggcag gagaatcgct tgaacccaag    110820
aggcagaggc tgcaatgagt tgagatcaca ccattgcact ccagcccggg caatagagca    110880
aagttctgtc tcaaaaaaaa aaaaattcag caataataaa ttcaacaatc tttttttttt    110940
ttttttttga gatggagcct agctttgtca ccagtctgga gtgcagtggc acgatatcag    111000
ctcactgcaa cctccgcgtg ggttcaagtg attctcctgc ctcagcctcc tgagtagctg    111060
ggactacagg agcacgccat cacacctggc taattttttgt attttttagta gaaacgggat    111120 ttcaccatgt tggccaggat ggtctcgatc tcttgacctc ctgatccgcc tgcctcagcc    111180
tcccatagtg ctgggattac aggcatgagc taccgcacct ggcctcaata atcattttta    111240
aacatgaacc aggtcccaag cttttgtcca tagttaactg tatatgcagt acttattttg    111300
tgcctggccc tgttctaagt acttacaata tattaatcaa tttggttctc ccaacgaccc    111360
tatgaggtag gtgccattaa cattcccatt ttactgatga gaagactgag gcacaaaaag    111420
gctagagcac ttgctggtgg tcacagaacc ataacctagg cattgtcact ccaaaatcca    111480
cgtgtttaag gactgtggtt gctgaccctt gaaatgcagt ccccaaaacc ctggaacttt    111540
gtccggggag ccccactggc ctgagaccca ttggcctgag acccagagac agcaagtgac    111600
aaggccaagg tcagagagtt aggaagcagc aaagtcagtg aaggccgcag ccaggaaatg    111660
agcagaagca tgggcctggg aaaacacgcc cgccaccagg agaacacact tgactcactt    111720 ttttttaaaaa actcggggga gattaagtga ttaagccttg aaatgtcaga agccagcagc    111780
agcctggaag cgacccagca ggactcttcc cgaacccaca gcgggtggca gggggcagg     111840 gggcggagga ctgggggcgc acaggggcg gtacaggcct tctgctcttc ttccctctgg    111900
gcaggaaacc tggcttggag gagggctgg ttctgcagac aggatgcaag cacctctgtg    111960
acaggtggca tgtggagagg aatccaggga cagcaggggc ctcgggtggg ggctgggct    112020 ttggagccgc tgacccctga aactccacga cagaaactgg cctgaaacct cagctcctgt    112080
ggcgcaatca gttagtcatg ctacttataa gaaaccagcc cagagcttcc tctggcttct    112140
gggacagctg ggctgggctg gcaggaagct aggcatgcac ttcttcctgg gacagtaacc    112200
tacctagaac tggggttttcc agaaatggca gccacgtcgg tggccccact gggatagtaa    112260
ggcaggccag gccagggccc cagaatggcc cgggatctgc ctggttggct ccgtccccag    112320
cccagccagt gggagggagg ggaggcaaca gactggctct gcagccacca ggaacacaaa    112380
tcggccccct ccaccaacag cacccaccag cctccctgtg ggcctgctgt ggctcaacca    112440
tcctcaccca cttgctcaag tacctcactt attctccttc tcttttttgc tttagagaca    112500
gggtctcatt ctgtggctag aatgcagtcg caccgtcacg gctcagtgca gccttgaact    112560
cctgggctca agtgatcctc ctgccttagc ctcccaagta gttgtgacta caggcacaca    112620
ccaccatgct cgaataattt ttaaattttt gtagagatgg gatctctct ctgtggccca     112680 agctggagtg ctatgcaca atcatagctc actgcaacct caaactcctg gcctcaagca    112740
aacctcctgc ctcggccttc caacatgcta caggcatgag ctgccgtgtc cagccatctc    112800
```

```
ctcatttatt cttgctgtgg gtgttttcca agtactgcct atgtgctggc tattacagat    112860
gcaaacaggc cattcattca ttcattcctt tcttcttttta acaaatatttt gagcaaggaa  112920 gaagttgcca gagcgttttg agcaaagaag tgacatgatg agactttaaa aaagacctct    112980
cttgcttggg tggtgggggc acgggtagaa gtgggtagca gtgaggaggc taccacactg    113040
gccccagaga gaggtgccag ggctcacacc aggctgcgga gatgggagg ttgagaaggg     113100 gctgaattct agatctgtgt tgaagacaga gcccacagga tttgctgaca ggatggatgc    113160
tgtggggcgg gagagagaac aggaaggcta ataggagtca agaatgattc cacagccatt    113220
ggccttttcc aagatggcgg cctgtggggg tagcccgtgt gacaagccag cctgctgggc    113280
aagctgcagg acttcagatt agcagaggag gctgttagca ggcgctcagg gaagaccctc    113340
cctcatccta gagggtcagg tttctttatc ggggatgcac cagagttctc tcggggaggg   113400
gcccgacata cagcaggcac tcaataagtg agcatgtgta ttttatttta ttcttatttt    113460
aacaggtata cagtgtttcc ttggtgccag acactggcct aggtgcttta agccctccct    113520
atgagataag tataattatt aaacccattt tatgattctg aaggttcttt ttttttttt    113580 gagacagagt ctcactgtgt agtccaggct ggagtgcaat ggtgggatct cagttcactg    113640
caacctctgt ctcccaggtt caagtagttc tcctgcctca gtctcccgag tagctgggac    113700
tacaggtgcc cacaacaacg cccagctaat ttttttgtat ttttagcaga cagggtttt    113760 tgccatgttg gccaagctgg tctcaaactc ctgacctcag gtgatccacc cacctcagcc    113820
tcccaaagtg ctgggattac aggcgtgagc cactgcgtct ggcagattct gaaggttctt   113880
atgagagggc ggggtgaggg agggaatgag ggaagaccca gcgaataggc aggcaggagg   113940
gagggcacgg cccacttccc accctacaag cggggcccctt ggctggagca agggggagaa  114000
ggactggctg ggatggcagc tggaaggttg gcaggccagg gacaacatcg tctgccaagc    114060
catggcagta gactcaaaact ctgtctctag ggcagtgggg agccagtgaa ggctcttaag   114120
caggagagga gcgggctgag ctgagagctg gcgaagaggg ggcaggtttg agcctgttttg  114180 ggaggaggag gcagcaggga cttggtggcg cttggtgggg aaagcaggct ggggagagcg    114240
gggacagagg gaaagtggcc tcaggctggg gtggtgggga ggatcccagg gacccttccc    114300
acgatggaga gccgagaaga gaagcagatt tgctggggaa gaccacgcgc tccggcgcac    114360
tgtggacact ttgagtccac acagtcaaca ggcaactcca tccgggatcc tggaagccag    114420
gcctgtcttc agaagattcc agaggcccaa aggaggaaac agagcctgag gaaactgtgt    114480
ccagaagcca cctacccagg aacagcagcc agcctggcct ccatctttct gcaacctgtt    114540
atcttgcttt atttctctgc aatctttgtg gcatattgca cactcgggcc ttatgtgttt    114600
ggtgctcata tcccctactg caaggccagc tcacacaagg ccagtgtcga tcccgctcac    114660
agccatctcc ccagagccta gcacggtgcc tggcacacag caggtgctcc atgaatattt    114720
gctgaatgga agaacgacag gatgaattcc cctggctgtg agcagggagg cctggttggt    114780
catccccaat tttccacctc tccctgctgg gcaaacacta gcaaatcctg gcttggagtc    114840
cccttaaatg tcctaatgca ggcacagatc tcagcccacc tcggggccct gacctccaga    114900
gagctggtta tcgactatca ctcactgtcc tgagcagcgg acaatggcct cttggcgcca    114960
gggtgctgat tagattttga ctgtcttagt gacagctatg ctcctagct ggcctccttc     115020 ttgaggtctg cagaggtcac tgtgactggc cacgtgtccc ctcttccttc agccatgaga    115080
ggccatgccc tgggcccttc tgcccttggt ttcgcccctc cccaactggg tgcaactttg    115140
ctcaccagcc ttggcattgg ttgtaccagt ctcactaaca aaaaaaagca cttgaaggct    115200
```

```
gggcgcggtg gctcctacct gtaatcacag ccatttggga ggctgaggca ggtagatcac 115260
ttgagtccag gagttcaaga ccagcctggg taacatggca agaccccgtc tctaccaaaa 115320
atacaaaaaa aaattgccag gcatggtggc acatgcctgt agtcccagct actaagggag 115380
atgaggcagg aggatggctt gagcccacga ggtcgcagct gcagtgaact gtgatcatgc 115440
cactgcactc cagcctgggc aacagagtga gaccctatct ctaaaaaaaa aaaagaagc 115500 ccttgagcct cactcactca cttaaccatg gacccaatcc aaggagcatt gcagatacaa 115560
ttaatatcat ctccattgca gagatggaga agccgaggcc cagagagggt caggaacctg 115620
cctaaggatg cacagctagt gagtgggctg ggatttgaac ccaggccttt ggctctggag 115680
tgcacagcac agtgcctggc acagaagcag tcataaactt gcttttttat acaccactct 115740
tttttgcttc tcctggaaag ctcactatgg aagatacagt aaaatattct ccctgcaagc 115800
acagatggag gaatgaggct gagggaggtt cagaatttgc ccgaggtgat ggtgacggag 115860
caggaagtaa ccaggtagga atttagaatc tggcctttgt caccatttgc tcggccctca 115920
gcagcagtga acttgtctca acaatgacca ggactttgcc ccctgggcaa acccaaagcc 115980
aggacaacac atgggcacag gtaagagctt cccgttcatt ttctgcttgc agactggcat 116040
atggaaggca gtgggtgggg actacccatg gagctcttcc tgttgtctca ccccatacca 116100
ttcctggatg ggtggggaca cacagacatg ggggccacct ttgtgggcag ggacccccaa 116160
gcatctgaga cacagaagca taactctggg cctaagtgca ggctccaacc tgactcggtg 116220
ggagaccgtg gcaggctgga gtccactcag agcctcagtc tcctcatctg tgaaatgaga 116280
ataagatcac ttgcttcatg gctggttgca aggctgctgt tgttttttaac tcatctggct 116340 tattagtaca ggagtactga catcaataaa atagaattca tgacaatgat gtcttgagta 116400
agtattagaa gagagaaggt ggatggtttt tttgtttttg ttttttttgag aatgtctcac 116460 tctgtcacct agactggagt gcagtggagc aatcatagct cactgcggcc ttgaattcct 116520
ggtctcaagt gattctccca cctcgccctc ccaagtagct ggaactacag gtgcacgcca 116580
ccacacccag ctaattttta gttttttggta gagatgggt ctcactatgc tgcccaggct 116640
ggaagttggc tcttttatac tgattaaagg aacaattcag ccagctgcgg tggctcatgc 116700
ctgtaatccc agcactttgg gaggctgagg tgggcagact gcttgaacct aggagtttga 116760
gactggcccg ggaaacatag cgaaatccca tctctacaaa aaacacaaac atcagctagg 116820
cgtggtagtg cacatctgta gtcccagcta ctcgggaaaa tgcaacaatt caccaaaaag 116880
gtataaaaat cctgaaccct tattctactc atatggctat gcacttaaca acatagcttc 116940
aaaaataaag caaaaactg acagactcaa aaggagaact taacaaagcc tctattatgg 117000
tgaattgtaa ttgtattacg gtgggaggta aatcaggtaa aaaaaaaaa aaccacatag 117060 tgacataaca aatatagata atataatagc tagcttgatc aaatagatac atttctagaa 117120
ccttataccc aacagaaaat atacattctt ttcaaacaca agaggaaaaa aatgaccaga 117180
aaatcctata aagatctcag caaattctct accactgata ttataggaac cacatatatt 117240
gaccacaaca accatgatga ccaaatttag aaatcaacaa taaaaagata acttaaaaaa 117300
ttctatctgt ctcaaaaatt taaaaagcat ataattaaat aagtcttaaa atgggaacca 117360
aaagggaaat tctaaactgg gcagtgaata acattgtgta acaagttgtg gaaagaaacc 117420
aaagcagtac tcaaagaaaa aatgatagca tgttagcctg aagtagattt attagagagc 117480
atgaaaaact ggaacctctt agctttagac aaggactctc agaatagaag aaacttggat 117540
```

-continued

```
taacagcagc tcatatagaa gagaaacatg gagattttag ctgacaagcc caatatgcac 117600
tccaagtggg atatggctgc tacacagtat gattccaggt tgcatcaaca gaagtataag 117660
ctctagatcc aaggaggtaa tagtctcctt cctctttgac caaacaaaca gtctttgcgt 117720
gggactccaa ccagttgact catgtgccaa ggcaggccaa acttataatt tcctgagtca 117780
gggagaatac ctgaaataac tacagttgtg tagtctgaat aagagaagta tccgagtttg 117840
gagggagatg gtcactacct ccaagaggca gaaacagact cagaaagtgg aagctcctag 117900
aaagctaatt tgggctgggc acggtggctc acacctgtaa taccagcact ttgggaggct 117960
gaggtgggcg gatcacccta ggtcaggagt ttgagaccag tctggccagc atggtgaaac 118020
cccattgcta ataaaaatac aaaaattagc caggcgtggt ggtgtgtgcc tgaaatccca 118080
gctactcggg aggttgaggc aggagaatca cttgaacccg ggaggcagag attgcagtga 118140
gccgagattg cgccactgca ctccagcctg gcagcagag tgagactcca tctcaaaaaa 118200 aaaaaaaga aagaaagaaa gctaatttgg ctaaatctca ggaagatttt ctcccagtta 118260
gagctgccca cctgtggaaa tgtggcttct ggaagaaata tgctagaggc aagaccgtcg 118320
ggaggctgtg gccctgccag cttggagacc tgcccagccc agagagctgg tgcctctcct 118380
ccctagaatt cagtcttccc ttttaaaaag gcagaatact tccctggccg cttcaggaaa 118440
acataggcct tctctgagtt tttcaaaaat ggttctgggc gactatgctc actgatttcc 118500
aaccaagaaa tgtaatcctt ttaaactctc ctctttgggc tggatagctc agaaccgtgg 118560
ttaaatgcac aggcttctgg gtccgtagcc ctgggtttga atctggactc tgccacttag 118620
gagccgtgtc acccaggtaa gtctctagcc tgagcctcag gttcctcctc agggaaatga 118680
gcaggacacc cactcatctc cattcctgca cccagcacag agcgtgatgt ggactccagc 118740
ctccactgcc agaggccgtg gttggggcca tggcttcggg atgattcaag cacattacat 118800
gtattacgta ctttatttct attattatta tatggtaaca tataatgaaa taattataca 118860
actcaccata atgcagaatc agtgggagcc ctgagcttat tttcctgcaa ttagatggtc 118920
ccatccaagg gcgatgggag acagtgacag atcatcaggc attagagtct cataagaagc 118980
acgcacccag ggccgcgtgc agtggctcat gcctgtaatc ccagcacttt gggagactga 119040
ggcaggtgga tcacctgagg ccaggagttc gacaccagcc tggccaacac agtgaaaccc 119100
tgtctctact aaaaatacaa aaattagctg ggtgtgatag cacaggcctg taatcccagc 119160
caccaggctg aggcaggaga atcacttgaa catgggagg tggagattgc agtgagccaa 119220
gatcgcacca ttgcactcca gtctgggcga caagagcgaa actccgtctt aaaaaaaaaa 119280
gaaaaagtac gcaacccaga tccctcacat gtgcagttca caaagggtt tgtgctcctg 119340 tgagaatcat ctaatgcctc agctgacctg acaggtggcc gagcttgggt ggtaatgcga 119400
gcgatgggga gcagctgtaa atacagataa aacttcgctc actcacctgc cactcacctc 119460
ctgctgtgtg gccctgctgt gtggggaccc tggtctgag acactgagga aggtgctcat 119520
tcataaaata atatgtaaaa tgattggact gtctgtaaaa tggggcttgg aggaaccagt 119580
cctgcgctgc ccacattcac agtatttctg gcagatggaa tggcagggag tacaccgaca 119640
atgtaaaaaa gtggatcgat ctaaatggca ggtgtgtctt cagcactcag gcatagattt 119700
tattgtgttt aaacaccatg gtgaggactg aggactctgg agcttctagg ttcacagccc 119760
tgctctgcca ccttcaggtg tgtgaccctg acaagtcac tgaacctctc tgtgcctctg 119820
ttacttcatc tgtaacattt gcatgagagt agctccatc tggtaggggtt attacacaag 119880 ttaaatgaga caatgcaggt atctggcccc agctccctcc ctgacctctg ctcctagacc 119940
```

```
tctttcttgt ttggttccat ccaaccacac cagcttcctt gctgtgggtc aaacacacca 120000
agctcattca tgcctctggg cctttgcact ctctgttccc actgccagga tcactctttc 120060
cccagatatc cacatgcctt ggtatttcag gtctcagttc aaaagccact tcctcaaagt 120120
caccaagccc agaatgcttt cagctccatg agggccctca tttctgggtc actcattccc 120180
gtgtccccag cccctggcac tttggctaag caagcgttaa gcacctagcc ccgggctggc 120240
actcgagata tgtgagcgcg tgttacgttc aactttgctt tgcaggcgag aggctctaag 120300
acccagaaca cagcccctcc ccaccaggaa ctcaattcca ccaaacccct ggaaggcccc 120360
acggctcctc ttcccctccc gggacccact tcctccaact ccagatgcaa gcccagctgg 120420
gcaccatcct cggccgagag gttacagcac ccaggctggc tttagcgcag acctcagatt 120480
tcttaagcaa acgagaagag gtgaggaggc ctgtggggc acctaaagag agaatgagtc 120540
agtcagagct agacttgaaa cgtaagagac atcagcactt cttggaaagg caagaacgga 120600
cgcatttaga cagaactgtg catgcagaat gagggtaag cacaggccag tcaggaagtg 120660
gagtcttccg tcctctgtga gtccctccac ctggccctct cttcctcatt tccctctcaa 120720
atgtcacctc ctcagggaag ccctccctga ttccacttgc acccagcttt gctttccttc 120780
ctagcacagt ctccacctga taggatattg caggtccatg ttctctcctg taaaatcctg 120840
ggggccagac atagttcaga attcaggatg actcaggctg tagaaaggtc accttgtata 120900
aaatacccac cgacatgccc atcatgcagg gcgggaaagc acccaaagat caattgcact 120960
aatatctctg cagaaagaca tctgagcatc acaccgaaga ggatgaagac tctaaaaagc 121020
ctcaagttta gcttcaaaat gagttatgaa aactttcgg ttttcagaaa tcgtggattt 121080
cagaataaca gataaagctg ccgatctgaa catatgtatt ggttgtacat tgcctgtatg 121140
ctcaactaga atctaaaccc caggagagca aaggacttgg tccgatgctc tggcacatat 121200
aggtgctcaa taaattcctg aggaagaaat gcaggaggaa gccaggtgct ggatacgcag 121260
aagggactcg gtccaaaatg cagagaaaaa cagcaatcac tgagcgcctt ccaagggcaa 121320
aatgtctata caaactatct catgaatgct ctccctgcaa atacccatga caaaacaaag 121380
ggaggctcag agaggttaaa caacttcctc cagattacac agtggagagc tgggaagtag 121440
ccagctccga tttaaacctg ggatcccctc ttcaagctca ggcccttctc tctgccttaa 121500
gctcagagac gcagagcaat ttgctggata tcataaaaca gtggtgatgc acccggtctg 121560
acagtggatc ccccagcctc tgtagcacct caagcctctg ccggggcgct ccgatccaca 121620
ttcaccaagg gcaggtctgt gcaacctcca gacaagctcc tggcctctct tctagcccag 121680
ccatggtaag tctagctaaa cgtggctggg catgtctcca ctgtgccagc caggaggaaa 121740
actcagaaat gtctttcttg gtcaccccag tgaactggta caagcaggaa agaatacatg 121800
ggaagaaaag taggatggag tctgtccctc agatgtggac ctgaggcaag gctactgcat 121860
tcatctccgg gtctcagttc tcacctgcaa aatgagtgga ctaaatccca accaataaag 121920
ctcaaaggag gcaacagtaa agatttattc atttaggcca ggcacgtttg ctcgcatcta 121980
taaatccaac actttaggag gctgaggcag gaggactgct tgagaccagc agttcaagac 122040
tagcctaggc aacatagcaa gatcctgtct ctaaaaatat aaaaacaatt agccagccgt 122100
ggtggcacac acctgtagtc ccagctactc aggaggctga ggtggaagga ttacttgaac 122160
ccaggtattg gatgctacag tgagctatga ttgtgccact gtgctccagc ctgggaaata 122220
gagagagacc atggctctaa aaaaaaaaaa aaaaggtatt catttaacaa atacatagtt 122280
```

```
tgtactacat accaggtact gttttgtatg cttgacatat attaactcat ttagtcatca    122340
ctacaatggc atagtcacta taatctcata aatgcagaaa ctgaggctct gggaagtcag    122400
ttacacagta agcagcaaag ccagcatttg cactgggtga tctggctcaa gtccatactg    122460
tcactcccca gctatacgtt ttgacaggta acaacagaca tatacattga ttgtggaccc    122520
actgggtgtt ggacattgtg tgaagtagct tataaaacat gtcatcaacc ctcaagaaag    122580
ttcacttttta caaatgtgag gaagaacagt acttaggcgg cttctgtcct ggcctcactc    122640
ccaggtacca gtgagggcag tcgagaggtg gggcatctaa tcccaaacgc tctcctccat    122700
cgtcccagat ggggtgggtg gaagagggca gggagatggg ggaggtagaa aaggttctct    122760
cttctcatgt atttatgtat ttgtttattt tgagacagag tctcgctctg tcacccaggc    122820
tacagtgcag tggcacaatc atagttcact gcagccttga ccacctgggc tcaagccatc    122880
ctcccacctc agcctcccaa atagctgggg ctagaggcac ctgctaccac gcctggctaa    122940
gttttttaaat ttttttttgta ggaacaggat ctcactatgt tgcccaggct ggtctcaaac    123000
tcctgggttc aagcgatcct ctctcagcct cccaaagtgc tgggattaca ggtgtgagtc    123060
actgcgccca gcttgtcact tctttgacaa ttcatttcag ctccttttg aactgggagc    123120
attagaaaac tgaacacccc caccccttgcc ctgggcattt tgcaaccggg attgtattgt    123180
attaaacata tcagtcattg agtcacttcc tagcatttgg aaaccettag gttatctcgg    123240
acctgccggt aactgcatgt gttgtaactg gggtgagtga ctgcaggttt tcctccctgc    123300
tgcctcccca gcgtctccct ccagattcag atccagaggc ccagggtggg gcccaggaat    123360
ctgcactgtt gcttttacaa ctcaagccaa ggtgaataca ctggcccaag ttccttggca    123420
tggcattcaa ggcttttccac aatgcagccc agcccaactt tccatccatc tctggcttct    123480
gcttactccc taggttctgt acacagtgcc ctttcacact tcccagcctc cgcccactct    123540
gtgcctccct ttacctccca tcctctacct gccagactcc cctgctctac tcacaaggct    123600
agctcagggt ccctgggtgc tgggaagcct ggcccagtgc cctttgaaga gctgatcccc    123660
tctggcttgt ggtcctgcag ccgctggtgc atccgcaccc tcccagccct cacgtctgtc    123720
ttcctgcaga gggggtgctc cttgaggcaa gcaccagtgc ccagaacacc cccagggcc    123780
tcgcaggagc tgaatgagtg ctagtgagtg aatgagtggc ttagcaggtc acctcccatt    123840
catgggctgg gctagccgag ttctaagaaa cccctgcagg accctggaat gccctaatgt    123900
gcaggacacc ctggccaaac ctacacctga gcctgtttcc ccattggact ttgggatttt    123960
gataaaggca ctgaggtccc agcaaatgcc ttgggctcct cataggctac tgggggcagg    124020
gaagtgcagt gggtcatgcc tcccagaggg ctggggaagg ggagagacta gaactggagc    124080
agggttagcg ctggcctggg ggcattcctt gaaccccaga agcagacaaa ctagtggtcc    124140
cctatcttgc ttaagtctaa gaaatccaga ttttgtttaa aaaaaaaatc agggctcagt    124200
ggctcacacc tgtaatccca gcattttggg aggccgaggt gggaggatca cttgaggcca    124260
gcctggacaa catagtgaga caccatcttt ataaataaa tttttaaaaa taaaataaag    124320
atcagattcc tgggtttact gaatctgaat ctcaggcaa ggacctggga atctgcattt    124380
taagcaaatc tcccggagat tctggttatt gtggggctc ctcaaacgtg attgagagat    124440
ggagagcagc tggctctggc gtgggattgc ctggctcta gtcctgctgc cccacggact    124500
cccaagtggg cggcacctta gggcaagtta ctaaagcggc tggggtcttg gtgacctcat    124560
ctgtacaatg tccatgacgc acagcaccgg ccacagagaa gttagtggga ggtttcactt    124620
ggcatccttt cagtaaaaca agtcccagtc aatgatcgcg attattgggt ccatctgata    124680
```

-continued

```
ttcggaggcg gagaccgccc cgattcactg acctactact caaatttaca gttctcagaa  124740
ctttccccac cctttctctc tccgaagtcc tcactgactt cctgagcgca gggctgggcg  124800
ccactgcccg gagaagaggg gctgcgtggc ctccgacagc ctaacccaa  gccccccacc  124860
cccgcaggcc gtcccggcgg aggtctcact gccagcaccg gctttgggga gcgctgggtg  124920
tccacgtacc ccgggcctcg cgcctccgct gccgttcggc ggcaaggacg gaaccgggcg  124980
ctgctccgcg cgcaccgaga gtcgcgggct cgggccccgc tcggagtcgg ggtggtcccc  125040
gtggtccccg ccggcggccg agcccttccc gaacgccctc agccggcgtg cccgggcgat  125100
accttcgcaa cccgatccgc gcgcgggccc cggatcctac ctgcgcgccc ctgctccatt  125160
cgccgtccgg gcgcccaagc gggaagtggg ggacccctgg gtggcccttc cctggcccgc  125220
gccgcgcggg gctttcctgg gcgcggagac ccagcccgcc ccggcttcct gctcccgcc  125280
ccggcgcccg gcagatttgc atgcgccgcc ccgcccggcg cgcccggccc gggtcccggc  125340
cacctcgcgc ccctgtcgct gtccccgccg ccgccgccgg acagtccgag ccgccgtcct  125400
ctcctgggg cgaccccagc acctcgctgg gtgtcttgcc gcgcgcttcc tcccacgctg  125460
cagcccgagg tcacgcccag cggagaactc tgcagtggat ccccttggtc tcggaataaa  125520
acgcccacgc cgaccaggcc tccaggacct gctcctgcct ggcctccgcg gcctcttttg  125580
cgccggggca gttgcgtttg tgggggagg gctggcgac tggaatcctc ctccccttcc  125640
taacagcccg gcttccaagt gagagtggtt gcacattctt caataaatgt ttacccaact  125700
cctactccag ccacatttgg atagtaaaac agcccttcaa tcagtaacta gtacaatctg  125760
tcgggcactg caaatgttaa ctcgttcaat cctggcaact accctataag ggagtgatac  125820
tatcaccggt tttacaaatc aggaaactga ggcacagagt ccttaagaaa ttcaaaatgg  125880
gttgggcaaa gtggctcatg cctgtaatcc cagcactttg ggaagctgag gcgggaggat  125940
cacttgaacc ccatagttcg agaccagcct gggcaaccct gttagcgaga cccctatcta  126000
caaaaattga catttataaa attttaaaaa agaaagaaa gaaactcaga atcactctgc  126060
aggtaagcag gagcagggat ggagctggga ttcgaacaca ggccccatag accattaacg  126120
tctggacacc ataagaaccc ggatgcagcc agatgactgg ggggaaaaca ctcaacaaag  126180
tatttcaggt caggagggcc caagaagaaa gtagggacct cttagaccag tggggcaggt  126240
ggtctggaag aggctttttg agtagaggcc atttgagctg agactctgaa gagcctatgg  126300
gggaagactt tgtagggag agggaagagc tagtgcaaag gccctgtggg aaccagctca  126360
gcctgcagga ggaattgctg aaggccggca tggctgtgga gccctgagtg aggaaagagc  126420
ggagacaggg gaggtgggag atatttggac tcacactggg cagtgctgag aacccagaga  126480
gtaatttgac cccctgctgc cctcaaggag ctctcagttt gagggtggaa gccaaggact  126540
gcccaatggg atcaagtgct gtggtggagg gtgagggttg gcttcccagg gcaggggcca  126600
ctgcacgtca atcattcttt tttttttttt gaagatgggg tctcattcca ttgcctaggc  126660
tggagtgcag tgggtgatct cagctcactg caacctccac ttcctgagtt caagcaattc  126720
tcctgcctca gcctcctgag tagctggaat tacaagcgtg caccaccacg tccggctcat  126780
ttttgtattt ttagtagaca tgaggtttca ctatgttggc caggctggta tcaaactcct  126840
gacctcaggt gatctgcctg cctctgcctc ccgaagtgct gggattacag gtgtgagcca  126900
ccacgcctgg cccatatgtc aatcattctt tcatgtactt ggtctgtctt ggtcctactg  126960
tgtgtctaac cttgtgacaa gcgctgatga cgcagacctg aagacatgaa acagacacaa  127020
```

```
tccctgccct ctgagacctt acaaccaagt gagcaagaca gccaccaacc cacccccaga 127080
agtgacagta aagataagtc agttccctgg ggtcagggat ggcttcctgg aggaggtgac 127140
ctctgaccag tgcctgaatc aatgcagaaa acatgcagg tggaagggac agcatgagca 127200
aatacctgga ggtggcgtgg gagtgtggaa aaactcccat ccttcggcat ctgtttgtgg 127260
atgcctccat atgccaagtc gtgagctggg ggctagggag agcaagaaat agatccagcc 127320
cctgcttcct agccctgagg acctggttgg ggcactgaca agtgagcaga cgtaagcaat 127380
tgaagtgaac agatgtaagc aattgagtgt aataaacccc gtactggggg cagcccaggc 127440
agacgctaag aggactaggg agagaaggcc acaggaaggg cttcctgga agcttgggtt 127500
tcaggaggaa taggaatcct ctggattagg tgtgacttcc actcccgtcc acactcatac 127560
tccctcacac tcattactca cacatccgca cacccacacg gttgatgctt catcccaggc 127620
agttcagccc tgcaagctgc ctttgtcctg tctgtgtttc tgagtttgtg ccccatgtca 127680
tcgggagacg acagcaaaag tctacctttg aagtcctttg ggaatgtatg gcttgggcta 127740
tatccctcc tggactccca aactgggctc ccatcctgtt ttcccagtca agtcatcctt 127800
cgtcggtttc ctcgcttgcc tctagactgc cggcattggc ataccaactc tgctacgtat 127860
tgactatgtg actttgggca aagtagatca tcctccctgt gcttcagttt ccccatctgt 127920
aaaatgggga taataataga cccacctcat agggctatga atggtgaaa tggcaaggta 127980
cgtatcgcag tgcctagaat agtgcctggc gtggattagg cattcaaaat gtcaattgct 128040
gttcttatca ggatgaaaat gagaaagaag caaagtcgaa gcctgttgcc ttggtctgtt 128100
gcttggttgt gaaatggaga tgaacgtggc attgagaaga caggcaaaga aagcacagct 128160
gtggtcagag gctaagacat tcaggaaatc tgggggaaga gacttcggga attcttttgta 128220
ctcttctccc aactttcccg ccagtctgaa attatgtcaa attacaaagt taaagaaaac 128280
agggcattgt tctcgggtgc aagagagata ataaatgtct tcttgcatac agtcccactg 128340
ttcaagttcc tgcccaagat gcccagactt tatctgtgac tgctccgtca gtcctgggag 128400
caggtccaaa ggcaccaaga tagtaaaacc tctgttcccc catctagggg ttcccaagtc 128460
ttgcctcagt ataagctcaa tcctcattat atcctaacac gcttacttgt ttccaagcct 128520
ttcggtcttt aaaactaata gagttttattt tttagaacca ttgtagatta tggaaaaatt 128580
gagccgatag tactgagagt tcccatacat ccctctcccc catgcaaaat ttcctctttt 128640
atcaacatct tgcattagtg tgtagtgcct tccttataat gctgatacat tattataaac 128700
taaagtccat agcatacatt gtttcactgt ttctcggggt ttttgttttgt tttgttttgt 128760
tttgtgtttg tttgcttgtt tggaaacaag gtctcactct gttgcccagg ctggagcagc 128820
ctggaactcc tggactcagg ggatcctcct gcttctgcct tctgagtagc ttgggctaca 128880
agaacatgcc accacactag gctttttttt ttttatactt ttagagacag tcttgctaca 128940
ttgcccaagc tggtctcaga ctcctaagct gaagttatcc ttccatctca gcctcctaaa 129000
gtgctgggat tacaagcatg agccactgtg cctaacctct gcagcacagt tctgagtctt 129060
tttttttttct ttgagacaga gtcttgttct gtcacccagg ctgggtaca gtggcgtgat 129120
ctcaactcac tgcaacctgt gcctcccagg ttcaagcgat tctcactcct cagccttcca 129180
agtagctggg actacaggtg cacgcctggc taattttttgt attttttagta gagacggagt 129240
ttccccatac tggccaagct ggttttgaac tcctgacctc aagtgatcca ccagcctcgg 129300
cctcccaaag tgttgggatt acaggcatga gccaatgcac ccagccaagt tctggtcttt 129360
aacaatgtat aatgccatgg atccacacat gtagcaacaa aaagaatagt ttcccagcct 129420
```

-continued

| | | | |
|---|---|---|---|
| gggcaacata | gcaagacccg | gtctctacca | aaaaacacaa acaaacaaca acaacaaaaa 129480 |
| acaggccagg | catggtggtg | cactgtagtc | ccagctactc agaggctgag gcaggaggat 129540 |
| cccttgagcc | caggagttcg | aggctgcagt | gaactatgat catgccactg cactccagcc 129600 |
| tgggcaacag | aatgagaccc | tgtctctaaa | aaaaaaaga aaaaaataaa gaatagtttt 129660 |
| acttccctaa | aaatccccaa | ttctctacct | attcttcctg gattctggaa accactgatt 129720 |
| ttttactgt | ctccatagtt | ttgccttttt | cagaatgtca cgtaattgaa atcagaaagt 129780 |
| atgtagtctc | ttaatactga | cttcttttac | ttagcaatat gcttttcagg ttcctcaatg 129840 |
| tcttttccag | gcttcacacc | tcatttcctt | ttgtggctga atagtgccct attgtatgga 129900 |
| tgtaccacag | tttatccatt | ctacctattg | aaagacatct ttgttgcttc caattttttgg 129960 |
| caattatgaa | taaagctgct | atcaacactc | atgtgcaagt ttttgggtgg acataagctt 130020 |

<210> SEQ ID NO 89
<211> LENGTH: 9900
<212> TYPE: DNA
<213> ORGANISM: Homo sapiens

<400> SEQUENCE: 89

| | | | | |
|---|---|---|---|---|
| gaattcaata | aaaacaagc | agggcgcgtg | gtggggcact gactaggagg gctgatttgt | 60 |
| aagttggtaa | gactgtagct | cttttttccta | attagctgag gatgtgttta ggttccattc | 120 |
| aaaaagtggg | cattcctggc | caggcatggt | ggctcacacc tgtaatctca gagctttggg | 180 |
| agactgaggt | aggaggatca | cttgagccca | ggaatttgag atgagcctag caacatagt | 240 |
| gagactctta | tctctatcaa | aaaataaaaa | taaaaatgag ccaggcatgg tgcggtggac | 300 |
| cacgcaccta | ctgctagggg | ggctgaggtg | ggaggatcat tgagcctggg aggttgaggc | 360 |
| tgcagtgatc | cctgatcaaa | cattgcattt | cagcctgggt gacagagtga gaccctgtct | 420 |
| cagaaaaaaa | aaaaaaagt | cattcctgaa | acctcagaat agacctacct tgccaagggc | 480 |
| ttccttatgg | gtaaggacct | tatggacctg | ctgggaccca aactaggcct cacctgatac | 540 |
| gacctgtcct | tctcaaaaca | ctaaacttgg | gagaacattg tcccccagtg ctgggggtagg | 600 |
| agagtctgcc | tgttattctg | cctctatgca | gagaaggagc cccagatcat cttttccatg | 660 |
| acaggacagt | ttccaagatg | ccacctgtac | ttggaagaag ccaggttaaa atacttttca | 720 |
| agtaaaactt | tcttgatatt | actctatctt | tccccaggag gactgcatta caacaaattc | 780 |
| ggacacctgt | ggcctctccc | ttctatgcaa | agcaaaaagc cagcagcagc cccaagctga | 840 |
| taagattaat | ctaaagagca | aattatggtg | taatttccta tgctgaaact ttgtagttaa | 900 |
| ttttttaaaa | aggtttcatt | ttcctattgg | tctgatttca caggaacatt ttacctgttt | 960 |
| gtgaggcatt | ttttctcctg | gaagagaggt | gctgattggc cccaagtgac tgacaatctg | 1020 |
| gtgtaacgaa | aatttccaat | gtaaactcat | tttccctcgg tttcagcaat tttaaatcta | 1080 |
| tatatagaga | tatctttgtc | agcattgcat | cgttagcttc tcctgataaa ctaattgcct | 1140 |
| cacattgtca | ctgcaaatcg | acacctatta | atgggtctca cctcccaact gcttcccct | 1200 |
| ctgttcttcc | tgctagcatg | tgccggcaac | tttgtccacg acacaagtg cgatatcacc | 1260 |
| ttacaggaga | tcatcaaaac | tttgaacagc | ctcacagagc agaaggtgag tacctatctg | 1320 |
| gcaccatctc | tccagatgtt | ctggtgatgc | tctcagtatt tctaggcatg aaaacgttaa | 1380 |
| cagctgctag | agaagttgga | actggtggtt | ggtggcagtc cagggcacac agcgaggctt | 1440 |
| ctccctgcca | ctcttttttc | tgagggtttg | taggaagttt cctcagttgg agggagtgag | 1500 |

-continued

```
agctgctcat caaggacttc tctgtccggt tggaggttaa ctctgtctct tgctctctca    1560
tttctgcctg gaccaagact ctgtgcaccg agttgaccgt aacagacatc tttgctgcct    1620
ccaaggtaag aagccgtccc acggtctgtt ttagcaaatg gggagatcca tccccaaatg    1680
tctgaacaag aaacttgtct aatggaaaac gagcgggccc aaattaactc taaggtgtta    1740
gatgttttca agaacgagaa agtctgatct ttactcttaa gcatgttttg gtctttctgg    1800
tttcacttga tttagaagac atgtaataga aagcttacat gctgtagtcc tgactcagat    1860
cctggtcaaa gaaaagccct cttgggtttt acttagcttt ggcatagtgc ctggaacgta    1920
ggaggcactc aataaatgcc tgttaatga gagaattttt ctggcccata catttctgaa     1980
aaaccaaata ctctcacaga aacagatatt gagatgacag gttgagggag ctttcatttt    2040
gtctaagaga cttcctatgg caacagaaaa ggtatcgcca gagcccctcc tcttccacag    2100
cctggccacc taacagccct ctggttccgg ggctgccgtc cagagctctc agcttgctct    2160
ggccggccga actcccctcc agctcggtct ggaaccatcc tgctgggcag cgtccagcac    2220
atccctgctt cgggctgcct gggcacctcg cctctctgcc tcctgtgctg cctcaccccc    2280 accctctat ctgtagtggg agggagatag atttgacagc tgatagtgca ttttctctga    2340
caaacacatg actacagccg tatcaatagt tttgtgcatt tcagttcctg ttttcatgga    2400
aacacacggc tgagaatgaa agccccaaag cctcaatttc acagtggtct cctaactacc    2460
tgctttccat gcaaactagg gagatgatat ggccaggagt gaagccctgt gtgttgggca    2520
gggtcacact ccagcaccca gaccatagaa cagggcccat cctgcttcat gagggaaact    2580
gctcttcggg cctttagctg gactatctca tttcattagt tatcccggga gtccgataca    2640
ggatgagatt ctgaagggca aatacacact tttttttttt ttttgagata gggtcttgtt    2700
ctgtcaccca ggctggagtg cagtggtgcg atttcagctc atagcagcct ccacctccca    2760
ggctcaagct atcttcctac ctcagcctcc caagtagccg ggacgacagg tgtgcaccac    2820
cacgcctggc taattttttgt attttttttgt agagatggag tcttgccatt ttgcccaggc    2880
ttgtctcgaa cttctgggct caagcaatcc gtccacctcg gcctctcaaa gtgctgggat    2940
tagccactgc acctgggcaa cagtttatgt gtgtgtgtgt gtgtgtgtgt atatatgtgt    3000
gtgtgtgtat atatatgtgt gtatgtatat atgtgtatgt atatgtgtgt gtgtgtgtgt    3060
gtgtgtgtgt gtgtataaaa tctccaagtc catccaaccg agatggctcc tactagaagc    3120
caagagtcca ccggggttgag cactgggtct ctggaggcct gtcggactgc tgagaaggct    3180
ctaacaaagc caagggaagg gccacctcac tagaagccag gcctggagga agggtgaggg    3240
ctgagggctg gaggtaagac tgcctgtggt tttagcccca ggctctgcca ctgactagct    3300
gtgtggctgg ccttcagaca tcttcacagc tctctgcacc tcagtttcca catgtgaaga    3360
tatgaaagtg attctgaagg tgattgcaag gttgattgga atccagctct tgagttagtg    3420
caaagtgtta ttgtgagatg atataaccac gattaaaagc aagaacaggt gcagagaagc    3480
gatgattcta agaaggaggg gaccgggttg gaaaggatca accatccag gatgccgagt    3540 ctggggcaat ccatctgggc tgtttctgga agaccccccgg gtgcaggcca ggacactgct    3600
gccctcccgt ccttaactcc cctcttcact cagtcctcac tcacctccct ctcacacaca    3660
caaacatctc ctagaataat ccccactgcc tgccttcact cttaccgtc tcatttgcct    3720 cccctgaact tcatcctcct ggagttcacg atctcactct tcactctttt cttccccctcg   3780 aagattcagc actgcttact tacatgttaa gatatttcag aacagtgaaa tgttgctatt    3840
ttcaaaaacc tacaaaggtg gtatgcagag gaaaaggtac ttctttgtgt tcccaaagaa    3900
```

-continued

```
aacatctttc caaaatccag cctattgatt ttatttcttc gggggaacaa gaattttagt      3960
atctctaagt tgggtagcat tctactcttg gcagttgctg gaaagaaggc actggtctag      4020
gtcctgggct tcacaggtaa cacctgtcag ggtgtctatg aagtcaaggc tgtctgagga      4080
acagcaaagt gggaagaagc aagctggctg gctgatgaag ggtttcttgg gtggacaagt      4140
agttggagcg atttcctatt taccaaagag agctaaagtt cataattcta cagagagttc      4200
cataatgaac ctcaaatacc tctgtttttt gaaggagttt ctcatataca gcactagctg      4260
actatcctgg gcaggatggg agataatgaa tgcagtgcca atcgggctgg atttatatgg      4320
tcctagtgag gctggtcaag aaccgagtta gaactctcac agagtcactg cccacagaag      4380
aaatctccca gtggctgttt cctgacatt cccgggaggc aggcctcctt ctgagtcact       4440
ccctaagcag ttctgaactg tgaggtcagc caggctgtcc aagtgcactc cctgagccac      4500
tggcagacac actcagcagc cagagctaga caggcaggtg gtaggagtcc agggccacgg      4560
cagggatgga gtgtcgcccc ctcgctgcga taccagagca agtaaaacgt taaggccttg      4620
cactaaagct gcccttagga tgcattcttt taaagttttt ccatttaatg cagactcttt      4680
tcaattctta ttttatcctt gtttccttta gaaagtcctt tgaaaaatat ctttagaggg      4740
ttttttccta tactatgtgg ccatatacgg gtcaaaatta agtttaattt ccaggctcca      4800
agccagcgtt tcagaaaaat ctcaccaagg tttgtggtaa aagaagcaaa gggctgactt      4860
tttggttttc ttgaatctca ctgttccctc tgcagcagca tgcatgtctg cccacctcca      4920
gacacacagg caccatctgc cgcccccat cagcccgtgt cccttccacc tcgactcgcc       4980
tacaaagccc agagaggtct gtttcttggc ccccagagcc caaagatact gacacactct      5040
tacatttcca actagaatca ggaacgagga gtgactctca gtcagttcat taagtaaatg      5100
tctttctaac cgctctgccc atgggacatc acgccccaca ggggaaaggg gaagcttctg      5160
tagcctggga ttctggtgcc tcagtctggg tctagacttt cctgaaaaaa cgttaaaata      5220
tgaactgcat tcctagaatt tagcctacat aaataagaga tgaacacaaa gatttctata      5280
gtttactcac tgccgcttat ttacagaagc aaaaatctgc cacgataggg gcctgacaaa      5340
tgacagtacc actgtgcaat gcgtttctac gcagctctca atcccatgtt ctctaatacc      5400
accgaaggct taggaaatgc ttatggtata tgtaaagagt aaagaagtta caaacagtat      5460
caacagttga cccctatttt aaaaagtatt tttgaaaagt gtgacgatat ttaccaaaat      5520
attaacgagc aatagttacc tctggctggt gggatgagtg aatgtatttt tgttgaatat      5580
atgttacctt tatagtaaat atatgttatc ttgatcatca gaaaaaaaaa tatgtaagaa      5640
cttgaaagct gcttggacag cgctgctgat agaaaccct gagcatcttg tcactgttct       5700
tctgattcag agggtctggg tggggcaggg gtggtctgag attctgtatt tctaagaagc      5760
tcccagtgat gtccatgctg ctgtccatgg accacacttt gagtatcaag ggaccagagc      5820
atgtcggggg agaggctggg gatagctttc tttatctgaa ctggataaag gaactgggct      5880
caagctaaga accctctcca ggttctgcat ctttgttctt cagtgaaaaa tgagaggaca      5940
caccaggcca ggttcagact gagacacaat ccctctcctg ggttcccaat gacttgtctc      6000
ttgtccattc cctttctctaa ggctaagggc cccccaggaa gagccatgtg gccagaccct     6060
cacagttgct ggcattccaa ggagattctc actccgcatc attggtccaa aaggccccttt     6120 acagaagctc tgcccaaggc tcagatcaat ggcacctgct cccagagctc ctctgatctc      6180
ccaggacacc tttccctgat ctgtgcactt atctcttgct gcctggcaaa atgtcttagc      6240
```

-continued

```
tcctcacttg ggccatgtgc tgctctcctc tcccatgggg agagccacac ggagagtgct    6300
ggccaaagca gcagagttca ggccaaagga tgtgcactca tttattcaac aggcatgcag    6360
gatttccagg gaaagctgga ttttaaaacc tctgggaaca agagcagaac ctgactgaga    6420
gctcatgtgg gcacttttca tagcagaata gctcatgagg tatagagaca cggacgcaga    6480
acgtgggctg tagcgacaga tggtcctgca ttctagtccc cactgtgcct tttcctcatg    6540
ggatgacttt attcaggtac cctttcggca aaatcctcca agagaaagga aactgggagg    6600
ttctggggag aaggctgctg cgtttgcaat gggagaggt tgttgacaga ggtttatgtc     6660
tgtggcaagc agccttcctt cagtggaata cttgaagaca ggtctgtagt tgagcaaact    6720
cacctccatt tgtcctcctg gaaagaagaa atcaagagga aaatctctc tcccatcctc     6780
caaatggagc tggcacattg ctatctgtgg catttgtctt tccagaacac aactgagaag    6840
gaaaccttct gcagggctgc gactgtgctc cggcagttct acagccacca tgagaaggac    6900
actcgctgcc tgggtgcgac tgcacagcag ttccacaggc acaagcagct gatccgattc    6960
ctgaaacggc tcgacaggaa cctctgggc ctggcgggct tggtaagctg cactgtattc     7020
ctggcaagcc ggccgcgtgg ctcctggtgg acagcagcct cacttctaaa cactccttag    7080
gagctgcagc acccttggtc aacccattca ttcattcact cattcaataa gtatttgctg    7140
aagttccaca agtgctgggt gtggttctag gtgctgagga cgtgtcacta aagacagcag    7200
gccgagtccc tgttctcatg gaatgttcta atgggagagt tagaaaaaca aacatgtaaa    7260
atgatggcca gcagtgatac gtgctacaaa gaaaaacata gaaataaaga acataagagt    7320
catgggggag ggggctgact taggagctgg tgacattatc tgagcagata tttgaattga    7380
gggagcaggc cacatgacta actagggaga ccattccagg gagaaggagg aggtatgcaa    7440
aggccttagg atggaaatga actaacttcc tgtatttaaa gaccagtagg aaggccagtg    7500
tggctggatc agagtgagtg agggggtagtt tccaggacag cagatcacac aaggcccttta   7560
gattccacca cgagtatgga gggaacacct gcagagcttt gggcaggaca aagactgtac    7620
aatctgattt acgtgattta aagggtcag tctggctact gtgtggtaaa taggctgaaa     7680
gggggaaagc atagaagcaa gatggcctgt tgggaggcta ccacagtaaa ccaggctaga    7740
gatgatggtg gcgtggacag aatgaagcaa gatggcctgt tgggaggcta ccacagtaaa    7800
ccaggctaga gatgatggtg gcgtggacag aatgaagcaa gatggcctgt tgggaggcta    7860
ccacagtaaa ccaggctaga gatgatggtg gcgtggacaa atggagcagt tgaggtgaac    7920
agatttggga tatgactaaa aataaaacca gaagatttgc tgacagatcg gttgtagggg    7980
gtaagataca ggggaggaaa agatgacctc tttgttcctg cccaaacccc tctggcgatg    8040
gtcagtactg tttacagaga gatgaaagac tggcggcaag gcaggctgg aggttcagca     8100
gaagatcaag agttcaattt tgtacatcgt acatgtaagg tggctcttgg atagccaagt    8160
gaaggtgttg agaagatggt tagaaaagtc tggaacttag gggagaggtc agaacttgca    8220
atacaaaaag gagagtcctt agatagatac tgctgaaaat ctgaatgaca gaaagggaga    8280
gatcaaagga ctgagcctga gatcaacaca tggaggtcag gagaggagga tccagccaag    8340
gggcctgagg aggagtgacc agtgaggcag gagaacatgg agagtgggcg tacccccagg    8400
aagccggtga ggacactcaa ggagggaggg ttgactgtgt caaatgtact gaaaggacag    8460
gtcaggtgag gaccaagaaa ggcccctggg tttggctgat ggaggccatg ggtgaggctg    8520
atgtaaatgg agaggcagga aggaaagccc agctggagtg ggctcaccga ggatagggtg    8580
gcgagaggag acaaagaagg aacagtgagg gcagacaact cttgaagat gtttagctat      8640
```

-continued

```
aaggctgcag agaaactgag cccacagctg cagggtggtt atggagtgag ggaagctctt    8700
ttaaggttgg gggtataccc agcatgttaa tgcacctggg ggaatggtcc agtggagcag    8760
gaagaactga agagagcaga aagaggaaga atcattaggg ggcagaagtc cttgtagccc    8820
agagtggatg ttatctaata tcgagtggag gaattaattg gctttagagg agaacaagga    8880
catgtatccc ctctctgggc ctatcacctt gtagacaatg gataggtca tgggatagga    8940
acttggcaca acacatgttc tctcttttaa ttctctccat tatcttatga agcaggcaag    9000
taggcaaaca attgtcccaa ctttacaaaa gaaactgaag cttttataaa ttaagtagta    9060
catcctaagc aatacaatta ataaatggta gagctgagat tcaaactgaa gcagtggcct    9120
gggggtagca tctggaatcc ttcccacctt tagggctgct gtgctgcggt gctgctgttt    9180
aatggcacag agggccagat gactgaatct ctctcagcag tccaggcagt catgcagaag    9240
gcccagtaga gcaccgggca ggtctgagcc agcatcttca agttccaccc tgtgagcaag    9300
cacttagctg tgacacactt ctcgagagac tggactcccc ccgcgcaac ccacccaaaa    9360
gcagataggt aatggtatac agtaaccatt tctagaagtg taagtagtat gcacccaaaa    9420
taggcaaaac ctgctggcct agtgatagag acaactccca gtcaggctag actggaggcc    9480
ttggttttat aagtgttcag gtgacaagtc ccacagtagg cttgatcaag tagacaggca    9540
ggcaagacaa atgcttacca atgcaagcta atgaaatgtt tcttttgcag aattcctgtc    9600
ctgtgaagga agccaaccag agtacgttgg aaaacttctt ggaaaggcta agacgatca    9660
tgagagaaa atattcaaag tgttcgagct gaatatttta atttatgagt ttttgatagc    9720
tttattttt aagtatttat atatttataa ctcatcataa aataaagtat atatagaatc    9780
taacagcaat ggcatttaat gtattggcta tgtttacttg acaaatgaaa ttatggtttg    9840
caactttag ggaaatcaat ttagtttacc aagagactat aaatgctatg gagccaaaac    9900
```

<210> SEQ ID NO 90
<211> LENGTH: 4740
<212> TYPE: DNA
<213> ORGANISM: Homo sapiens

<400> SEQUENCE: 90

```
ggatccccgc tgacaatcta gaaacaagca acaggaccct ctgatgtagc catctgtgcc      60
gcgcctctcc gcaccgcccg ccacgccttg gtccctggag accaccctcc agggcagggg     120
ctgccgctcg gccgggcccg cggggtccct cggcctgaca tggccggtgc tggagcggca     180
cgtgcgcgcc tcggcccctc ggccgctccc gcccctcgcc ggtgcgcacc ggcgctcggg     240
gagccgctgg cccgggtgtc cagccggcc ttgccctgcc tggcgctcgg accgccacct     300
ttgccgcccc ctcgccagcc tccgcagctt ccagactggc cggtctgcgc gcccacccct     360
gcctcccgga ccgccaccg ccgaggcgcg gaggagggcc cggccgcgca gatcccgctt     420
atcggcccat ctcccgttac ataaggccac cccctatct ccgcgggcca tcgccgccgc     480
aaccgccgcg ccagcgcctt ctcccacgcg cgggggcgcc cctgcccacc gctcccggca     540
gggcttttgg tggccatggg ggataagggg cgttgactca cccgggcggg gctccgggag     600
ttgcacagac caaggtagtt ccccgctcct tcccccatca cggagaccct gtgggagatg     660
ccgtgggccc tctactacag attaggaaac aggcccgtag agggggtcaca cggccaagta     720
gcggcactcc aggcactggg ggccctcgag gggaagggc agacttctgg gagtcagagc     780
cagcagctgg gctgggaagc ttcgagtgtg gacagagagg gtgggaatga cgttccctgt     840
```

```
gggaagagag  ggtggcaagc  ctgggatgcc  tctgagcggg  aatccagcat  gccttgtgag     900
gagggtcaca  agcacaccct  tgtgaggagg  ttgagcccca  tcgaggacag  gacggaggga     960
gcctgagcag  gcagagaggg  ggcctgggga  ggcgctggtt  cggggaggaa  gtgggtaggg    1020
gagaaatctt  gacatcaaca  cccaacaggc  aaatgccgtg  gcctctgctg  tgggggtttc    1080
tggaggactt  ctaggaaaac  gagggaagag  caggaaaagg  cgacatgctg  cagagactgg    1140
tgagcaaagg  ggatcacccc  aagccccagt  ggcactagga  acacttacaa  tctctgacct    1200
ggactaaggc  tgccagctgg  cccagttaag  agtttcccag  aaggatggcc  catacacttt    1260
aaattaaagg  ggccagacac  gtgcacacta  cttccagcca  ctctggaagc  tgaggtgggg    1320
ggatcgcttg  agtctgggag  ttggaggcca  gcctaggcag  gcaacatagt  gagacccat    1380
ctccaaaaaa  acaaaacaaa  acaaaacaaa  aaacaccaa  aaaagctccc  agaaagacct    1440
ctgaatcttt  ctggatctct  cagtggagac  cttggaaatc  tgaactttga  caatccctct    1500
cacagtgggg  ccaaggagga  attaggcaag  ccaaaagaag  tgaactttac  tcttctattg    1560
cctgtttgaa  ttttgtatcc  aagcaagtgt  tacttaagta  atttaagaga  ctggttcatc    1620
gaaaaaataa  aactccccaa  attcccatag  ctggtagact  gtggtcacag  ccacagtgca    1680
ctaagactat  ctgctcagca  cttctggtga  cccaaaaggg  tctgaggaca  ggagctcaga    1740
gttgggtcag  ctgtccaggt  actcagggtt  gtcacaggca  aaactgctgg  aactcagggc    1800
agcattgcaa  atgccacgcc  gctctcaggg  ccccttgcct  gccgctggaa  ttaaacccac    1860
ccagatcttg  gaaactctgc  cctggaccct  tctcaataag  tccatgagaa  atcaaactct    1920
ttcctttatg  cgacactgga  ttttccacaa  agtaaaatca  agatgagtaa  agatgtggtt    1980
tctagatagt  gcctgaaaaa  gcagagacca  tggtgtcagg  cgtcaccact  tgggcctata    2040
aaagctgcca  caagacgcca  aggccacaag  ccacccagcc  tatgcatccg  ctcctcaatc    2100
ctctcctgtt  ggcactgggc  tcatggcgc   ttttgttgac  cacggtcatt  gctctcactt    2160
gccttggcgg  ctttgcctcc  ccaggccctg  tgcctccctc  tacagccctc  agggagctca    2220
ttgaggagct  ggtcaacatc  acccagaacc  agaaggtgag  tgtcggctag  ccagggtcct    2280
agctatgagg  gctccagggt  gggtgattcc  caagatgagg  tcatgagcag  gctgggcctg    2340
gtcctaagat  gcctgtaggt  caggaaaaat  ctccatggac  caaggcccgg  cccagccatg    2400
agggagagag  gagctgggct  gggggctca   gcactgtgga  tggacctatg  gaggtgtctg    2460
gcagactccc  cagggactac  ctgctctcct  ggcctggcct  tgtctgccac  tgccagctcc    2520
tactcagcca  ttcctgaaca  gaggacagca  gagaagggtc  cagcaccctc  ccagaaccat    2580
gtggcatttg  ccaactggat  tttgaccata  acaatgcagc  cattctcccc  agcaccatca    2640
taggcccgcc  cttacaggag  gattcgttag  tagagtcgct  ccttgcccca  ctagtaacag    2700
ctcacatgtc  ttgagcactg  cttacaccag  gcctggtgca  cgtgctttat  gtgtcatttc    2760
atcactgcca  gccacctcaa  gaggcaggta  cgatgaaccc  attctgctaa  ggttcgtgag    2820
gttaagtgac  agaggctgga  ttcaagccag  gcctggccaa  caccagagtg  tccatgctcc    2880
taactgcagt  gttccctcac  catcagaagg  cagggcattt  aatacaccag  atccccaccg    2940
cctcccatct  gatttgtctt  ggtcaacatg  gcccaggcca  ctcctacttc  actcgtcccc    3000
accctgaccc  ttcccgcagg  cccctgtcct  cctgccctga  ctatggcaag  ccttgcatgc    3060
agcttgtccc  ttactagtgg  tgtcaatttt  tttctctcag  ctccaagacc  ctaaacagtg    3120
ggacctcacc  cctatgcctg  ctgttcaaag  cagaaaacga  agctcaggaa  tgctgagggg    3180
ctgccaggcc  tgcctctgtg  ccacaccagg  gatgcttgtg  gggcctgtgc  tggggcagac    3240
```

```
ctggcctggg ctgccagggc aggcccacaa cccctgccag cactctgctc actgtcactt    3300
tgctcccaca gcgtccgctc tgcaatggca gcatggtatg gagcatcaac ctgacagctg    3360
gcatggtaag gacctttggg tgcagggagg atggggcaga ggctccaggc cttgggctta    3420
tcttctctga gcctcccttc catggctggg gttccaagca agcttcaagt gctctcctcc    3480
ctcccgccat aatctggccc cttcccgccc accacccaga ctcacctgcg ccaggcatct    3540
cagccccatc ttcctgcaga ctcacaaaag gcagctgccc aagcagggcc tgaccectcg    3600 gtgtcccctc cccacagtac tgtgcagccc tggaatccct gatcaacgtg tcaggctgca    3660
gtgccatcga gaagacccag aggatgctga gcggattctg cccgcacaag gtctcagctg    3720
gggtaaggca tcccccaccc tctcacaccc accctgcacc ccctcctgcc aaccctgggc    3780
tcgctgaagg gaagctggct gaatatccat ggtgtgtgtc cacccagggg tggggccatt    3840
gtggcagcag ggacgtggcc ttcgggattt acaggatctg ggctcaaggg ctcctaactc    3900
ctacctgggc ctcaatttcc acatctgtac agtagaggta ctaacagtac ccacctcatg    3960
gggacttccg tgaggactga atgagacagt ccctggaaag ccctggttt gtgcgagtcg    4020 tcccggcctc tggcgttcta ctcacgtgct gacctctttg tcctgcagca gttttccagc    4080
ttgcatgtcc gagacaccaa aatcgaggtg gcccagtttg taaaggacct gctcttacat    4140
ttaaagaaac tttttcgcga gggacggttc aactgaaact tcgaaagcat cattatttgc    4200
agagacagga cctgactatt gaagttgcag attcattttt ctttctgatg tcaaaaatgt    4260
cttgggtagg cgggaaggag ggttagggag gggtaaaatt ccttagctta gacctcagcc    4320
tgtgctgccc gtcttcagcc tagccgacct cagccttccc cttgcccagg gctcagcctg    4380
gtgggcctcc tctgtccagg gccctgagct cggtggaccc agggatgaca tgtccctaca    4440 cccctccct gccctagagc acactgtagc attacagtgg gtgcccccct tgccagacat    4500
gtggtgggac agggacccac ttcacacaca ggcaactgag gcagacagca gctcaggcac    4560
acttcttctt ggtcttattt attattgtgt gttatttaaa tgagtgtgtt tgtcaccgtt    4620
ggggattggg gaagactgtg gctgctggca cttggagcca agggttcaga gactcagggc    4680
cccagcacta aagcagtgga ccccaggagt ccctggtaat aagtactgtg tacagaattc    4740
```